(12) United States Patent
Chen et al.

(10) Patent No.: US 8,673,602 B2
(45) Date of Patent: Mar. 18, 2014

(54) RECOMBINANT BACTERIA HAVING IMPROVED SUCROSE UTILIZATION

(75) Inventors: Qi Chen, Wallingford, PA (US); Qiong Cheng, Wilmington, DE (US); Jian Ping Lai, Wallingford, PA (US); Kristin Ruebling-Jass, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 202 days.

(21) Appl. No.: 13/210,550

(22) Filed: Aug. 16, 2011

(65) Prior Publication Data

US 2013/0045519 A1  Feb. 21, 2013

(51) Int. Cl.
*C12P 7/42*  (2006.01)
*C12N 1/20*  (2006.01)

(52) U.S. Cl.
USPC ........................................ 435/146; 435/252.3

(58) Field of Classification Search
USPC .............................................. 435/146, 252.3
See application file for complete search history.

(56) References Cited

U.S. PATENT DOCUMENTS

| 6,960,455 B2 | 11/2005 | Livshits et al. |
| 2011/0136190 A1 | 6/2011 | Eliot et al. |

FOREIGN PATENT DOCUMENTS

| WO | 2009078687 | 6/2009 |
| WO | 2010051849 | 5/2010 |

OTHER PUBLICATIONS

Olson et al., "Production of tyrosine from sucrose or glucose achieved by rapid genetic changes to phenylalaine-producing *Escherichia coli* strains", Appl. Microbiol. Biotechnol. (2007) vol. 74, pp. 1031-1040.

Jahreis et al., "Adaptation of sucrose metabolism in the *Escherichia coli* wild-type strain EC3132", J. Bacteriol., Oct. 2002, pp. 5307-5316.

Lee et al., "Development of sucrose-utilizing *Escherichia coli* K-12 strain by cloning β-fructofuranosidases and its application for L-threonine production", Appl. Microbiol. Biotechnol. (2010) vol. 88, pp. 905-913.

U.S. Appl. No. 12/960,634, filed Dec. 6, 2010.
U.S. Appl. No. 12/960,646, filed Dec. 6, 2010.
U.S. Appl. No. 13/210,488, filed Aug. 16, 2011.

*Primary Examiner* — Tekchand Saidha

(57) ABSTRACT

Recombinant bacteria having an improved ability to utilize sucrose are provided. These recombinant bacteria have nucleotide sequences encoding sucrose utilization polypeptides integrated into their genome between the yihP gene or its homolog and the yihO gene or its homolog. Additionally, methods of utilizing the recombinant bacteria to produce products such as glycerol and glycerol-derived products are provided.

5 Claims, 1 Drawing Sheet

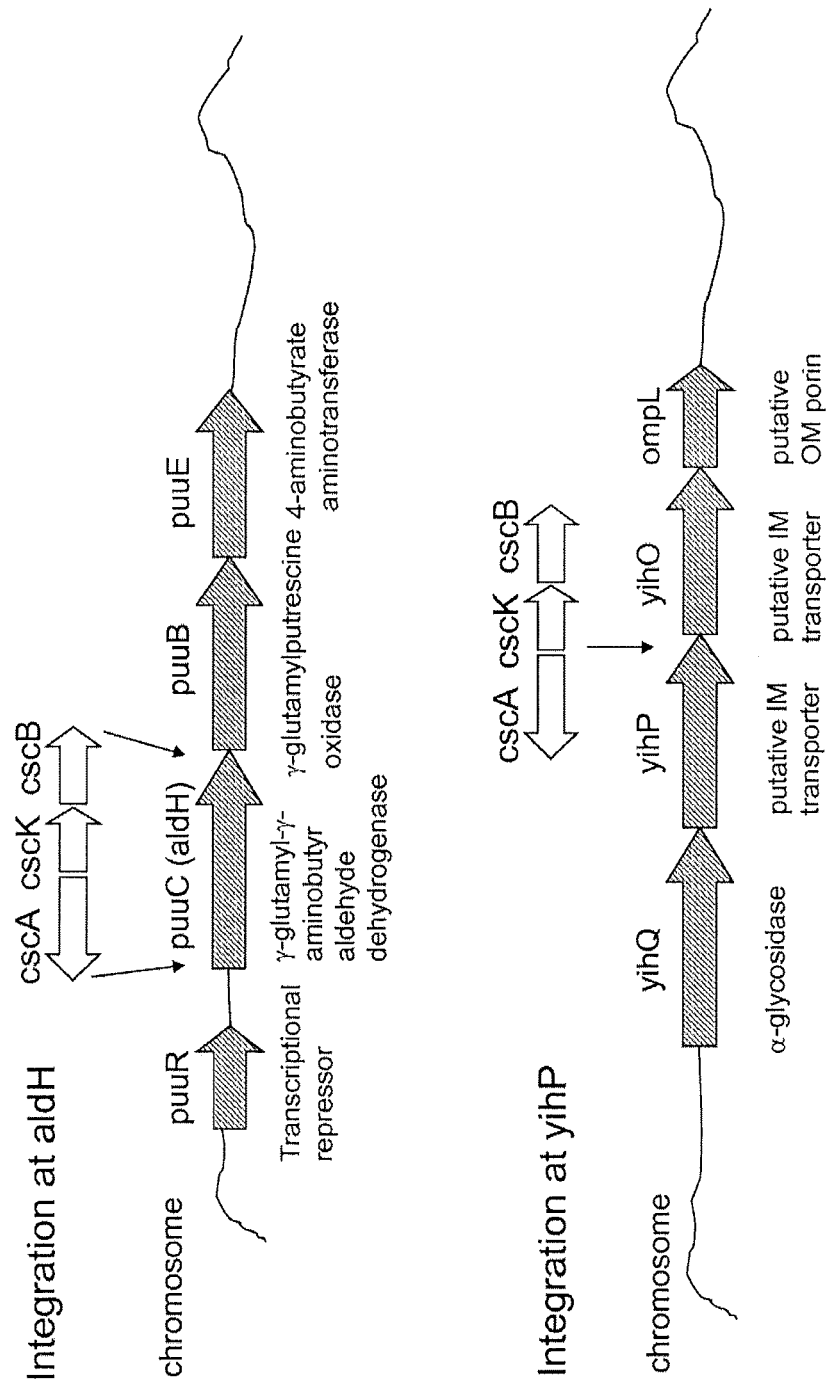

SEQUENCE LISTING

<160> NUMBER OF SEQ ID NOS: 124

<210> SEQ ID NO 1
<211> LENGTH: 1176
<212> TYPE: DNA
<213> ORGANISM: Saccharomyces cerevisiae

<400> SEQUENCE: 1

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actgggtac tactattgcc aaggtggttg ccgaaaattg taagggatac     180
ccagaagttt tcgctccaat agtacaaatg tgggtgttcg aagaagagat caatggtgaa     240
aaattgactg aaatcataaa tactagacat caaaacgtga aatacttgcc tggcatcact     300
ctacccgaca atttggttgc taatccagac ttgattgatt cagtcaagga tgtcgacatc     360
atcgttttca acattccaca tcaattttg ccccgtatct gtagccaatt gaaaggtcat     420
gttgattcac acgtcagagc tatctcctgt ctaaagggtt ttgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac     600
cacattccaa aggatttcag aggcgagggc aaggacgtcg accataaggt tctaaaggcc     660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tccagaaatc tagagaagaa acatactacc aagagtctgc tggtgttgct     900
gatttgatca ccacctgcgc tggtgtagga aacgtcaagg ttgctaggct aatggctact     960
```

-continued

```
tctggtaagg acgcctggga atgtgaaaag gagttgttga atggccaatc cgctcaaggt    1020
ttaattacct gcaagaagt tcacgaatgg ttggaaacat gtggctctgt cgaagacttc     1080
ccattatttg aagccgtata ccaaatcgtt tacaacaact acccaatgaa gaacctgccg    1140
gacatgattg aagaattaga tctacatgaa gattag                              1176
```

<210> SEQ ID NO 2
<211> LENGTH: 391
<212> TYPE: PRT
<213> ORGANISM: Saccharomyces cerevisiae

<400> SEQUENCE: 2

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335
```

Ser Ala Gln Gly Leu Ile Thr Cys Lys Glu Val His Glu Trp Leu Glu
        340                 345                 350

Thr Cys Gly Ser Val Glu Asp Phe Pro Leu Phe Glu Ala Val Tyr Gln
    355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 3
<211> LENGTH: 1323
<212> TYPE: DNA
<213> ORGANISM: Saccharomyces cerevisiae

<400> SEQUENCE: 3

```
atgcttgctg tcagaagatt aacaagatac acattcctta agcgaacgca tccggtgtta      60
tatactcgtc gtgcatataa aattttgcct tcaagatcta ctttcctaag aagatcatta     120
ttacaaacac aactgcactc aaagatgact gctcatacta atatcaaaca gcacaaacac     180
tgtcatgagg accatcctat cagaagatcg gactctgccg tgtcaattgt acatttgaaa     240
cgtgcgccct tcaaggttac agtgattggt tctggtaact gggggaccac catcgccaaa     300
gtcattgcgg aaaacacaga attgcattcc catatcttcg agccagaggt gagaatgtgg     360
gttttgatg aaaagatcgg cgacgaaaat ctgacggata tcataaatac aagacaccag     420
aacgttaaat atctacccaa tattgacctg ccccataatc tagtggccga tcctgatctt     480
ttacactcca tcaagggtgc tgacatcctt gtttttcaaca tccctcatca atttttacca     540
aacatagtca acaattgca aggccacgtg gcccctcatg taagggccat ctcgtgtcta     600
aaagggttcg agttgggctc caagggtgtg caattgctat cctcctatgt tactgatgag     660
ttaggaatcc aatgtggcgc actatctggt gcaaacttgg caccggaagt ggccaaggag     720
cattggtccg aaaccaccgt ggcttaccaa ctaccaaagg attatcaagg tgatggcaag     780
gatgtagatc ataagatttt gaaattgctg ttccacagac cttacttcca cgtcaatgtc     840
atcgatgatg ttgctggtat atccattgcc ggtgccttga gaacgtcgt ggcacttgca     900
tgtggtttcg tagaaggtat gggatggggt aacaatgcct ccgcagccat tcaaaggctg     960
ggtttaggtg aaattatcaa gttcggtaga atgttttttcc cagaatccaa agtcgagacc    1020
tactatcaag aatccgctgg tgttgcagat ctgatcacca cctgctcagg cggtagaaac    1080
gtcaaggttg ccacatacat ggccaagacc ggtaagtcag ccttggaagc agaaaaggaa    1140
ttgcttaacg gtcaatccgc ccaagggata atcacatgca gagaagttca cgagtggcta    1200
caaacatgtg agttgaccca agaattccca ttattcgagg cagtctacca gatagtctac    1260
aacaacgtcc gcatggaaga cctaccggag atgattgaag agctagacat cgatgacgaa    1320
tag                                                                  1323
```

<210> SEQ ID NO 4
<211> LENGTH: 440
<212> TYPE: PRT
<213> ORGANISM: Saccharomyces cerevisiae

<400> SEQUENCE: 4

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

```
Ser Thr Phe Leu Arg Arg Ser Leu Leu Gln Thr Gln Leu His Ser Lys
         35                  40                  45

Met Thr Ala His Thr Asn Ile Lys Gln His Lys Cys His Glu Asp
 50                  55                  60

His Pro Ile Arg Arg Ser Asp Ser Ala Val Ser Ile Val His Leu Lys
 65                  70                  75                  80

Arg Ala Pro Phe Lys Val Thr Val Ile Gly Ser Gly Asn Trp Gly Thr
                 85                  90                  95

Thr Ile Ala Lys Val Ile Ala Glu Asn Thr Glu Leu His Ser His Ile
                100                 105                 110

Phe Glu Pro Glu Val Arg Met Trp Val Phe Asp Glu Lys Ile Gly Asp
            115                 120                 125

Glu Asn Leu Thr Asp Ile Ile Asn Thr Arg His Gln Asn Val Lys Tyr
130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
            195                 200                 205

Gly Val Gln Leu Leu Ser Ser Tyr Val Thr Asp Glu Leu Gly Ile Gln
210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
            275                 280                 285

Ile Ala Gly Ala Leu Lys Asn Val Val Ala Leu Ala Cys Gly Phe Val
290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
            355                 360                 365

Lys Thr Gly Lys Ser Ala Leu Glu Ala Glu Lys Glu Leu Leu Asn Gly
370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430

Glu Glu Leu Asp Ile Asp Asp Glu
            435                 440

<210> SEQ ID NO 5
```

<211> LENGTH: 816
<212> TYPE: DNA
<213> ORGANISM: Saccharomyces cerevisiae

<400> SEQUENCE: 5

```
atgaaacgtt tcaatgtttt aaaatatatc agaacaacaa aagcaaatat acaaaccatc    60
gcaatgcctt tgaccacaaa acctttatct ttgaaaatca acgccgctct attcgatgtt   120
gacggtacca tcatcatctc tcaaccagcc attgctgctt tctggagaga tttcggtaaa   180
gacaagcctt acttcgatgc cgaacacgtt attcacatct ctcacggttg agaacttac    240
gatgccattg ccaagttcgc tccagacttt gctgatgaag aatacgttaa caagctagaa   300
ggtgaaatcc agaaaagta cggtgaacac tccatcgaag ttccaggtgc tgtcaagttg   360
tgtaatgctt tgaacgcctt gccaaaggaa aatgggctg tcgccacctc tggtacccgt    420
gacatggcca agaaatggtt cgacattttg aagatcaaga gaccagaata cttcatcacc   480
gccaatgatg tcaagcaagg taagcctcac ccagaaccat acttaaaggg tagaaacggt   540
ttgggtttcc caattaatga acaagaccca tccaaatcta aggttgttgt ctttgaagac   600
gcaccagctg gtattgctgc tggtaaggct gctggctgta aaatcgttgg tattgctacc   660
actttcgatt tggacttctt gaaggaaaag ggttgtgaca tcattgtcaa gaaccacgaa   720
tctatcagag tcggtgaata aacgctgaa accgatgaag tcgaattgat ctttgatgac   780
tacttatacg ctaaggatga cttgttgaaa tggtaa                            816
```

<210> SEQ ID NO 6
<211> LENGTH: 271
<212> TYPE: PRT
<213> ORGANISM: Saccharomyces cerevisiae

<400> SEQUENCE: 6

```
Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
        35                  40                  45

Pro Ala Ile Ala Ala Phe Trp Arg Asp Phe Gly Lys Asp Lys Pro Tyr
    50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
        195                 200                 205
```

```
Lys Ala Ala Gly Cys Lys Ile Val Gly Ile Ala Thr Thr Phe Asp Leu
    210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
                245                 250                 255

Ile Phe Asp Asp Tyr Leu Tyr Ala Lys Asp Asp Leu Leu Lys Trp
            260                 265                 270

<210> SEQ ID NO 7
<211> LENGTH: 753
<212> TYPE: DNA
<213> ORGANISM: Saccharomyces cerevisiae

<400> SEQUENCE: 7
atgggattga ctactaaacc tctatctttg aaagttaacg ccgctttgtt cgacgtcgac      60
ggtaccatta tcatctctca accagccatt gctgcattct ggagggattt cggtaaggac     120
aaaccttatt tcgatgctga acacgttatc caagtctcgc atggttggag aacgtttgat     180
gccattgcta agttcgctcc agactttgcc aatgaagagt atgttaacaa attagaagct     240
gaaattccgg tcaagtacgg tgaaaaatcc attgaagtcc aggtgcagt taagctgtgc      300 aacgctttga cgctctacc aaaagagaaa tgggctgtgg caacttccgg tacccgtgat     360
atggcacaaa atggttcga gcatctggga atcaggagac caagtactt cattaccgct      420 aatgatgtca acagggtaa gcctcatcca gaaccatatc tgaagggcag gaatggctta     480
ggatatccga tcaatgagca agacccttcc aaatctaagg tagtagtatt tgaagacgct     540
ccagcaggta ttgccgccgg aaaagccgcc ggttgtaaga tcattggtat tgccactact     600
ttcgacttgg acttcctaaa ggaaaaaggc tgtgacatca ttgtcaaaaa ccacgaatcc     660
atcagagttg gcggctacaa tgccgaaaca gacgaagttg aattcatttt tgacgactac     720
ttatatgcta aggacgatct gttgaaatgg taa                                  753

<210> SEQ ID NO 8
<211> LENGTH: 250
<212> TYPE: PRT
<213> ORGANISM: Saccharomyces cerevisiae

<400> SEQUENCE: 8

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
```

```
                    130                 135                 140
Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
                195                 200                 205

Lys Gly Cys Asp Ile Ile Val Lys Asn His Glu Ser Ile Arg Val Gly
            210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 9
<211> LENGTH: 1668
<212> TYPE: DNA
<213> ORGANISM: Klebsiella pneumoniae
<220> FEATURE:
<221> NAME/KEY: CDS
<222> LOCATION: (1)..(1668)

<400> SEQUENCE: 9
```

| | | | | | | | | | | | | | | | | |
|---|---|---|---|---|---|---|---|---|---|---|---|---|---|---|---|---|
| atg | aaa | aga | tca | aaa | cga | ttt | gca | gta | ctg | gcc | cag | cgc | ccc | gtc | aat | 48 |
| Met | Lys | Arg | Ser | Lys | Arg | Phe | Ala | Val | Leu | Ala | Gln | Arg | Pro | Val | Asn | |
| 1 | | | | 5 | | | | | 10 | | | | | 15 | | |
| cag | gac | ggg | ctg | att | ggc | gag | tgg | cct | gaa | gag | ggg | ctg | atc | gcc | atg | 96 |
| Gln | Asp | Gly | Leu | Ile | Gly | Glu | Trp | Pro | Glu | Glu | Gly | Leu | Ile | Ala | Met | |
| | 20 | | | | | 25 | | | | | 30 | | | | | |
| gac | agc | ccc | ttt | gac | ccg | gtc | tct | tca | gta | aaa | gtg | gac | aac | ggt | ctg | 144 |
| Asp | Ser | Pro | Phe | Asp | Pro | Val | Ser | Ser | Val | Lys | Val | Asp | Asn | Gly | Leu | |
| | | 35 | | | | | 40 | | | | | 45 | | | | |
| atc | gtc | gaa | ctg | gac | ggc | aaa | cgc | cgg | gac | cag | ttt | gac | atg | atc | gac | 192 |
| Ile | Val | Glu | Leu | Asp | Gly | Lys | Arg | Arg | Asp | Gln | Phe | Asp | Met | Ile | Asp | |
| 50 | | | | | 55 | | | | | 60 | | | | | | |
| cga | ttt | atc | gcc | gat | tac | gcg | atc | aac | gtt | gag | cgc | aca | gag | cag | gca | 240 |
| Arg | Phe | Ile | Ala | Asp | Tyr | Ala | Ile | Asn | Val | Glu | Arg | Thr | Glu | Gln | Ala | |
| 65 | | | | | 70 | | | | | 75 | | | | | 80 | |
| atg | cgc | ctg | gag | gcg | gtg | gaa | ata | gcc | cgt | atg | ctg | gtg | gat | att | cac | 288 |
| Met | Arg | Leu | Glu | Ala | Val | Glu | Ile | Ala | Arg | Met | Leu | Val | Asp | Ile | His | |
| | 85 | | | | | 90 | | | | | 95 | | | | | |
| gtc | agc | cgg | gag | gag | atc | att | gcc | atc | act | acc | gcc | atc | acg | ccg | gcc | 336 |
| Val | Ser | Arg | Glu | Glu | Ile | Ile | Ala | Ile | Thr | Thr | Ala | Ile | Thr | Pro | Ala | |
| | | 100 | | | | | 105 | | | | | 110 | | | | |
| aaa | gcg | gtc | gag | gtg | atg | gcg | cag | atg | aac | gtg | gtg | gag | atg | atg | atg | 384 |
| Lys | Ala | Val | Glu | Val | Met | Ala | Gln | Met | Asn | Val | Val | Glu | Met | Met | Met | |
| | | | 115 | | | | | 120 | | | | | 125 | | | |
| gcg | ctg | cag | aag | atg | cgt | gcc | cgc | cgg | acc | ccc | tcc | aac | cag | tgc | cac | 432 |
| Ala | Leu | Gln | Lys | Met | Arg | Ala | Arg | Arg | Thr | Pro | Ser | Asn | Gln | Cys | His | |
| 130 | | | | | 135 | | | | | 140 | | | | | | |
| gtc | acc | aat | ctc | aaa | gat | aat | ccg | gtg | cag | att | gcc | gct | gac | gcc | gcc | 480 |
| Val | Thr | Asn | Leu | Lys | Asp | Asn | Pro | Val | Gln | Ile | Ala | Ala | Asp | Ala | Ala | |
| 145 | | | | | 150 | | | | | 155 | | | | | 160 | |
| gag | gcc | ggg | atc | cgc | ggc | ttc | tca | gaa | cag | gag | acc | acg | gtc | ggt | atc | 528 |
| Glu | Ala | Gly | Ile | Arg | Gly | Phe | Ser | Glu | Gln | Glu | Thr | Thr | Val | Gly | Ile | |
| | 165 | | | | | 170 | | | | | 175 | | | | | |
| gcg | cgc | tac | gcg | ccg | ttt | aac | gcc | ctg | gcg | ctg | ttg | gtc | ggt | tcg | cag | 576 |
| Ala | Arg | Tyr | Ala | Pro | Phe | Asn | Ala | Leu | Ala | Leu | Leu | Val | Gly | Ser | Gln | |

```
                                          180                 185                 190
tgc ggc cgc ccc ggc gtg ttg acg cag tgc tcg gtg gaa gag gcc acc         624
Cys Gly Arg Pro Gly Val Leu Thr Gln Cys Ser Val Glu Glu Ala Thr
195                 200                 205 gag ctg gag ctg ggc atg cgt ggc tta acc agc tac gcc gag acg gtg         672
Glu Leu Glu Leu Gly Met Arg Gly Leu Thr Ser Tyr Ala Glu Thr Val
210                 215                 220 tcg gtc tac ggc acc gaa gcg gta ttt acc gac ggc gat gat acg ccg         720
Ser Val Tyr Gly Thr Glu Ala Val Phe Thr Asp Gly Asp Asp Thr Pro
225                 230                 235                 240 tgg tca aag gcg ttc ctc gcc tcg gcc tac gcc tcc cgc ggg ttg aaa         768
Trp Ser Lys Ala Phe Leu Ala Ser Ala Tyr Ala Ser Arg Gly Leu Lys
245                 250                 255 atg cgc tac acc tcc ggc acc gga tcc gaa gcg ctg atg ggc tat tcg         816
Met Arg Tyr Thr Ser Gly Thr Gly Ser Glu Ala Leu Met Gly Tyr Ser
260                 265                 270 gag agc aag tcg atg ctc tac ctc gaa tcg cgc tgc atc ttc att act         864
Glu Ser Lys Ser Met Leu Tyr Leu Glu Ser Arg Cys Ile Phe Ile Thr
275                 280                 285 aaa ggc gcc ggg gtt cag gga ctg caa aac ggc gcg gtg agc tgt atc         912
Lys Gly Ala Gly Val Gln Gly Leu Gln Asn Gly Ala Val Ser Cys Ile
290                 295                 300 ggc atg acc ggc gct gtg ccg tcg ggc att cgg gcg gtg ctg gcg gaa         960
Gly Met Thr Gly Ala Val Pro Ser Gly Ile Arg Ala Val Leu Ala Glu
305                 310                 315                 320 aac ctg atc gcc tct atg ctc gac ctc gaa gtg gcg tcc gcc aac gac        1008
Asn Leu Ile Ala Ser Met Leu Asp Leu Glu Val Ala Ser Ala Asn Asp
325                 330                 335 cag act ttc tcc cac tcg gat att cgc cgc acc gcg cgc acc ctg atg        1056
Gln Thr Phe Ser His Ser Asp Ile Arg Arg Thr Ala Arg Thr Leu Met
340                 345                 350 cag atg ctg ccg ggc acc gac ttt att ttc tcc ggc tac agc gcg gtg        1104
Gln Met Leu Pro Gly Thr Asp Phe Ile Phe Ser Gly Tyr Ser Ala Val
355                 360                 365 ccg aac tac gac aac atg ttc gcc ggc tcg aac ttc gat gcg gaa gat        1152
Pro Asn Tyr Asp Asn Met Phe Ala Gly Ser Asn Phe Asp Ala Glu Asp
370                 375                 380 ttt gat gat tac aac atc ctg cag cgt gac ctg atg gtt gac ggc ggc        1200
Phe Asp Asp Tyr Asn Ile Leu Gln Arg Asp Leu Met Val Asp Gly Gly
385                 390                 395                 400 ctg cgt ccg gtg acc gag gcg gaa acc att gcc att cgc cag aaa gcg        1248
Leu Arg Pro Val Thr Glu Ala Glu Thr Ile Ala Ile Arg Gln Lys Ala
405                 410                 415 gcg cgg gcg atc cag gcg gtt ttc cgc gag ctg ggg ctg ccg cca atc        1296
Ala Arg Ala Ile Gln Ala Val Phe Arg Glu Leu Gly Leu Pro Pro Ile
420                 425                 430 gcc gac gag gag gtg gag gcc gcc acc tac gcg cac ggc agc aac gag        1344
Ala Asp Glu Glu Val Glu Ala Ala Thr Tyr Ala His Gly Ser Asn Glu
435                 440                 445 atg ccg ccg cgt aac gtg gtg gag gat ctg agt gcg gtg gaa gag atg        1392
Met Pro Pro Arg Asn Val Val Glu Asp Leu Ser Ala Val Glu Glu Met
450                 455                 460 atg aag cgc aac atc acc ggc ctc gat att gtc ggc gcg ctg agc cgc        1440
Met Lys Arg Asn Ile Thr Gly Leu Asp Ile Val Gly Ala Leu Ser Arg
465                 470                 475                 480 agc ggc ttt gag gat atc gcc agc aat att ctc aat atg ctg cgc cag        1488
Ser Gly Phe Glu Asp Ile Ala Ser Asn Ile Leu Asn Met Leu Arg Gln
485                 490                 495 cgg gtc acc ggc gat tac ctg cag acc tcg gcc att ctc gat cgg cag        1536
Arg Val Thr Gly Asp Tyr Leu Gln Thr Ser Ala Ile Leu Asp Arg Gln
```

```
                           500                 505                 510
ttc gag gtg gtg agt gcg gtc aac gac atc aat gac tat cag ggg ccg              1584
Phe Glu Val Val Ser Ala Val Asn Asp Ile Asn Asp Tyr Gln Gly Pro
515                 520                 525 ggc acc ggc tat cgc atc tct gcc gaa cgc tgg gcg gag atc aaa aat              1632
Gly Thr Gly Tyr Arg Ile Ser Ala Glu Arg Trp Ala Glu Ile Lys Asn
530                 535                 540 att ccg ggc gtt cag ccc gac acc att gaa taa                                  1668
Ile Pro Gly Val Gln Pro Asp Thr Ile Glu
545                 550                 555

<210> SEQ ID NO 10
<211> LENGTH: 555
<212> TYPE: PRT
<213> ORGANISM: Klebsiella pneumoniae

<400> SEQUENCE: 10

Met Lys Arg Ser Lys Arg Phe Ala Val Leu Ala Gln Arg Pro Val Asn
1               5                   10                  15

Gln Asp Gly Leu Ile Gly Glu Trp Pro Glu Gly Leu Ile Ala Met
                20                  25                  30

Asp Ser Pro Phe Asp Pro Val Ser Ser Val Lys Val Asp Asn Gly Leu
            35                  40                  45

Ile Val Glu Leu Asp Gly Lys Arg Arg Asp Gln Phe Asp Met Ile Asp
        50                  55                  60

Arg Phe Ile Ala Asp Tyr Ala Ile Asn Val Glu Arg Thr Glu Gln Ala
65                  70                  75                  80

Met Arg Leu Glu Ala Val Gly Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Glu Met Met Met
        115                 120                 125

Ala Leu Gln Lys Met Arg Ala Arg Thr Pro Ser Asn Gln Cys His
        130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
```

```
                        305                 310                 315                 320
Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555

<210> SEQ ID NO 11
<211> LENGTH: 585
<212> TYPE: DNA
<213> ORGANISM: Klebsiella pneumoniae
<220> FEATURE:
<221> NAME/KEY: CDS
<222> LOCATION: (1)..(585)

<400> SEQUENCE: 11 gtg caa cag aca acc caa att cag ccc tct ttt acc ctg aaa acc cgc      48
Val Gln Gln Thr Thr Gln Ile Gln Pro Ser Phe Thr Leu Lys Thr Arg
1               5                   10                  15 gag ggc ggg gta gct tct gcc gat gaa cgc gcc gat gaa gtg gtg atc      96
Glu Gly Gly Val Ala Ser Ala Asp Glu Arg Ala Asp Glu Val Val Ile
            20                  25                  30 ggc gtc ggc cct gcc ttc gat aaa cac cag cat cac act ctg atc gat     144
Gly Val Gly Pro Ala Phe Asp Lys His Gln His His Thr Leu Ile Asp
 35                 40                  45 atg ccc cat ggc gcg atc ctc aaa gag ctg att gcc ggg gtg gaa gaa     192
Met Pro His Gly Ala Ile Leu Lys Glu Leu Ile Ala Gly Val Glu Glu
 50              55                  60 gag ggg ctt cac gcc cgg gtg gtg cgc att ctg cgc acg tcc gac gtc     240
Glu Gly Leu His Ala Arg Val Val Arg Ile Leu Arg Thr Ser Asp Val
 65              70                  75                  80 tcc ttt atg gcc tgg gat gcg gcc aac ctg agc ggc tcg ggg atc ggc     288
Ser Phe Met Ala Trp Asp Ala Ala Asn Leu Ser Gly Ser Gly Ile Gly
```

-continued

```
                    85                  90                  95
atc ggt atc cag tcg aag ggg acc acg gtc atc cat cag cgc gat ctg        336
Ile Gly Ile Gln Ser Lys Gly Thr Thr Val Ile His Gln Arg Asp Leu
100                 105                 110 ctg ccg ctc agc aac ctg gag ctg ttc tcc cag gcg ccg ctg ctg acg        384
Leu Pro Leu Ser Asn Leu Glu Leu Phe Ser Gln Ala Pro Leu Leu Thr
115                 120                 125 ctg gag acc tac cgg cag att ggc aaa aac gct gcg cgc tat gcg cgc        432
Leu Glu Thr Tyr Arg Gln Ile Gly Lys Asn Ala Ala Arg Tyr Ala Arg
130                 135                 140 aaa gag tca cct tcg ccg gtg ccg gtg gtg aac gat cag atg gtg cgg        480
Lys Glu Ser Pro Ser Pro Val Pro Val Val Asn Asp Gln Met Val Arg
145                 150                 155                 160 ccg aaa ttt atg gcc aaa gcc gcg cta ttt cat atc aaa gag acc aaa        528
Pro Lys Phe Met Ala Lys Ala Ala Leu Phe His Ile Lys Glu Thr Lys
165                 170                 175 cat gtg gtg cag gac gcc gag ccc gtc acc ctg cac atc gac tta gta        576
His Val Val Gln Asp Ala Glu Pro Val Thr Leu His Ile Asp Leu Val
180                 185                 190 agg gag tga                                                            585
Arg Glu
```

<210> SEQ ID NO 12
<211> LENGTH: 194
<212> TYPE: PRT
<213> ORGANISM: Klebsiella pneumoniae

<400> SEQUENCE: 12

```
Val Gln Gln Thr Thr Gln Ile Gln Pro Ser Phe Thr Leu Lys Thr Arg
1               5                   10                  15

Glu Gly Gly Val Ala Ser Ala Asp Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu
```

<210> SEQ ID NO 13
<211> LENGTH: 426
<212> TYPE: DNA
<213> ORGANISM: Klebsiella pneumoniae

<220> FEATURE:
<221> NAME/KEY: CDS
<222> LOCATION: (1)..(426)

<400> SEQUENCE: 13

```
atg agc gag aaa acc atg cgc gtg cag gat tat ccg tta gcc acc cgc      48
Met Ser Glu Lys Thr Met Arg Val Gln Asp Tyr Pro Leu Ala Thr Arg
1               5                  10                  15 tgc ccg gag cat atc ctg acg cct acc ggc aaa cca ttg acc gat att      96
Cys Pro Glu His Ile Leu Thr Pro Thr Gly Lys Pro Leu Thr Asp Ile
            20                  25                  30 acc ctc gag aag gtg ctc tct ggc gag gtg ggc ccg cag gat gtg cgg     144
Thr Leu Glu Lys Val Leu Ser Gly Glu Val Gly Pro Gln Asp Val Arg
35                  40                  45 atc tcc cgc cag acc ctt gag tac cag gcg cag att gcc gag cag atg     192
Ile Ser Arg Gln Thr Leu Glu Tyr Gln Ala Gln Ile Ala Glu Gln Met
50                  55                  60 cag cgc cat gcg gtg gcg cgc aat ttc cgc cgc gcg gcg gag ctt atc     240
Gln Arg His Ala Val Ala Arg Asn Phe Arg Arg Ala Ala Glu Leu Ile
65                  70                  75                  80 gcc att cct gac gag cgc att ctg gct atc tat aac gcg ctg cgc ccg     288
Ala Ile Pro Asp Glu Arg Ile Leu Ala Ile Tyr Asn Ala Leu Arg Pro
            85                  90                  95 ttc cgc tcc tcg cag gcg gag ctg ctg gcg atc gcc gac gag ctg gag     336
Phe Arg Ser Ser Gln Ala Glu Leu Leu Ala Ile Ala Asp Glu Leu Glu
            100                 105                 110 cac acc tgg cat gcg aca gtg aat gcc gcc ttt gtc cgg gag tcg gcg     384
His Thr Trp His Ala Thr Val Asn Ala Ala Phe Val Arg Glu Ser Ala
        115                 120                 125 gaa gtg tat cag cag cgg cat aag ctg cgt aaa gga agc taa             426
Glu Val Tyr Gln Gln Arg His Lys Leu Arg Lys Gly Ser
130                 135                 140
```

<210> SEQ ID NO 14
<211> LENGTH: 141
<212> TYPE: PRT
<213> ORGANISM: Klebsiella pneumoniae

<400> SEQUENCE: 14

```
Met Ser Glu Lys Thr Met Arg Val Gln Asp Tyr Pro Leu Ala Thr Arg
1               5                  10                  15

Cys Pro Glu His Ile Leu Thr Pro Thr Gly Lys Pro Leu Thr Asp Ile
            20                  25                  30

Thr Leu Glu Lys Val Leu Ser Gly Glu Val Gly Pro Gln Asp Val Arg
        35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
            100                 105                 110

His Thr Trp His Ala Thr Val Asn Ala Ala Phe Val Arg Glu Ser Ala
        115                 120                 125

Glu Val Tyr Gln Gln Arg His Lys Leu Arg Lys Gly Ser
    130                 135                 140
```

<210> SEQ ID NO 15
<211> LENGTH: 1539

<212> TYPE: DNA
<213> ORGANISM: Escherichia coli
<220> FEATURE:
<221> NAME/KEY: CDS
<222> LOCATION: (1)..(1539)

<400> SEQUENCE: 15

| | | | | | | | | | | | | | | | | |
|---|---|---|---|---|---|---|---|---|---|---|---|---|---|---|---|---|
| atg | acc | aat | aat | ccc | cct | tca | gca | cag | att | aag | ccc | ggc | gag | tat | ggt | 48 |
| Met | Thr | Asn | Asn | Pro | Pro | Ser | Ala | Gln | Ile | Lys | Pro | Gly | Glu | Tyr | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | ccc | ctc | aag | tta | aaa | gcc | cgc | tat | gac | aac | ttt | att | ggc | ggc | gaa | 96 |
| Phe | Pro | Leu | Lys | Leu | Lys | Ala | Arg | Tyr | Asp | Asn | Phe | Ile | Gly | Gly | Glu | |
| | 20 | | | | 25 | | | | | 30 | | | | | | |

| | | | | | | | | | | | | | | | | |
|---|---|---|---|---|---|---|---|---|---|---|---|---|---|---|---|---|
| tgg | gta | gcc | cct | gcc | gac | ggc | gag | tat | tac | cag | aat | ctg | acg | ccg | gtg | 144 |
| Trp | Val | Ala | Pro | Ala | Asp | Gly | Glu | Tyr | Tyr | Gln | Asn | Leu | Thr | Pro | Val | |
| 35 | | | | | 40 | | | | | 45 | | | | | | |

| | | | | | | | | | | | | | | | | |
|---|---|---|---|---|---|---|---|---|---|---|---|---|---|---|---|---|
| acc | ggg | cag | ctg | ctg | tgc | gaa | gtg | gcg | tct | tcg | ggc | aaa | cga | gac | atc | 192 |
| Thr | Gly | Gln | Leu | Leu | Cys | Glu | Val | Ala | Ser | Ser | Gly | Lys | Arg | Asp | Ile | |
| 50 | | | | 55 | | | | | 60 | | | | | | | |

| | | | | | | | | | | | | | | | | |
|---|---|---|---|---|---|---|---|---|---|---|---|---|---|---|---|---|
| gat | ctg | gcg | ctg | gat | gct | gcg | cac | aaa | gtg | aaa | gat | aaa | tgg | gcg | cac | 240 |
| Asp | Leu | Ala | Leu | Asp | Ala | Ala | His | Lys | Val | Lys | Asp | Lys | Trp | Ala | His | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| acc | tcg | gtg | cag | gat | cgt | gcg | gcg | att | ctg | ttt | aag | att | gcc | gat | cga | 288 |
| Thr | Ser | Val | Gln | Asp | Arg | Ala | Ala | Ile | Leu | Phe | Lys | Ile | Ala | Asp | Arg | |
| | 85 | | | | 90 | | | | | 95 | | | | | | |

| | | | | | | | | | | | | | | | | |
|---|---|---|---|---|---|---|---|---|---|---|---|---|---|---|---|---|
| atg | gaa | caa | aac | ctc | gag | ctg | tta | gcg | aca | gct | gaa | acc | tgg | gat | aac | 336 |
| Met | Glu | Gln | Asn | Leu | Glu | Leu | Leu | Ala | Thr | Ala | Glu | Thr | Trp | Asp | Asn | |
| 100 | | | | | 105 | | | | | 110 | | | | | | |

| | | | | | | | | | | | | | | | | |
|---|---|---|---|---|---|---|---|---|---|---|---|---|---|---|---|---|
| ggc | aaa | ccc | att | cgc | gaa | acc | agt | gct | gcg | gat | gta | ccg | ctg | gcg | att | 384 |
| Gly | Lys | Pro | Ile | Arg | Glu | Thr | Ser | Ala | Ala | Asp | Val | Pro | Leu | Ala | Ile | |
| 115 | | | | 120 | | | | | 125 | | | | | | | |

| | | | | | | | | | | | | | | | | |
|---|---|---|---|---|---|---|---|---|---|---|---|---|---|---|---|---|
| gac | cat | ttc | cgc | tat | ttc | gcc | tcg | tgt | att | cgg | gcg | cag | gaa | ggt | ggg | 432 |
| Asp | His | Phe | Arg | Tyr | Phe | Ala | Ser | Cys | Ile | Arg | Ala | Gln | Glu | Gly | Gly | |
| 130 | | | | | 135 | | | | | 140 | | | | | | |

| | | | | | | | | | | | | | | | | |
|---|---|---|---|---|---|---|---|---|---|---|---|---|---|---|---|---|
| atc | agt | gaa | gtt | gat | agc | gaa | acc | gtg | gcc | tat | cat | ttc | cat | gaa | ccg | 480 |
| Ile | Ser | Glu | Val | Asp | Ser | Glu | Thr | Val | Ala | Tyr | His | Phe | His | Glu | Pro | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| tta | ggc | gtg | gtg | ggg | cag | att | atc | ccg | tgg | aac | ttc | ccg | ctg | ctg | atg | 528 |
| Leu | Gly | Val | Val | Gly | Gln | Ile | Ile | Pro | Trp | Asn | Phe | Pro | Leu | Leu | Met | |
| 165 | | | | | 170 | | | | | 175 | | | | | | |

| | | | | | | | | | | | | | | | | |
|---|---|---|---|---|---|---|---|---|---|---|---|---|---|---|---|---|
| gcg | agc | tgg | aaa | atg | gct | ccc | gcg | ctg | gcg | gcg | ggc | aac | tgt | gtg | gtg | 576 |
| Ala | Ser | Trp | Lys | Met | Ala | Pro | Ala | Leu | Ala | Ala | Gly | Asn | Cys | Val | Val | |
| 180 | | | | 185 | | | | | 190 | | | | | | | |

| | | | | | | | | | | | | | | | | |
|---|---|---|---|---|---|---|---|---|---|---|---|---|---|---|---|---|
| ctg | aaa | ccc | gca | cgt | ctt | acc | ccg | ctt | tct | gta | ctg | ctg | cta | atg | gaa | 624 |
| Leu | Lys | Pro | Ala | Arg | Leu | Thr | Pro | Leu | Ser | Val | Leu | Leu | Leu | Met | Glu | |
| 195 | | | | 200 | | | | | 205 | | | | | | | |

| | | | | | | | | | | | | | | | | |
|---|---|---|---|---|---|---|---|---|---|---|---|---|---|---|---|---|
| att | gtc | ggt | gat | tta | ctg | ccg | ccg | ggc | gtg | gtg | aac | gtg | gtc | aat | ggc | 672 |
| Ile | Val | Gly | Asp | Leu | Leu | Pro | Pro | Gly | Val | Val | Asn | Val | Val | Asn | Gly | |
| 210 | | | | | 215 | | | | | 220 | | | | | | |

| | | | | | | | | | | | | | | | | |
|---|---|---|---|---|---|---|---|---|---|---|---|---|---|---|---|---|
| gca | ggt | ggg | gta | att | ggc | gaa | tat | ctg | gcg | acc | tcg | aaa | cgc | atc | gcc | 720 |
| Ala | Gly | Gly | Val | Ile | Gly | Glu | Tyr | Leu | Ala | Thr | Ser | Lys | Arg | Ile | Ala | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| aaa | gtg | gcg | ttt | acc | ggc | tca | acg | gaa | gtg | ggc | caa | caa | att | atg | caa | 768 |
| Lys | Val | Ala | Phe | Thr | Gly | Ser | Thr | Glu | Val | Gly | Gln | Gln | Ile | Met | Gln | |
| 245 | | | | | 250 | | | | | 255 | | | | | | |

| | | | | | | | | | | | | | | | | |
|---|---|---|---|---|---|---|---|---|---|---|---|---|---|---|---|---|
| tac | gca | acg | caa | aac | att | att | ccg | gtg | acg | ctg | gag | ttg | ggc | ggt | aag | 816 |
| Tyr | Ala | Thr | Gln | Asn | Ile | Ile | Pro | Val | Thr | Leu | Glu | Leu | Gly | Gly | Lys | |
| 260 | | | | 265 | | | | | 270 | | | | | | | |

| | | | | | | | | | | | | | | | | |
|---|---|---|---|---|---|---|---|---|---|---|---|---|---|---|---|---|
| tcg | cca | aat | atc | ttc | ttt | gct | gat | gtg | atg | gat | gaa | gaa | gat | gcc | ttt | 864 |
| Ser | Pro | Asn | Ile | Phe | Phe | Ala | Asp | Val | Met | Asp | Glu | Glu | Asp | Ala | Phe | |
| 275 | | | | | 280 | | | | | 285 | | | | | | |

```
ttc gat aaa gcg ctg gaa ggc ttt gca ctg ttt gcc ttt aac cag ggc        912
Phe Asp Lys Ala Leu Glu Gly Phe Ala Leu Phe Ala Phe Asn Gln Gly
290             295                 300 gaa gtt tgc acc tgt ccg agt cgt gct tta gtg cag gaa tct atc tac        960
Glu Val Cys Thr Cys Pro Ser Arg Ala Leu Val Gln Glu Ser Ile Tyr
305             310                 315                 320 gaa cgc ttt atg gaa cgc gcc atc cgc cgt gtc gaa agc att cgt agc       1008
Glu Arg Phe Met Glu Arg Ala Ile Arg Arg Val Glu Ser Ile Arg Ser
        325                 330                 335 ggt aac ccg ctc gac agc gtg acg caa atg ggc gcg cag gtt tct cac       1056
Gly Asn Pro Leu Asp Ser Val Thr Gln Met Gly Ala Gln Val Ser His
340                 345                 350 ggg caa ctg gaa acc atc ctc aac tac att gat atc ggt aaa aaa gag       1104
Gly Gln Leu Glu Thr Ile Leu Asn Tyr Ile Asp Ile Gly Lys Lys Glu
355                 360                 365 ggc gct gac gtg ctc aca ggc ggg cgg cgc aag ctg ctg gaa ggt gaa       1152
Gly Ala Asp Val Leu Thr Gly Gly Arg Arg Lys Leu Leu Glu Gly Glu
370                 375                 380 ctg aaa gac ggc tac tac ctc gaa ccg acg att ctg ttt ggt cag aac       1200
Leu Lys Asp Gly Tyr Tyr Leu Glu Pro Thr Ile Leu Phe Gly Gln Asn
385                 390                 395                 400 aat atg cgg gtg ttc cag gag gag att ttt ggc ccg gtg ctg gcg gtg       1248
Asn Met Arg Val Phe Gln Glu Glu Ile Phe Gly Pro Val Leu Ala Val
405                 410                 415 acc acc ttc aaa acg atg gaa gaa gcg ctg gag ctg gcg aac gat acg       1296
Thr Thr Phe Lys Thr Met Glu Glu Ala Leu Glu Leu Ala Asn Asp Thr
420                 425                 430 caa tat ggc ctg ggc gcg ggc gtc tgg agc cgc aac ggt aat ctg gcc       1344
Gln Tyr Gly Leu Gly Ala Gly Val Trp Ser Arg Asn Gly Asn Leu Ala
435                 440                 445 tat aag atg ggg cgc ggc ata cag gct ggg cgc gtg tgg acc aac tgt       1392
Tyr Lys Met Gly Arg Gly Ile Gln Ala Gly Arg Val Trp Thr Asn Cys
450                 455                 460 tat cac gct tac ccg gca cat gcg gcg ttt ggt ggc tac aaa caa tca       1440
Tyr His Ala Tyr Pro Ala His Ala Ala Phe Gly Gly Tyr Lys Gln Ser
465                 470                 475                 480 ggt atc ggt cgc gaa acc cac aag atg atg ctg gag cat tac cag caa       1488
Gly Ile Gly Arg Glu Thr His Lys Met Met Leu Glu His Tyr Gln Gln
485                 490                 495 acc aag tgc ctg ctg gtg agc tac tcg gat aaa ccg ttg ggg ctg ttc       1536
Thr Lys Cys Leu Leu Val Ser Tyr Ser Asp Lys Pro Leu Gly Leu Phe
500                 505                 510 tga                                                                    1539

<210> SEQ ID NO 16
<211> LENGTH: 512
<212> TYPE: PRT
<213> ORGANISM: Escherichia coli

<400> SEQUENCE: 16

Met Thr Asn Asn Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
                20                  25                  30

Trp Val Ala Pro Ala Asp Gly Glu Tyr Tyr Gln Asn Leu Thr Pro Val
            35                  40                  45

Thr Gly Gln Leu Leu Cys Glu Val Ala Ser Ser Gly Lys Arg Asp Ile
        50                  55                  60

Asp Leu Ala Leu Asp Ala Ala His Lys Val Lys Asp Lys Trp Ala His
65                  70                  75                  80
```

```
Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270

Ser Pro Asn Ile Phe Phe Ala Asp Val Met Asp Glu Glu Asp Ala Phe
        275                 280                 285

Phe Asp Lys Ala Leu Glu Gly Phe Ala Leu Phe Ala Phe Asn Gln Gly
290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Val Leu Thr Gly Gly Arg Arg Lys Leu Leu Glu Gly Glu
370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                405                 410                 415

Thr Thr Phe Lys Thr Met Glu Glu Ala Leu Glu Leu Ala Asn Asp Thr
            420                 425                 430

Gln Tyr Gly Leu Gly Ala Gly Val Trp Ser Arg Asn Gly Asn Leu Ala
        435                 440                 445

Tyr Lys Met Gly Arg Gly Ile Gln Ala Gly Arg Val Trp Thr Asn Cys
450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
```

<210> SEQ ID NO 17
<211> LENGTH: 1440
<212> TYPE: DNA
<213> ORGANISM: Escherichia coli
<220> FEATURE:
<221> NAME/KEY: CDS
<222> LOCATION: (1)..(1440)

<400> SEQUENCE: 17

| | | | | | | | | | | | | | | | | |
|---|---|---|---|---|---|---|---|---|---|---|---|---|---|---|---|---|
| atg | tca | gta | ccc | gtt | caa | cat | cct | atg | tat | atc | gat | gga | cag | ttt | gtt | 48 |
| Met | Ser | Val | Pro | Val | Gln | His | Pro | Met | Tyr | Ile | Asp | Gly | Gln | Phe | Val | |
| 1 | | | | 5 | | | | | 10 | | | | | 15 | | |
| acc | tgg | cgt | gga | gac | gca | tgg | att | gat | gtg | gta | aac | cct | gct | aca | gag | 96 |
| Thr | Trp | Arg | Gly | Asp | Ala | Trp | Ile | Asp | Val | Val | Asn | Pro | Ala | Thr | Glu | |
| 20 | | | | | 25 | | | | | 30 | | | | | | |
| gct | gtc | att | tcc | cgc | ata | ccc | gat | ggt | cag | gcc | gag | gat | gcc | cgt | aag | 144 |
| Ala | Val | Ile | Ser | Arg | Ile | Pro | Asp | Gly | Gln | Ala | Glu | Asp | Ala | Arg | Lys | |
| 35 | | | | 40 | | | | | 45 | | | | | | | |
| gca | atc | gat | gca | gca | gaa | cgt | gca | caa | cca | gaa | tgg | gaa | gcg | ttg | cct | 192 |
| Ala | Ile | Asp | Ala | Ala | Glu | Arg | Ala | Gln | Pro | Glu | Trp | Glu | Ala | Leu | Pro | |
| 50 | | | | 55 | | | | | 60 | | | | | | | |
| gct | att | gaa | cgc | gcc | agt | tgg | ttg | cgc | aaa | atc | tcc | gcc | ggg | atc | cgc | 240 |
| Ala | Ile | Glu | Arg | Ala | Ser | Trp | Leu | Arg | Lys | Ile | Ser | Ala | Gly | Ile | Arg | |
| 65 | | | | 70 | | | | | 75 | | | | | 80 | | |
| gaa | cgc | gcc | agt | gaa | atc | agt | gcg | ctg | att | gtt | gaa | gaa | ggg | ggc | aag | 288 |
| Glu | Arg | Ala | Ser | Glu | Ile | Ser | Ala | Leu | Ile | Val | Glu | Glu | Gly | Gly | Lys | |
| 85 | | | | | 90 | | | | | 95 | | | | | | |
| atc | cag | cag | ctg | gct | gaa | gtc | gaa | gtg | gct | ttt | act | gcc | gac | tat | atc | 336 |
| Ile | Gln | Gln | Leu | Ala | Glu | Val | Glu | Val | Ala | Phe | Thr | Ala | Asp | Tyr | Ile | |
| 100 | | | | 105 | | | | | 110 | | | | | | | |
| gat | tac | atg | gcg | gag | tgg | gca | cgg | cgt | tac | gag | ggc | gag | att | att | caa | 384 |
| Asp | Tyr | Met | Ala | Glu | Trp | Ala | Arg | Arg | Tyr | Glu | Gly | Glu | Ile | Ile | Gln | |
| 115 | | | | 120 | | | | | 125 | | | | | | | |
| agc | gat | cgt | cca | gga | gaa | aat | att | ctt | ttg | ttt | aaa | cgt | gcg | ctt | ggt | 432 |
| Ser | Asp | Arg | Pro | Gly | Glu | Asn | Ile | Leu | Leu | Phe | Lys | Arg | Ala | Leu | Gly | |
| 130 | | | | 135 | | | | | 140 | | | | | | | |
| gtg | act | acc | ggc | att | ctg | ccg | tgg | aac | ttc | ccg | ttc | ttc | ctc | att | gcc | 480 |
| Val | Thr | Thr | Gly | Ile | Leu | Pro | Trp | Asn | Phe | Pro | Phe | Phe | Leu | Ile | Ala | |
| 145 | | | | 150 | | | | | 155 | | | | | 160 | | |
| cgc | aaa | atg | gct | ccc | gct | ctt | ttg | acc | ggt | aat | acc | atc | gtc | att | aaa | 528 |
| Arg | Lys | Met | Ala | Pro | Ala | Leu | Leu | Thr | Gly | Asn | Thr | Ile | Val | Ile | Lys | |
| 165 | | | | 170 | | | | | 175 | | | | | | | |
| cct | agt | gaa | ttt | acg | cca | aac | aat | gcg | att | gca | ttc | gcc | aaa | atc | gtc | 576 |
| Pro | Ser | Glu | Phe | Thr | Pro | Asn | Asn | Ala | Ile | Ala | Phe | Ala | Lys | Ile | Val | |
| 180 | | | | 185 | | | | | 190 | | | | | | | |
| gat | gaa | ata | ggc | ctt | ccg | cgc | ggc | gtg | ttt | aac | ctt | gta | ctg | ggg | cgt | 624 |
| Asp | Glu | Ile | Gly | Leu | Pro | Arg | Gly | Val | Phe | Asn | Leu | Val | Leu | Gly | Arg | |
| 195 | | | | 200 | | | | | 205 | | | | | | | |
| ggt | gaa | acc | gtt | ggg | caa | gaa | ctg | gcg | ggt | aac | cca | aag | gtc | gca | atg | 672 |
| Gly | Glu | Thr | Val | Gly | Gln | Glu | Leu | Ala | Gly | Asn | Pro | Lys | Val | Ala | Met | |
| 210 | | | | 215 | | | | | 220 | | | | | | | |
| gtc | agt | atg | aca | ggc | agc | gtc | tct | gca | ggt | gag | aag | atc | atg | gcg | act | 720 |
| Val | Ser | Met | Thr | Gly | Ser | Val | Ser | Ala | Gly | Glu | Lys | Ile | Met | Ala | Thr | |
| 225 | | | | 230 | | | | | 235 | | | | | 240 | | |
| gcg | gcg | aaa | aac | atc | acc | aaa | gtg | tgt | ctg | gaa | ttg | ggg | ggt | aaa | gca | 768 |
| Ala | Ala | Lys | Asn | Ile | Thr | Lys | Val | Cys | Leu | Glu | Leu | Gly | Gly | Lys | Ala | |
| 245 | | | | 250 | | | | | 255 | | | | | | | |
| cca | gct | atc | gta | atg | gac | gat | gcc | gat | ctt | gaa | ctg | gca | gtc | aaa | gcc | 816 |
| Pro | Ala | Ile | Val | Met | Asp | Asp | Ala | Asp | Leu | Glu | Leu | Ala | Val | Lys | Ala | |
| 260 | | | | 265 | | | | | 270 | | | | | | | |

-continued

| | |
|---|---|
| atc gtt gat tca cgc gtc att aat agt ggg caa gtg tgt aac tgt gca<br>Ile Val Asp Ser Arg Val Ile Asn Ser Gly Gln Val Cys Asn Cys Ala<br>275                        280                        285 | 864 |
| gaa cgt gtt tat gta cag aaa ggc att tat gat cag ttc gtc aat cgg<br>Glu Arg Val Tyr Val Gln Lys Gly Ile Tyr Asp Gln Phe Val Asn Arg<br>290                        295                        300 | 912 |
| ctg ggt gaa gcg atg cag gcg gtt caa ttt ggt aac ccc gct gaa cgc<br>Leu Gly Glu Ala Met Gln Ala Val Gln Phe Gly Asn Pro Ala Glu Arg<br>305                        310                        315                        320 | 960 |
| aac gac att gcg atg ggg ccg ttg att aac gcc gcg gcg ctg gaa agg<br>Asn Asp Ile Ala Met Gly Pro Leu Ile Asn Ala Ala Ala Leu Glu Arg<br>325                        330                        335 | 1008 |
| gtc gag caa aaa gtg gcg cgc gca gta gaa gaa ggg gcg aga gtg gcg<br>Val Glu Gln Lys Val Ala Arg Ala Val Glu Glu Gly Ala Arg Val Ala<br>340                        345                        350 | 1056 |
| ttc ggt ggc aaa gcg gta gag ggg aaa gga tat tat tat ccg ccg aca<br>Phe Gly Gly Lys Ala Val Glu Gly Lys Gly Tyr Tyr Tyr Pro Pro Thr<br>355                        360                        365 | 1104 |
| ttg ctg ctg gat gtt cgc cag gaa atg tcg att atg cat gag gaa acc<br>Leu Leu Leu Asp Val Arg Gln Glu Met Ser Ile Met His Glu Glu Thr<br>370                        375                        380 | 1152 |
| ttt ggc ccg gtg ctg cca gtt gtc gca ttt gac acg ctg gaa gat gct<br>Phe Gly Pro Val Leu Pro Val Val Ala Phe Asp Thr Leu Glu Asp Ala<br>385                        390                        395                        400 | 1200 |
| atc tca atg gct aat gac agt gat tac ggc ctg acc tca tca atc tat<br>Ile Ser Met Ala Asn Asp Ser Asp Tyr Gly Leu Thr Ser Ser Ile Tyr<br>405                        410                        415 | 1248 |
| acc caa aat ctg aac gtc gcg atg aaa gcc att aaa ggg ctg aag ttt<br>Thr Gln Asn Leu Asn Val Ala Met Lys Ala Ile Lys Gly Leu Lys Phe<br>420                        425                        430 | 1296 |
| ggt gaa act tac atc aac cgt gaa aac ttc gaa gct atg caa ggc ttc<br>Gly Glu Thr Tyr Ile Asn Arg Glu Asn Phe Glu Ala Met Gln Gly Phe<br>435                        440                        445 | 1344 |
| cac gcc gga tgg cgt aaa tcc ggt att ggc ggc gca gat ggt aaa cat<br>His Ala Gly Trp Arg Lys Ser Gly Ile Gly Gly Ala Asp Gly Lys His<br>450                        455                        460 | 1392 |
| ggc ttg cat gaa tat ctg cag acc cag gtg gtt tat tta cag tct taa<br>Gly Leu His Glu Tyr Leu Gln Thr Gln Val Val Tyr Leu Gln Ser<br>465                        470                        475 | 1440 |

<210> SEQ ID NO 18
<211> LENGTH: 479
<212> TYPE: PRT
<213> ORGANISM: Escherichia coli

<400> SEQUENCE: 18

Met Ser Val Pro Val Gln His Pro Met Tyr Ile Asp Gly Gln Phe Val
1                  5                    10                  15

Thr Trp Arg Gly Asp Ala Trp Ile Asp Val Val Asn Pro Ala Thr Glu
                 20                    25                    30

Ala Val Ile Ser Arg Ile Pro Asp Gly Gln Ala Glu Asp Ala Arg Lys
                 35                    40                    45

Ala Ile Asp Ala Ala Glu Arg Ala Gln Pro Glu Trp Glu Ala Leu Pro
 50                   55                    60

Ala Ile Glu Arg Ala Ser Trp Leu Arg Lys Ile Ser Ala Gly Ile Arg
65                  70                    75                    80

Glu Arg Ala Ser Glu Ile Ser Ala Leu Ile Val Glu Glu Gly Gly Lys
                 85                    90                    95

Ile Gln Gln Leu Ala Glu Val Glu Val Ala Phe Thr Ala Asp Tyr Ile

Asp Tyr Met Ala Glu Trp Ala Arg Arg Tyr Glu Gly Glu Ile Ile Gln
            115                 120                 125

Ser Asp Arg Pro Gly Glu Asn Ile Leu Leu Phe Lys Arg Ala Leu Gly
        130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
            340                 345                 350

Phe Gly Gly Lys Ala Val Glu Gly Lys Gly Tyr Tyr Tyr Pro Pro Thr
        355                 360                 365

Leu Leu Leu Asp Val Arg Gln Glu Met Ser Ile Met His Glu Glu Thr
370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
450                 455                 460

Gly Leu His Glu Tyr Leu Gln Thr Gln Val Val Tyr Leu Gln Ser
465                 470                 475

<210> SEQ ID NO 19
<211> LENGTH: 1488
<212> TYPE: DNA
<213> ORGANISM: Escherichia coli
<220> FEATURE:
<221> NAME/KEY: CDS
<222> LOCATION: (1)..(1488)

<400> SEQUENCE: 19

```
atg aat ttt cat cat ctg gct tac tgg cag gat aaa gcg tta agt ctc    48
Met Asn Phe His His Leu Ala Tyr Trp Gln Asp Lys Ala Leu Ser Leu
1               5                   10                  15 gcc att gaa aac cgc tta ttt att aac ggt gaa tat act gct gcg gcg    96
Ala Ile Glu Asn Arg Leu Phe Ile Asn Gly Glu Tyr Thr Ala Ala Ala
            20                  25                  30 gaa aat gaa acc ttt gaa acc gtt gat ccg gtc acc cag gca ccg ctg   144
Glu Asn Glu Thr Phe Glu Thr Val Asp Pro Val Thr Gln Ala Pro Leu
35                  40                  45 gcg aaa att gcc cgc ggc aag agc gtc gat atc gac cgt gcg atg agc   192
Ala Lys Ile Ala Arg Gly Lys Ser Val Asp Ile Asp Arg Ala Met Ser
        50                  55                  60 gca gca cgc ggc gta ttt gaa cgc ggc gac tgg tca ctc tct tct ccg   240
Ala Ala Arg Gly Val Phe Glu Arg Gly Asp Trp Ser Leu Ser Ser Pro
65                  70                  75                  80 gct aaa cgt aaa gcg gta ctg aat aaa ctc gcc gat tta atg gaa gcc   288
Ala Lys Arg Lys Ala Val Leu Asn Lys Leu Ala Asp Leu Met Glu Ala
                85                  90                  95 cac gcc gaa gag ctg gca ctg ctg gaa act ctc gac acc ggc aaa ccg   336
His Ala Glu Glu Leu Ala Leu Leu Glu Thr Leu Asp Thr Gly Lys Pro
            100                 105                 110 att cgt cac agt ctg cgt gat gat att ccc ggc gcg gcg cgc gcc att   384
Ile Arg His Ser Leu Arg Asp Asp Ile Pro Gly Ala Ala Arg Ala Ile
        115                 120                 125 cgc tgg tac gcc gaa gcg atc gac aaa gtg tat ggc gaa gtg gcg acc   432
Arg Trp Tyr Ala Glu Ala Ile Asp Lys Val Tyr Gly Glu Val Ala Thr
130                 135                 140 acc agt agc cat gag ctg gcg atg atc gtg cgt gaa ccg gtc ggc gtg   480
Thr Ser Ser His Glu Leu Ala Met Ile Val Arg Glu Pro Val Gly Val
145                 150                 155                 160 att gcc gcc atc gtg ccg tgg aac ttc ccg ctg ttg ctg act tgc tgg   528
Ile Ala Ala Ile Val Pro Trp Asn Phe Pro Leu Leu Leu Thr Cys Trp
                165                 170                 175 aaa ctc ggc ccg gcg ctg gcg gcg gga aac agc gtg att cta aaa ccg   576
Lys Leu Gly Pro Ala Leu Ala Ala Gly Asn Ser Val Ile Leu Lys Pro
            180                 185                 190 tct gaa aaa tca ccg ctc agt gcg att cgt ctc gcg ggg ctg gcg aaa   624
Ser Glu Lys Ser Pro Leu Ser Ala Ile Arg Leu Ala Gly Leu Ala Lys
        195                 200                 205 gaa gca ggc ttg ccg gat ggt gtg ttg aac gtg gtg acg ggt ttt ggt   672
Glu Ala Gly Leu Pro Asp Gly Val Leu Asn Val Val Thr Gly Phe Gly
210                 215                 220 cat gaa gcc ggg cag gcg ctg tcg cgt cat aac gat atc gac gcc att   720
His Glu Ala Gly Gln Ala Leu Ser Arg His Asn Asp Ile Asp Ala Ile
225                 230                 235                 240 gcc ttt acc ggt tca acc cgt acc ggg aaa cag ctg ctg aaa gat gcg   768
Ala Phe Thr Gly Ser Thr Arg Thr Gly Lys Gln Leu Leu Lys Asp Ala
                245                 250                 255 ggc gac agc aac atg aaa cgc gtc tgg ctg gaa gcg ggc ggc aaa agc   816
Gly Asp Ser Asn Met Lys Arg Val Trp Leu Glu Ala Gly Gly Lys Ser
            260                 265                 270 gcc aac atc gtt ttc gct gac tgc ccg gat ttg caa cag gcg gca agc   864
Ala Asn Ile Val Phe Ala Asp Cys Pro Asp Leu Gln Gln Ala Ala Ser
        275                 280                 285 gcc acc gca gca ggc att ttc tac aac cag gga cag gtg tgc atc gcc   912
Ala Thr Ala Ala Gly Ile Phe Tyr Asn Gln Gly Gln Val Cys Ile Ala
290                 295                 300 gga acg cgc ctg ttg ctg gaa gag agc atc gcc gat gaa ttc tta gcc   960
Gly Thr Arg Leu Leu Leu Glu Glu Ser Ile Ala Asp Glu Phe Leu Ala
```

```
ctg tta aaa cag cag gcg caa aac tgg cag ccg ggc cat cca ctt gat    1008
Leu Leu Lys Gln Gln Ala Gln Asn Trp Gln Pro Gly His Pro Leu Asp
325                 330                 335 ccc gca acc acc atg ggc acc tta atc gac tgc gcc cac gcc gac tcg    1056
Pro Ala Thr Thr Met Gly Thr Leu Ile Asp Cys Ala His Ala Asp Ser
340                 345                 350 gtc cat agc ttt att cgg gaa ggc gaa agc aaa ggg caa ctg ttg ttg    1104
Val His Ser Phe Ile Arg Glu Gly Glu Ser Lys Gly Gln Leu Leu Leu
355                 360                 365 gat ggc cgt aac gcc ggg ctg gct gcc gcc atc ggc ccg acc atc ttt    1152
Asp Gly Arg Asn Ala Gly Leu Ala Ala Ala Ile Gly Pro Thr Ile Phe
370                 375                 380 gtg gat gtg gac ccg aat gcg tcc tta agt cgc gaa gag att ttc ggt    1200
Val Asp Val Asp Pro Asn Ala Ser Leu Ser Arg Glu Glu Ile Phe Gly
385                 390                 395                 400 ccg gtg ctg gtg gtc acg cgt ttc aca tca gaa gaa cag gcg cta cag    1248
Pro Val Leu Val Val Thr Arg Phe Thr Ser Glu Glu Gln Ala Leu Gln
405                 410                 415 ctt gcc aac gac agc cag tac ggc ctt ggc gcg gcg gta tgg acg cgc    1296
Leu Ala Asn Asp Ser Gln Tyr Gly Leu Gly Ala Ala Val Trp Thr Arg
420                 425                 430 gac ctc tcc cgc gcg cac cgc atg agc cga cgc ctg aaa gcc ggt tcc    1344
Asp Leu Ser Arg Ala His Arg Met Ser Arg Arg Leu Lys Ala Gly Ser
435                 440                 445 gtc ttc gtc aat aac tac aac gac ggc gat atg acc gtg ccg ttt ggc    1392
Val Phe Val Asn Asn Tyr Asn Asp Gly Asp Met Thr Val Pro Phe Gly
450                 455                 460 ggc tat aag cag agc ggc aac ggt cgc gac aaa tcc ctg cat gcc ctt    1440
Gly Tyr Lys Gln Ser Gly Asn Gly Arg Asp Lys Ser Leu His Ala Leu
465                 470                 475                 480 gaa aaa ttc act gaa ctg aaa acc atc tgg ata agc ctg gag gcc tga    1488
Glu Lys Phe Thr Glu Leu Lys Thr Ile Trp Ile Ser Leu Glu Ala
485                 490                 495

<210> SEQ ID NO 20
<211> LENGTH: 495
<212> TYPE: PRT
<213> ORGANISM: Escherichia coli

<400> SEQUENCE: 20

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Ile Asp Lys Val Tyr Gly Glu Val Ala Thr
    130                 135                 140
```

```
Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Thr Cys Trp
            165                 170                 175

Lys Leu Gly Pro Ala Leu Ala Ala Gly Asn Ser Val Ile Leu Lys Pro
        180                 185                 190

Ser Glu Lys Ser Pro Leu Ser Ala Ile Arg Leu Ala Gly Leu Ala Lys
            195                 200                 205

Glu Ala Gly Leu Pro Asp Gly Val Leu Asn Val Val Thr Gly Phe Gly
        210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
            245                 250                 255

Gly Asp Ser Asn Met Lys Arg Val Trp Leu Glu Ala Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
            325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ala Ile Gly Pro Thr Ile Phe
        370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
            405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
        435                 440                 445

Val Phe Val Asn Asn Tyr Asn Asp Gly Asp Met Thr Val Pro Phe Gly
        450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
            485                 490                 495

<210> SEQ ID NO 21
<211> LENGTH: 1395
<212> TYPE: DNA
<213> ORGANISM: Escherichia coli

<400> SEQUENCE: 21
atgcctgacg ctaaaaaaca ggggcggtca aacaaggcaa tgacgttttt cgtctgcttc      60
cttgccgctc tggcgggatt actctttggc ctggatatcg gtgtaattgc tggcgcactg     120
ccgtttattg cagatgaatt ccagattact tcgcacacgc aagaatgggt cgtaagctcc     180
```

```
atgatgttcg gtgcggcagt cggtgcggtg ggcagcggct ggctctcctt taaactcggg      240
cgcaaaaaga gcctgatgat cggcgcaatt ttgtttgttg ccggttcgct gttctctgcg      300
gctgcgccaa acgttgaagt actgattctt tcccgcgttc tactggggct ggcggtgggt      360
gtggcctctt ataccgcacc gctgtacctc tctgaaattg cgccggaaaa aattcgtggc      420
agtatgatct cgatgtatca gttgatgatc actatcggga tcctcggtgc ttatctttct      480
gataccgcct tcagctacac cggtgcatgg cgctggatgc tgggtgtgat tatcatcccg      540
gcaattttgc tgctgattgg tgtcttcttc ctgccagaca gcccacgttg gtttgccgcc      600
aaacgccgtt ttgttgatgc cgaacgcgtg ctgctacgcc tgcgtgacac cagcgcggaa      660
gcgaaacgcg aactggatga atccgtgaaa gtttgcaggt taaacagag tggctgggcg       720 ctgtttaaag agaacagcaa cttccgccgc gcggtgttcc ttggcgtact gttgcaggta      780
atgcagcaat tcaccgggat gaacgtcatc atgtattacg cgccgaaaat cttcgaactg      840
gcgggttata ccaacactac cgagcaaatg tgggggaccg tgattgtcgg cctgaccaac      900
gtacttgcca cctttatcgc aatcggcctt gttgaccgct ggggacgtaa ccaacgcta      960 acgctgggct tcctggtgat ggctgctggc atgggcgtac tcggtacaat gatgcatatc     1020
ggtattcact ctccgtcggc gcagtatttc gccatcgcca tgctgctgat gtttattgtc     1080
ggttttgcca tgagtgccgg tccgctgatt tgggtactgt gctccgaaat tcagccgctg     1140
aaaggccgcg attttggcat cacctgctcc actgccacca actggattgc aacatgatc      1200 gttggcgcaa cgttcctgac catgctcaac acgctgggta acgccaacac cttctgggtg     1260
tatgcggctc tgaacgtact gtttatcctg ctgacattgt ggctggtacc ggaaaccaaa     1320
cacgtttcgc tggaacatat tgaacgtaat ctgatgaaag gtcgtaaact gcgcgaaata     1380
ggcgctcacg attaa                                                      1395
```

<210> SEQ ID NO 22
<211> LENGTH: 464
<212> TYPE: PRT
<213> ORGANISM: Escherichia coli

<400> SEQUENCE: 22

```
Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
                20                  25                  30

Ile Gly Val Ile Ala Gly Ala Leu Pro Phe Ile Ala Asp Glu Phe Gln
            35                  40                  45

Ile Thr Ser His Thr Gln Glu Trp Val Val Ser Met Met Phe Gly
        50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Pro Asn Val Glu Val Leu Ile Leu Ser Arg
            100                 105                 110

Val Leu Leu Gly Leu Ala Val Gly Val Ala Ser Tyr Thr Ala Pro Leu
        115                 120                 125

Tyr Leu Ser Glu Ile Ala Pro Glu Lys Ile Arg Gly Ser Met Ile Ser
    130                 135                 140

Met Tyr Gln Leu Met Ile Thr Ile Gly Ile Leu Gly Ala Tyr Leu Ser
145                 150                 155                 160
```

```
Asp Thr Ala Phe Ser Tyr Thr Gly Ala Trp Arg Trp Met Leu Gly Val
                165                 170                 175

Ile Ile Ile Pro Ala Ile Leu Leu Ile Gly Val Phe Phe Leu Pro
        180                 185                 190

Asp Ser Pro Arg Trp Phe Ala Ala Lys Arg Arg Phe Val Asp Ala Glu
                195                 200                 205

Arg Val Leu Leu Arg Leu Arg Asp Thr Ser Ala Glu Ala Lys Arg Glu
        210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
                275                 280                 285

Gln Met Trp Gly Thr Val Ile Val Gly Leu Thr Asn Val Leu Ala Thr
            290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350

Ala Met Leu Leu Met Phe Ile Val Gly Phe Ala Met Ser Ala Gly Pro
                355                 360                 365

Leu Ile Trp Val Leu Cys Ser Glu Ile Gln Pro Leu Lys Gly Arg Asp
        370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
                420                 425                 430

Leu Trp Leu Val Pro Glu Thr Lys His Val Ser Leu Glu His Ile Glu
        435                 440                 445

Arg Asn Leu Met Lys Gly Arg Lys Leu Arg Glu Ile Gly Ala His Asp
        450                 455                 460

<210> SEQ ID NO 23
<211> LENGTH: 1248
<212> TYPE: DNA
<213> ORGANISM: Escherichia coli

<400> SEQUENCE: 23
atggcactga atattccatt cagaaatgcg tactatcgtt ttgcatccag ttactcattt       60 ctcttttta tttcctggtc gctgtggtgg tcgttatacg ctatttggct gaaaggacat      120
ctaggattaa cagggacgga attaggtaca ctttattcgg tcaaccagtt taccagcatt      180
ctatttatga tgttctacgg catcgttcag gataaactcg gtctgaagaa accgctcatc      240
tggtgtatga gtttcattct ggtcttgacc ggaccgttta tgatttacgt ttatgaaccg      300
ttactgcaaa gcaattttc tgtaggtcta attctggggg cgctcttttt tggcctgggg      360
tatctggcgg gatgcggttt gcttgacagc ttcaccgaaa aaatgcgcg aaattttcat      420
```

```
ttcgaatatg gaacagcgcg cgcctgggga tcttttggct atgctattgg cgcgttcttt    480
gccggtatat tttttagtat cagtccccat atcaacttct ggttggtctc gctatttggc    540
gctgtattta tgatgatcaa catgcgtttt aaagataagg atcaccagtg catagcggcg    600
gatgcgggag gggtaaaaaa agaggatttt atcgcagttt tcaaggatcg aaacttctgg    660
gttttcgtca tatttattgt ggggacgtgg tctttctata acattttga tcaacaactc    720 tttcctgtct tttatgcagg tttattcgaa tcacacgatg taggaacgcg cctgtatggt    780
tatctcaact cattccaggt ggtactcgaa gcgctgtgca tggcgattat cctttctttt    840
gtgaatcggg tagggccaaa aaatgcatta cttatcggtg ttgtgattat ggcgttgcgt    900
atcctttcct gcgcgttgtt cgttaacccc tggattattt cattagtgaa gctgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg cattttctt cctgagtaaa   1200 aaacgcgagc aaatagttat ggaaacgcct gtaccttcag caatatag                1248
```

<210> SEQ ID NO 24
<211> LENGTH: 415
<212> TYPE: PRT
<213> ORGANISM: Escherichia coli

<400> SEQUENCE: 24

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Ile Ala Ala Asp Ala Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240
```

| Phe | Pro | Val | Phe | Tyr | Ala | Gly | Leu | Phe | Glu | Ser | His | Asp | Val | Gly | Thr |
|---|---|---|---|---|---|---|---|---|---|---|---|---|---|---|---|
| | | | | 245 | | | | | 250 | | | | | 255 | |

Arg Leu Tyr Gly Tyr Leu Asn Ser Phe Gln Val Val Leu Glu Ala Leu
            260                       265                   270

Cys Met Ala Ile Ile Pro Phe Phe Val Asn Arg Val Gly Pro Lys Asn
            275                       280                   285

Ala Leu Leu Ile Gly Val Val Ile Met Ala Leu Arg Ile Leu Ser Cys
            290                       295                   300

Ala Leu Phe Val Asn Pro Trp Ile Ile Ser Leu Val Lys Leu Leu His
305                  310                       315                   320

Ala Ile Glu Val Pro Leu Cys Val Ile Ser Val Phe Lys Tyr Ser Val
            325                       330                   335

Ala Asn Phe Asp Lys Arg Leu Ser Ser Thr Ile Phe Leu Ile Gly Phe
            340                       345                   350

Gln Ile Ala Ser Ser Leu Gly Ile Val Leu Leu Ser Thr Pro Thr Gly
            355                       360                   365

Ile Leu Phe Asp His Ala Gly Tyr Gln Thr Val Phe Phe Ala Ile Ser
            370                       375                   380

Gly Ile Val Cys Leu Met Leu Leu Phe Gly Ile Phe Phe Leu Ser Lys
385                  390                       395                   400

Lys Arg Glu Gln Ile Val Met Glu Thr Pro Val Pro Ser Ala Ile
            405                       410                   415

<210> SEQ ID NO 25
<211> LENGTH: 1248
<212> TYPE: DNA
<213> ORGANISM: Escherichia coli

<400> SEQUENCE: 25

| | | | | | |
|---|---|---|---|---|---|
| atggcactga | atattccatt | cagaaatgcg | tactatcgtt | ttgcatccag | ttactcattt     60 |
| ctcttttta | tttcctggtc | gctgtggtgg | tcgttatacg | ctatttggct | gaaaggacat    120 |
| ctagggttga | cagggacgga | attaggtaca | ctttattcgg | tcaaccagtt | taccagcatt    180 |
| ctatttatga | tgttctacgg | catcgttcag | gataaactcg | gtctgaagaa | accgctcatc    240 |
| tggtgtatga | gtttcatcct | ggtcttgacc | ggaccgttta | tgatttacgt | ttatgaaccg    300 |
| ttactgcaaa | gcaattttc | tgtaggtcta | attctggggg | cgctattttt | tggcttgggg    360 |
| tatctggcgg | gatgcggttt | gcttgatagc | ttcaccgaaa | aaatggcgcg | aaattttcat    420 |
| ttcgaatatg | aacagcgcg | cgcctgggga | tcttttggct | atgctattgg | cgcgttcttt    480 |
| gccggcatat | tttttagtat | cagtccccat | atcaacttct | ggttggtctc | gctatttggc    540 |
| gctgtattta | tgatgatcaa | catgcgtttt | aaagataagg | atcaccagtg | cgtagcggca    600 |
| gatgcgggag | gggtaaaaaa | agaggatttt | atcgcagttt | tcaaggatcg | aaacttctgg    660 |
| gttttcgtca | tatttattgt | ggggacgtgg | tcttttctata | acattttttga | tcaacaactt    720 |
| tttcctgtct | tttattcagg | tttattcgaa | tcacacgatg | taggaacgcg | cctgtatggt    780 |
| tatctcaact | cattccaggt | ggtactcgaa | gcgctgtgca | tggcgattat | tccttttcttt    840 |
| gtgaatcggg | tagggccaaa | aaatgcatta | cttatcggag | ttgtgattat | ggcgttgcgt    900 |
| atcctttcct | gcgcgctgtt | cgttaacccc | tggattattt | cattagtgaa | gttgttacat    960 |
| gccattgagg | ttccactttg | tgtcatatcc | gtcttcaaat | acagcgtggc | aaactttgat   1020 |
| aagcgcctgt | cgtcgacgat | cttttctgatt | ggttttcaaa | ttgccagttc | gcttgggatt   1080 |
| gtgctgcttt | caacgccgac | tgggatactc | tttgaccacg | caggctacca | gacagttttc   1140 |

```
ttcgcaattt cgggtattgt ctgcctgatg ttgctatttg cattttctt cttgagtaaa    1200 aaacgcgagc aaatagttat ggaaacgcct gtaccttcag caatatag              1248
```

<210> SEQ ID NO 26
<211> LENGTH: 415
<212> TYPE: PRT
<213> ORGANISM: Escherichia coli

<400> SEQUENCE: 26

```
Met Ala Leu Asn Ile Pro Phe Arg Asn Ala Tyr Tyr Arg Phe Ala Ser
 1               5                  10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365
```

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415

<210> SEQ ID NO 27
<211> LENGTH: 1326
<212> TYPE: DNA
<213> ORGANISM: Bifidobacterium lactis

<400> SEQUENCE: 27
atggcaacaa ccacgaaggt gtggaggaac ccctcctacc tgcaaagctc aaccggcatc      60
ttcctgttct tctgctcctg gggcatctgg tggtcgttct tccagcgctg gctcaactcg     120
atgggactca acggcgcgaa agtgggcacg atctattcga tcaactcgct ggccacgctc     180
atcctcatgt tcgggtacgg cctcatccag gacaatctcg gactcaagcg ccgtcttgtg     240
ctcgtcatct cggcgatcgc cgcactcgtc ggacccttcg tgcagttcgt gtacgcgccg     300
ctgatgagga cgaacatgat ggccgccgca ctcgtgggct ccgtcgttct ctccgcgggc     360
ttcatggcag gctgctcgct catagagccc gtgaccgaac ggtacagccg ccgtttcaac     420
ttagagtacg gccaatcccg cgcatggggt tccttcggat atgccattgt ggcgcttgtc     480
gccggcttcg tgttcaacat caacccgatg atcaacttct ggctcggctc cgcattcggc     540
gtgggcatgc tcatcgtgta cctcacctgg tatccggccg agcagcgcga agcgctcaag     600
gaagccgccg atccgaatgc cgcgccaact aacccgacca tcaaagacat gctcggcgtg     660
ctcaagatgc ccacgctgtg ggtgctcatc gtgttcatgc tgctcaccaa cacgttctac     720
accgtattcg accagcagat gttccccacc tactacgcct cgctcttccc gaatgaggcc     780
accggcaacg ccgtctacgg cacgctcaac tcggtgcagg tgttctgcga atccgcgatg     840
atgggcgtcg tgccgatcat catgcgcaag gtaggtgtgc gcaacgcgtt gctgctcgga     900
tccacggtga tgttccttcg catcgggctg tgcggcatct tccacgatcc ggtgtccatc     960
tcgatcgtca aaatgttcca cgccattgaa gttccgctgt tctgcctgcc ggcgttccgc    1020
tacttcacgc tccacttcaa tccgaagctc tccgcgacgc tctacatggt cggcttccag    1080
attgcctcac agatcggcca ggtcgtcttc tccacccccgc tcggcatgct gcatgaccgc    1140
atgggcgacc gcacgacgtt cctgacgatc tccgccatcg tgcttgctgc caccgtctac    1200
ggattcttcg tgatcaagcg cgacgacgag caggtggatg cgatccgtt catccgcgat    1260 tcgaagaagc tgccgtcgct cgccaccgac gaggcgatcc tctccgcgga ttccgaggat    1320
atgtaa                                                               1326

<210> SEQ ID NO 28
<211> LENGTH: 441
<212> TYPE: PRT
<213> ORGANISM: Bifidobacterium lactis

<400> SEQUENCE: 28

Met Ala Thr Thr Thr Lys Val Trp Arg Asn Pro Ser Tyr Leu Gln Ser
1               5                   10                  15

Ser Thr Gly Ile Phe Leu Phe Phe Cys Ser Trp Gly Ile Trp Trp Ser
            20                  25                  30

Phe Phe Gln Arg Trp Leu Asn Ser Met Gly Leu Asn Gly Ala Lys Val
        35                  40                  45

Gly Thr Ile Tyr Ser Ile Asn Ser Leu Ala Thr Leu Ile Leu Met Phe
 50                  55                  60

Gly Tyr Gly Leu Ile Gln Asp Asn Leu Gly Leu Lys Arg Arg Leu Val
 65                  70                  75                  80

Leu Val Ile Ser Ala Ile Ala Ala Leu Val Gly Pro Phe Val Gln Phe
                 85                  90                  95

Val Tyr Ala Pro Leu Met Arg Thr Asn Met Met Ala Ala Ala Leu Val
            100                 105                 110

Gly Ser Val Val Leu Ser Ala Gly Phe Met Ala Gly Cys Ser Leu Ile
        115                 120                 125

Glu Pro Val Thr Glu Arg Tyr Ser Arg Arg Phe Asn Leu Glu Tyr Gly
    130                 135                 140

Gln Ser Arg Ala Trp Gly Ser Phe Gly Tyr Ala Ile Val Ala Leu Val
145                 150                 155                 160

Ala Gly Phe Val Phe Asn Ile Asn Pro Met Ile Asn Phe Trp Leu Gly
                165                 170                 175

Ser Ala Phe Gly Val Gly Met Leu Ile Val Tyr Leu Thr Trp Tyr Pro
            180                 185                 190

Ala Glu Gln Arg Glu Ala Leu Lys Glu Ala Ala Asp Pro Asn Ala Ala
        195                 200                 205

Pro Thr Asn Pro Thr Ile Lys Asp Met Leu Gly Val Leu Lys Met Pro
    210                 215                 220

Thr Leu Trp Val Leu Ile Val Phe Met Leu Thr Asn Thr Phe Tyr
225                 230                 235                 240

Thr Val Phe Asp Gln Gln Met Phe Pro Thr Tyr Tyr Ala Ser Leu Phe
                245                 250                 255

Pro Asn Glu Ala Thr Gly Asn Ala Val Tyr Gly Thr Leu Asn Ser Val
            260                 265                 270

Gln Val Phe Cys Glu Ser Ala Met Met Gly Val Val Pro Ile Ile Met
        275                 280                 285

Arg Lys Val Gly Val Arg Asn Ala Leu Leu Leu Gly Ser Thr Val Met
    290                 295                 300

Phe Leu Arg Ile Gly Leu Cys Gly Ile Phe His Asp Pro Val Ser Ile
305                 310                 315                 320

Ser Ile Val Lys Met Phe His Ala Ile Glu Val Pro Leu Phe Cys Leu
                325                 330                 335

Pro Ala Phe Arg Tyr Phe Thr Leu His Phe Asn Pro Lys Leu Ser Ala
            340                 345                 350

Thr Leu Tyr Met Val Gly Phe Gln Ile Ala Ser Gln Ile Gly Gln Val
        355                 360                 365

Val Phe Ser Thr Pro Leu Gly Met Leu His Asp Arg Met Gly Asp Arg
    370                 375                 380

Thr Thr Phe Leu Thr Ile Ser Ala Ile Val Leu Ala Ala Thr Val Tyr
385                 390                 395                 400

Gly Phe Phe Val Ile Lys Arg Asp Asp Glu Gln Val Asp Gly Asp Pro
                405                 410                 415

Phe Ile Arg Asp Ser Lys Lys Leu Pro Ser Leu Ala Thr Asp Glu Ala
            420                 425                 430

Ile Leu Ser Ala Asp Ser Glu Asp Met
        435                 440

<210> SEQ ID NO 29
<211> LENGTH: 858
<212> TYPE: DNA

<213> ORGANISM: Streptococcus pneumoniae

<400> SEQUENCE: 29

```
ttattgatga ctgtccccgg tttagtttta acctttatct ttaaatacat ccctatgtat      60
ggggttttaa tcgcatttaa agattacaat cctttaaaag gaattttagg gagtgattgg     120
attggttttt ctgagtttac aaaattcata tcctctccca actttggtat cttgttagcc     180
aacacattaa aattaagtat ctatggttta ttgcttggct ttttaccacc aatcattctc     240
gcgattatgc tcaatcaact cttgagtgaa aaagtcaaaa acgaattca gctcatttta      300
tacgcaccaa actttatctc agtcgttgtt attgtcggta tgattttcct cttcttttca     360
gtgggaggac caatcaacaa ttttctttct atgtttggaa tgaaggctga cttcttgaca     420
aatccagact tctttagacc tttatacatc tttagtggta tctggcaagg aatgggctgg     480
gcttcaacgc tctacacggc aacattggta aatgtagatc cagccttagt agaagcagcc     540
cgactggatg gagccaatat cttccaacga atctggcaca ttgatattcc agctcttaag     600
cctattatgg ttatccaatt tgttttagct gcaggtggaa ttatgaatgt cggatatgaa     660
aaagcattct tgatgcagac atcgttaaat ttgccaactt ctgaaattat ctcgacatat     720
gtctataaag ttggtcttgt atcaggagac tattcttact caacagcggt tggtttgttt     780
aatgcagtga ttaacgtagt attgcttgtt gcagttaacc aaatcgttaa acgcatgaat     840
aatggtgaag gaatttaa                                                   858
```

<210> SEQ ID NO 30
<211> LENGTH: 305
<212> TYPE: PRT
<213> ORGANISM: Streptococcus pneumoniae

<400> SEQUENCE: 30

```
Met Asn Ser Lys Ala Lys Gln Val Ser Leu Trp Glu Arg Ile Lys Lys
1               5                   10                  15

Gln Lys Leu Leu Leu Met Thr Val Pro Gly Leu Val Leu Thr Phe
            20                  25                  30

Ile Phe Lys Tyr Ile Pro Met Tyr Gly Val Leu Ile Ala Phe Lys Asp
        35                  40                  45

Tyr Asn Pro Leu Lys Gly Ile Leu Gly Ser Asp Trp Ile Gly Phe Ser
    50                  55                  60

Glu Phe Thr Lys Phe Ile Ser Ser Pro Asn Phe Gly Ile Leu Leu Ala
65                  70                  75                  80

Asn Thr Leu Lys Leu Ser Ile Tyr Gly Leu Leu Gly Phe Leu Pro
            85                  90                  95

Pro Ile Ile Leu Ala Ile Met Leu Asn Gln Leu Leu Ser Glu Lys Val
            100                 105                 110

Lys Lys Arg Ile Gln Leu Ile Leu Tyr Ala Pro Asn Phe Ile Ser Val
        115                 120                 125

Val Val Ile Val Gly Met Ile Phe Leu Phe Phe Ser Val Gly Gly Pro
    130                 135                 140

Ile Asn Asn Phe Leu Ser Met Phe Gly Met Lys Ala Asp Phe Leu Thr
145                 150                 155                 160

Asn Pro Asp Phe Phe Arg Pro Leu Tyr Ile Phe Ser Gly Ile Trp Gln
                165                 170                 175

Gly Met Gly Trp Ala Ser Thr Leu Tyr Thr Ala Thr Leu Val Asn Val
            180                 185                 190

Asp Pro Ala Leu Val Glu Ala Ala Arg Leu Asp Gly Ala Asn Ile Phe
        195                 200                 205
```

```
Gln Arg Ile Trp His Ile Asp Ile Pro Ala Leu Lys Pro Ile Met Val
    210                 215                 220

Ile Gln Phe Val Leu Ala Ala Gly Gly Ile Met Asn Val Gly Tyr Glu
225                 230                 235                 240

Lys Ala Phe Leu Met Gln Thr Ser Leu Asn Leu Pro Thr Ser Glu Ile
                245                 250                 255

Ile Ser Thr Tyr Val Tyr Lys Val Gly Leu Val Ser Gly Asp Tyr Ser
            260                 265                 270

Tyr Ser Thr Ala Val Gly Leu Phe Asn Ala Val Ile Asn Val Val Leu
        275                 280                 285

Leu Val Ala Val Asn Gln Ile Val Lys Arg Met Asn Asn Gly Glu Gly
    290                 295                 300

Ile
305

<210> SEQ ID NO 31
<211> LENGTH: 918
<212> TYPE: DNA
<213> ORGANISM: Streptococcus pneumoniae

<400> SEQUENCE: 31
atggtgaagg aatttaagga ggaaagtatg aaaaattcga ttatggatac aaaatttgat      60
agacgtatct tactcttaaa taaaatcatt attgtcttta tcgttttgat gactttgctt     120
cctttacttt atatcgtcgt agcatccttt atggatccta aggttctggt tagtagaggg     180
attagcttta atccagccga ttggactgta gaaggttacc agcgtgtatt cagtgaccaa     240
tctattctaa gaggttttat caattctcta ctatactctt ttggatttgc agctttaaca     300
gtcttgctat ctgtgtttac agcttatcct ctttctaaga aagacttggt tggacgtcgt     360
tggattaact acttcttgat tgtaactatg ttctttggtg gtggtttagt cccaacttac     420
ttgctcgtaa agaattggga atgctcaat actccatggg ctatcattgt tccaggtgct     480
gttaacgttt ggaatattat tcttgctagg gcctatttcc aaggattgcc tgaagaatta     540
gttgaagctg ctgtcattga tggtgcaaat gatttacaga ttttcttcaa aatcatgctt     600
cctcttgcaa aaccaattat gtttgttctc ttcctttatg cttttgtagg acagtggaac     660
tcatactttg atgcaatgat ttatatcaag gatccaaact ggaaccatt gcaacttgta     720 cttcgtaaaa ttctcattca gagccaacca ggtcaagaca tgattggagc acaagcggct     780
atgaatgaaa tgaaacgttt agctgaattg attaaatacg caactattgt catttccagc     840
ttgccattga ttgttatgta tccattcttc caaaaatact ttgataaagg aattatggct     900
ggttcactta aaggataa                                                   918

<210> SEQ ID NO 32
<211> LENGTH: 305
<212> TYPE: PRT
<213> ORGANISM: Streptococcus pneumoniae

<400> SEQUENCE: 32

Met Val Lys Glu Phe Lys Glu Glu Ser Met Lys Asn Ser Ile Met Asp
1               5                   10                  15

Thr Lys Phe Asp Arg Arg Ile Leu Leu Leu Asn Lys Ile Ile Ile Val
            20                  25                  30

Phe Ile Val Leu Met Thr Leu Leu Pro Leu Leu Tyr Ile Val Val Ala
        35                  40                  45

Ser Phe Met Asp Pro Lys Val Leu Val Ser Arg Gly Ile Ser Phe Asn
```

```
            50                  55                  60
Pro Ala Asp Trp Thr Val Glu Gly Tyr Gln Arg Val Phe Ser Asp Gln
 65                  70                  75                  80

Ser Ile Leu Arg Gly Phe Ile Asn Ser Leu Leu Tyr Ser Phe Gly Phe
                 85                  90                  95

Ala Ala Leu Thr Val Leu Leu Ser Val Phe Thr Ala Tyr Pro Leu Ser
            100                 105                 110

Lys Lys Asp Leu Val Gly Arg Arg Trp Ile Asn Tyr Phe Leu Ile Val
        115                 120                 125

Thr Met Phe Phe Gly Gly Leu Val Pro Thr Tyr Leu Leu Val Lys
    130                 135                 140

Glu Leu Gly Met Leu Asn Thr Pro Trp Ala Ile Val Pro Gly Ala
145                 150                 155                 160

Val Asn Val Trp Asn Ile Ile Leu Ala Arg Ala Tyr Phe Gln Gly Leu
                165                 170                 175

Pro Glu Glu Leu Val Glu Ala Val Ile Asp Gly Ala Asn Asp Leu
            180                 185                 190

Gln Ile Phe Phe Lys Ile Met Leu Pro Leu Ala Lys Pro Ile Met Phe
        195                 200                 205

Val Leu Phe Leu Tyr Ala Phe Val Gly Gln Trp Asn Ser Tyr Phe Asp
210                 215                 220

Ala Met Ile Tyr Ile Lys Asp Pro Asn Leu Glu Pro Leu Gln Leu Val
225                 230                 235                 240

Leu Arg Lys Ile Leu Ile Gln Ser Gln Pro Gly Gln Asp Met Ile Gly
                245                 250                 255

Ala Gln Ala Ala Met Asn Glu Met Lys Arg Leu Ala Glu Leu Ile Lys
            260                 265                 270

Tyr Ala Thr Ile Val Ile Ser Ser Leu Pro Leu Ile Val Met Tyr Pro
        275                 280                 285

Phe Phe Gln Lys Tyr Phe Asp Lys Gly Ile Met Ala Gly Ser Leu Lys
    290                 295                 300

Gly
305

<210> SEQ ID NO 33
<211> LENGTH: 1617
<212> TYPE: DNA
<213> ORGANISM: Streptococcus pneumoniae

<400> SEQUENCE: 33
atgaaattca aaacattctc aaaatcagca gttttgttga cagctagttt agcagtactt    60
gcagcctgtg ctcaaaaaaa tacagcttca agtccagatt ataagttgga aggtgtaaca   120
ttcccgcttc aagaaaagaa acattgaag tttatgacag ccagttcacc gttatctcct   180
aaagacccaa tgaaaagtt aattttgcaa cgtttggaga aggaaactgg cgttcatatt   240
gactggacca actaccaatc cgactttgca gaaaaacgta acttggatat ttctagtggt   300
gatttaccag atgctatcca caacgacgga gcttcagatg tggacttgat gaactgggct   360
aaaaaaggtg ttattattcc agttgaagat ttgattgata atacatgcc aaatcttaag   420 aaaattttgg atgagaaacc agagtacaag gccttgatga cagcacctga tgggcacatt   480
tactcatttc catggattga agagcttgga gatggtaaag agtctattca cagtgtcaac   540
gatatggctt ggattaacaa agattggctt aagaaacttg gtcttgaaat gccaaaaact   600
actgatgatt tgattaaagt cctagaagct ttcaaaaacg ggatccaaa tggaaatgga   660
```

```
gaggctgatg aaattccatt ttcatttatt agtggtaacg gaaacgaaga ttttaaattc    720
ctatttgctg catttggtat aggggataac gatgatcatt tagtagtagg aaatgatggc    780
aaagttgact tcacagcaga taacgataac tataagaag gtgtcaaatt tatccgtcaa     840
ttgcaagaaa aaggcctgat tgataaagaa gctttcgaac atgattggaa tagttacatt    900
gctaaaggtc atgatcagaa atttggtgtt tactttacat gggataagaa taatgttact    960
ggaagtaacg aaagttatga tgttttacca gtacttgctg gaccaagtgg tcaaaaacac   1020
gtagctcgta caaacggtat gggatttgca cgtgacaaga tggttattac cagtgtaaac   1080
aaaaacctag aattgacagc taatggatt gatgcacaat acgctccact ccaatctgtg    1140
caaaataact ggggaactta cggagatgac aaacaacaaa acatctttga attggatcaa   1200
gcgtcaaata gtctaaaaca cttaccacta acggaactg caccagcaga acttcgtcaa    1260
aagactgaag taggaggacc actagctatc ctagattcat actatggtaa agtaacaacc   1320
atgcctgatg atgccaaatg gcgtttggat cttatcaaag aatattatgt tccttacatg   1380
agcaatgtca ataactatcc aagagtcttt atgacacagg aagatttgga caagattgcc   1440
catatcgaag cagatatgaa tgactatatc taccgtaaac gtgctgaatg gattgtaaat   1500
ggcaatattg atactgagtg ggatgattac aagaaagaac ttgaaaaata cggactttct   1560
gattacctcg ctattaaaca aaaatactac gaccaatacc aagcaaacaa aaactag      1617

<210> SEQ ID NO 34
<211> LENGTH: 538
<212> TYPE: PRT
<213> ORGANISM: Streptococcus pneumoniae

<400> SEQUENCE: 34

Met Lys Phe Lys Thr Phe Ser Lys Ser Ala Val Leu Leu Thr Ala Ser
1               5                   10                  15

Leu Ala Val Leu Ala Ala Cys Gly Ser Lys Asn Thr Ala Ser Ser Pro
            20                  25                  30

Asp Tyr Lys Leu Glu Gly Val Thr Phe Pro Leu Gln Glu Lys Lys Thr
        35                  40                  45

Leu Lys Phe Met Thr Ala Ser Ser Pro Leu Ser Pro Lys Asp Pro Asn
    50                  55                  60

Glu Lys Leu Ile Leu Gln Arg Leu Glu Lys Glu Thr Gly Val His Ile
65                  70                  75                  80

Asp Trp Thr Asn Tyr Gln Ser Asp Phe Ala Glu Lys Arg Asn Leu Asp
                85                  90                  95

Ile Ser Ser Gly Asp Leu Pro Asp Ala Ile His Asn Asp Gly Ala Ser
            100                 105                 110

Asp Val Asp Leu Met Asn Trp Ala Lys Lys Gly Val Ile Pro Val
            115                 120                 125

Glu Asp Leu Ile Asp Lys Tyr Met Pro Asn Leu Lys Lys Ile Leu Asp
    130                 135                 140

Glu Lys Pro Glu Tyr Lys Ala Leu Met Thr Ala Pro Asp Gly His Ile
145                 150                 155                 160

Tyr Ser Phe Pro Trp Ile Glu Glu Leu Gly Asp Gly Lys Glu Ser Ile
                165                 170                 175

His Ser Val Asn Asp Met Ala Trp Ile Asn Lys Asp Trp Leu Lys Lys
            180                 185                 190

Leu Gly Leu Glu Met Pro Lys Thr Thr Asp Asp Leu Ile Lys Val Leu
        195                 200                 205

Glu Ala Phe Lys Asn Gly Asp Pro Asn Gly Asn Gly Glu Ala Asp Glu
```

```
                210                 215                 220
Ile Pro Phe Ser Phe Ile Ser Gly Asn Gly Asn Glu Asp Phe Lys Phe
225                 230                 235                 240

Leu Phe Ala Ala Phe Gly Ile Gly Asp Asn Asp Asp His Leu Val Val
                245                 250                 255

Gly Asn Asp Gly Lys Val Asp Phe Thr Ala Asp Asn Asp Asn Tyr Lys
                260                 265                 270

Glu Gly Val Lys Phe Ile Arg Gln Leu Gln Glu Lys Gly Leu Ile Asp
                275                 280                 285

Lys Glu Ala Phe Glu His Asp Trp Asn Ser Tyr Ile Ala Lys Gly His
290                 295                 300

Asp Gln Lys Phe Gly Val Tyr Phe Thr Trp Asp Lys Asn Asn Val Thr
305                 310                 315                 320

Gly Ser Asn Glu Ser Tyr Asp Val Leu Pro Val Leu Ala Gly Pro Ser
                325                 330                 335

Gly Gln Lys His Val Ala Arg Thr Asn Gly Met Gly Phe Ala Arg Asp
                340                 345                 350

Lys Met Val Ile Thr Ser Val Asn Lys Asn Leu Glu Leu Thr Ala Lys
                355                 360                 365

Trp Ile Asp Ala Gln Tyr Ala Pro Leu Gln Ser Val Gln Asn Asn Trp
370                 375                 380

Gly Thr Tyr Gly Asp Asp Lys Gln Gln Asn Ile Phe Glu Leu Asp Gln
385                 390                 395                 400

Ala Ser Asn Ser Leu Lys His Leu Pro Leu Asn Gly Thr Ala Pro Ala
                405                 410                 415

Glu Leu Arg Gln Lys Thr Glu Val Gly Gly Pro Leu Ala Ile Leu Asp
                420                 425                 430

Ser Tyr Tyr Gly Lys Val Thr Thr Met Pro Asp Asp Ala Lys Trp Arg
                435                 440                 445

Leu Asp Leu Ile Lys Glu Tyr Tyr Val Pro Tyr Met Ser Asn Val Asn
                450                 455                 460

Asn Tyr Pro Arg Val Phe Met Thr Gln Glu Asp Leu Asp Lys Ile Ala
465                 470                 475                 480

His Ile Glu Ala Asp Met Asn Asp Tyr Ile Tyr Arg Lys Arg Ala Glu
                485                 490                 495

Trp Ile Val Asn Gly Asn Ile Asp Thr Glu Trp Asp Asp Tyr Lys Lys
                500                 505                 510

Glu Leu Glu Lys Tyr Gly Leu Ser Asp Tyr Leu Ala Ile Lys Gln Lys
                515                 520                 525

Tyr Tyr Asp Gln Tyr Gln Ala Asn Lys Asn
530                 535

<210> SEQ ID NO 35
<211> LENGTH: 1248
<212> TYPE: DNA
<213> ORGANISM: Streptococcus mutans

<400> SEQUENCE: 35
atgaaaacat ggcaaaaaat cgtcgttggc ggtgcaggcc ttatgcttgc aagcagtatt       60
cttgttgcct gtggatcaaa ggattcaaaa tcaagttcat ctgatcccaa aaccattaaa      120
ctttgggttc aacaggagc caagaaatct tatcaaagta ttgttcacaa atttgaaaag      180
gattctaact ataagtaaa gattattgaa tctgaagacc aaaagctca ggaaaagatc       240 aaaaaagatc ctagtactgc tgcagatgtt ttctcgctgc cgcatgatca gctgggccag      300
```

```
ttagttgact ctggtgttat ccaagagatt cctcaaaaat attcaaagaa aataaataaa    360
aatgaaacac agcaggctgc aacaggagct atgtacaaag gtaagactta tgcttttcct    420
tttggaatcg agtctcaagt actttactat aataaatcaa aactctcagc tgatgatgtc    480
acatcatatg agactattac cagcaaggca actttcggag caaaattcaa acaagttaat    540
gcctatgcga ctgcaccact tttctattca gtaggtgata cactctttgg taaaaatggc    600
gaagatgcca aaggaactaa ctggggaaat gatgctggtg tatctgtttt gaaatggatt    660
gccagtcaaa aaggtaacgc tggctttgtc aatcttgacg ataacaatgt catgtctaaa    720
tttggtgatg ttctgtagc ttcttttgaa tcaggtcctt gggattatga agccgcacaa    780
aaggcagttg gcaaaaacaa cctcggtgtt acggtttatc aacaataaaa tattaatggt    840
caagaagttc aacagaaagc tttcttaggt gttaaactct acgctgttaa tcaagctcct    900
tctaaaggaa ataccaaacg tattgctgct agttataaat tagcttctta cttaacaagt    960
gctgaaagcc aagaaaatca atttaagaca aaaggacgca acatcatccc atctaataag    1020
accgttcaaa actctgatac agtcaaaaat catgaactcg cacaggctgt tatccaaatg    1080
ggatcttctt cagattatac tgttgttatg cctaaactca accaaatgtc aacattctgg    1140
acggaaagcg cagctattct tagtgatact tacaatggta aaattaaaga aagtgattac    1200
cttgctaaat taaacaatt tgataaagat ttagcagctg ctaaataa                  1248
```

<210> SEQ ID NO 36
<211> LENGTH: 415
<212> TYPE: PRT
<213> ORGANISM: Streptococcus mutans
<400> SEQUENCE: 36

```
Met Lys Thr Trp Gln Lys Ile Val Val Gly Gly Ala Gly Leu Met Leu
1               5                   10                  15

Ala Ser Ser Ile Leu Val Ala Cys Gly Ser Lys Asp Ser Lys Ser Ser
                20                  25                  30

Ser Ser Asp Pro Lys Thr Ile Lys Leu Trp Val Pro Thr Gly Ala Lys
            35                  40                  45

Lys Ser Tyr Gln Ser Ile Val His Lys Phe Glu Lys Asp Ser Asn Tyr
        50                  55                  60

Lys Val Lys Ile Ile Glu Ser Glu Asp Pro Lys Ala Gln Glu Lys Ile
65                  70                  75                  80

Lys Lys Asp Pro Ser Thr Ala Ala Asp Val Phe Ser Leu Pro His Asp
                85                  90                  95

Gln Leu Gly Gln Leu Val Asp Ser Gly Val Ile Gln Glu Ile Pro Gln
            100                 105                 110

Lys Tyr Ser Lys Glu Ile Asn Lys Asn Glu Thr Gln Gln Ala Ala Thr
        115                 120                 125

Gly Ala Met Tyr Lys Gly Lys Thr Tyr Ala Phe Pro Phe Gly Ile Glu
    130                 135                 140

Ser Gln Val Leu Tyr Tyr Asn Lys Ser Lys Leu Ser Ala Asp Asp Val
145                 150                 155                 160

Thr Ser Tyr Glu Thr Ile Thr Ser Lys Ala Thr Phe Gly Ala Lys Phe
                165                 170                 175

Lys Gln Val Asn Ala Tyr Ala Thr Ala Pro Leu Phe Tyr Ser Val Gly
            180                 185                 190

Asp Thr Leu Phe Gly Lys Asn Gly Glu Asp Ala Lys Gly Thr Asn Trp
        195                 200                 205

Gly Asn Asp Ala Gly Val Ser Val Leu Lys Trp Ile Ala Ser Gln Lys
```

```
                210                 215                 220
Gly Asn Ala Gly Phe Val Asn Leu Asp Asp Asn Val Met Ser Lys
225                 230                 235                 240

Phe Gly Asp Gly Ser Val Ala Ser Phe Glu Ser Gly Pro Trp Asp Tyr
                245                 250                 255

Glu Ala Ala Gln Lys Ala Val Gly Lys Asn Asn Leu Gly Val Thr Val
                260                 265                 270

Tyr Pro Thr Ile Asn Ile Asn Gly Gln Glu Val Gln Lys Ala Phe
                275                 280                 285

Leu Gly Val Lys Leu Tyr Ala Val Asn Gln Ala Pro Ser Lys Gly Asn
                290                 295                 300

Thr Lys Arg Ile Ala Ala Ser Tyr Lys Leu Ala Ser Tyr Leu Thr Ser
305                 310                 315                 320

Ala Glu Ser Gln Glu Asn Gln Phe Lys Thr Lys Gly Arg Asn Ile Ile
                325                 330                 335

Pro Ser Asn Lys Thr Val Gln Asn Ser Asp Thr Val Lys Asn His Glu
                340                 345                 350

Leu Ala Gln Ala Val Ile Gln Met Gly Ser Ser Ser Asp Tyr Thr Val
                355                 360                 365

Val Met Pro Lys Leu Asn Gln Met Ser Thr Phe Trp Thr Glu Ser Ala
370                 375                 380

Ala Ile Leu Ser Asp Thr Tyr Asn Gly Lys Ile Lys Glu Ser Asp Tyr
385                 390                 395                 400

Leu Ala Lys Leu Lys Gln Phe Asp Lys Asp Leu Ala Ala Ala Lys
                405                 410                 415

<210> SEQ ID NO 37
<211> LENGTH: 1362
<212> TYPE: DNA
<213> ORGANISM: Streptococcus mutans

<400> SEQUENCE: 37
atgattcagt catcttctca tgatcagtta tctgtacttg aaactttttaa aaagggcggg      60 atagatatca aattatcgtt tgtcatcatg ggatttgcca atttgatgaa taagcaattc     120
ataaaaggcc tcctctttct attaagtgag atagcttttc taattgcttt tgtcacacag     180
gttattccag cttttcagg cttactcact ctcggtacta aaacacaagg gatgcaagaa     240
aaaattgtgg atggcgttaa attacaggtg gcagttgaag gcgataattc gatgctgatg     300
ctcatttttg gattagcctc actaatcttt tgtttggttt ttgcctacat ttattggtgt     360
aatcttaaaa gtgccagaaa tctctatatg ttaaaaaaag agggacgtca cattccatct     420
ttcaaagaag attttatgac tttggcaaac ggccgattcc atatgacttt gatgtttatt     480
cctttgattg gtgttcttct ttttaccatt ttgccactcg tttatatgat tgcctggcc      540 tttaccaatt atgatcacaa tcatcttccg cctaaatccc ttttttgattg ggtagggttg     600 gctaattttg gtaatgtttt gaatggccgc atggctggaa ccttcttccc tgtcctttct     660
tggacactta tctgggctgt tttcgcaact gtgacaaact ttcttttttgg agtcatcttg     720 gcacttatta tcaatgctaa gggattaaaa ttgaaaaaaa tgtggcggac tatctttgtt     780
attaccattg ctgtgccgca gttcatttca cttttgctga tgagaaattt ccttaatgat     840
caaggtccgc tcaatgcttt cctagaaaaa attggcctga tttctcattc tctgccatttt     900 ctatcagatc ctacttgggc aaaattttca attatcttcg ttaatatgtg ggttggtatt     960
ccttttacca tgttagtcgc aacaggaatt atcatgaatc ttccgagtga gcaaattgag    1020
```

```
gctgcagaaa ttgacggcgc tagtaagttc caaattttta aatccatcac tttcccgcag    1080
attcttttaa ttatgatgcc atctttaatc cagcaattta ttggaaatat caataatttt    1140
aatgtcatct acctttaac cggtggcgga ccaactaatt cacaattcta tcaagcaggc     1200
agcacagact tattggtcac ttggctttat aaactaacaa tgaatgctgc agactataat    1260
ttagcttctg ttattggtat ctttatcttt gccatttcag ctatcttcag tcttttagct    1320
tatacgcata cagcatcata caaggaagga gctgttaaat aa                       1362
```

<210> SEQ ID NO 38
<211> LENGTH: 453
<212> TYPE: PRT
<213> ORGANISM: Streptococcus mutans

<400> SEQUENCE: 38

```
Met Ile Gln Ser Ser His Asp Gln Leu Ser Val Leu Glu Thr Phe
 1               5                  10                  15

Lys Lys Gly Gly Ile Asp Ile Lys Leu Ser Phe Val Ile Met Gly Phe
                20                  25                  30

Ala Asn Leu Met Asn Lys Gln Phe Ile Lys Gly Leu Leu Phe Leu Leu
            35                  40                  45

Ser Glu Ile Ala Phe Leu Ile Ala Phe Val Thr Gln Val Ile Pro Ala
        50                  55                  60

Phe Ser Gly Leu Leu Thr Leu Gly Thr Lys Thr Gln Gly Met Gln Glu
65                  70                  75                  80

Lys Ile Val Asp Gly Val Lys Leu Gln Val Ala Val Glu Gly Asp Asn
                85                  90                  95

Ser Met Leu Met Leu Ile Phe Gly Leu Ala Ser Leu Ile Phe Cys Leu
            100                 105                 110

Val Phe Ala Tyr Ile Tyr Trp Cys Asn Leu Lys Ser Ala Arg Asn Leu
        115                 120                 125

Tyr Met Leu Lys Lys Glu Gly Arg His Ile Pro Ser Phe Lys Glu Asp
    130                 135                 140

Phe Met Thr Leu Ala Asn Gly Arg Phe His Met Thr Leu Met Phe Ile
145                 150                 155                 160

Pro Leu Ile Gly Val Leu Leu Phe Thr Ile Leu Pro Leu Val Tyr Met
                165                 170                 175

Ile Cys Leu Ala Phe Thr Asn Tyr Asp His Asn His Leu Pro Pro Lys
            180                 185                 190

Ser Leu Phe Asp Trp Val Gly Leu Ala Asn Phe Gly Asn Val Leu Asn
        195                 200                 205

Gly Arg Met Ala Gly Thr Phe Phe Pro Val Leu Ser Trp Thr Leu Ile
    210                 215                 220

Trp Ala Val Phe Ala Thr Val Thr Asn Phe Leu Phe Gly Val Ile Leu
225                 230                 235                 240

Ala Leu Ile Ile Asn Ala Lys Gly Leu Lys Leu Lys Lys Met Trp Arg
                245                 250                 255

Thr Ile Phe Val Ile Thr Ile Ala Val Pro Gln Phe Ile Ser Leu Leu
            260                 265                 270

Leu Met Arg Asn Phe Leu Asn Asp Gln Gly Pro Leu Asn Ala Phe Leu
        275                 280                 285

Glu Lys Ile Gly Leu Ile Ser His Ser Leu Pro Phe Leu Ser Asp Pro
    290                 295                 300

Thr Trp Ala Lys Phe Ser Ile Ile Phe Val Asn Met Trp Val Gly Ile
305                 310                 315                 320
```

```
Pro Phe Thr Met Leu Val Ala Thr Gly Ile Ile Met Asn Leu Pro Ser
            325                 330                 335

Glu Gln Ile Glu Ala Ala Glu Ile Asp Gly Ala Ser Lys Phe Gln Ile
        340                 345                 350

Phe Lys Ser Ile Thr Phe Pro Gln Ile Leu Leu Ile Met Met Pro Ser
    355                 360                 365

Leu Ile Gln Gln Phe Ile Gly Asn Ile Asn Asn Phe Asn Val Ile Tyr
370                 375                 380

Leu Leu Thr Gly Gly Gly Pro Thr Asn Ser Gln Phe Tyr Gln Ala Gly
385                 390                 395                 400

Ser Thr Asp Leu Leu Val Thr Trp Leu Tyr Lys Leu Thr Met Asn Ala
            405                 410                 415

Ala Asp Tyr Asn Leu Ala Ser Val Ile Gly Ile Phe Ile Phe Ala Ile
        420                 425                 430

Ser Ala Ile Phe Ser Leu Leu Ala Tyr Thr His Thr Ala Ser Tyr Lys
    435                 440                 445

Glu Gly Ala Val Lys
    450

<210> SEQ ID NO 39
<211> LENGTH: 837
<212> TYPE: DNA
<213> ORGANISM: Streptococcus mutans

<400> SEQUENCE: 39
atgaaaagaa aaaacaact tcagatcggc tctatctatg ctttactgat tctcttatcc      60
ttcatttggc tatttccgat catttgggtt atactgacga gttttcgcgg tgaaggcaca     120
gcttatgttc cttatattat tccaaaaacg tggactttag ataattatat taaattattt     180
accaattctt ctttcccatt tggacgctgg tttttaaata ccttaatcgt ttcaacagcc     240
acttgtgttc tgtcaacttc tatcacagtg gcaatggctt attcgcttag ccgtattaaa     300
tttaaacacc gtaacggctt tttaaaatta gctcttgttc tgaatatgtt tccgggattt     360
atgagtatga ttgcagttta ctacattcta aaagcactca atctcaccca aacattaaca     420
tctcttgttt tggtctattc ttcaggagct gccttaactt tctatatcgc taaaggcttt     480
tttgatacga ttccttattc attggatgaa tcagctatga ttgatggggc tacgcgtaaa     540
gatatttttct taaaaatcac tctgccgcta tctaagccca tcatcgttta tcggccctg     600
ttggcattta ttgccccttg gattgacttt atttttgctc aggttattct tggagatgcc     660
accagcaaat ataccgtagc gattggactc ttctctatgc ttcaagctga taccattaat     720
aattggttca tggcctttgc agcaggttct gtactgatcg ccattccaat cacgatactt     780
tttatcttca tgcaaaagta ttacgttgaa ggcattactg gcggatctgt taaataa       837

<210> SEQ ID NO 40
<211> LENGTH: 278
<212> TYPE: PRT
<213> ORGANISM: Streptococcus mutans

<400> SEQUENCE: 40

Met Lys Arg Lys Lys Gln Leu Gln Ile Gly Ser Ile Tyr Ala Leu Leu
1               5                   10                  15

Ile Leu Leu Ser Phe Ile Trp Leu Phe Pro Ile Ile Trp Val Ile Leu
            20                  25                  30

Thr Ser Phe Arg Gly Glu Gly Thr Ala Tyr Val Pro Tyr Ile Ile Pro
        35                  40                  45
```

Lys Thr Trp Thr Leu Asp Asn Tyr Ile Lys Leu Phe Thr Asn Ser Ser
    50                  55                  60

Phe Pro Phe Gly Arg Trp Phe Leu Asn Thr Leu Ile Val Ser Thr Ala
65                  70                  75                  80

Thr Cys Val Leu Ser Thr Ser Ile Thr Val Ala Met Ala Tyr Ser Leu
                85                  90                  95

Ser Arg Ile Lys Phe Lys His Arg Asn Gly Phe Leu Lys Leu Ala Leu
            100                 105                 110

Val Leu Asn Met Phe Pro Gly Phe Met Ser Met Ile Ala Val Tyr Tyr
            115                 120                 125

Ile Leu Lys Ala Leu Asn Leu Thr Gln Thr Leu Thr Ser Leu Val Leu
            130                 135                 140

Val Tyr Ser Ser Gly Ala Ala Leu Thr Phe Tyr Ile Ala Lys Gly Phe
145                 150                 155                 160

Phe Asp Thr Ile Pro Tyr Ser Leu Asp Glu Ser Ala Met Ile Asp Gly
                165                 170                 175

Ala Thr Arg Lys Asp Ile Phe Leu Lys Ile Thr Leu Pro Leu Ser Lys
            180                 185                 190

Pro Ile Ile Val Tyr Thr Ala Leu Leu Ala Phe Ile Ala Pro Trp Ile
            195                 200                 205

Asp Phe Ile Phe Ala Gln Val Ile Leu Gly Asp Ala Thr Ser Lys Tyr
            210                 215                 220

Thr Val Ala Ile Gly Leu Phe Ser Met Leu Gln Ala Asp Thr Ile Asn
225                 230                 235                 240

Asn Trp Phe Met Ala Phe Ala Ala Gly Ser Val Leu Ile Ala Ile Pro
                245                 250                 255

Ile Thr Ile Leu Phe Ile Phe Met Gln Lys Tyr Tyr Val Glu Gly Ile
            260                 265                 270

Thr Gly Gly Ser Val Lys
            275

<210> SEQ ID NO 41
<211> LENGTH: 1134
<212> TYPE: DNA
<213> ORGANISM: Streptococcus mutans

<400> SEQUENCE: 41
atgacaactt taaaacttga taacatctac aaaagatatc ccaatgcaaa gcattattcc        60
gttgaaaatt ttaatcttga cattcatgat aaagaattta ttgtctttgt cggtccttca       120
ggatgcggaa agtcaaccac tcttcgcatg attgctgggc tggaagatat tacagaaggc       180 aaccttata ttgatgataa actcatgaat gatgcctctc ctaaagatcg cgatattgct       240 atggttttc aaaattatgc tctttatcct catatgagcg tttatgaaaa tatggctttt       300
ggcctaaaac ttcgtaaata caaaaaagat gatattaata acgtgtaca cgaagctgct       360 gaaattcttg actgacaga atttcttgaa agaaagcctg cggacctctc tggcggacag       420
cggcagcggg ttgctatggg acgtgctatt gtccgagatg ctaaggtctt cttaatggac       480
gaacctttgt caaatttaga tgccaaactt cgagttgcca tgcgagccga aatcgctaaa       540
attcaccgcc gcattgggc aacgactatc tatgttaccc atgaccaaac agaagccatg       600
accttagcag atcgtattgt tatcatgagc gctactccaa acccagataa aaccggctct       660
atcggtcgta ttgagcagat tggaacacca caggaactct acaatgaacc tgctaataaa       720
tttgttgctg gcttcatcgg aagccccgct atgaatttct ttgaagtgac cgttgaaaaa       780
gagcgtttgg ttaaccaaga tggtctaagc cttgcgcttc ctcagggaca ggaaaaaatt       840

```
cttgaggaga aaggttatct tggtaaaaaa gtcactttag gtattcgacc agaagacatc    900
tcaagtgatc aaattgtcca cgagactttc ccaaatgcca gtgttacagc tgacatacta    960
gtatcagaac ttttaggcag cgaaagcatg ttatatgtca aatttggcag tactgaattt   1020
acagctcgcg tcaatgctcg tgactctcac agtcccggag aaaaagtaca attaaccttt   1080
aatattgcta agggacactt ctttgattta gagactgaaa aacgaatcaa ttaa         1134
```

<210> SEQ ID NO 42
<211> LENGTH: 377
<212> TYPE: PRT
<213> ORGANISM: Streptococcus mutans

<400> SEQUENCE: 42

```
Met Thr Thr Leu Lys Leu Asp Asn Ile Tyr Lys Arg Tyr Pro Asn Ala
1               5                   10                  15

Lys His Tyr Ser Val Glu Asn Phe Asn Leu Asp Ile His Asp Lys Glu
            20                  25                  30

Phe Ile Val Phe Val Gly Pro Ser Gly Cys Gly Lys Ser Thr Thr Leu
        35                  40                  45

Arg Met Ile Ala Gly Leu Glu Asp Ile Thr Glu Gly Asn Leu Tyr Ile
    50                  55                  60

Asp Asp Lys Leu Met Asn Asp Ala Ser Pro Lys Asp Arg Asp Ile Ala
65                  70                  75                  80

Met Val Phe Gln Asn Tyr Ala Leu Tyr Pro His Met Ser Val Tyr Glu
                85                  90                  95

Asn Met Ala Phe Gly Leu Lys Leu Arg Lys Tyr Lys Lys Asp Asp Ile
            100                 105                 110

Asn Lys Arg Val His Glu Ala Ala Glu Ile Leu Gly Leu Thr Glu Phe
        115                 120                 125

Leu Glu Arg Lys Pro Ala Asp Leu Ser Gly Gly Gln Arg Gln Arg Val
    130                 135                 140

Ala Met Gly Arg Ala Ile Val Arg Asp Ala Lys Val Phe Leu Met Asp
145                 150                 155                 160

Glu Pro Leu Ser Asn Leu Asp Ala Lys Leu Arg Val Ala Met Arg Ala
                165                 170                 175

Glu Ile Ala Lys Ile His Arg Arg Ile Gly Ala Thr Thr Ile Tyr Val
            180                 185                 190

Thr His Asp Gln Thr Glu Ala Met Thr Leu Ala Asp Arg Ile Val Ile
        195                 200                 205

Met Ser Ala Thr Pro Asn Pro Asp Lys Thr Gly Ser Ile Gly Arg Ile
    210                 215                 220

Glu Gln Ile Gly Thr Pro Gln Glu Leu Tyr Asn Glu Pro Ala Asn Lys
225                 230                 235                 240

Phe Val Ala Gly Phe Ile Gly Ser Pro Ala Met Asn Phe Phe Glu Val
                245                 250                 255

Thr Val Glu Lys Glu Arg Leu Val Asn Gln Asp Gly Leu Ser Leu Ala
            260                 265                 270

Leu Pro Gln Gly Gln Glu Lys Ile Leu Glu Lys Gly Tyr Leu Gly
        275                 280                 285

Lys Lys Val Thr Leu Gly Ile Arg Pro Glu Asp Ile Ser Ser Asp Gln
    290                 295                 300

Ile Val His Glu Thr Phe Pro Asn Ala Ser Val Thr Ala Asp Ile Leu
305                 310                 315                 320

Val Ser Glu Leu Leu Gly Ser Glu Ser Met Leu Tyr Val Lys Phe Gly
```

```
                    325                 330                 335
Ser Thr Glu Phe Thr Ala Arg Val Asn Ala Arg Asp Ser His Ser Pro
                340                 345                 350

Gly Glu Lys Val Gln Leu Thr Phe Asn Ile Ala Lys Gly His Phe Phe
            355                 360                 365

Asp Leu Glu Thr Glu Lys Arg Ile Asn
        370                 375

<210> SEQ ID NO 43
<211> LENGTH: 927
<212> TYPE: DNA
<213> ORGANISM: Agrobacterium tumefaciens

<400> SEQUENCE: 43
atgatcctgt gttgtggtga agccctgatc gacatgctgc cccggcagac gacgctgggt    60
gaggcgggct ttgcccctta cgcaggcgga gcggtcttca acacggcaat tgcgctgggg   120
cgtcttggcg tcccttcagc cttttttacc ggtctttccg acgacatgat gggcgatatc   180
ctgcgggaga ccctgcgggc cagcaaggtg gatttcagct attgcgccac cctgtcgcgc   240
cccaccacca ttgcgttcgt taagctggtt gatggccatg cgacctacgc tttttacgac   300
gagaacaccg ccggccggat gatcaccgag gccgaacttc cggccttggg agcggattgc   360
gaagcgctgc atttcggcgc catcagcctt attcccgaac cctgcggcag cacctatgag   420
gcgctgatga cgcgcgagca tgagacccgc gtcatctcgc tcgatccgaa cattcgtccc   480
ggcttcatcc agaacaagca gtcgcacatg cccgcatcc gccgcatggc ggcgatgtct   540
gacatcgtca gttctcgga tgaggacctg gcgtggttcg gtctggaagg cgacgaggac   600
acgcttgccc gccactggct gcaccacggt gcaaaactcg tcgttgtcac ccgtggcgcc   660
aagggtgccg tgggttacag cgccaatctc aaggtggaag tggcctccga gcgcgtcgaa   720
gtggtcgata cggtcggcgc cggcgatacg ttcgatgccg gcattcttgc ttcgctgaaa   780
atgcagggcc tgctgaccaa agcgcaggtg gcttcgctga gcgaagagca gatcagaaaa   840 gctttgcgc ttggcgcgaa agccgctgcg gtcactgtct cgcgggctgg cgcaaatccg   900
cctttcgcgc atgaaatcgg tttgtga                                       927

<210> SEQ ID NO 44
<211> LENGTH: 308
<212> TYPE: PRT
<213> ORGANISM: Agrobacterium tumefaciens

<400> SEQUENCE: 44

Met Ile Leu Cys Cys Gly Glu Ala Leu Ile Asp Met Leu Pro Arg Gln
1               5                   10                  15

Thr Thr Leu Gly Glu Ala Gly Phe Ala Pro Tyr Ala Gly Gly Ala Val
            20                  25                  30

Phe Asn Thr Ala Ile Ala Leu Gly Arg Leu Gly Val Pro Ser Ala Phe
        35                  40                  45

Phe Thr Gly Leu Ser Asp Asp Met Met Gly Asp Ile Leu Arg Glu Thr
    50                  55                  60

Leu Arg Ala Ser Lys Val Asp Phe Ser Tyr Cys Ala Thr Leu Ser Arg
65                  70                  75                  80

Pro Thr Thr Ile Ala Phe Val Lys Leu Val Asp Gly His Ala Thr Tyr
                85                  90                  95

Ala Phe Tyr Asp Glu Asn Thr Ala Gly Arg Met Ile Thr Glu Ala Glu
            100                 105                 110
```

```
Leu Pro Ala Leu Gly Ala Asp Cys Glu Ala Leu His Phe Gly Ala Ile
        115                 120                 125

Ser Leu Ile Pro Glu Pro Cys Gly Ser Thr Tyr Glu Ala Leu Met Thr
    130                 135                 140

Arg Glu His Glu Thr Arg Val Ile Ser Leu Asp Pro Asn Ile Arg Pro
145                 150                 155                 160

Gly Phe Ile Gln Asn Lys Gln Ser His Met Ala Arg Ile Arg Arg Met
                165                 170                 175

Ala Ala Met Ser Asp Ile Val Lys Phe Ser Asp Glu Asp Leu Ala Trp
            180                 185                 190

Phe Gly Leu Glu Gly Asp Glu Asp Thr Leu Ala Arg His Trp Leu His
        195                 200                 205

His Gly Ala Lys Leu Val Val Val Thr Arg Gly Ala Lys Gly Ala Val
    210                 215                 220

Gly Tyr Ser Ala Asn Leu Lys Val Glu Val Ala Ser Glu Arg Val Glu
225                 230                 235                 240

Val Val Asp Thr Val Gly Ala Gly Asp Thr Phe Asp Ala Gly Ile Leu
                245                 250                 255

Ala Ser Leu Lys Met Gln Gly Leu Leu Thr Lys Ala Gly Val Ala Ser
            260                 265                 270

Leu Ser Glu Glu Gln Ile Arg Lys Ala Leu Ala Leu Gly Ala Lys Ala
        275                 280                 285

Ala Ala Val Thr Val Ser Arg Ala Gly Ala Asn Pro Pro Phe Ala His
    290                 295                 300

Glu Ile Gly Leu
305

<210> SEQ ID NO 45
<211> LENGTH: 1404
<212> TYPE: DNA
<213> ORGANISM: Streptococcus mutans

<400> SEQUENCE: 45
cagctgatta tgcgtcagtt gaaaccctcg cttcttcagg aactgttgct gtaggtgata      60
gcttacttga agttaaaaaa taagaaatat tatcagaaag accgtaaggt cttttttgact    120 gcttaaaaga ttcagtaaca atagtattaa agccttttgg ctaactaata cttgaaattt     180
agcaaattat gatataatgt taagtagtcc ttaagggtag attaagggta ttcaaatcca     240
aaaattgatt tggtaagtta agtaaaatat aagaggttta ttatgtctaa attatatggc     300
agcatcgaag ctggcggaac aaaatttgtc tgtgctgtag gtgatgaaaa ttttcaaatt     360
ttagaaaaag ttcagttccc aacaacaaca cctatgaaaa caatagaaaa aacagttgct     420 ttcttttaaaa aatttgaagc tgatttagcc agtgttgcca ttggttcttt tggcccctatt   480 gatattgatc aaaattcaga cacttatggt tacattactt caacaccaaa gccaaactgg     540
gctaacgttg attttgtcgg cttaatttct aaagatttta aaattccatt ttactttacg     600
acagatgtta attcttctgc ttatggggaa acaattgctc gttcaaatgt taaaagtctg     660
gtttattata ctattggaac aggcattgga gcagggggcta ttcaaaatgg cgaattcatt    720
ggcggtatgg acatacggga agctggacac gtttacatgg ctccgcatcc caatgatgtt    780
catcatggtt ttgtaggcac ctgtcctttc cataaaggct gtttagaagg acttgcagcg    840
ggtcctagct tagaggctcg tactggtatt cgtggtgagt taattgagca aaactcagaa    900
gtttgggata ttcaggcata ctacattgct caggcggcta ttcaagcgac tgtcctttat    960
cgtccgcaag tcattgtatt tggcggaggc gttatggcac aagaacatat gctcaatcgg  1020
```

```
gttcgtgaaa aatttacttc acttttgaat gactatcttc cagttccaga tgttaaagat    1080
tatattgtga caccagctgt tgcagaaaat ggttcagcaa cattgggaaa tctcgcttta    1140
gctaaaaaga tagcagcgcg ttaattaaaa atgaattgga agattaaagc accttctaat    1200
attcaatatt aaactgttag aatttacgtg aacgaaattt tcattttatg aggataatga    1260
agtgaatata attactcttg atttcctctg aaactagata gtggtatatt gaaaaacaga    1320
aaggagaaca ctatggaagg acctttgttt ttacaatcac aaatgcataa aaaaatctgg    1380
ggcggcaatc ggctcagaaa agaa                                           1404
```

<210> SEQ ID NO 46
<211> LENGTH: 293
<212> TYPE: PRT
<213> ORGANISM: Streptococcus mutans

<400> SEQUENCE: 46

Met Ser Lys Leu Tyr Gly Ser Ile Glu Ala Gly Gly Thr Lys Phe Val
1               5                   10                  15

Cys Ala Val Gly Asp Glu Asn Phe Gln Ile Leu Glu Lys Val Gln Phe
            20                  25                  30

Pro Thr Thr Thr Pro Tyr Glu Thr Ile Glu Lys Thr Val Ala Phe Phe
        35                  40                  45

Lys Lys Phe Glu Ala Asp Leu Ala Ser Val Ala Ile Gly Ser Phe Gly
    50                  55                  60

Pro Ile Asp Ile Asp Gln Asn Ser Asp Thr Tyr Gly Tyr Ile Thr Ser
65                  70                  75                  80

Thr Pro Lys Pro Asn Trp Ala Asn Val Asp Phe Val Gly Leu Ile Ser
                85                  90                  95

Lys Asp Phe Lys Ile Pro Phe Tyr Phe Thr Asp Val Asn Ser Ser
            100                 105                 110

Ala Tyr Gly Glu Thr Ile Ala Arg Ser Asn Val Lys Ser Leu Val Tyr
        115                 120                 125

Tyr Thr Ile Gly Thr Gly Ile Gly Ala Gly Ala Ile Gln Asn Gly Glu
    130                 135                 140

Phe Ile Gly Gly Met Gly His Thr Glu Ala Gly His Val Tyr Met Ala
145                 150                 155                 160

Pro His Pro Asn Asp Val His His Gly Phe Val Gly Thr Cys Pro Phe
                165                 170                 175

His Lys Gly Cys Leu Glu Gly Leu Ala Ala Gly Pro Ser Leu Glu Ala
            180                 185                 190

Arg Thr Gly Ile Arg Gly Glu Leu Ile Glu Gln Asn Ser Glu Val Trp
        195                 200                 205

Asp Ile Gln Ala Tyr Tyr Ile Ala Gln Ala Ala Ile Gln Ala Thr Val
    210                 215                 220

Leu Tyr Arg Pro Gln Val Ile Val Phe Gly Gly Val Met Ala Gln
225                 230                 235                 240

Glu His Met Leu Asn Arg Val Arg Glu Lys Phe Thr Ser Leu Leu Asn
                245                 250                 255

Asp Tyr Leu Pro Val Pro Asp Val Lys Asp Tyr Ile Val Thr Pro Ala
            260                 265                 270

Val Ala Glu Asn Gly Ser Ala Thr Leu Gly Asn Leu Ala Leu Ala Lys
        275                 280                 285

Lys Ile Ala Ala Arg
    290

<210> SEQ ID NO 47
<211> LENGTH: 915
<212> TYPE: DNA
<213> ORGANISM: Escherichia coli

<400> SEQUENCE: 47

```
atgtcagcca aagtatgggt tttaggggat gcggtcgtag atctcttgcc agaatcagac      60
gggcgcctac tgccttgtcc tggcggcgcg ccagctaacg ttgcggtggg aatcgccaga     120
ttaggcggaa caagtgggtt tataggtcgg gtggggatg atccttttgg tgcgttaatg      180
caaagaacgc tgctaactga gggagtcgat atcacgtatc tgaagcaaga tgaatggcac     240
cggacatcca cggtgcttgt cgatctgaac gatcaagggg aacgttcatt tacgtttatg     300
gtccgcccca gtgccgatct ttttttagag acgacagact tgccctgctg gcgacatggc     360
gaatggttac atctctgttc aattgcgttg tctgccgagc cttcgcgtac cagcgcattt     420
actgcgatga cggcgatccg gcatgccgga ggttttgtca gcttcgatcc taatattcgt     480
gaagatctat ggcaagacga gcatttgctc cgcttgtgtt tgcggcaggc gctacaactg     540
gcggatgtcg tcaagctctc ggaagaagaa tggcgactta tcagtggaaa acacagaac     600
gatcaggata tatgcgccct ggcaaaagag tatgagatcg ccatgctgtt ggtgactaaa     660
ggtgcagaag gggtggtggt ctgttatcga ggacaagttc accattttgc tggaatgtct     720
gtgaattgtg tcgatagcac ggggggcggga gatgcgttcg ttgccgggtt actcacaggt     780
ctgtcctcta cgggattatc tacagatgag agagaaatgc gacgaattat cgatctcgct     840
caacgttgcg gagcgcttgc agtaacggcg aaagggggcaa tgacagcgct gccatgtcga     900
caagaactgg aatag                                                      915
```

<210> SEQ ID NO 48
<211> LENGTH: 304
<212> TYPE: PRT
<213> ORGANISM: Escherichia coli

<400> SEQUENCE: 48

```
Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175
```

Ala Leu Gln Leu Ala Asp Val Val Lys Leu Ser Glu Glu Trp Arg
            180                 185                 190

Leu Ile Ser Gly Lys Thr Gln Asn Asp Gln Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300

<210> SEQ ID NO 49
<211> LENGTH: 879
<212> TYPE: DNA
<213> ORGANISM: Enterococcus faecalis

<400> SEQUENCE: 49
atgacagaaa aacttttagg aagtatcgaa gccggtggca caaaatttgt atgtggcgtt      60
gggacagatg atttgaccat cgtagaacgt gtcagttttc ccacaacaac cccagaagaa     120
acaatgaaaa agtaataga  attttttccaa caatatcctt taaaagcgat tgggattggt    180
tcatttggtc cgattgatat tcacgttgat tctcctacgt atggttatat cacttctaca     240
ccaaaattag cttggcgtaa ctttgacttg ttaggaacta tgaaacaaca ttttgatgtg     300
ccaatggctt ggacaacgga tgtgaatgct gcggcatatg gtgagtatgt tgctggaaat     360
gggcaacata catctagttg tgtatattat acaattggaa ctggtgttgg cgctggagcg     420
attcaaaacg gtgagtttat tgaaggcttt agccacccag aaatggggca tgcgttagtt     480
cgtcgtcatc ctgaagatac gtatgcagga aattgtcctt atcatggaga ttgtttagaa     540
gggattgcag caggaccagc agttgaaggt cgttctggta aaaaaggaca tttattggaa     600
gaggatcata aaacttggga attagaagct tattatttag cgcaagcggc gtacaatacg     660
actttattat tagcgccaga agtgatcatt ttaggtggcg gcgtcatgaa acaacgtcat     720 tgatgccga  aagttcgtga aaaatttgct gaattagtca atggatatgt ggaaacaccg     780
cctttagaaa aatacttggt gacgcctctt ttagaagata tccaggaac  aatcggttgc    840 tttgccttgg caaaaaaagc tttaatggct caaaaataa                             879

<210> SEQ ID NO 50
<211> LENGTH: 292
<212> TYPE: PRT
<213> ORGANISM: Enterococcus faecalis

<400> SEQUENCE: 50

Met Thr Glu Lys Leu Leu Gly Ser Ile Glu Ala Gly Gly Thr Lys Phe
1               5                   10                  15

Val Cys Gly Val Gly Thr Asp Asp Leu Thr Ile Val Glu Arg Val Ser
                20                  25                  30

Phe Pro Thr Thr Thr Pro Glu Glu Thr Met Lys Lys Val Ile Glu Phe
            35                  40                  45

```
Phe Gln Gln Tyr Pro Leu Lys Ala Ile Gly Ile Gly Ser Phe Gly Pro
         50                  55                  60

Ile Asp Ile His Val Asp Ser Pro Thr Tyr Gly Tyr Ile Thr Ser Thr
 65                  70                  75                  80

Pro Lys Leu Ala Trp Arg Asn Phe Asp Leu Leu Gly Thr Met Lys Gln
                 85                  90                  95

His Phe Asp Val Pro Met Ala Trp Thr Thr Asp Val Asn Ala Ala Ala
            100                 105                 110

Tyr Gly Glu Tyr Val Ala Gly Asn Gly Gln His Thr Ser Ser Cys Val
        115                 120                 125

Tyr Tyr Thr Ile Gly Thr Gly Val Gly Ala Gly Ile Gln Asn Gly
130                 135                 140

Glu Phe Ile Glu Gly Phe Ser His Pro Glu Met Gly His Ala Leu Val
145                 150                 155                 160

Arg Arg His Pro Glu Asp Thr Tyr Ala Gly Asn Cys Pro Tyr His Gly
                165                 170                 175

Asp Cys Leu Glu Gly Ile Ala Ala Gly Pro Ala Val Glu Gly Arg Ser
            180                 185                 190

Gly Lys Lys Gly His Leu Leu Glu Glu Asp His Lys Thr Trp Glu Leu
        195                 200                 205

Glu Ala Tyr Tyr Leu Ala Gln Ala Ala Tyr Asn Thr Thr Leu Leu Leu
210                 215                 220

Ala Pro Glu Val Ile Ile Leu Gly Gly Gly Val Met Lys Gln Arg His
225                 230                 235                 240

Leu Met Pro Lys Val Arg Glu Lys Phe Ala Glu Leu Val Asn Gly Tyr
                245                 250                 255

Val Glu Thr Pro Pro Leu Glu Lys Tyr Leu Val Thr Pro Leu Leu Glu
            260                 265                 270

Asp Asn Pro Gly Thr Ile Gly Cys Phe Ala Leu Ala Lys Lys Ala Leu
        275                 280                 285

Met Ala Gln Lys
        290

<210> SEQ ID NO 51
<211> LENGTH: 1458
<212> TYPE: DNA
<213> ORGANISM: Saccharomyces cerevisiae

<400> SEQUENCE: 51
atggttcatt taggtccaaa gaaaccacag gctagaaagg gttccatggc tgatgtgccc      60
aaggaattga tggatgaaat tcatcagttg gaagatatgt ttacagttga cagcgagacc     120
ttgagaaagg ttgttaagca ctttatcgac gaattgaata aaggtttgac aaagaaggga     180
ggtaacattc caatgattcc cggttgggtc atggaattcc caacaggtaa agaatctggt     240
aactatttgg ccattgattt gggtggtact aacttaagag tcgtgttggt caagttgagc     300
ggtaaccata cctttgacac cactcaatcc aagtataaac taccacatga catgagaacc     360
actaagcacc aagaggagtt atggtccttt attgccgact cttttgaagga ctttatggtc     420 gagcaagaat tgctaaacac caaggacacc ttaccattag gtttcaccctt ctcgtaccca     480 gcttcccaaa acaagattaa cgaaggtatt ttgcaaagat ggaccaaggg tttcgatatt     540
ccaaatgtcg aaggccacga tgtcgtccca ttgctacaaa acgaaatttc aagagagag      600 ttgcctattg aaattgtagc attgattaat gatactgttg gtactttaat tgcctcatac     660
tacactgacc cagagactaa gatgggtgtg attttcggta ctggtgtcaa cggtgctttc     720
```

-continued

```
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc caagacctgg tcaacaagct    900
tttgaaaaga tgacctccgg ttactacttg ggtgaattgt tgcgtctagt gttacttgaa    960
ttaaacgaga agggcttgat gttgaaggat caagatctaa gcaagttgaa acaaccatac   1020
atcatggata cctcctaccc agcaagaatc gaggatgatc catttgaaaa cttggaagat   1080
actgatgaca tcttccaaaa ggactttggt gtcaagacca ctctgccaga acgtaagttg   1140
attagaagac tttgtgaatt gatcggtacc agagctgcta gattagctgt ttgtggtatt   1200
gccgctattt gccaaaagag aggttacaag actggtcaca ttgccgctga cggttctgtc   1260
tataacaaat acccaggttt caaggaagcc gccgctaagg gtttgagaga tatctatgga   1320
tggactggtg acgcaagcaa agatccaatt acgattgttc cagctgagga tggttcaggt   1380
gcaggtgctg ctgttattgc tgcattgtcc gaaaaaagaa ttgccgaagg taagtctctt   1440
ggtatcattg gcgcttaa                                                 1458
```

<210> SEQ ID NO 52
<211> LENGTH: 485
<212> TYPE: PRT
<213> ORGANISM: Saccharomyces cerevisiae

<400> SEQUENCE: 52

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
                20                  25                  30

Met Phe Thr Val Asp Ser Glu Thr Leu Arg Lys Val Lys His Phe
            35                  40                  45

Ile Asp Glu Leu Asn Lys Gly Leu Thr Lys Lys Gly Gly Asn Ile Pro
        50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
    210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
```

```
                        245                 250                 255
Asp Ile Pro Ser Asn Ser Pro Met Ala Ile Asn Cys Glu Tyr Gly Ser
                260                 265                 270

Phe Asp Asn Glu His Leu Val Leu Pro Arg Thr Lys Tyr Asp Val Ala
            275                 280                 285

Val Asp Glu Gln Ser Pro Arg Pro Gly Gln Gln Ala Phe Glu Lys Met
        290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Ile Phe Gln Lys Asp
        355                 360                 365

Phe Gly Val Lys Thr Thr Leu Pro Glu Arg Lys Leu Ile Arg Arg Leu
        370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
        435                 440                 445

Pro Ile Thr Ile Val Pro Ala Glu Asp Gly Ser Gly Ala Gly Ala Ala
        450                 455                 460

Val Ile Ala Ala Leu Ser Glu Lys Arg Ile Ala Glu Gly Lys Ser Leu
465                 470                 475                 480

Gly Ile Ile Gly Ala
                485

<210> SEQ ID NO 53
<211> LENGTH: 1461
<212> TYPE: DNA
<213> ORGANISM: Saccharomyces cerevisiae

<400> SEQUENCE: 53
atggttcatt taggtccaaa aaaaccacaa gccagaaagg gttccatggc cgatgtgcca      60
aaggaattga tgcaacaaat tgagaatttt gaaaaaattt tcactgttcc aactgaaact     120
ttacaagccg ttaccaagca cttcatttcc gaattggaaa agggtttgtc caagaagggt     180
ggtaacattc aatgattcc aggttgggtt atggatttcc caactggtaa ggaatccggt     240
gatttcttgg ccattgattt gggtggtacc aacttgagag ttgtcttagt caagttgggc     300
ggtgaccgta cctttgacac cactcaatct aagtacagat accagatgc tatgagaact     360 actcaaaatc cagacgaatt gtgggaattt attgccgact cttttgaaagc tttttattgat     420 gagcaattcc cacaaggtat ctctgagcca attccattgg gttcacctt tctttccca       480 gcttctcaaa acaaaatcaa tgaaggtatc ttgcaaagat ggactaaagg ttttgatatt     540
ccaaacattg aaaccacga tgttgttcca atgttgcaaa agcaaatcac taagaggaat     600
atcccaattg aagttgttgc tttgataaac gacactaccg gtactttggt tgcttcttac     660
tacactgacc cagaaactaa gatgggtgtt atcttcggta ctggtgtcaa tggtgcttac     720
tacgatgttt gttccgatat cgaaaagcta caaggaaaac tatctgatga cattccacca     780
```

```
tctgctccaa tggccatcaa ctgtgaatac ggttccttcg ataatgaaca tgtcgttttg    840
ccaagaacta aatacgatat caccattgat gaagaatctc aagaccagg ccaacaaacc    900 tttgaaaaaa tgtcttctgg ttactactta ggtgaaattt tgcgtttggc cttgatggac    960
atgtacaaac aaggtttcat cttcaagaac caagacttgt ctaagttcga caagcctttc   1020
gtcatggaca cttcttaccc agccagaatc gaggaagatc cattcgagaa cctagaagat   1080
accgatgact tgttccaaaa tgagttcggt atcaacacta ctgttcaaga acgtaaattg   1140
atcagacgtt tatctgaatt gattggtgct agagctgcta gattgtccgt ttgtggtatt   1200
gctgctatct gtcaaaagag aggttacaag accggtcaca tcgctgcaga cggttccgtt   1260
tacaacagat acccaggttt caaagaaaag gctgccaatg ctttgaagga catttacggc   1320
tggactcaaa cctcactaga cgactaccca atcaagattg ttcctgctga agatggttcc   1380
ggtgctggtg ccgctgttat tgctgctttg gcccaaaaaa gaattgctga aggtaagtcc   1440
gttggtatca tcggtgctta a                                              1461
```

<210> SEQ ID NO 54
<211> LENGTH: 486
<212> TYPE: PRT
<213> ORGANISM: Saccharomyces cerevisiae

<400> SEQUENCE: 54

```
Met Val His Leu Gly Pro Lys Pro Gln Ala Arg Lys Gly Ser Met
1               5                   10                  15

Ala Asp Val Pro Lys Glu Leu Met Gln Gln Ile Glu Asn Phe Glu Lys
                20                  25                  30

Ile Phe Thr Val Pro Thr Glu Thr Leu Gln Ala Val Thr Lys His Phe
            35                  40                  45

Ile Ser Glu Leu Glu Lys Gly Leu Ser Lys Lys Gly Gly Asn Ile Pro
        50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255
```

```
Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Leu Phe Gln Asn Glu
        355                 360                 365

Phe Gly Ile Asn Thr Thr Val Gln Glu Arg Lys Leu Ile Arg Arg Leu
370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
        435                 440                 445

Tyr Pro Ile Lys Ile Val Pro Ala Glu Asp Gly Ser Gly Ala Gly Ala
    450                 455                 460

Ala Val Ile Ala Ala Leu Ala Gln Lys Arg Ile Ala Glu Gly Lys Ser
465                 470                 475                 480

Val Gly Ile Ile Gly Ala
                485

<210> SEQ ID NO 55
<211> LENGTH: 1434
<212> TYPE: DNA
<213> ORGANISM: Escherichia coli

<400> SEQUENCE: 55
atgacgcaat ctcgattgca tgcggcgcaa aacgcactag caaaacttca cgagcgccga      60
ggtaacactt tctatcccca ttttcacctc gcgcctcctg ccgggtggat gaacgatcca     120
aacggcctga tctggtttaa cgatcgttat cacgcgtttt atcaacatca cccgatgagc     180
gaacactggg ggccaatgca ctggggacat gccaccagcg acgatatgat ccactggcag     240
catgagccta ttgcgctagc gccaggagac gagaatgaca agacgggtg ttttcaggt      300 agtgctgtcg atgacaatgg tgtcctctca cttatctaca ccggacacgt ctggctcgat     360
ggtgcaggta atgacgatgc aattcgcgaa gtacaatgtc tggctaccag tcgggatggt     420
attcatttcg agaaacaggg tgtgatcctc actccaccag aaggcatcat gcacttccgc     480
gatcctaaag tgtggcgtga agccgacaca tggtggatgg tagtcggggc gaaagaccca     540
ggcaacacgg ggcagatcct gctttatcgc ggcagttcat tgcgtgaatg actttcgat     600 cgcgtactgg cccacgctga tgcgggtgaa agctatatgt gggaatgtcc ggacttttc      660 agccttggcg atcagcatta tctgatgttt tcccgcagg gaatgaatgc cgagggatac     720
agttatcgaa atcgctttca aagtggcgta ataccgaa tgtggtcgcc aggacgactt     780
```

-continued

```
tttgcacaat ccgggcattt tactgaactt gataacgggc atgactttta tgcaccacaa    840
agctttgtag cgaaggatgg tcggcgtatt gttatcggct ggatggatat gtgggaatcg    900
ccaatgccct caaaacgtga aggctgggca ggctgcatga cgctggcgcg cgagctatca    960
gagagcaatg caaactcct acaacgcccg gtacacgaag ctgagtcgtt acgccagcag    1020
catcaatcta tctctccccg cacaatcagc aataaatatg ttttgcagga aaacgcgcaa    1080
gcagttgaga ttcagttgca gtgggcgctg aagaacagtg atgccgaaca ttacggatta    1140
cagctcggcg ctggaatgcg gctgtatatt gataaccaat ctgagcgact tgttttgtgg    1200
cggtattacc cacacgagaa tttagatggc taccgtagta ttcccctccc gcagggtgac    1260
atgctcgccc taaggatatt tatcgataca tcatccgtgg aagtatttat taacgacggg    1320
gaggcggtga tgagtagccg aatatatccg cagccagaag aacgggaact gtcgctctat    1380
gcctcccacg gagtggctgt gctgcaacat ggagcactct ggcaactggg ttaa          1434
```

<210> SEQ ID NO 56
<211> LENGTH: 477
<212> TYPE: PRT
<213> ORGANISM: Escherichia coli

<400> SEQUENCE: 56

```
Met Thr Gln Ser Arg Leu His Ala Ala Gln Asn Ala Leu Ala Lys Leu
1               5                   10                  15

His Glu Arg Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Glu Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270
```

```
Gly His Asp Phe Tyr Ala Pro Gln Ser Phe Val Ala Lys Asp Gly Arg
            275                 280                 285

Arg Ile Val Ile Gly Trp Met Asp Met Trp Glu Ser Pro Met Pro Ser
        290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Ile Ser Pro Arg Thr Ile Ser Asn Lys
            340                 345                 350

Tyr Val Leu Gln Glu Asn Ala Gln Ala Val Glu Ile Gln Leu Gln Trp
        355                 360                 365

Ala Leu Lys Asn Ser Asp Ala Glu His Tyr Gly Leu Gln Leu Gly Ala
    370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
                405                 410                 415

Pro Gln Gly Asp Met Leu Ala Leu Arg Ile Phe Ile Asp Thr Ser Ser
            420                 425                 430

Val Glu Val Phe Ile Asn Asp Gly Glu Ala Val Met Ser Ser Arg Ile
        435                 440                 445

Tyr Pro Gln Pro Glu Glu Arg Glu Leu Ser Leu Tyr Ala Ser His Gly
    450                 455                 460

Val Ala Val Leu Gln His Gly Ala Leu Trp Gln Leu Gly
465                 470                 475
```

```
<210> SEQ ID NO 57
<211> LENGTH: 1434
<212> TYPE: DNA
<213> ORGANISM: Escherichia coli

<400> SEQUENCE: 57
atgacgcaat ctcgattgca tgcggcgcaa aacgccctag caaaacttca tgagcaccgg      60
ggtaacactt tctatcccca ttttcacctc gcgcctcctg ccgggtggat gaacgatcca     120
aacggcctga tctggtttaa cgatcgttat cacgcgtttt atcaacatca tccgatgagc     180
gaacactggg ggccaatgca ctggggacat gccaccagcg acgatatgat ccactggcag     240
catgagccta ttgcgctagc gccaggagac gataatgaca agacgggtg tttttcaggt      300 agtgctgtcg atgacaatgg tgtcctctca cttatctaca ccggacacgt ctggctcgat     360
ggtgcaggta tgacgatgc aattcgcgaa gtacaatgtc tggctaccag tcgggatggt      420
attcatttcg agaaacaggg tgtgatcctc actccaccag aaggaatcat gcacttccgc     480
gatcctaaag tgtggcgtga agccgacaca tggtggatgg tagtcgggc gaaagatcca      540 ggcaacacgg ggcagatcct gctttatcgc ggcagttcgt tgcgtgaatg gaccttcgat     600
cgcgtactgg cccacgctga tgcgggtgaa agctatatgt gggaatgtcc ggactttttc     660
agccttggcg atcagcatta tctgatgttt tccccgcagg gaatgaatgc cgagggatac     720
agttaccgaa atcgctttca agtggcgta atacccggaa tgtggtcgcc aggacgactt     780
tttgcacaat ccgggcattt tactgaactt gataacgggc atgactttta tgcaccacaa     840
agctttttag cgaaggatgg tcggcgtatt gttatcggct ggatggatat gtgggaatcg     900
ccaatgccct caaaacgtga aggatgggca ggctgcatga cgctggcgcg cgagctatca     960
```

-continued

```
gagagcaatg gcaaacttct acaacgcccg gtacacgaag ctgagtcgtt acgccagcag    1020
catcaatctg tctctccccg cacaatcagc aataaatatg ttttgcagga aaacgcgcaa    1080
gcagttgaga ttcagttgca gtgggcgctg aagaacagtg atgccgaaca ttacggatta    1140
cagctcggca ctggaatgcg gctgtatatt gataaccaat ctgagcgact tgttttgtgg    1200
cggtattacc cacacgagaa tttagacggc taccgtagta ttcccctccc gcagcgtgac    1260
acgctcgccc taaggatatt tatcgataca tcatccgtgg aagtatttat taacgacggg    1320
gaagcggtga tgagtagtcg aatctatccg cagccagaag aacgggaact gtcgctttat    1380
gcctcccacg gagtggctgt gctgcaacat ggagcactct ggctactggg ttaa          1434
```

<210> SEQ ID NO 58
<211> LENGTH: 477
<212> TYPE: PRT
<213> ORGANISM: Escherichia coli

<400> SEQUENCE: 58

```
Met Thr Gln Ser Arg Leu His Ala Ala Gln Asn Ala Leu Ala Lys Leu
1               5                   10                  15

His Glu His Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Asp Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Leu Ala Lys Asp Gly Arg
        275                 280                 285

Arg Ile Val Ile Gly Trp Met Asp Met Trp Glu Ser Pro Met Pro Ser
    290                 295                 300
```

| | | | | | | | | | | | | | | | |
|---|---|---|---|---|---|---|---|---|---|---|---|---|---|---|---|
Lys | Arg | Glu | Gly | Trp | Ala | Gly | Cys | Met | Thr | Leu | Ala | Arg | Glu | Leu | Ser
305 | | | | 310 | | | | 315 | | | | 320

Glu Ser Asn Gly Lys Leu Leu Gln Arg Pro Val His Glu Ala Glu Ser
              325                    330                  335

Leu Arg Gln Gln His Gln Ser Val Ser Pro Arg Thr Ile Ser Asn Lys
            340                    345                  350

Tyr Val Leu Gln Glu Asn Ala Gln Ala Val Glu Ile Gln Leu Gln Trp
    355                    360                  365

Ala Leu Lys Asn Ser Asp Ala Glu His Tyr Gly Leu Gln Leu Gly Thr
370                    375                  380

Gly Met Arg Leu Tyr Ile Asp Asn Gln Ser Glu Arg Leu Val Leu Trp
385                    390                  395                  400

Arg Tyr Tyr Pro His Glu Asn Leu Asp Gly Tyr Arg Ser Ile Pro Leu
            405                    410                  415

Pro Gln Arg Asp Thr Leu Ala Leu Arg Ile Phe Ile Asp Thr Ser Ser
        420                    425                  430

Val Glu Val Phe Ile Asn Asp Gly Glu Ala Val Met Ser Ser Arg Ile
            435                    440                  445

Tyr Pro Gln Pro Glu Glu Arg Glu Leu Ser Leu Tyr Ala Ser His Gly
    450                    455                  460

Val Ala Val Leu Gln His Gly Ala Leu Trp Leu Leu Gly
465                    470                  475

<210> SEQ ID NO 59
<211> LENGTH: 1599
<212> TYPE: DNA
<213> ORGANISM: Bifidobacterium lactis

<400> SEQUENCE: 59

```
atggcaaccc ttcccaccaa tattcccgcc aacggcattc tgaccccga cccggcgctc      60 gaccctgtgc tcacgccgat ctcggaccat gccgagcagc tgtcactcgc cgaagcaggc     120
gtgtcggcac tggaaaccac ccgcaacgac cgctggtacc cgaagttcca cattgcctcc     180
aatggcgggt ggatcaacga cccgaacggc ctgtgccgct acaacggacg ctggcacgtg     240
ttctaccagc tgcatcccca cggcacacag tggggcccga tgcattgggg ccacgtctcc     300
tccgacaaca tggtcgactg gcaccgcgaa cccatcgcct tcgcgccaag cctcgaacag     360
gaacgccacg gtgtgttctc cggttccgcc gtgattggcg acgacggcaa gccgtggatt     420
ttctacaccg ccaccgctg gccaacggc aaggacaaca ccggaggcga ctggcaggtg     480
cagatgctcg ccaagccgaa cgacgacgaa ctgaagacct tcacgaagga gggcatgatc     540
atcgactgcc ccaccgacga ggtggaccac cacttccgcg acccgaaggt gtggaagacc     600
ggtgacacct ggtatatgac cttcggtgtc tcgtcgaagg agcatcgtgg ccagatgtgg     660
ctgtacacgt cgagcgacat ggtgcactgg agcttcgatc gggtgctgtt cgagcatccg     720
gatccgaacg tgttcatgct tgaatgcccc gatttcttcc gatccgcga tgcgcggggc     780 aacgagaaat gggtcatcgg cttctccgcg atgggtgcca agccaaatgg cttcatgaac     840
cgcaacgtga acaatgccgg ctacatggtg ggcacatgga agccaggcga gagcttcaag     900
ccggagaccg agttccgcct gtgggacgaa ggccataact tctatgcacc acagtcgttc     960
aacaccgaag gcgccagat catgtacggc tggatgagcc cgttcgtcgc ccccatcccg    1020
atggaggagg acggctggtg cggcaacctc accctccccc gcgagatcac gctgggcgat    1080
gacggtgacc tggtcaccgc ccccaccatc gaaatggagg ggctgcgcga gaataccata    1140
```

-continued

```
ggcttcgact cgctcgacct tggtacgaac cagacctcca cgatcctcga cgatgacggc    1200
ggcgccctgg aaatcgagat gagactcgat ctgaacaaaa ccaccgccga acgcgccgga    1260
ctgcatgtgc atgccacaag cgacggccac tacacggcaa tcgtattcga cgcgcagatc    1320
ggcggcgtcg tcatcgaccg gcagaacgtg gcgaacggag acaaaggcta ccgggtggcc    1380
aagctcagcg acaccgagct cgcagccgat acgcttgact tgcgcgtgtt catcgaccgc    1440
ggatgcgtcg aggtctacgt cgacggcggc aagcatgcga tgagctcgta ctcgttccct    1500
ggcgatggcg cacgcgccgt cgaactcgtg agcgaatccg gcaccacgca catcgacacc    1560
ctcaccatgc actcgctcaa gtccatcgga ctcgagtga                          1599
```

<210> SEQ ID NO 60
<211> LENGTH: 532
<212> TYPE: PRT
<213> ORGANISM: Bifidobacterium lactis

<400> SEQUENCE: 60

```
Met Ala Thr Leu Pro Thr Asn Ile Pro Ala Asn Gly Ile Leu Thr Pro
1               5                   10                  15

Asp Pro Ala Leu Asp Pro Val Leu Thr Pro Ile Ser Asp His Ala Glu
            20                  25                  30

Gln Leu Ser Leu Ala Glu Ala Gly Val Ser Ala Leu Glu Thr Thr Arg
        35                  40                  45

Asn Asp Arg Trp Tyr Pro Lys Phe His Ile Ala Ser Asn Gly Gly Trp
    50                  55                  60

Ile Asn Asp Pro Asn Gly Leu Cys Arg Tyr Asn Gly Arg Trp His Val
65                  70                  75                  80

Phe Tyr Gln Leu His Pro His Gly Thr Gln Trp Gly Pro Met His Trp
                85                  90                  95

Gly His Val Ser Ser Asp Asn Met Val Asp Trp His Arg Glu Pro Ile
            100                 105                 110

Ala Phe Ala Pro Ser Leu Glu Gln Glu Arg His Gly Val Phe Ser Gly
        115                 120                 125

Ser Ala Val Ile Gly Asp Gly Lys Pro Trp Ile Phe Tyr Thr Gly
    130                 135                 140

His Arg Trp Ala Asn Gly Lys Asp Asn Thr Gly Gly Asp Trp Gln Val
145                 150                 155                 160

Gln Met Leu Ala Lys Pro Asn Asp Asp Glu Leu Lys Thr Phe Thr Lys
                165                 170                 175

Glu Gly Met Ile Ile Asp Cys Pro Thr Asp Glu Val Asp His His Phe
            180                 185                 190

Arg Asp Pro Lys Val Trp Lys Thr Gly Asp Thr Trp Tyr Met Thr Phe
        195                 200                 205

Gly Val Ser Ser Lys Glu His Arg Gly Gln Met Trp Leu Tyr Thr Ser
    210                 215                 220

Ser Asp Met Val His Trp Ser Phe Asp Arg Val Leu Phe Glu His Pro
225                 230                 235                 240

Asp Pro Asn Val Phe Met Leu Glu Cys Pro Asp Phe Phe Pro Ile Arg
                245                 250                 255

Asp Ala Arg Gly Asn Glu Lys Trp Val Ile Gly Phe Ser Ala Met Gly
            260                 265                 270

Ala Lys Pro Asn Gly Phe Met Asn Arg Asn Val Asn Asn Ala Gly Tyr
        275                 280                 285

Met Val Gly Thr Trp Lys Pro Gly Glu Ser Phe Lys Pro Glu Thr Glu
    290                 295                 300
```

| | | | | | | | | | | | |
|---|---|---|---|---|---|---|---|---|---|---|---|
| Phe | Arg | Leu | Trp | Asp | Glu | Gly | His | Asn | Phe | Tyr | Ala | Pro | Gln | Ser | Phe |
| 305 | | | | 310 | | | | 315 | | | 320 |

Phe Arg Leu Trp Asp Glu Gly His Asn Phe Tyr Ala Pro Gln Ser Phe
305                 310                 315                 320

Asn Thr Glu Gly Arg Gln Ile Met Tyr Gly Trp Met Ser Pro Phe Val
            325                 330                 335

Ala Pro Ile Pro Met Glu Glu Asp Gly Trp Cys Gly Asn Leu Thr Leu
            340                 345                 350

Pro Arg Glu Ile Thr Leu Gly Asp Asp Gly Asp Leu Val Thr Ala Pro
            355                 360                 365

Thr Ile Glu Met Glu Gly Leu Arg Glu Asn Thr Ile Gly Phe Asp Ser
    370                 375                 380

Leu Asp Leu Gly Thr Asn Gln Thr Ser Thr Ile Leu Asp Asp Asp Gly
385                 390                 395                 400

Gly Ala Leu Glu Ile Glu Met Arg Leu Asp Leu Asn Lys Thr Thr Ala
            405                 410                 415

Glu Arg Ala Gly Leu His Val His Ala Thr Ser Asp Gly His Tyr Thr
            420                 425                 430

Ala Ile Val Phe Asp Ala Gln Ile Gly Gly Val Val Ile Asp Arg Gln
    435                 440                 445

Asn Val Ala Asn Gly Asp Lys Gly Tyr Arg Val Ala Lys Leu Ser Asp
450                 455                 460

Thr Glu Leu Ala Ala Asp Thr Leu Asp Leu Arg Val Phe Ile Asp Arg
465                 470                 475                 480

Gly Cys Val Glu Val Tyr Val Asp Gly Gly Lys His Ala Met Ser Ser
            485                 490                 495

Tyr Ser Phe Pro Gly Asp Gly Ala Arg Ala Val Glu Leu Val Ser Glu
            500                 505                 510

Ser Gly Thr Thr His Ile Asp Thr Leu Thr Met His Ser Leu Lys Ser
            515                 520                 525

Ile Gly Leu Glu
    530

<210> SEQ ID NO 61
<211> LENGTH: 1599
<212> TYPE: DNA
<213> ORGANISM: Saccharomyces cerevisiae

<400> SEQUENCE: 61

```
atgcttttgc aagctttcct tttccttttg gctggttttg cagccaaaat atctgcatca     60
atgacaaacg aaactagcga tagacctttg gtccacttca cacccaacaa gggctggatg    120
aatgacccaa atgggttgtg gtacgatgaa aaagatgcca atggcatctg tactttcaa    180
tacaacccaa atgacaccgt atggggtacg ccattgtttt ggggccatgc tacttccgat    240
gatttgacta attgggaaga tcaacccatt gctatcgctc caagcgtaac gattcaggt    300
gctttctctg ctccatggt ggttgattac aacaacacga gtgggttttt caatgatact    360
attgatccaa gacaaagatg cgttgcgatt tggacttata cactcctga agtgaagag    420
caatacatta gctattctct tgatggtggt tacactttta ctgaatacca aaagaaccct    480
gttttagctg ccaactccac tcaattcaga gatccaaagg tgttctggta tgaaccttct    540
caaaaatgga ttatgacggc tgccaaatca caagactaca aaattgaaat ttactcctct    600
gatgacttga agtcctggaa gctagaatct gcatttgcca atgaaggttt cttaggctac    660
caatacgaat gtccaggttt gattgaagtc ccaactgagc aagatccttc caatctttat    720
tgggtcatgt ttatttctat caacccaggt gcacctgctg gcggttcctt caaccaatat    780
```

```
tttgttggat ccttcaatgg tactcatttt gaagcgtttg acaatcaatc tagagtggta    840
gattttggta aggactacta tgccttgcaa actttcttca acactgaccc aacctacggt    900
tcagcattag gtattgcctg ggcttcaaac tgggagtaca gtgcctttgt cccaactaac    960
ccatggagat catccatgtc tttggtccgc aagtttttctt tgaacactga atatcaagct   1020
aatccagaga ctgaattgat caatttgaaa gccgaaccaa tattgaacat tagtaatgct   1080
ggtccctggt ctcgttttgc tactaacaca actctaacta aggccaattc ttacaatgtc   1140
gatttgagca actcgactgg taccctagag tttgagttgg tttacgctgt taacaccaca   1200
caaaccatat ccaaatccgt cttcgccgac ttatcacttt ggttcaaggg tttagaagat   1260
cctgaagaat atttgagaat gggttttgaa gtcagtgctt cttccttctt tttggaccgt   1320
ggtaactcta aggtcaagtt tgtcaaggag aacccatatt tcacaaacag aatgtctgtc   1380
aacaaccaac cattcaagtc tgagaacgac ctaagttact ataaagtgta cggcctactg   1440
gatcaaaaca tcttggaatt gtacttcaac gatggagatg tggtttctac aaataccatc   1500
ttcatgacca ccggtaacgc tctaggatct gtgaacatga ccactggtgt cgataatttg   1560
ttctacattg acaagttcca agtaagggaa gtaaaatag                          1599

<210> SEQ ID NO 62
<211> LENGTH: 532
<212> TYPE: PRT
<213> ORGANISM: Saccharomyces cerevisiae

<400> SEQUENCE: 62

Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
                20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
        50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240
```

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
                260                 265                 270

Phe Asp Asn Gln Ser Arg Val Val Asp Phe Gly Lys Asp Tyr Tyr Ala
                275                 280                 285

Leu Gln Thr Phe Phe Asn Thr Asp Pro Thr Tyr Gly Ser Ala Leu Gly
                290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
                340                 345                 350

Pro Ile Leu Asn Ile Ser Asn Ala Gly Pro Trp Ser Arg Phe Ala Thr
                355                 360                 365

Asn Thr Thr Leu Thr Lys Ala Asn Ser Tyr Asn Val Asp Leu Ser Asn
                370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
                420                 425                 430

Ala Ser Ser Phe Phe Leu Asp Arg Gly Asn Ser Lys Val Lys Phe Val
                435                 440                 445

Lys Glu Asn Pro Tyr Phe Thr Asn Arg Met Ser Val Asn Asn Gln Pro
                450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
                500                 505                 510

Met Thr Thr Gly Val Asp Asn Leu Phe Tyr Ile Asp Lys Phe Gln Val
                515                 520                 525

Arg Glu Val Lys
        530

<210> SEQ ID NO 63
<211> LENGTH: 1302
<212> TYPE: DNA
<213> ORGANISM: Corynebacterium glutamicum

<400> SEQUENCE: 63
gtgtgtgggg ctatgcacac agaactttcc agtttgcgcc ctgcgtacca tgtgactcct      60
ccgcagggca ggctcaatga tcccaacgga atgtacgtcg atggcgatac cctccacgtc     120
tactaccagc acgatccagg tttccccttc gcaccaaagc gcaccggctg ggctcacacc     180
accacgccgt tgaccggacc gcagcgattg cagtggacgc acctgcccga cgctctttac     240
ccggatgcat cctatgacct ggatggatgc tattccggtg gagccgtatt tactgacggc     300
acacttaaac ttttctacac cggcaaccta aaaattgacg gcaagcgccg cgccacccaa     360
aacctcgtcg aagtcgagga cccaactggg ctgatgggcg gcattcatcg ccgttcgcct     420

-continued

```
aaaaatccgc ttatcgacgg acccgccagc ggtttcacac cccattaccg cgatcccatg    480
atcagccctg atggtgatgg ttggaaaatg gttcttgggg cccaacgcga aacctcacc     540 ggtgcagcgg ttctataccg ctcgacagat cttgaaaact gggaattctc cggtgaaatc    600
acctttgacc tcagtgatgc acaacctggt tctgctcctg atctcgttcc cggtggctac    660
atgtgggaat gccccaacct ttttacgctt cgcgatgaag aaactggcga gatctcgac     720 gtgctgattt tctgtccaca aggattggac cgaatccacg atgaggttac tcactacgca    780
agctctgacc agtgcggata tgtcgtcggc aagcttgaag aacgacctt ccgcgtcttg     840 cgaggattca gcgagctgga tttcggccat gaattctacg caccgcaggt tgcagtaaac    900
ggttctgatg cctggctcgt gggctggatg gggctgcccg cgcaggatga tcacccaaca    960
gttgcacggg aaggatgggt gcactgcctg actgtgcccc gcaagcttca tttgcgcaac   1020
cacgcgatct atcaagagct tcttctccca gaggggagt cagggtaat cagatctgta    1080 ttaggttctg aacctgtccg agtagacatc cgaggcaata tttccctcga gtgggatggt   1140
gtccgtttgt ctgtggatcg tggtggtgat cgtcgcgtag ctgaggtaaa acctggcgaa   1200
ttagtgatcg cggacgataa tacagccatt gagataactg caggtgatgg acaggtttca   1260
ttcgctttcc gggctttcaa aggtgacact attgagagat aa                     1302
```

<210> SEQ ID NO 64
<211> LENGTH: 433
<212> TYPE: PRT
<213> ORGANISM: Corynebacterium glutamicum

<400> SEQUENCE: 64

```
Met Cys Gly Ala Met His Thr Glu Leu Ser Ser Leu Arg Pro Ala Tyr
  1               5                  10                  15

His Val Thr Pro Pro Gln Gly Arg Leu Asn Asp Pro Asn Gly Met Tyr
             20                  25                  30

Val Asp Gly Asp Thr Leu His Val Tyr Gln His Asp Pro Gly Phe
         35                  40                  45

Pro Phe Ala Pro Lys Arg Thr Gly Trp Ala His Thr Thr Thr Pro Leu
     50                  55                  60

Thr Gly Pro Gln Arg Leu Gln Trp Thr His Leu Pro Asp Ala Leu Tyr
 65                  70                  75                  80

Pro Asp Ala Ser Tyr Asp Leu Asp Gly Cys Tyr Ser Gly Gly Ala Val
                 85                  90                  95

Phe Thr Asp Gly Thr Leu Lys Leu Phe Tyr Thr Gly Asn Leu Lys Ile
            100                 105                 110

Asp Gly Lys Arg Arg Ala Thr Gln Asn Leu Val Glu Val Glu Asp Pro
        115                 120                 125

Thr Gly Leu Met Gly Gly Ile His Arg Arg Ser Pro Lys Asn Pro Leu
    130                 135                 140

Ile Asp Gly Pro Ala Ser Gly Phe Thr Pro His Tyr Arg Asp Pro Met
145                 150                 155                 160

Ile Ser Pro Asp Gly Asp Gly Trp Lys Met Val Leu Gly Ala Gln Arg
                165                 170                 175

Glu Asn Leu Thr Gly Ala Ala Val Leu Tyr Arg Ser Thr Asp Leu Glu
            180                 185                 190

Asn Trp Glu Phe Ser Gly Glu Ile Thr Phe Asp Leu Ser Asp Ala Gln
        195                 200                 205

Pro Gly Ser Ala Pro Asp Leu Val Pro Gly Gly Tyr Met Trp Glu Cys
    210                 215                 220
```

```
Pro Asn Leu Phe Thr Leu Arg Asp Glu Glu Thr Gly Glu Asp Leu Asp
225                 230                 235                 240

Val Leu Ile Phe Cys Pro Gln Gly Leu Asp Arg Ile His Asp Glu Val
            245                 250                 255

Thr His Tyr Ala Ser Ser Asp Gln Cys Gly Tyr Val Val Gly Lys Leu
        260                 265                 270

Glu Gly Thr Thr Phe Arg Val Leu Arg Gly Phe Ser Glu Leu Asp Phe
    275                 280                 285

Gly His Glu Phe Tyr Ala Pro Gln Val Ala Val Asn Gly Ser Asp Ala
290                 295                 300

Trp Leu Val Gly Trp Met Gly Leu Pro Ala Gln Asp Asp His Pro Thr
305                 310                 315                 320

Val Ala Arg Glu Gly Trp Val His Cys Leu Thr Val Pro Arg Lys Leu
            325                 330                 335

His Leu Arg Asn His Ala Ile Tyr Gln Glu Leu Leu Leu Pro Glu Gly
        340                 345                 350

Glu Ser Gly Val Ile Arg Ser Val Leu Gly Ser Glu Pro Val Arg Val
    355                 360                 365

Asp Ile Arg Gly Asn Ile Ser Leu Glu Trp Asp Gly Val Arg Leu Ser
370                 375                 380

Val Asp Arg Gly Gly Asp Arg Arg Val Ala Glu Val Lys Pro Gly Glu
385                 390                 395                 400

Leu Val Ile Ala Asp Asp Asn Thr Ala Ile Glu Ile Thr Ala Gly Asp
            405                 410                 415

Gly Gln Val Ser Phe Ala Phe Arg Ala Phe Lys Gly Asp Thr Ile Glu
        420                 425                 430

Arg

<210> SEQ ID NO 65
<211> LENGTH: 1473
<212> TYPE: DNA
<213> ORGANISM: Leuconostoc mesenteroides

<400> SEQUENCE: 65
atggaaattc aaaacaaagc aatgttgatc acttatgctg attcgttggg caaaaactta      60
aaagatgttc atcaagtctt gaagaagat attggagatg cgattggtgg ggttcatttg      120
ttgccttcct tcccttcaac aggtgatcgc ggttttgcgc cagccgatta tactcgtgtt      180
gatgccgcat ttggtgattg gcagatgtc gaagcattgg gtgaagaata ctatttgatg      240
tttgacttca tgattaacca tatttctcgt gaatcagtga tgtatcaaga ttttaagaag      300
aatcatgacg attcaaagta taagatttc tttattcgtt gggaaaagtt ctgggcaaag      360
gccggcgaaa accgtccaac acaagccgat gttgacttaa tttacaagcg taaagataag      420
gcaccaacgc aagaaatcac ttttgatgat ggcacaacag aaaacttgtg gaatactttt      480
ggtgaagaac aaattgacat tgatgttaat tcagccattg ccaaggaatt tattaagaca      540
acccttgaag acatggtaaa acatggtgct aacttgattc gtttggatgc ctttgcgtat      600
gcagttaaaa aagttgacac aaatgacttc ttcgttgagc agaaatctg ggacactttg      660 aatgaagtac gtgaaatttt gacaccatta aaggctgaaa ttttaccaga aattcatgaa      720
cattactcaa tccctaaaaa gatcaatgat catggttact tcacctatga ctttgcatta      780
ccaatgacaa cgctttacac attgtattca ggtaagacaa atcaattggc aaagtggttg      840
aagatgtcac caatgaagca attcacaaca ttggacacgc atgatggtat tggtgtcgtt      900
gatgcccgtg atattctaac tgatgatgaa attgactacg cttctgaaca actttacaag      960
```

```
gttggcgcga atgtcaaaaa gacatattca tctgcttcat acaacaacct tgatatttac    1020
caaattaact caacttatta ttcagcattg ggaaatgatg atgcagcata cttgttgagt    1080
cgtgtcttcc aagtctttgc gcctggaatt ccacaaattt attacgttgg tttgttggca    1140
ggtgaaaacg atatcgcgct tttggagtca actaaagaag gtcgtaatat taaccgtcat    1200
tactatacgc gtgaagaagt taagtcagaa gttaagcgac cagttgttgc taacttattg    1260
aagctattgt catggcgtaa tgaaagccct gcatttgatt tggctggctc aatcacagtt    1320
gacacgccaa ctgataacaa aattgtggtg acacgtcaag atgaaaatgg tcaaaacaaa    1380
gctgtattaa cagccgatgc ggccaacaaa acttttgaaa tcgttgagaa tggtcaaact    1440
gttatgagca gtgataattt gactcagaac taa                                  1473
```

<210> SEQ ID NO 66
<211> LENGTH: 490
<212> TYPE: PRT
<213> ORGANISM: Leuconostoc mesenteroides

<400> SEQUENCE: 66

```
Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Asp Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Lys Asp Lys Ala Pro Thr Gln
    130                 135                 140

Glu Ile Thr Phe Asp Asp Gly Thr Thr Glu Asn Leu Trp Asn Thr Phe
145                 150                 155                 160

Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285
```

```
Thr Thr Leu Asp Thr His Asp Gly Ile Gly Val Val Asp Ala Arg Asp
    290                 295                 300

Ile Leu Thr Asp Asp Glu Ile Asp Tyr Ala Ser Glu Gln Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Val Phe Gln Val Phe Ala Pro
        355                 360                 365

Gly Ile Pro Gln Ile Tyr Tyr Val Gly Leu Leu Ala Gly Glu Asn Asp
    370                 375                 380

Ile Ala Leu Leu Glu Ser Thr Lys Glu Gly Arg Asn Ile Asn Arg His
385                 390                 395                 400

Tyr Tyr Thr Arg Glu Glu Val Lys Ser Glu Val Lys Arg Pro Val Val
                405                 410                 415

Ala Asn Leu Leu Lys Leu Leu Ser Trp Arg Asn Glu Ser Pro Ala Phe
            420                 425                 430

Asp Leu Ala Gly Ser Ile Thr Val Asp Thr Pro Thr Asp Thr Thr Ile
        435                 440                 445

Val Val Thr Arg Gln Asp Glu Asn Gly Gln Asn Lys Ala Val Leu Thr
    450                 455                 460

Ala Asp Ala Ala Asn Lys Thr Phe Glu Ile Val Glu Asn Gly Gln Thr
465                 470                 475                 480

Val Met Ser Ser Asp Asn Leu Thr Gln Asn
                485                 490

<210> SEQ ID NO 67
<211> LENGTH: 1515
<212> TYPE: DNA
<213> ORGANISM: Bifidobacterium adolescentis

<400> SEQUENCE: 67
atgaaaaaca aggtgcagct catcacttac gccgaccgcc ttggcgacgg caccatcaag     60
tcgatgaccg acattctgcg cacccgcttc gacggcgtgt acgacggcgt tcacatcctg    120
ccgttcttca ccccgttcga cggcgccgac gcaggcttcg acccgatcga ccacaccaag    180
gtcgacgaac gtctcggcag ctgggacgac gtcgccgaac tctccaagac ccacaacatc    240
atggtcgacg ccatcgtcaa ccacatgagt tgggaatcca agcagttcca ggacgtgctg    300
gccaagggcg aggagtccga atactatccg atgttcctca ccatgagctc cgtgttcccg    360
aacggcgcca ccgaagagga cctggccggc atctaccgtc cgcgtccggg cctgccgttc    420
acccactaca agttcgccgg caagacccgc ctcgtgtggg tcagcttcac cccgcagcag    480
gtggacatcg acaccgattc cgacaagggt tgggaatacc tcatgtcgat tttcgaccag    540
atggccgcct ctcacgtcag ctacatccgc ctcgacgccg tcggctatgg cgccaaggaa    600
gccggcacca gctgcttcat gaccccgaag accttcaagc tgatctcccg tctgcgtgag    660
gaaggcgtca agcgcggtct ggaaatcctc atcgaagtgc actcctacta caagaagcag    720
gtcgaaatcg catccaaggt ggaccgcgtc tacgacttcg ccctgcctcc gctgctgctg    780
cacgcgctga gcaccggcca cgtcgagccc gtcgcccact ggaccgacat cgcccgaac     840 aacgccgtca ccgtgctcga tacgcacgac ggcatcggcg tgatcgacat cggtccgac     900 cagctcgacc gctcgctcaa gggtctcgtg ccggatgagg acgtggacaa cctcgtcaac    960
```

-continued

```
accatccacg ccaacaccca cggcgaatcc caggcagcca ctggcgccgc cgcatccaat      1020
ctcgacctct accaggtcaa cagcacctac tattcggcgc tcgggtgcaa cgaccagcac      1080
tacatcgccg cccgcgcggt gcagttcttc ctgccgggcg tgccgcaagt ctactacgtc      1140
ggcgcgctcg ccggcaagaa cgacatggag ctgctgcgta agacgaataa cggccgcgac      1200
atcaatcgcc attactactc caccgcggaa atcgacgaga acctcaagcg tccggtcgtc      1260
aaggccctga cgcgctcgc caagttccgc aacgagctcg acgcgttcga cggcacgttc      1320
tcgtacacca ccgatgacga cacgtccatc agcttcacct ggcgcggcga aaccagccag      1380
gccacgctga cgttcgagcc gaagcgcggt ctcggtgtgg acaacactac gccggtcgcc      1440
atgttggaat gggaggattc cgcgggagac caccgttcgg atgatctgat cgccaatccg      1500
cctgtcgtcg cctga                                                      1515
```

<210> SEQ ID NO 68
<211> LENGTH: 504
<212> TYPE: PRT
<213> ORGANISM: Bifidobacterium adolescentis

<400> SEQUENCE: 68

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
```

```
                275                 280                 285
His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
            355                 360                 365

Phe Phe Leu Pro Gly Val Pro Gln Val Tyr Tyr Val Gly Ala Leu Ala
        370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Asp Thr
        435                 440                 445

Ser Ile Ser Phe Thr Trp Arg Gly Glu Thr Ser Gln Ala Thr Leu Thr
    450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
                485                 490                 495

Ile Ala Asn Pro Pro Val Val Ala
            500

<210> SEQ ID NO 69
<211> LENGTH: 1164
<212> TYPE: DNA
<213> ORGANISM: Klebsiella pneumoniae

<400> SEQUENCE: 69
atgagctatc gtatgtttga ttatctggtg ccaaacgtta acttttttgg ccccaacgcc      60
atttccgtag tcggcgaacg ctgccagctg ctgggggga aaaagcccct gctggtcacc     120
gacaaaggcc tgcgggcaat taagatggc gcagtgaca aaacccctgca ttatctgcgg     180 gaggccggga tcgaggtggc gatctttgac ggcgtcgagc cgaacccgaa agacaccaac    240
gtgcgcgacg gcctcgccgt gtttcgccgc gaacagtgcg acatcatcgt caccgtgggc    300
ggcggcagcc gcacgattg cggcaaaggc atcggcatcg ccgccaccca tgagggcgat    360
ctgtaccagt atgccggaat cgagaccctg accaacccgc tgccgcctat cgtcgcggtc    420
aataccaccg ccggcaccgc cagcgaggtc accgccact gcgtcctgac caacaccgaa    480
accaaagtga agtttgtgat cgtcagctgg cgcaacctgc cgtcggtctc tatcaacgat    540
ccgctgctga tgatcggtaa accggccgcc ctgaccgcgg cgaccgggat ggatgccctg    600
acccacgccg tagaggccta tatctccaaa gacgctaacc cggtgacgga cgccgccgcc    660
atgcaggcga tccgcctcat cgcccgcaac ctgcgccagg ccgtggccct cggcagcaat    720
ctgcaggcgc gggaaaacat ggcctatgcc tctctgctgg ccgggatggc ttttaataac    780
gccaacctcg gctacgtgca cgccatggcg caccagctgg gcggcctgta cgacatgccg    840
```

```
cacggcgtgg ccaacgctgt cctgctgccg catgtggccc gctacaacct gatcgccaac    900
ccggagaaat cgccgatat cgctgaactg atgggcgaaa atatcaccgg actgtccact    960
ctcgacgcgg cggaaaaagc catcgccgct atcacgcgtc tgtcgatgga tatcggtatt   1020
ccgcagcatc tgcgcgatct gggagtaaaa gaggccgact tcccctacat ggcggagatg   1080
gctctgaaag acggcaatgc gttctcgaac ccgcgtaaag caacgagca ggagattgcc    1140 gcgattttcc gccaggcatt ctga                                          1164

<210> SEQ ID NO 70
<211> LENGTH: 387
<212> TYPE: PRT
<213> ORGANISM: Klebsiella pneumoniae

<400> SEQUENCE: 70
```

Met Ser Tyr Arg Met Phe Asp Tyr Leu Val Pro Asn Val Asn Phe
1               5                   10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Met Gln Ala Ile
    210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Leu Met Gly Glu Asn Ile Thr Gly Leu Ser Thr
305                 310                 315                 320

```
Leu Asp Ala Ala Glu Lys Ala Ile Ala Ala Ile Thr Arg Leu Ser Met
            325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
    370                 375                 380

Gln Ala Phe
385

<210> SEQ ID NO 71
<211> LENGTH: 1824
<212> TYPE: DNA
<213> ORGANISM: Klebsiella pneumoniae

<400> SEQUENCE: 71
atgccgttaa tagccgggat tgatatcggc aacgccacca ccgaggtggc gctggcgtcc      60
gactacccgc aggcgagggc gtttgttgcc agcgggatcg tcgcgacgac gggcatgaaa     120
gggacgcggg acaatatcgc cgggaccctc gccgcgctgg agcaggccct ggcgaaaaca     180
ccgtggtcga tgagcgatgt ctctcgcatc tatcttaacg aagccgcgcc ggtgattggc     240
gatgtgcgat ggagaccat caccgagacc attatcaccg aatcgaccat gatcggtcat     300
aacccgcaga cgccgggcgg ggtgggcgtt ggcgtgggga cgactatcgc cctcgggcgg     360
ctggcgacgt gccggcggc gcagtatgcc gaggggtgga tcgtactgat tgacgacgcc     420
gtcgatttcc ttgacgccgt gtggtggctc aatgaggcgc tcgaccgggg gatcaacgtg     480
gtggcggcga tcctcaaaaa ggacgacggc gtgctggtga caaccgcct gcgtaaaacc     540 ctgccggtgg tggatgaagt gacgctgctg agcaggtcc ccgagggggt aatggcggcg     600
gtggaagtgg ccgcgccggg ccaggtggtg cggatcctgt cgaatcccta cgggatcgcc     660
accttcttcg ggctaagccc ggaagagacc caggccatcg tccccatcgc ccgcgccctg     720
attggcaacc gttccgcggt ggtgctcaag accccgcagg gggatgtgca gtcgcgggtg     780
atcccggcgg gcaacctcta cattagcggc gaaaagcgcc gcggagaggc cgatgtcgcc     840
gagggcgcgg aagccatcat gcaggcgatg agcgcctgcg ctccggtacg cgacatccgc     900
ggcgaaccgg gcacccacgc cggcggcatg cttgagcggg tgcgcaaggt aatggcgtcc     960
ctgaccggcc atgagatgag cgcgatatac atccaggatc tgctggcggt ggatacgttt    1020
attccgcgca aggtgcaggg cggatggcc ggcgagtgcg ccatggagaa tgccgtcggg    1080
atggcggcga tggtgaaagc ggatcgtctg caaatgcagg ttatcgcccg cgaactgagc    1140
gcccgactgc agaccgaggt ggtggtgggc ggcgtggagg ccaacatggc catcgccggg    1200
gcgttaacca ctcccggctg tgcggcgccg ctggcgatcc tcgacctcgg cgccggctcg    1260
acggatgcgg cgatcgtcaa cgcggagggg cagataacgg cggtccatct cgccggggcg    1320
gggaatatgg tcagcctgtt gattaaaacc gagctgggcc tcgaggatct ttcgctggcg    1380
gaagcgataa aaaatacccc gctggccaaa gtggaaagcc tgttcagtat tcgtcacgag    1440
aatggcgcgg tggagttctt tcgggaagcc ctcagcccgg cggtgttcgc caaagtggtg    1500
tacatcaagg agggcgaact ggtgccgatc gataacgcca gcccgctgga aaaaattcgt    1560
ctcgtgcgcc ggcaggcgaa agagaaagtg tttgtcacca actgcctgcg cgcgctgcgc    1620
caggtctcac ccgcggttc cattcgcgat atcgcctttg tggtgctggt gggcggctca    1680
tcgctggact ttgagatccc gcagcttatc acggaagcct tgtcgcacta tggcgtggtc    1740
```

| gccgggcagg gcaatattcg gggaacagaa gggccgcgca atgcggtcgc caccgggctg | 1800 |
| ctactggccg gtcaggcgaa ttaa | 1824 |

<210> SEQ ID NO 72
<211> LENGTH: 13669
<212> TYPE: DNA
<213> ORGANISM: Artificial Sequence
<220> FEATURE:
<223> OTHER INFORMATION: Plasmid

<400> SEQUENCE: 72

| tagtaaagcc ctcgctagat tttaatgcgg atgttgcgat tacttcgcca actattgcga | 60 |
| taacaagaaa aagccagcct ttcatgatat atctcccaat ttgtgtaggg cttattatgc | 120 |
| acgcttaaaa ataataaaag cagacttgac ctgatagttt ggctgtgagc aattatgtgc | 180 |
| ttagtgcatc taacgcttga gttaagccgc gccgcgaagc ggcgtcggct tgaacgaatt | 240 |
| gttagacatt atttgccgac taccttggtg atctcgcctt tcacgtagtg acaaattct | 300 |
| tccaactgat ctgcgcgcga ggccaagcga tcttcttctt gtccaagata agcctgtcta | 360 |
| gcttcaagta tgacgggctg atactgggcc ggcaggcgct ccattgccca gtcggcagcg | 420 |
| acatccttcg gcgcgatttt gccggttact gcgctgtacc aaatgcggga caacgtaagc | 480 |
| actcatttc gctcatcgcc agcccagtcg ggcggcgagt tccatagcgt taaggtttca | 540 |
| tttagcgcct caaatagatc ctgttcagga accggatcaa agagttcctc cgccgctgga | 600 |
| cctaccaagg caacgctatg ttctcttgct tttgtcagca agatagccag atcaatgtcg | 660 |
| atcgtggctg gctcgaagat acctgcaaga atgtcattgc gctgccattc tccaaattgc | 720 |
| agttcgcgct tagctggata cgccacggaa tgatgtcgt cgtgcacaac aatggtgact | 780 |
| tctacagcgc ggagaatctc gctctctcca ggggaagccg aagtttccaa aaggtcgttg | 840 |
| atcaaagctc gccgcgttgt ttcatcaagc cttacggtca ccgtaaccag caaatcaata | 900 |
| tcactgtgtg gcttcaggcc gccatccact gcggagccgt acaaatgtac ggccagcaac | 960 |
| gtcggttcga gatggcgctc gatgacgcca actacctctg atagttgagt cgatacttcg | 1020 |
| gcgatcaccg cttccctcat gatgtttaac tttgttttag ggcgactgcc ctgctgcgta | 1080 |
| acatcgttgc tgctccataa catcaaacat cgacccacgg cgtaacgcgc ttgctgcttg | 1140 |
| gatgcccgag gcatagactg taccccaaaa aaacagtcat aacaagccat gaaaaccgcc | 1200 |
| actgcgccgt taccaccgct gcgttcggtc aaggttctgg accagttgcg tgagcgcata | 1260 |
| cgctacttgc attacagctt acgaaccgaa caggcttatg tccactgggt tcgtgccttc | 1320 |
| atccgtttcc acggtgtgcg tcacccggca accttgggca gcagcgaagt cgaggcattt | 1380 |
| ctgtcctggc tggcgaacga gcgcaaggtt tcggtctcca cgcatcgtca ggcattggcg | 1440 |
| gccttgctgt tcttctacgg caaggtgctg tgcacggatc tgccctggct tcaggagatc | 1500 |
| ggaagacctc ggccgtcgcg gcgcttgccg gtggtgctga ccccggatga agtggttcgc | 1560 |
| atcctcggtt ttctggaagg cgagcatcgt ttgttcgccc agcttctgta tggaacgggc | 1620 |
| atgcggatca gtgagggttt gcaactgcgg gtcaaggatc tggatttcga tcacggcacg | 1680 |
| atcatcgtgc gggagggcaa gggctccaag gatcgggcct tgatgttacc cgagagcttg | 1740 |
| gcacccagcc tgcgcgagca ggggaattaa ttcccacggg ttttgctgcc cgcaaacggg | 1800 |
| ctgttctggt gttgctagtt tgttatcaga atcgcagatc cggcttcagc cggtttgccg | 1860 |
| gctgaaagcg ctatttcttc cagaattgcc atgattttt ccccacggga ggcgtcactg | 1920 |
| gctcccgtgt tgtcggcagc tttgattcga taagcagcat cgcctgtttc aggctgtcta | 1980 |

```
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgttttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttctttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttttcgct tgagaacttg   2940 gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtccttttt cctttgagtt gtgggtatct gtaaattctg ctagacctttt   3360 gctggaaaac ttgtaaattc tgctagaccc tctgtaaatt ccgctagacc tttgtgtgtt   3420
ttttttgttt atattcaagt ggttataatt tatagaataa agaaagaata aaaaagata   3480 aaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgacttttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
```

```
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac aacagcgaa ttattatttt tggcggcggc    4560
ctgccagtta ttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacggaggc ggtgacgccg ctgcgctggg cgccctgcg gccagaagct    4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca cgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc    5700 tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagcccctt tgaccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcg ctgcagaaga    6300 tgcgtgcccg ccggacccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacgcacc gaagcggtat    6600 ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
```

```
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttct  ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacgcag  caacgagatg ccgccgcgta    7260
acgtggtgga ggatctgagt gcggtggaag agatgatgaa cgcaacatc  accggcctcg    7320 atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620 tgaaacccg  cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg agacctacc     7980 ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt ttgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccgggga  tcaacgtggt ggcggcgatc ctcaaaaagg acgacggcgt    9120
gctggtgaac aaccgcctgc gtaaaaccct gccggtggtg gatgaagtga cgctgctgga    9180
```

```
gcaggtcccc gaggggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca agtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc ttttttcttg  10500
tctagagtac tggcgaaagg gggatgtgct gcaaggcgat taagttgggt aacgccaggg  10560
ttttcccagt cacgacgttg taaaacgacg gccagtgaat tcgagctcgg tacccggggc  10620
ggccgcgcta gcgcccgatc cagctggagt ttgtagaaac gcaaaaaggc catccgtcag  10680
gatggccttc tgcttaattt gatgcctggc agtttatggc gggcgtcctg cccgccaccc  10740
tccgggccgt tgcttcgcaa cgttcaaatc cgctcccggc ggatttgtcc tactcaggag  10800
agcgttcacc gacaaacaac agataaaacg aaaggcccag tctttcgact gagcctttcg  10860
ttttatttga tgcctggcag ttccctactc tcgcatgggg agaccccaca ctaccatcgg  10920
cgctacggcg tttcacttct gagttcggca tggggtcagg tgggaccacc gcgctactgc  10980
cgccaggcaa attctgtttt atcagaccgc ttctgcgttc tgatttaatc tgtatcaggc  11040
tgaaaatctt ctctcatccg ccaaaacagc caagcttgca tgcctgcagc ccgggttacc  11100
atttcaacag atcgtcctta gcatataagt agtcgtcaaa aatgaattca acttcgtctg  11160
tttcggcatt gtagccgcca actctgatgg attcgtggtt tttgacaatg atgtcacagc  11220
cttttttcctt taggaagtcc aagtcgaaag tagtggcaat accaatgatc ttacaaccgg  11280
cggcttttcc ggcggcaata cctgctggag cgtcttcaaa tactactacc ttagatttgg  11340
aagggtcttg ctcattgatc ggatatccta agcattcct gccttcaga tatggttctg  11400
gatgaggctt accctgtttg acatcattag cggtaatgaa gtactttggt ctcctgattc  11460
ccagatgctc gaaccatttt tgtgccatat cacgggtacc ggaagttgcc acagcccatt  11520
tctctttttgg tagagcgttc aaagcgttgc acagcttaac tgcacctggg acttcaatgg  11580
```

```
atttttcacc gtacttgacc ggaatttcag cttctaattt gttaacatac tcttcattgg   11640
caaagtctgg agcgaactta gcaatggcat caaacgttct ccaaccatgc gagacttgga   11700
taacgtgttc agcatcgaaa taaggtttgt ccttaccgaa atccctccag aatgcagcaa   11760
tggctggttg agagatgata atggtaccgt cgacgtcgaa caaagcggcg ttaactttca   11820
aagatagagg tttagtagtc aatcccataa ttctagtctg tttcctggat ccaataaatc   11880
taatcttcat gtagatctaa ttcttcaatc atgtccggca ggttcttcat tgggtagttg   11940
ttgtaaacga tttggtatac ggcttcaaat aatgggaagt cttcgacaga gccacatgtt   12000
tccaaccatt cgtgaacttc tttgcaggta attaaacctt gagcggattg gccattcaac   12060 aactccttt  cacattccca ggcgtcctta ccagaagtag ccattagcct agcaaccttg   12120
acgtttctac caccagcgca ggtggtgatc aaatcagcaa caccagcaga ctcttggtag   12180
tatgtttctt ctctagattc tgggaaaaac atttgaccga atctgatgat ctcacccaaa   12240
ccgactcttt ggatggcagc agaagcgttg ttaccccagc ctagaccttc gacgaaacca   12300
caacctaagg caacaacgtt cttcaaagca ccacagatgg agataccagc aacatcttcg   12360
atgacactaa cgtggaagta aggtctgtgg aacaaggcct ttagaacctt atggtcgacg   12420
tccttgccct cgcctctgaa atcctttgga atgtggtaag caactgttgt ttcagaccag   12480
tgttcttgag cgacttcggt ggcaatgtta gcaccagata gagcaccaca ttgaatacct   12540
agttcctcag tgatgtaaga ggatagcaat tggacacctt agcaccaac  ttcaaaaccc   12600 tttagacagg agatagctct gacgtgtgaa tcaacatgac cttcaattg  gctacagata   12660 cggggcaaaa attgatgtgg aatgttgaaa acgatgatgt cgacatcctt gactgaatca   12720
atcaagtctg gattagcaac caaattgtcg ggtagagtga tgccaggcaa gtatttcacg   12780
ttttgatgtc tagtatttat gatttcagtc aattttttcac cattgatctc ttcttcgaac   12840
acccacattt gtactattgg agcgaaaact tctgggtatc ccttacaatt ttcggcaacc   12900
accttggcaa tagtagtacc ccagttacca gatccaatca cagtaacctt gaaaggcttt   12960
tcggcagcct tcaaagaaac agaagaggaa cttctctttc taccagcatt caagtggccg   13020
gaagttaagt ttaatctatc agcagcagca gccatggaat tgtcctcctt actagtcatg   13080
gtctgtttcc tgtgtgaaat tgttatccgc tcacaattcc acacattata cgagccggat   13140
gattaattgt caacagctca tttcagaata tttgccagaa ccgttatgat gtcggcgcaa   13200
aaaacattat ccagaacggg agtgcgcctt gagcgacacg aattatgcag tgatttacga   13260
cctgcacagc cataccacag cttccgatgg ctgcctgacg ccagaagcat tggtgcacgc   13320
tagccagtac atttaaatgg taccctctag tcaaggcctt aagtgagtcg tattacggac   13380
tggccgtcgt tttacaacgt cgtgactggg aaaaccctgg cgttacccaa cttaatcgcc   13440
ttgcagcaca tcccccttc  gccagctggg gtaatagcga agaggcccgc accgatcgcc   13500
cttcccaaca gttgcgcagc ctgaatggcg aatggcgcct gatgcggtat tttctcctta   13560
cgcatctgtg cggtatttca caccgcatat ggtgcactct cagtacaatc tgctctgatg   13620
ccgcatagtt aagccagccc cgacacccgc caacacccgc tgacgagct                13669
```

<210> SEQ ID NO 73
<211> LENGTH: 13543
<212> TYPE: DNA
<213> ORGANISM: Artificial Sequence
<220> FEATURE:
<223> OTHER INFORMATION: Plasmid

<400> SEQUENCE: 73

-continued

```
tagtaaagcc ctcgctagat tttaatgcgg atgttgcgat tacttcgcca actattgcga    60
taacaagaaa aagccagcct ttcatgatat atctcccaat ttgtgtaggg cttattatgc   120
acgcttaaaa ataataaaag cagacttgac ctgatagttt ggctgtgagc aattatgtgc   180
ttagtgcatc taacgcttga gttaagccgc gccgcgaagc ggcgtcggct tgaacgaatt   240
gttagacatt atttgccgac taccttggtg atctcgcctt tcacgtagtg gacaaattct   300
tccaactgat ctgcgcgcga ggccaagcga tcttcttctt gtccaagata agcctgtcta   360
gcttcaagta tgacgggctg atactgggcc ggcaggcgct ccattgccca gtcggcagcg   420
acatccttcg gcgcgatttt gccggttact gcgctgtacc aaatgcggga caacgtaagc   480
actacatttc gctcatcgcc agcccagtcg ggcggcgagt tccatagcgt taaggtttca   540
tttagcgcct caaatagatc ctgttcagga accggatcaa agagttcctc cgccgctgga   600
cctaccaagg caacgctatg ttctcttgct tttgtcagca agatagccag atcaatgtcg   660
atcgtggctg gctcgaagat acctgcaaga atgtcattgc gctgccattc tccaaattgc   720
agttcgcgct tagctggata acgccacgga atgatgtcgt cgtgcacaac aatggtgact   780
tctacagcgc ggagaatctc gctctctcca ggggaagccg aagtttccaa aaggtcgttg   840
atcaaagctc gccgcgttgt ttcatcaagc cttacggtca ccgtaaccag caaatcaata   900
tcactgtgtg gcttcaggcc gccatccact gcggagccgc acaaatgtac ggccagcaac   960
gtcggttcga gatggcgctc gatgacgcca actacctctg atagttgagt cgatacttcg  1020
gcgatcaccg cttccctcat gatgtttaac tttgttttag ggcgactgcc ctgctgcgta  1080
acatcgttgc tgctccataa catcaaacat cgacccacgg cgtaacgcgc ttgctgcttg  1140
gatgcccgag gcatagactg taccccaaaa aaacagtcat aacaagccat gaaaaccgcc  1200
actgcgccgt taccaccgct gcgttcggtc aaggttctgg accagttgcg tgagcgcata  1260
cgctacttgc attacagctt acgaaccgaa caggcttatg tccactgggt tcgtgccttc  1320
atccgtttcc acggtgtgcg tcacccggca accttgggca gcagcgaagt cgaggcattt  1380
ctgtcctggc tggcgaacga gcgcaaggtt tcggtctcca cgcatcgtca ggcattggcg  1440
gccttgctgt tcttctacgg caaggtgctg tgcacggatc tgccctggct tcaggagatc  1500
ggaagacctc ggccgtcgcg gcgcttgccg gtggtgctga ccccggatga agtggttcgc  1560
atcctcggtt ttctggaagg cgagcatcgt tgttcgccc agcttctgta tggaacgggc  1620
atgcggatca gtgagggttt gcaactgcgg gtcaaggatc tggatttcga tcacggcacg  1680
atcatcgtgc gggagggcaa gggctccaag gatcgggcct tgatgttacc cgagagcttg  1740
gcacccagcc tgcgcgagca ggggaattaa ttcccacggg ttttgctgcc cgcaaacggg  1800
ctgttctggt gttgctagtt tgttatcaga atcgcagatc cggcttcagc cggtttgccg  1860
gctgaaagcg ctatttcttc cagaattgcc atgatttttt ccccacggga ggcgtcactg  1920
gctcccgtgt tgtcggcagc tttgattcga taagcagcat cgcctgtttc aggctgtcta  1980
tgtgtgactg ttgagctgta acaagttgtc tcaggtgttc aatttcatgt tctagttgct  2040
ttgtttact ggtttcacct gttctattag gtgttacatg ctgttcatct gttacattgt   2100
cgatctgttc atggtgaaca gctttgaatg caccaaaaac tcgtaaaagc tctgatgtat  2160
ctatctttt tacaccgttt tcatctgtgc atatggacag ttttcccttt gatatgtaac   2220
ggtgaacagt tgttctactt ttgtttgtta gtcttgatgc ttcactgata gatacaagag  2280
ccataagaac ctcagatcct tccgtattta gccagtatgt tctctagtgt ggttcgttgt  2340
ttttgcgtga gccatgagaa cgaaccattg agatcatact tactttgcat gtcactcaaa  2400
```

```
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact     2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttttcgct tgagaacttg   2940 gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg gctagtcaa     3300 tgataattac tagtccttttt cctttgagtt gtgggtatct gtaaattctg ctagacctttt  3360 gctggaaaac ttgtaaattc tgctagaccc tctgtaaatt ccgctagacc tttgtgtgtt    3420 tttttttgttt atattcaagt ggttataatt tatagaataa agaagaata aaaaaagata    3480 aaagaatag atcccagccc tgtgtataac tcactacttt agtcagttcc gcagtattac     3540
aaaaggatgt cgcaaacgct gtttgctcct ctacaaaaca gaccttaaaa ccctaaaggc    3600
ttaagtagca ccctcgcaag ctcgggcaaa tcgctgaata ttcctttttgt ctccgaccat   3660 caggcacctg agtcgctgtc ttttttcgtga cattcagttc gctgcgctca cggctctggc   3720
agtgaatggg ggtaaatggc actacaggcg cctttttatgg attcatgcaa ggaaactacc   3780
cataatacaa gaaaagcccg tcacgggctt tcagggcgt tttatggcgg gtctgctatg    3840
tggtgctatc tgacttttttg ctgttcagca gttcctgccc tctgattttc cagtctgacc   3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga ctatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atattcccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
```

```
atgccggcgc catcaatgag ctgtgctggg ggctggagga gcaggggtc ccctgccaga    4860
ccataaccta tgacggaggc ggtgacgccg ctgcgctggg cgccctggcg gccagaagct    4920
cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc    5700
tgtgctgttt gccacggtat gcagcaccag cgcgagatta tgggctcgca cgctcgactg    5760
tcggacgggg gcactggaac gagaagtcag gcgagccgtc acgcccttga ctatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgcggccaa    6240
aagcggtcga ggtgatggcg cagatgaacg tggtggagat gatgatggcg ctgcagaaga    6300
tgcgtgcccg ccgacccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta cgcccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc acctgatgc    6960
agatgctgcc gggcaccgac tttattttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga gcggaaaacc attgccattc    7140
gccagaaagc ggcgcgggcg atccaggcgg ttttccgcga gctggggctg ccgccaatcg    7200
```

```
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620
tgaaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cggtggtgc     7800 gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220 cccgagcat atcctgacgc ctaccggcaa accattgacc gatattaccc tcgagaaggt    8280
gctctctggc gaggtgggcc gcaggatgt gcggatctcc cgccagaccc ttgagtacca     8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgccttg tccgggagtc ggcggaagtg tatcagcagc ggcataagct     8580
gcgtaaagga agctaagcgg aggtcagcat gccgttaata gccgggattg atatcggcaa    8640
cgccaccacc gaggtggcgc tggcgtccga ctaccgcag gcgagggcgt tgttgccag      8700 cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccggcggg tgggcgttgg      8940 cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gaggggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
```

```
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca agtggtgta catcaaggag ggcgaactgg tgccgatcga   10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc ttttttcttg  10500
tctagcgtgc accaatgctt ctggcgtcag gcagccatcg gaagctgtgg tatggctgtg  10560
caggtcgtaa atcactgcat aattcgtgtc gctcaaggcg cactcccgtt ctggataatg  10620
ttttttgcgc cgacatcata acggttctgg caaatattct gaaatgagct gttgacaatt  10680
aatcatccgg ctcgtataat gtgtggaatt gtgagcggat aacaatttca cacaggaaac  10740
agaccatgac tagtaaggag gacaattcca tggctgctgc tgctgataga ttaaacttaa  10800
cttccggcca cttgaatgct ggtagaaaga gaagttcctc ttctgttttct ttgaaggctg  10860 ccgaaaagcc tttcaaggtt actgtgattg gatctggtaa ctggggtact actattgcca  10920
aggtggttgc cgaaaattgt aagggatacc agaagttttt cgctccaata gtacaaatgt  10980
gggtgttcga agaagagatc aatggtgaaa aattgactga atcataaat actagacatc  11040 aaaacgtgaa atacttgcct ggcatcactc tacccgacaa tttggttgct aatccagact  11100
tgattgattc agtcaaggat gtcgacatca tcgttttcaa cattccacat caattttgc  11160 cccgtatctg tagccaattg aaaggtcatg ttgattcaca cgtcagagct atctcctgtc  11220
taaagggttt tgaagttggt gctaaaggtg tccaattgct atcctcttac atcactgagg  11280
aactaggtat tcaatgtggt gctctatctg gtgctaacat tgccaccgaa gtcgctcaag  11340
aacactggtc tgaaacaaca gttgcttacc acattccaaa ggatttcaga ggcgagggca  11400
aggacgtcga ccataaggtt ctaaaggcct tgttccacag accttacttc cacgttagtg  11460
tcatcgaaga tgttgctggt atctccatct gtggtgcttt gaagaacgtt gttgccttag  11520
gttgtggttt cgtcgaaggt ctaggctggg gtaacaacgc ttctgctgcc atccaaagag  11580
tcggtttggg tgagatcatc agattcggtc aaatgtttt cccagaatct agagaagaaa  11640
catactacca agagtctgct ggtgttgctg atttgatcac cacctgcgct ggtggtagaa  11700
acgtcaaggt tgctaggcta atggctactt ctggtaagga cgcctgggaa tgtgaaaagg  11760
agttgttgaa tggccaatcc gctcaaggtt taattacctg caaagaagtt cacgaatggt  11820
tggaaacatg tggctctgtc gaagacttcc cattatttga agccgtatac caaatcgttt  11880
acaacaacta cccaatgaag aacctgccgg acatgattga agaattagat ctacatgaag  11940
attagattta ttggatccag gaaacagact agaattatgg gattgactac taaacctcta  12000
```

```
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
aaatccattg aagtcccagg tgcagttaag ctgtgcaacg ctttgaacgc tctaccaaaa   12300
gagaaatggg ctgtggcaac ttccggtacc cgtgatatgg cacaaaaatg gttcgagcat   12360
ctgggaatca ggagaccaaa gtacttcatt accgctaatg atgtcaaaca gggtaagcct   12420
catccagaac catatctgaa gggcaggaat ggcttaggat atccgatcaa tgagcaagac   12480
ccttccaaat ctaaggtagt agtatttgaa gacgctccag caggtattgc cgccggaaaa   12540
gccgccggtt gtaagatcat tggtattgcc actactttcg acttggactt cctaaaggaa   12600
aaaggctgtg acatcattgt caaaaaccac gaatccatca gagttggcgg ctacaatgcc   12660
gaaacagacg aagttgaatt cattttttgac gactacttat atgctaagga cgatctgttg   12720
aaatggtaac ccgggctgca ggcatgcaag cttggctgtt ttggcggatg agagaagatt   12780
ttcagcctga tacagattaa atcagaacgc agaagcggtc tgataaaaca gaatttgcct   12840
ggcggcagta gcgcggtggt cccacctgac cccatgccga actcagaagt gaaacgccgt   12900
agcgccgatg gtagtgtggg gtctccccat gcgagagtag ggaactgcca ggcatcaaat   12960
aaaacgaaag gctcagtcga aagactgggc ctttcgtttt atctgttgtt tgtcggtgaa   13020
cgctctcctg agtaggacaa atccgccggg agcggatttg aacgttgcga agcaacggcc   13080
cggagggtgg cgggcaggac gcccgccata aactgccagg catcaaatta gcagaaggc   13140 catcctgacg gatggccttt ttgcgtttct acaaactcca gctggatcgg cgctagagt   13200 atacatttaa atggtaccct ctagtcaagg ccttaagtga gtcgtattac ggactggccg   13260
tcgttttaca acgtcgtgac tgggaaaacc ctggcgttac ccaacttaat cgccttgcag   13320
cacatccccc tttcgccagc tggcgtaata gcgaagaggc ccgcaccgat cgcccttccc   13380
aacagttgcg cagcctgaat ggcgaatggc gcctgatgcg gtattttctc cttacgcatc   13440
tgtgcggtat ttcacaccgc atatggtgca ctctcagtac aatctgctct gatgccgcat   13500
agttaagcca gccccgacac ccgccaacac ccgctgacga gct                     13543
```

<210> SEQ ID NO 74
<211> LENGTH: 13543
<212> TYPE: DNA
<213> ORGANISM: Artificial Sequence
<220> FEATURE:
<223> OTHER INFORMATION: Plasmid

<400> SEQUENCE: 74

```
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg gacaaattct    300
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
```

```
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg tacccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgtttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtattt gtcaccattc   2520
attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgtttta aatctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttcgct tgagaacttg    2940
```

```
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagacctttt   3360 gctggaaaac ttgtaaattc tgctagaccc tctgtaaatt ccgctagacc tttgtgtgtt    3420
ttttttgttt atattcaagt ggttataatt tatagaataa agaaagaata aaaaagata    3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttttcgtga cattcagttc gctgcgctca cggctctggc   3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttttg ctgttcagca gttcctgccc tctgattttc cagtctgacc   3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcacccct ggccgccgcc cagcaaatgg cggcggcggt ggaaaaaaaa   4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacggaggc ggtgacgccg ctgcgctggg cgccctggcg gccagaagct    4920 cgccctgcg ggtgggtatc gggctcagcc cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
```

```
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcaagagac taggcctga tgcttgcgct tgaactggcc   5640
tagcaaacac agaaaaaagc ccgcacctga cagtgcgggc tttttttttc ctaggcgatc   5700
tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940
gccccgtcaa tcaggacggg ctgattggcg agtggcctga agagggctg atcgccatgg   6000 acagccccct tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatgcg ctgcagaaga   6300 tgcgtgcccg ccggaccccc tccaaccagt gccacgtcac caatctcaaa gataatccgg   6360
tgcagattgc cgctgacgcc gccgaggcg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc accctgatgc   6960
agatgctgcc gggcaccgac tttatttttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct tgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
```

```
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgccttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tgtgggcgg   9780 cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctt ttcagtattc gtcacgagaa tggcgcggtg gagttctttc gggaagccct  10080
cagcccggcg gtgttcgcca aagtggtgta catcaaggag ggcgaactgg tgccgatcga  10140
```

```
taacgccagc ccgctggaaa aaattcgtct cgtgcgccgg caggcgaaag agaaagtgtt    10200
tgtcaccaac tgcctgcgcg cgctgcgcca ggtctcaccc ggcggttcca ttcgcgatat    10260
cgcctttgtg gtgctggtgg gcggctcatc gctggacttt gagatcccgc agcttatcac    10320
ggaagccttg tcgcactatg gcgtggtcgc cgggcagggc aatattcggg gaacagaagg    10380
gccgcgcaat gcggtcgcca ccgggctgct actggccggt caggcgaatt aaacgggcgc    10440
tcgcgccagc ctctaggtac aaataaaaaa ggcacgtcag atgacgtgcc ttttttcttg    10500
tctagcgtgc accaatgctt ctggcgtcag gcagccatcg gaagctgtgg tatggctgtg    10560
caggtcgtaa atcactgcat aattcgtgtc gctcaaggcg cactcccgtt ctggataatg    10620
ttttttgcgc cgacatcata acggttctgg caaatattct gaaatgagct gttgacaatt    10680
aatcatccgg ctcgtataat gtgtggaatt gtgagcggat aacaatttca cacaggaaac    10740
agaccatgac tagtaaggag acaattcca tggctgctgc tgctgataga ttaaacttaa    10800
cttccggcca cttgaatgct ggtagaaaga gaagttcctc ttctgtttct ttgaaggctg    10860
ccgaaaagcc tttcaaggtt actgtgattg gatctggtaa ctggggtact actattgcca    10920
aggtggttgc cgaaaattgt aagggatacc cagaagtttt cgctccaata gtacaaatgt    10980
gggtgttcga agaagagatc aatggtgaaa aattgactga atcataaat actagacatc    11040 aaaacgtgaa atacttgcct ggcatcactc tacccgacaa tttggttgct aatccagact    11100
tgattgattc agtcaaggat gtcgacatca tcgttttcaa cattccacat caattttttgc    11160 cccgtatctg tagccaattg aaaggtcatg ttgattcaca cgtcagagct atctcctgtc    11220
taaagggttt tgaagttggt gctaaaggtg tccaattgct atcctcttac atcactgagg    11280
aactaggtat tcaatgtggt gctctatctg gtgctaacat tgccaccgaa gtcgctcaag    11340
aacactggtc tgaaacaaca gttgcttacc acattccaaa ggatttcaga ggcgagggca    11400
aggacgtcga ccataaggtt ctaaaggcct tgttccacag accttacttc cacgttagtg    11460
tcatcgaaga tgttgctggt atctccatct gtggtgcttt gaagaacgtt gttgccttag    11520
gttgtggttt cgtcgaaggt ctaggctggg gtaacaacgc ttctgctgcc atccaaagag    11580
tcggtttggg tgagatcatc agattcggtc aaatgttttt cccagaatct agagaagaaa    11640
catactacca agagtctgct ggtgttgctg atttgatcac cacctgcgct ggtggtagaa    11700
acgtcaaggt tgctaggcta atggctactt ctggtaagga cgcctgggaa tgtgaaaagg    11760
agttgttgaa tggccaatcc gctcaaggtt taattacctg caaagaagtt cacgaatggt    11820
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta gaagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
```

```
gccgccggtt gtaagatcat tggtattgcc actactttcg acttggactt cctaaaggaa    12600
aaaggctgtg acatcattgt caaaaaccac gaatccatca gagttggcgg ctacaatgcc    12660
gaaacagacg aagttgaatt cattttgac gactacttat atgctaagga cgatctgttg     12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
aaaacgaaag gctcagtcga agactgggc cttccgtttt atctgttgtt tgtcggtgaa     13020
cgctctcctg agtaggacaa atccgccggg agcggatttg aacgttgcga agcaacggcc    13080
cggagggtgg cgggcaggac gcccgccata aactgccagg catcaaatta gcagaaggc     13140 catcctgacg gatggccttt ttgcgtttct acaaactcca gctggatcgg gcgctagagt    13200
atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgcccttccc    13380
aacagttgcg cagcctgaat ggcgaatggc gcctgatgcg gtattttctc cttacgcatc    13440
tgtgcggtat ttcacaccgc atatggtgca ctctcagtac aatctgctct gatgccgcat    13500
agttaagcca gccccgacac ccgccaacac ccgctgacga gct                      13543

<210> SEQ ID NO 75
<211> LENGTH: 13402
<212> TYPE: DNA
<213> ORGANISM: Artificial Sequence
<220> FEATURE:
<223> OTHER INFORMATION: Plamid

<400> SEQUENCE: 75
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg acaaattct     300 tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg    1020
gcgatcaccg cttccctcat gatgtttaac tttgttttag ggcgactgcc ctgctgcgta   1080
```

```
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctgaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgattttt ccccacggga ggcgtcactg    1920
gctcccgtgt tgtcggcagc tttgattcga taagcagcat cgcctgtttc aggctgtcta    1980
tgtgtgactt tgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaagc tctgatgtat    2160 ctatcttttt tacaccgttt tcatctgtgc atatggacag ttttcccttt gatatgtaac    2220
ggtgaacagt tgttctactt tgttttgtta gtccttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520
atttttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta aatctttact tattggttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttcgct tgagaacttg    2940 gcatagtttg tccactggaa aatctcaaag cctttaacca aaggattcct gatttccaca    3000
gttctcgtca tcagctctct ggttgcttta gctaatacac cataagcatt tccctactg    3060 atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgatttaa tcactatacc aattgagatg ggctagtcaa    3300
tgataattac tagtccttt cctttgagtt gtgggtatct gtaaattctg ctagacctt    3360 gctgaaaac ttgtaaattc tgctagaccc tctgtaaatt ccgctagacc tttgtgtgtt    3420
ttttttgttt atattcaagt ggttataatt tatagaataa agaaagaata aaaaaagata    3480
```

-continued

```
aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga cattcagttc gctgcgctca cggctctggc    3720
agtgaatggg ggtaaatggc actacaggcg cctttatgg attcatgcaa ggaaactacc    3780
cataatacaa gaaaagcccg tcacgggctt ctcagggcgt tttatggcgg gtctgctatg    3840
tggtgctatc tgactttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcgacggggg cactggaac gagaagtcag    4140 gcgagccgtc acgcccttga caatgccaca tcctgagcaa ataattcaac cactaaacaa    4200
atcaaccgcg tttccggag gtaaccaagc ttgcgggaga aatgatgaa caagagccaa    4260 caagttcaga caatcaccct ggccgccgcc agcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acgtctgca gctaaccaac caacagcgaa ttattatttt tggcggcggc    4560
ctgccagtta ttttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacggaggc ggtgacgccg ctgcgctggg cgcccggcg gccagaagct    4920 cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcaccctgat gcttgcgctt gaactggcct agcaaacaca gaaaaaagcc    5520
cgcacctgac agtgcgggct ttttttttcc taggcgatct gtgctgtttg ccacggtatg    5580
cagcaccagc gcgagattat gggctcgcac gctcgactgt cggacggggg cactggaacg    5640
agaagtcagg cgagccgtca cgcccttgac aatgccacat cctgagcaaa taattcaacc    5700
actaaacaaa tcaaccgcgt ttccggagg taaccaagct tcacctttg agccgatgaa    5760 caatgaaaag atcaaaacga tttgcagtac tggcccagcg ccccgtcaat caggacgggc    5820
tgattggcga gtggcctgaa gaggggctga tcgccatgga cagccccttt gacccggtct    5880
```

-continued

```
cttcagtaaa agtggacaac ggtctgatcg tcgaactgga cggcaaacgc cgggaccagt    5940
ttgacatgat cgaccgattt atcgccgatt acgcgatcaa cgttgagcgc acagagcagg    6000
caatgcgcct ggaggcggtg gaaatagccc gtatgctggt ggatattcac gtcagccggg    6060
aggagatcat tgccatcact accgccatca cgccggccaa agcggtcgag gtgatggcgc    6120
agatgaacgt ggtggagatg atgatggcgc tgcagaagat gcgtgcccgc cggaccccct    6180
ccaaccagtg ccacgtcacc aatctcaaag ataatccggt gcagattgcc gctgacgccg    6240
ccgaggccgg gatccgcggc ttctcagaac aggagaccac ggtcggtatc gcgcgctacg    6300
cgccgtttaa cgccctggcg ctgttggtcg gttcgcagtg cggccgcccc ggcgtgttga    6360
cgcagtgctc ggtggaagag gccaccgagc tggagctggg catgcgtggc ttaaccagct    6420
acgccgagac ggtgtcggtc tacggcaccg aagcggtatt taccgacggc gatgatacgc    6480
cgtggtcaaa ggcgttcctc gcctcggcct acgcctcccg cgggttgaaa atgcgctaca    6540
cctccggcac cggatccgaa gcgctgatgg gctattcgga gagcaagtcg atgctctacc    6600
tcgaatcgcg ctgcatcttc attactaaag gcgccggggt tcagggactg caaaacggcg    6660
cggtgagctg tatcggcatg accggcgctg tgccgtcggg cattcgggcg gtgctggcgg    6720
aaaacctgat cgcctctatg ctcgacctcg aagtggcgtc cgccaacgac cagactttct    6780
cccactcgga tattcgccgc accgcgcgca ccctgatgca gatgctgccg ggcaccgact    6840
ttattttctc cggctacagc gcggtgccga actacgacaa catgttcgcc ggctcgaact    6900
tcgatgcgga agattttgat gattacaaca tcctgcagcg tgacctgatg gttgacggcg    6960
gcctgcgtcc ggtgaccgag gcggaaacca ttgccattcg ccagaaagcg cgcgggcga    7020 tccaggcggt tttccgcgag ctggggctgc cgccaatcgc cgacgaggag gtggaggccg    7080
ccacctacgc gcacggcagc aacgagatgc cgccgcgtaa cgtggtggag gatctgagtg    7140
cggtggaaga gatgatgaag cgcaacatca ccggcctcga tattgtcggc gcgctgagcc    7200
gcagcggctt tgaggatatc gccagcaata ttctcaatat gctgcgccag cgggtcaccg    7260
gcgattacct gcagacctcg gccattctcg atcggcagtt cgaggtggtg agtgcggtca    7320
acgacatcaa tgactatcag gggccgggca ccggctatcg catctctgcc gaacgctggg    7380
cggagatcaa aaatattccg ggcgtggttc agcccgacac cattgaataa ggcggtattc    7440
ctgtgcaaca gacaacccaa attcagccct cttttaccct gaaaacccgc gagggcgggg    7500
tagcttctgc cgatgaacgc gccgatgaag tggtgatcgg cgtcggccct gccttcgata    7560
aacaccagca tcacactctg atcgatatgc cccatggcgc gatcctcaaa gagctgattg    7620
ccggggtgga agaagagggg cttcacgccc gggtggtgcg cattctgcgc acgtccgacg    7680
tctcctttat ggcctgggat gcggccaacc tgagcggctc ggggatcggc atcggtatcc    7740
agtcgaaggg gaccacggtc atccatcagc gcgatctgct gccgctcagc aacctggagc    7800
tgttctccca ggcgccgctg ctgacgctgg agacctaccg gcagattggc aaaaacgctg    7860
cgcgctatgc gcgcaaagag tcaccttcgc cggtgccggt ggtgaacgat cagatggtgc    7920
ggccgaaatt tatggccaaa gccgcgctat ttcatatcaa agagaccaaa catgtggtgc    7980
aggacgccga gcccgtcacc ctgcacatcg acttagtaag ggagtgacca tgagcgagaa    8040
aaccatgcgc gtgcaggatt atccgttagc caccgctgc ccggagcata tcctgacgcc    8100
taccggcaaa ccattgaccg atattaccct cgagaaggtg ctctctggcg aggtgggccc    8160
gcaggatgtg cggatctccc gccagaccct tgagtaccag gcgcagattg ccgagcagat    8220
gcagcgccat gcggtggcgc gcaatttccg ccgcgcggcg gagcttatcg ccattcctga    8280
```

```
cgagcgcatt ctggctatct ataacgcgct gcgcccgttc cgctcctcgc aggcggagct   8340
gctggcgatc gccgacgagc tggagcacac ctggcatgcg acagtgaatg ccgcctttgt   8400
ccgggagtcg gcggaagtgt atcagcagcg gcataagctg cgtaaaggaa gctaagcgga   8460
ggtcagcatg ccgttaatag ccgggattga tatcggcaac gccaccaccg aggtggcgct   8520
ggcgtccgac tacccgcagg cgagggcgtt tgttgccagc gggatcgtcg cgacgacggg   8580
catgaaaggg acgcgggaca atatcgccgg gaccctcgcc gcgctggagc aggccctggc   8640
gaaaacaccg tggtcgatga gcgatgtctc tcgcatctat cttaacgaag ccgcgccggt   8700
gattggcgat gtggcgatgg agaccatcac cgagaccatt atcaccgaat cgaccatgat   8760
cggtcataac ccgcagacgc cgggcggggt gggcgttggc gtggggacga ctatcgccct   8820
cgggcggctg gcgacgctgc cggcggcgca gtatgccgag gggtggatcg tactgattga   8880
cgacgccgtc gatttccttg acgccgtgtg gtggctcaat gaggcgctcg accgggggat   8940
caacgtggtg gcggcgatcc tcaaaaagga cgacggcgtg ctggtgaaca accgcctgcg   9000 taaaccctg ccggtggtgg atgaagtgac gctgctggag caggtccccg aggggtaat    9060 ggcggcggtg gaagtggccg cgccgggcca ggtggtgcgg atcctgtcga atccctacgg   9120
gatcgccacc ttcttcgggc taagcccgga agagacccag gccatcgtcc ccatcgcccg   9180
cgccctgatt ggcaaccgtt ccggcggtggt gctcaagacc ccgcagggg atgtgcagtc   9240 gcgggtgatc ccggcgggca acctctacat tagcggcgaa aagcgccgcg gagaggccga   9300
tgtcgccgag ggcgcggaag ccatcatgca ggcgatgagc cctgcgctc cggtacgcga   9360 catccgcggc gaaccgggca cccacgccgg cggcatgctt gagcgggtgc gcaaggtaat   9420
ggcgtccctg accggccatg agatgagcgc gatatacatc caggatctgc tggcggtgga   9480
tacgtttatt ccgcgcaagg tgcagggcgg gatggccggc gagtgcgcca tggagaatgc   9540
cgtcgggatg gcggcgatgg tgaaagcgga tcgtctgcaa atgcaggtta tcgcccgcga   9600
actgagcgcc cgactgcaga ccgaggtggt ggtgggcggc gtggaggcca acatggccat   9660
cgccggggcg ttaaccactc ccggctgtgc ggcgccgctg gcgatcctcg acctcggcgc   9720
cggctcgacg gatgcggcga tcgtcaacgc ggaggggcag ataacggcgg tccatctcgc   9780
cggggcgggg aatatggtca gcctgttgat taaaaccgag ctgggcctcg aggatctttc   9840
gctggcggaa gcgataaaaa aatacccgct ggccaaagtg gaaagcctgt tcagtattcg   9900
tcacgagaat ggcgcggtgg agttctttcg ggaagccctc agcccggcgg tgttcgccaa   9960
agtggtgtac atcaaggagg gcgaactggt gccgatcgat aacgccagcc cgctggaaaa  10020
aattcgtctc gtgcgccggc aggcgaaaga gaaagtgttt gtcaccaact gcctgcgcgc  10080
gctgcgccag gtctcacccg gcggttccat tcgcgatatc gcctttgtgg tgctggtggg  10140
cggctcatcg ctggactttg agatcccgca gcttatcacg gaagccttgt cgcactatgg  10200
cgtggtcgcc gggcagggca atattcgggg aacagaaggg ccgcgcaatg cggtcgccac  10260
cgggctgcta ctggccggtc aggcgaatta acgggcgct cgcgccagcc tctaggtaca  10320
aataaaaaag gcacgtcaga tgacgtgcct tttttcttgt ctagcgtgca ccaatgcttc  10380
tggcgtcagg cagccatcgg aagctgtggt atggctgtgc aggtcgtaaa tcactgcata  10440
attcgtgtcg ctcaaggcgc actccgttc tggataatgt ttttgcgcc gacatcataa   10500 cggttctggc aaatattctg aaatgagctg ttgacaatta atcatccggc tcgtataatg  10560
tgtggaattg tgagcggata acaatttcac acaggaaaca gaccatgact agtaaggagg  10620
acaattccat ggctgctgct gctgatagat taaacttaac ttccggccac ttgaatgctg  10680
```

```
gtagaaagag aagttcctct tctgtttctt tgaaggctgc cgaaaagcct ttcaaggtta   10740
ctgtgattgg atctggtaac tggggtacta ctattgccaa ggtggttgcc gaaaattgta   10800
agggataccc agaagttttc gctccaatag tacaaatgtg ggtgttcgaa gaagagatca   10860
atggtgaaaa attgactgaa atcataaata ctagacatca aaacgtgaaa tacttgcctg   10920
gcatcactct acccgacaat ttggttgcta atccagactt gattgattca gtcaaggatg   10980
tcgacatcat cgttttcaac attccacatc aattttttgcc ccgtatctgt agccaattga   11040
aaggtcatgt tgattcacac gtcagagcta tctcctgtct aaagggtttt gaagttggtg   11100
ctaaaggtgt ccaattgcta tcctcttaca tcactgagga actaggtatt caatgtggtg   11160
ctctatctgg tgctaacatt gccaccgaag tcgctcaaga acactggtct gaaacaacag   11220
ttgcttacca cattccaaag gatttcagag gcgagggcaa ggacgtcgac cataaggttc   11280
taaaggcctt gttccacaga ccttacttcc acgttagtgt catcgaagat gttgctggta   11340
tctccatctg tggtgctttg aagaacgttg ttgccttagg ttgtggtttc gtcgaaggtc   11400
taggctgggg taacaacgct tctgctgcca tccaaagagt cggtttgggt gagatcatca   11460
gattcggtca aatgtttttc ccagaatcta gagaagaaac atactaccaa gagtctgctg   11520
gtgttgctga tttgatcacc acctgcgctg gtggtagaaa cgtcaaggtt gctaggctaa   11580
tggctacttc tggtaaggac gcctgggaat gtgaaaagga gttgttgaat ggccaatccg   11640
ctcaaggttt aattacctgc aaagaagttc acgaatggtt ggaaacatgt ggctctgtcg   11700
aagacttccc attatttgaa gccgtatacc aaatcgttta caacaactac ccaatgaaga   11760
acctgccgga catgattgaa gaattagatc tacatgaaga ttagatttat tggatccagg   11820
aaacagacta gaattatggg attgactact aaacctctat ctttgaaagt taacgccgct   11880
ttgttcgacg tcgacggtac cattatcatc tctcaaccag ccattgctgc attctggagg   11940
gatttcggta aggacaaacc ttatttcgat gctgaacacg ttatccaagt ctcgcatggt   12000
tggagaacgt ttgatgccat tgctaagttc gctccagact ttgccaatga agagtatgtt   12060
aacaaattag aagctgaaat tccggtcaag tacggtgaaa aatccattga agtcccaggt   12120
gcagttaagc tgtgcaacgc tttgaacgct ctaccaaaag agaaatgggc tgtggcaact   12180
tccggtaccc gtgatatggc acaaaaatgg ttcgagcatc tgggaatcag gagaccaaag   12240
tacttcatta ccgctaatga tgtcaaacag ggtaagcctc atccagaacc atatctgaag   12300
ggcaggaatg gcttaggata tccgatcaat gagcaagacc cttccaaatc taaggtagta   12360
gtatttgaag acgctccagc aggtattgcc gccggaaaag ccgccggttg taagatcatt   12420
ggtattgcca ctactttcga cttggacttc ctaaaggaaa aaggctgtga catcattgtc   12480
aaaaaccacg aatccatcag agttggcggc tacaatgccg aaacagacga agttgaattc   12540 attttttgacg actacttata tgctaaggac gatctgttga atggtaacc cgggctgcag   12600 gcatgcaagc ttggctgttt tggcggatga gagaagattt tcagcctgat acagattaaa   12660
tcagaacgca gaagcggtct gataaaacag aatttgcctg gcggcagtag cgcggtggtc   12720
ccacctgacc ccatgccgaa ctcagaagtg aaacgccgta gcgccgatgg tagtgtgggg   12780
tctccccatg cgagagtagg gaactgccag gcatcaaata aaacgaaagg ctcagtcgaa   12840
agactgggcc tttcgtttta tctgttgttt gtcggtgaac gctctcctga gtaggacaaa   12900
tccgccggga gcggatttga acgttgcgaa gcaacggccc ggagggtggc gggcaggacg   12960
cccgccataa actgccaggc atcaaattaa gcagaaggcc atcctgacgg atggcctttt   13020
tgcgtttcta caaactccag ctggatcggg cgctagagta tacatttaaa tggtaccctc   13080
```

| | |
|---|---|
| tagtcaaggc cttaagtgag tcgtattacg gactggccgt cgttttacaa cgtcgtgact | 13140 |
| gggaaaaccc tggcgttacc caacttaatc gccttgcagc acatccccct ttcgccagct | 13200 |
| ggcgtaatag cgaagaggcc cgcaccgatc gcccttccca acagttgcgc agcctgaatg | 13260 |
| gcgaatggcg cctgatgcgg tatttttctcc ttacgcatct gtgcggtatt tcacaccgca | 13320 |
| tatggtgcac tctcagtaca atctgctctg atgccgcata gttaagccag ccccgacacc | 13380 |
| cgccaacacc cgctgacgag ct | 13402 |

<210> SEQ ID NO 76
<211> LENGTH: 14443
<212> TYPE: DNA
<213> ORGANISM: Artificial Sequence
<220> FEATURE:
<223> OTHER INFORMATION: Plasmid

<400> SEQUENCE: 76

| | |
|---|---|
| ttctgataac aaactagcaa caccagaaca gcccgtttgc gggcagcaaa acccgtggga | 60 |
| attaattccc ctgctcgcgc aggctgggtg ccaagctctc gggtaacatc aaggcccgat | 120 |
| ccttggagcc cttcttacag agatgaaaaa caaaccgcga cgccaggcgg catcgcggtc | 180 |
| tcagagatat gtttacgtag atcgaagagc accggtgttt aaacgcccct tgacgatgcca | 240 |
| catcctgagc aaataattca accactaaac aaatcaaccg cgtttcccgg aggtaaccga | 300 |
| gctcatgatc ctgtgttgtg gtgaagccct gatcgacatg ctgccccggc agacgacgct | 360 |
| gggtgaggcg ggctttgccc cttacgcagg cggagcggtc ttcaacacgg caattgcgct | 420 |
| ggggcgtctt ggcgtccctt cagccttttt taccggtctt tccgacgaca tgatgggcga | 480 |
| tatcctgcgg gagaccctgc gggccagcaa ggtggatttc agctattgcg ccaccctgtc | 540 |
| gcgccccacc accattgcgt tcgttaagct ggttgatggc catgcgacct acgctttttta | 600 |
| cgacgagaac accgccggcc ggatgatcac cgaggccgaa cttccggcct tgggagcgga | 660 |
| ttgcgaagcg ctgcatttcg gcgccatcag ccttattccc gaaccctgcg gcagcaccta | 720 |
| tgaggcgctg atgacgcgcg agcatgagac ccgcgtcatc tcgctcgatc cgaacattcg | 780 |
| tcccggcttc atccagaaca agcagtcgca catggcccgc atccgccgca tggcggcgat | 840 |
| gtctgacatc gtcaagttct cggatgagga cctggcgtgg ttcggtctgg aaggcgacga | 900 |
| ggacacgctt gcccgccact ggctgcacca cggtgcaaaa ctcgtcgttg tcacccgtgg | 960 |
| cgccaagggt gccgtggggtt acagcgccaa tctcaaggtg gaagtggcct ccgagcgcgt | 1020 |
| cgaagtggtc gatacggtcg gcgccggcga tacgttcgat gccggcattc ttgcttcgct | 1080 |
| gaaaatgcag ggcctgctga ccaaagcgca ggtggcttcg ctgagcgaag agcagatcag | 1140 |
| aaaagctttg gcgcttggcg cgaaagccgc tgcggtcact gtctcgcggg ctggcgcaaa | 1200 |
| tccgcctttc gcgcatgaaa tcggtttgtg attaattaaa gcacgcagtc aaacaaaaaa | 1260 |
| cccgcgccat tgcgcgggtt ttttttatgcc cgaaggcgcg ccagcacgca gtcaaacaaa | 1320 |
| aaacccgcgc cattgcgcgg gttttttttat gcccgaacgg ccgaggtctt ccgatctcct | 1380 |
| gaagccaggg cagatccgtg cacagcacct tgccgtagaa gaacagcaag gccgccaatg | 1440 |
| cctgacgatg cgtggagacc gaaaccttgc gctcgttcgc cagccaggac agaaatgcct | 1500 |
| cgacttcgct gctgcccaag gttgccgggt gacgcacacc gtggaaacgg atgaaggcac | 1560 |
| gaacccagtg gacataagcc tgttcggttc gtaagctgta atgcaagtag cgtatgcgct | 1620 |
| cacgcaactg gtccagaacc ttgaccgaac gcagcggtgg taacggcgca gtggcggttt | 1680 |
| tcatggcttg ttatgactgt ttttttgggg tacagtctat gcctcgggca tccaagcagc | 1740 |

-continued

```
aagcgcgtta cgccgtgggt cgatgtttga tgttatggag cagcaacgat gttacgcagc    1800
agggcagtcg ccctaaaaca aagttaaaca tcatgaggga agcggtgatc gccgaagtat    1860
cgactcaact atcagaggta gttggcgtca tcgagcgcca tctcgaaccg acgttgctgg    1920
ccgtacattt gtacggctcc gcagtggatg gcggcctgaa gccacacagt gatattgatt    1980
tgctggttac ggtgaccgta aggcttgatg aaacaacgcg gcgagctttg atcaacgacc    2040
ttttggaaac ttcggcttcc cctggagaga gcagagattct ccgcgctgta gaagtcacca    2100
ttgttgtgca cgacgacatc attccgtggc gttatccagc taagcgcgaa ctgcaatttg    2160
gagaatggca gcgcaatgac attcttgcag gtatcttcga gccagccacg atcgacattg    2220
atctggctat cttgctgaca aaagcaagag aacatagcgt tgccttggta ggtccagcgg    2280
cggaggaact ctttgatccg gttcctgaac aggatctatt tgaggcgcta aatgaaacct    2340
taacgctatg gaactcgccg cccgactggg ctggcgatga gcgaaatgta gtgcttacgt    2400
tgtcccgcat ttggtacagc gcagtaaccg gcaaaatcgc gccgaaggat gtcgctgccg    2460
actgggcaat ggagcgcctg ccggcccagt atcagcccgt catacttgaa gctagacagg    2520
cttatcttgg acaagaagaa gatcgcttgg cctcgcgcgc agatcagttg gaagaatttg    2580
tccactacgt gaaaggcgag atcaccaagg tagtcggcaa ataatgtcta acaattcgtt    2640
caagccgacg ccgcttcgcg gcgcggctta actcaagcgt tagatgcact aagcacataa    2700
ttgctcacag ccaaactatc aggtcaagtc tgcttttatt atttttaagc gtgcataata    2760
agccctacac aaattgggag atatatcatg aaaggctggc ttttcttgt tatcgcaata    2820 gttggcgaag taatcgcaac atccgcatta aaatctagcg agggctttac taagctcgtc    2880
agcgggtgtt ggcgggtgtc ggggctggct taactatgcg gcatcagagc agattgtact    2940
gagagtgcac catatgcggt gtgaaatacc gcacagatgc gtaaggagaa ataccgcat    3000 caggcgccat tcgccattca ggctgcgcaa ctgttgggaa gggcgatcgg tgcgggcctc    3060
ttcgctatta cgccagctgg cgaaagggggg atgtgctgca aggcgattaa gttgggtaac    3120
gccagggttt tcccagtcac gacgttgtaa aacgacggcc agtccgtaat acgactcact    3180
taaggccttg actagagggt accatttaaa tgtatactct agcgcccgat ccagctggag    3240
tttgtagaaa cgcaaaaagg ccatccgtca ggatggcctt ctgcttaatt tgatgcctgg    3300
cagtttatgg cgggcgtcct gcccgccacc ctccgggccg ttgcttcgca acgttcaaat    3360
ccgctcccgg cggatttgtc ctactcagga gagcgttcac cgacaaacaa cagataaaac    3420
gaaaggccca gtctttcgac tgagcctttc gttttatttg atgcctggca gttccctact    3480
ctcgcatggg gagaccccac actaccatcg gcgctacggc gtttcacttc tgagttcggc    3540
atggggtcag gtgggaccac cgcgctactg ccgccaggca aattctgttt tatcagaccg    3600
cttctgcgtt ctgatttaat ctgtatcagg ctgaaaatct tctctcatcc gccaaaacag    3660
ccaagcttgc atgcctgcag cccgggttac catttcaaca gatcgtcctt agcatataag    3720
tagtcgtcaa aaatgaattc aacttcgtct gtttcggcat tgtagccgcc aactctgatg    3780
gattcgtggt ttttgacaat gatgtcacag cctttttcct ttaggaagtc caagtcgaaa    3840
gtagtggcaa taccaatgat cttacaaccg gcggcttttc cggcggcaat acctgctgga    3900
gcgtcttcaa atactactac cttagatttg aagggtctt gctcattgat cggatatcct    3960
aagccattcc tgcccttcag atatggttct ggatgaggct taccctgttt gacatcatta    4020
gcggtaatga agtactttgg tctcctgatt cccagatgcc cgaaccattt ttgtgccata    4080
tcacgggtac cggaagttgc cacagcccat ttctcttttg gtagagcgtt caaagcgttg    4140
```

```
cacagcttaa ctgcacctgg gacttcaatg gattttttcac cgtacttgac cggaatttca   4200
gcttctaatt tgttaacata ctcttcattg gcaaagtctg gagcgaactt agcaatggca   4260
tcaaacgttc tccaaccatg cgagacttgg ataacgtgtt cagcatcgaa ataaggtttg   4320
tccttaccga aatccctcca gaatgcagca atggctggtt gagagatgat aatggtaccg   4380
tcgacgtcga acaaagcggc gttaactttc aaagatagag gtttagtagt caatcccata   4440
attctagtct gtttcctgga tccaataaat ctaatcttca tgtagatcta attcttcaat   4500
catgtccggc aggttcttca ttgggtagtt gttgtaaacg atttggtata cggcttcaaa   4560
taatgggaag tcttcgacag agccacatgt ttccaaccat tcgtgaactt ctttgcaggt   4620 aattaaaccct tgagcggatt ggccattcaa caactccttt tcacattccc aggcgtcctt   4680
accagaagta gccattagcc tagcaacctt gacgtttcta ccaccagcgc aggtggtgat   4740
caaatcagca acaccagcag actcttggta gtatgtttct tctctagatt ctgggaaaaa   4800
catttgaccg aatctgatga tctcacccaa accgactctt tggatggcag cagaagcgtt   4860
gttaccccag cctagacctt cgacgaaacc acaacctaag gcaacaacgt tcttcaaagc   4920
accacagatg gagataccag caacatcttc gatgacacta acgtggaagt aaggtctgtg   4980
gaacaaggcc tttagaacct tatggtcgac gtccttgccc tcgcctctga aatcctttgg   5040
aatgtggtaa gcaactgttg tttcagacca gtgttcttga gcgacttcgg tggcaatgtt   5100
agcaccagat agagcaccac attgaatacc tagttcctca gtgatgtaag aggatagcaa   5160
ttggacacct ttagcaccaa cttcaaaacc ctttagacag gagatagctc tgacgtgtga   5220
atcaacatga ccttttcaatt ggctacagat acggggcaaa aattgatgtg gaatgttgaa   5280
aacgatgatg tcgacatcct tgactgaatc aatcaagtct ggattagcaa ccaaattgtc   5340
gggtagagtg atgccaggca agtatttcac gttttgatgt ctagtattta tgatttcagt   5400 caattttttca ccattgatct cttcttcgaa cacccacatt tgtactattg gagcgaaaac   5460
ttctgggtat cccttacaat tttcggcaac caccttggca atagtagtac cccagttacc   5520
agatccaatc acagtaacct tgaaaggctt ttcggcagcc ttcaaagaaa cagaagagga   5580
acttctcttt ctaccagcat tcaagtggcc ggaagttaag tttaatctat cagcagcagc   5640
agccatggaa ttgtcctcct tactagtcat ggtctgtttc ctgtgtgaaa ttgttatccg   5700
ctcacaattc cacacattat acgagccgga tgattaattg tcaacagctc atttcagaat   5760
atttgccaga accgttatga tgtcggcgca aaaacatta tccagaacgg gagtgcgcct   5820
tgagcgacac gaattatgca gtgatttacg acctgcacag ccataccaca gcttccgatg   5880
gctgcctgac gccagaagca ttggtgcacg ctagacaaga aaaaaggcac gtcatctgac   5940
gtgccttttt tatttgtacc tagaggctgg cgcgagcgcc cgtttaattc gcctgaccgg   6000
ccagtagcag cccggtggcg accgcattgc gcggcccttc tgttcccga atattgccct   6060 gcccggcgac cacgccatag tgcgacaagg cttccgtgat aagctgcggg atctcaaagt   6120
ccagcgatga gccgcccacc agcaccacaa aggcgatatc gcgaatggaa ccgccgggtg   6180
agacctggcg cagcgcgcgc aggcagttgg tgacaaaacac tttctctttc gcctgccggc   6240
gcacgagacg aatttttttcc agcgggctgg cgttatcgat cggcaccagt tcgccctcct   6300
tgatgtacac cactttggcg aacaccgccg ggctgagggc ttcccgaaag aactccaccg   6360
cgccattctc gtgacgaata ctgaacaggc tttccacttt ggccagcggg tatttttta   6420 tcgcttccgc cagcgaaaga tcctcgaggc ccagctcggt tttaatcaac aggctgacca   6480
tattccccgc cccggcgaga tggaccgccg ttatctgccc ctccgcgttg acgatcgccg   6540
```

```
catccgtcga gccggcgccg aggtcgagga tcgccagcgg cgccgcacag ccggagtgg     6600
ttaacgcccc ggcgatggcc atgttggcct ccacgccgcc caccaccacc tcggtctgca    6660
gtcgggcgct cagttcgcgg gcgataacct gcatttgcag acgatccgct ttcaccatcg    6720
ccgccatccc gacggcattc tccatggcgc actcgccggc catcccgccc tgcaccttgc    6780
gcggaataaa cgtatccacc gccagcagat cctggatgta tatcgcgctc atctcatggc    6840
cggtcaggga cgccattacc ttgcgcaccc gctcaagcat gccgccggcg tgggtgcccg    6900
gttcgccgcg gatgtcgcgt accggagcgc aggcgctcat cgcctgcatg atggcttccg    6960
cgccctcggc gacatcggcc tctccgcggc gcttttcgcc gctaatgtag aggttgcccg    7020
ccggatcac ccgcgactgc acatcccct gcgggtctt gagcaccacc gcggaacggt       7080
tgccaatcag ggcgcgggcg atggggacga tggcctgggt ctcttccggg cttagcccga    7140
agaaggtggc gatcccgtag ggattcgaca ggatccgcac cacctggccc ggcgcggcca    7200
cttccaccgc cgccattacc ccctcgggga cctgctccag cagcgtcact tcatccacca    7260
ccggcagggt tttacgcagg cggttgttca ccagcacgcc gtcgtccttt ttgaggatcg    7320
ccgccaccac gttgatcccc cggtcgagcg cctcattgag ccaccacacg cgtcaagga    7380
aatcgacggc gtcgtcaatc agtacgatcc acccctcggc atactgcgcc gccggcagcg    7440
tcgccagccg cccgagggcg atagtcgtcc ccacgccaac gcccacccg cccggcgtct     7500
gcgggttatg accgatcatg gtcgattcgg tgataatggt ctcggtgatg gtctccatcg    7560
ccacatcgcc aatcaccggc gcggcttcgt taagatagat gcgagagaca tcgctcatcg    7620
accacggtgt tttcgccagg gcctgctcca gcgcggcgag ggtcccggcg atattgtccc    7680
gcgtcccttt catgcccgtc gtcgcgacga tcccgctggc aacaaacgcc ctcgcctgcg    7740
ggtagtcgga cgccagcgcc acctcggtgg tggcgttgcc gatatcaatc ccggctatta    7800
acggcatgct gacctccgct tagcttcctt tacgcagctt atgccgctgc tgatacactt    7860
ccgccgactc ccggacaaag gcggcattca ctgtcgcatg ccaggtgtgc tccagctcgt    7920
cggcgatcgc cagcagctcc gcctgcgagg agcggaacgg gcgcagcgcg ttatagatag    7980
ccagaatgcg ctcgtcagga atggcgataa gctccgccgc gcggcggaaa ttgcgcgcca    8040
ccgcatggcg ctgcatctgc tcggcaatct gcgcctggta tcaagggtc tggcgggaga    8100
tccgcacatc ctgcgggccc acctcgccag agagcacctt ctcgagggta atatcggtca    8160
atggtttgcc ggtaggcgtc aggatatgct ccgggcagcg ggtggctaac ggataatcct    8220
gcacgcgcat ggttttctcg ctcatggtca ctcccttact aagtcgatgt gcagggtgac    8280
gggctcggcg tcctgcacca catgtttggt ctctttgata tgaaatagcg ggcctttggc    8340
cataaatttc ggccgcacca tctgatcgtt caccaccggc accggcgaag gtgactcttt    8400
gcgcgcatag cgcgcagcgt ttttgccaat ctgccggtag gtctccagcg tcagcagcgg    8460
cgcctgggag aacagctcca ggttgctgag cggcagcaga tcgcgctgat ggatgaccgt    8520
ggtccccttc gactggatac cgatgccgat ccccgagccg ctcaggttgg ccgcatccca    8580
ggccataaag gagacgtcgg acgtgcgcag aatgcgcacc accgggcgt gaagcccctc     8640
ttcttccacc ccggcaatca gctctttgag gatcgcgcca tggggcatat cgatcagagt    8700
gtgatgctgg tgtttatcga aggcagggcc gacgccgatc accacttcat cggcgcgttc    8760
atcggcagaa gctaccccgc cctcgcgggt tttcagggta aagagggct gaatttgggt      8820
tgtctgttgc acaggaatac cgccttgttc aatggtgtcg ggctgaacca cgcccggaat    8880
attttttgatc tccgcccagc gttcggcaga gatgcgatag ccggtgcccg gccctgata    8940
```

```
gtcattgatg tcgttgaccg cactcaccac ctcgaactgc cgatcgaaaa tggccgaggt    9000
ctgcaggtaa tcgccggtga cccgctggcg cagcatattg agaatattgc tggcgatatc    9060
ctcaaagccg ctgcggctca gcgcgccgac aatatcgagg ccggtgatgt tgcgcttcat    9120
catctcttcc accgcactca gatcctccac cacgttacgc ggcggcatct cgttgctgcc    9180
gtgcgcgtag gtggcggcct ccacctcctc gtcggcgatt ggcggcagcc ccagctcgcg    9240
gaaaaccgcc tggatcgccc gcgccgcttt ctggcgaatg gcaatggttt ccgcctcggt    9300
caccggacgc aggccgccgt caaccatcag gtcacgctgc aggatgttgt aatcatcaaa    9360
atcttccgca tcgaagttcg agccggcgaa catgttgtcg tagttcggca ccgcgctgta    9420
gccggagaaa ataaagtcgg tgcccggcag catctgcatc agggtgcgcg cggtgcggcg    9480
aatatccgag tgggagaaag tctggtcgtt ggcggacgcc acttcgaggt cgagcataga    9540
ggcgatcagg ttttccgcca gcaccgcccg aatgcccgac ggcacagcgc cggtcatgcc    9600
gatacagctc accgcgccgt tttgcagtcc ctgaaccccg cgcctttag taatgaagat    9660
gcagcgcgat tcgaggtaga gcatcgactt gctctccgaa tagcccatca gcgcttcgga    9720
tccggtgccg gaggtgtagc gcattttcaa cccgcgggag gcgtaggccg aggcgaggaa    9780
cgcctttgac cacggcgtat catcgccgtc ggtaaatacc gcttcggtgc cgtagaccga    9840
caccgtctcg gcgtagctgg ttaagccacg catgcccagc tccagctcgg tggcctcttc    9900
caccgagcac tgcgtcaaca cgccggggcg gccgcactgc gaaccgacca acagcgccag    9960
ggcgttaaac ggcgcgtagc gcgcgatacc gaccgtggtc tcctgttctg agaagccgcg   10020
gatcccggcc tcggcggcgt cagcggcaat ctgcaccgga ttatctttga gattggtgac   10080
gtggcactgg ttggaggggg tccggcgggc acgcatcttc tgcagcgcca tcatcatctc   10140
caccacgttc atctgcgcca tcacctcgac cgctttggcc ggcgtgatgg cggtagtgat   10200
ggcaatgatc tcctcccggc tgacgtgaat atccaccagc atacgggcta tttccaccgc   10260
ctccaggcgc attgcctgct ctgtgcgctc aacgttgatc gcgtaatcgg cgataaatcg   10320
gtcgatcatg tcaaactggt cccggcgttt gccgtccagt tcgacgatca gaccgttgtc   10380
cactttact gaagagaccg ggtcaaaggg gctgtccatg gcgatcagcc cctcttcagg   10440
ccactcgcca atcagcccgt cctgattgac ggggcgctgg gccagtactg caaatcgttt   10500
tgatcttttc attgttcatc ggctcaaaag gtgaagcttg gttacctccg ggaaacgcgg   10560
ttgatttgtt tagtggttga attatttgct caggatgtgg cattgtcaag ggcgtgacgg   10620
ctcgcctgac ttctcgttcc agtgcccccg tccgacagtc gagcgtgcga gcccataatc   10680
tcgcgctggt gctgcatacc gtggcaaaca gcacagatcg cctaggaaaa aaaaagcccg   10740
cactgtcagg tgcgggcttt tttctgtgtt tgctaggcca gttcaagcgc aagcatcagg   10800
gtgcagctgg gcagaggcga gattcctccc cgggatcacg aactgtttta acggccgct   10860
ctcggccata ttgcggtcga taagccgctc cagggcggtg atctcctctt cgccgatcgt   10920
ctggctcagg cgggtcaggc cccgcgcatc gctggccagt tcagcccca gcacgaacag   10980
cgtctgctga atatggtgca ggcttttccg cagcccggcg tcgcgggtcg tggcgtagca   11040
gacgcccagc tgggatatca gttcatcgac ggtgccgtag gcctcgacgc gaatatggtc   11100
tttctcgatg cggctgccgc cgtacagggc ggtggtgcct ttatccccgg tgcgggtata   11160
gatacgatac attcagtttc tctcacttaa cggcaggact ttaaccagct gcccggcgtt   11220
ggcgccgagc gtacgcagtt gatcgtcgct atcggtgacg tgtccggtag ccagcggcgc   11280
gtccgccggc agctgggcat gagtgagggc tatctcgccg gacgcgctga gcccgatacc   11340
```

```
cacccgcagg ggcgagcttc tggccgccag ggcgcccagc gcagcggcgt caccgcctcc    11400
gtcataggtt atggtctggc aggggacccc ctgctcctcc agccccagc acagctcatt     11460 gatggcgccg gcatggtgcc cgcgcggatc gtaaaacagg cgtacgcctg gcggtgaaag    11520
cgacatgacg gtcccctcgt taacactcag aatgcctggc ggaacatacg atagctcata    11580
atataccttc tcgcttcagg ttataatgcg gaaaaacaat ccaggcgca ctgggctaat     11640 aattgatcct gctcgaccgt accgccgcta acgccgacgg cgccaattac ctgctcatta    11700
aaaataactg gcaggccgcc gccaaaaata ataattcgct gttggttggt tagctgcaga    11760
ccgtacagag attgtcctgg ctggaccgct gacgtaattt catgggtacc ttgcttcagg    11820
ctgcaggcgc tccaggcttt attcagggaa atatcgcagc tggagacgaa ggcctcgtcc    11880
atccgctgga taagcagcgt gttgcctccg cggtcaacta cggaaaacac caccgccacg    11940
ttgatctcag tggcttttttt ttccaccgcc gccgccattt gctgggcggc ggccagggtg   12000
attgtctgaa cttgttggct cttgttcatc attctctccc gcaagcttgg ttacctccgg    12060
gaaacgcggt tgatttgttt agtggttgaa ttatttgctc aggatgtggc attgtcaagg    12120
gcgtgacggc tcgcctgact tctcgttcca gtgccccgt ccgacagtcg agcgtgcgag     12180
cccataatct cgcgctggtg ctgcataccg tggcaaacag cacagatcgc ctagcagtca    12240
aaagcctccg gtcggaggct tttgactatt taaatgaatt cccgacagta agacgggtaa    12300
gcctgttgat gataccgctg ccttactggg tgcattagcc agtctgaatg acctgtcacg    12360
ggataatccg aagtggtcag actggaaaat cagagggcag gaactgctga cagcaaaaa    12420 gtcagatagc accacatagc agacccgcca taaaacgccc tgagaagccc gtgacgggct    12480
tttcttgtat tatgggtagt ttccttgcat gaatccataa aaggcgcctg tagtgccatt    12540
taccccattt cactgccaga gccgtgagcg cagcgaactg aatgtcacga aaaagacagc    12600
gactcaggtg cctgatggtc ggagacaaaa ggaatattca gcgatttgcc cgagcttgcg    12660
agggtgctac ttaagccttt agggttttaa ggtctgtttt gtagaggagc aaacagcgtt    12720
tgcgacatcc ttttgtaata ctgcggaact gactaaagta gtgagttata cacagggctg    12780
ggatctattc tttttatctt tttttattct ttctttattc tataaattat aaccacttga    12840
atataaacaa aaaaaacaca caaaggtcta gcggaattta cagagggtct agcagaattt    12900
acaagttttc cagcaaaggt ctagcagaat ttacagatac ccacaactca aggaaaagg    12960 actagtaatt atcattgact agcccatctc aattggtata gtgattaaaa tcacctagac    13020
caattgagat gtatgtctga attagttgtt ttcaaagcaa atgaactagc gattagtcgc    13080
tatgacttaa cggagcatga aaccaagcta atttatgct gtgtggcact actcaacccc    13140
acgattgaaa accctacaag gaaagaacgg acggtatcgt tcacttataa ccaatacgct    13200
cagatgatga acatcagtag ggaaaatgct tatggtgtat tagctaaagc aaccagagag    13260
ctgatgacga gaactgtgga aatcaggaat cctttggtta aaggctttga gattttccag    13320
tggacaaact atgccaagtt ctcaagcgaa aaattagaat tagttttag tgaagagata    13380 ttgccttatc ttttccagtt aaaaaaattc ataaatata atctggaaca tgttaagtct    13440
tttgaaaaca atactctat gaggatttat gagtggttat taaaagaact aacacaaaag    13500
aaaactcaca aggcaaatat agagattagc cttgatgaat ttaagttcat gttaatgctt    13560
gaaaataact accatgagtt taaaggctt aaccaatggg ttttgaaacc aataagtaaa    13620
gatttaaaca cttacagcaa tatgaaattg gtggttgata agcgaggccg cccgactgat    13680
acgttgattt tccaagttga actagataga caaatggatc tcgtaaccga acttgagaac    13740
```

| | |
|---|---|
| aaccagataa aaatgaatgg tgacaaaata ccaacaacca ttacatcaga ttcctaccta | 13800 |
| cataacggac taagaaaaac actacacgat gctttaactg caaaaattca gctcaccagt | 13860 |
| tttgaggcaa aatttttgag tgacatgcaa agtaagtatg atctcaatgg ttcgttctca | 13920 |
| tggctcacgc aaaaacaacg aaccacacta gagaacatac tggctaaata cggaaggatc | 13980 |
| tgaggttctt atggctcttg tatctatcag tgaagcatca agactaacaa acaaaagtag | 14040 |
| aacaactgtt caccgttaca tatcaaaggg aaaactgtcc atatgcacag atgaaaacgg | 14100 |
| tgtaaaaaag atagatacat cagagctttt acgagttttt ggtgcattca aagctgttca | 14160 |
| ccatgaacag atcgacaatg taacagatga acagcatgta acacctaata gaacaggtga | 14220 |
| aaccagtaaa acaaagcaac tagaacatga aattgaacac ctgagacaac ttgttacagc | 14280 |
| tcaacagtca cacatagaca gcctgaaaca ggcgatgctg cttatcgaat caaagctgcc | 14340 |
| gacaacacgg gagccagtga cgcctcccgt ggggaaaaaa tcatggcaat tctggaagaa | 14400 |
| atagcgcttt cagccggcaa accggctgaa gccggatctg cga | 14443 |

<210> SEQ ID NO 77
<211> LENGTH: 1407
<212> TYPE: DNA
<213> ORGANISM: Escherichia coli

<400> SEQUENCE: 77

| | |
|---|---|
| atgggcaaag ggagaacatc gatgagtcac atcacaacgg aagatccagc aactttacgc | 60 |
| ctgccctta aagagaaact ctcttacggt attggcgacc tggcctctaa catcctgctg | 120 |
| gatatcggta cgctttatct tttgaagttt tataccgacg ttctggggct gccaggcacc | 180 |
| tatggcggca ttatcttttt gatttcaaaa ttctttactg cgtttaccga tatgggtacc | 240 |
| ggcattatgt tggattcccg acgcaagatc ggtccaaaag gtaagttccg tccttttatt | 300 |
| ctgtatgcgt cattcccggt caccttactg gcgatcgcca actttgtcgg cacaccgttt | 360 |
| gatgtcaccg gtaaaacggt gatggccact attctgttta tgctttacgg actgttttc | 420 |
| agcatgatga actgctccta cggcgcaatg gttcccgcta tcaccaaaaa ccccaacgaa | 480 |
| cgcgcctcac tggcggcatg gcgtcagggc ggcgctacgc tgggcctgct gctgtgcacg | 540 |
| gtgggattcg tgccagttat gaatcttatc gaaggtaatc agcaacttgg ctatatcttc | 600 |
| gccgccacgc tgttttcact gtttggcctg ctgtttatgt ggatctgcta ctcgggcgtg | 660 |
| aaagagcgtt atgtcgaaac ccagcctgct aatccggcgc aaaagccggg cctgctgcaa | 720 |
| tctttccgcg caattgcggg taaccgcccg ctgttcattc tgtgcattgc caacctctgc | 780 |
| actttagggg cgtttaacgt caagctcgcc atccaggtct attacaccca gtacgtgctt | 840 |
| aacgatccca tcctgttgtc gtatatggga ttttcagca tgggctgtat tttcatcggc | 900 |
| gtattcctga tgcctgcctc agtcagacgt tttggcaaga gaaagtttta tcggcggc | 960 |
| ctgctgattt gggtgctggg cgatctgctc aactatttct tcggcggcgg ttcggtcagc | 1020 |
| ttcgtggcgt tctcctgcct ggcgttcttt ggctcagcgt ttgttaacag cctgaactgg | 1080 |
| gcgctggttt ccgacaccgt cgagtacggc gagtggcgca ccggcgtgcg ttcggaagga | 1140 |
| acggtctaca ccggttttac cttctttcgc aaagtgtctc aggcgctggc tggtttcttc | 1200 |
| cccggctgga tgctgacgca aattggctat gtgccgaacg tcgcacaggc tgaccacacc | 1260 |
| attgaagggt tacgccagtt gatcttcatc tacccaagcg cactggcggt agtcaccatt | 1320 |
| gtggcgatgg gttgcttcta cagcctgaac gagaagatgt atgtccgcat tgtggaagag | 1380 |
| atagaagccc gtaaacgcac ggcgtaa | 1407 |

<210> SEQ ID NO 78
<211> LENGTH: 468
<212> TYPE: PRT
<213> ORGANISM: Escherichia coli

<400> SEQUENCE: 78

| | | | | | | | | | | | | | | |
|---|---|---|---|---|---|---|---|---|---|---|---|---|---|---|
| Met | Gly | Lys | Gly | Arg | Thr | Ser | Met | Ser | His | Ile | Thr | Thr | Glu | Asp | Pro |
| 1 | | | | 5 | | | | | 10 | | | | | 15 | |
| Ala | Thr | Leu | Arg | Leu | Pro | Phe | Lys | Glu | Lys | Leu | Ser | Tyr | Gly | Ile | Gly |
| | | | 20 | | | | | 25 | | | | | 30 | | |
| Asp | Leu | Ala | Ser | Asn | Ile | Leu | Leu | Asp | Ile | Gly | Thr | Leu | Tyr | Leu | Leu |
| | | 35 | | | | | 40 | | | | | 45 | | | |
| Lys | Phe | Tyr | Thr | Asp | Val | Leu | Gly | Leu | Pro | Gly | Thr | Tyr | Gly | Gly | Ile |
| 50 | | | | | 55 | | | | | 60 | | | | | |
| Ile | Phe | Leu | Ile | Ser | Lys | Phe | Phe | Thr | Ala | Phe | Thr | Asp | Met | Gly | Thr |
| 65 | | | | | 70 | | | | | 75 | | | | | 80 |
| Gly | Ile | Met | Leu | Asp | Ser | Arg | Arg | Lys | Ile | Gly | Pro | Lys | Gly | Lys | Phe |
| | | | | 85 | | | | | 90 | | | | | 95 | |
| Arg | Pro | Phe | Ile | Leu | Tyr | Ala | Ser | Phe | Pro | Val | Thr | Leu | Leu | Ala | Ile |
| | | | 100 | | | | | 105 | | | | | 110 | | |
| Ala | Asn | Phe | Val | Gly | Thr | Pro | Phe | Asp | Val | Thr | Gly | Lys | Thr | Val | Met |
| | | | 115 | | | | | 120 | | | | | 125 | | |
| Ala | Thr | Ile | Leu | Phe | Met | Leu | Tyr | Gly | Leu | Phe | Phe | Ser | Met | Met | Asn |
| | 130 | | | | | 135 | | | | | 140 | | | | |
| Cys | Ser | Tyr | Gly | Ala | Met | Val | Pro | Ala | Ile | Thr | Lys | Asn | Pro | Asn | Glu |
| 145 | | | | | 150 | | | | | 155 | | | | | 160 |
| Arg | Ala | Ser | Leu | Ala | Ala | Trp | Arg | Gln | Gly | Gly | Ala | Thr | Leu | Gly | Leu |
| | | | | 165 | | | | | 170 | | | | | 175 | |
| Leu | Leu | Cys | Thr | Val | Gly | Phe | Val | Pro | Val | Met | Asn | Leu | Ile | Glu | Gly |
| | | | 180 | | | | | 185 | | | | | 190 | | |
| Asn | Gln | Gln | Leu | Gly | Tyr | Ile | Phe | Ala | Ala | Thr | Leu | Phe | Ser | Leu | Phe |
| | | 195 | | | | | 200 | | | | | 205 | | | |
| Gly | Leu | Leu | Phe | Met | Trp | Ile | Cys | Tyr | Ser | Gly | Val | Lys | Glu | Arg | Tyr |
| | 210 | | | | | 215 | | | | | 220 | | | | |
| Val | Glu | Thr | Gln | Pro | Ala | Asn | Pro | Ala | Gln | Lys | Pro | Gly | Leu | Leu | Gln |
| 225 | | | | | 230 | | | | | 235 | | | | | 240 |
| Ser | Phe | Arg | Ala | Ile | Ala | Gly | Asn | Arg | Pro | Leu | Phe | Ile | Leu | Cys | Ile |
| | | | | 245 | | | | | 250 | | | | | 255 | |
| Ala | Asn | Leu | Cys | Thr | Leu | Gly | Ala | Phe | Asn | Val | Lys | Leu | Ala | Ile | Gln |
| | | | 260 | | | | | 265 | | | | | 270 | | |
| Val | Tyr | Tyr | Thr | Gln | Tyr | Val | Leu | Asn | Asp | Pro | Ile | Leu | Leu | Ser | Tyr |
| | | 275 | | | | | 280 | | | | | 285 | | | |
| Met | Gly | Phe | Phe | Ser | Met | Gly | Cys | Ile | Phe | Ile | Gly | Val | Phe | Leu | Met |
| | 290 | | | | | 295 | | | | | 300 | | | | |
| Pro | Ala | Ser | Val | Arg | Arg | Phe | Gly | Lys | Lys | Lys | Val | Tyr | Ile | Gly | Gly |
| 305 | | | | | 310 | | | | | 315 | | | | | 320 |
| Leu | Leu | Ile | Trp | Val | Leu | Gly | Asp | Leu | Leu | Asn | Tyr | Phe | Phe | Gly | Gly |
| | | | | 325 | | | | | 330 | | | | | 335 | |
| Gly | Ser | Val | Ser | Phe | Val | Ala | Phe | Ser | Cys | Leu | Ala | Phe | Phe | Gly | Ser |
| | | | 340 | | | | | 345 | | | | | 350 | | |
| Ala | Phe | Val | Asn | Ser | Leu | Asn | Trp | Ala | Leu | Val | Ser | Asp | Thr | Val | Glu |
| | | | 355 | | | | | 360 | | | | | 365 | | |
| Tyr | Gly | Glu | Trp | Arg | Thr | Gly | Val | Arg | Ser | Glu | Gly | Thr | Val | Tyr | Thr |
| | 370 | | | | | 375 | | | | | 380 | | | | |

```
Gly Phe Thr Phe Phe Arg Lys Val Ser Gln Ala Leu Ala Gly Phe
385                 390                 395                 400

Pro Gly Trp Met Leu Thr Gln Ile Gly Tyr Val Pro Asn Val Ala Gln
            405                 410                 415

Ala Asp His Thr Ile Glu Gly Leu Arg Gln Leu Ile Phe Ile Tyr Pro
            420                 425                 430

Ser Ala Leu Ala Val Val Thr Ile Val Ala Met Gly Cys Phe Tyr Ser
            435                 440                 445

Leu Asn Glu Lys Met Tyr Val Arg Ile Val Glu Ile Glu Ala Arg
    450                 455                 460

Lys Arg Thr Ala
465

<210> SEQ ID NO 79
<211> LENGTH: 2037
<212> TYPE: DNA
<213> ORGANISM: Escherichia coli

<400> SEQUENCE: 79
atggatacgc cacgtccaca gttattagat tttcaatttc atcagaataa cgacagtttt      60
accctacatt ttcaacaacg tcttatttta acccatagca agataatcc ttgtttatgg     120 attggctcag gtatagcgga tatcgatatg ttccgcggta atttcagcat aaagataaa     180 ctacaggaga aaattgcgct taccgacgcc atcgtcagcc agtcaccgga tggttggtta     240
attcatttca gccgtggttc tgacattagc gccacgctga atatctctgc cgacgatcag     300
gggcgtttat tgctggaact acaaaacgac aaccttaacc acaaccgtat ctggctgcgc     360
cttgccgctc aaccagagga ccatatctac ggctgcggcg aacagttttc ctacttcgat     420
ctgcgtggca aaccgttccc gctatggacc agtgaacaag gcgttggtcg caacaaacaa     480
acctatgtca cctggcaggc cgactgcaaa gaaaatgcgg cggcgactact tactggact      540 ttcttcccac agcctacgtt tgtcagcacg cagaagtatt actgccatgt tgataacagt     600
tgctatatga acttcgactt tagtgccccg gaataccatg aactggcgct gtgggaagac     660
aaagcaacgc tgcgttttga atgtgctgac acatacattt ccctgctgga aaaattaacc     720
gccctgctgg gacgccagcc agaactgccc gactggattt atgacggagt aacgctcggc     780
attcagggcg ggacggaagt gtgccagaag aaactggaca ccatgcgtaa cgcgggcgtg     840
aaggtcaacg gcatctgggc gcaggactgg tccggtattc gtatgacctc ttttggcaaa     900
cgcgtgatgt ggaactggaa gtggaacagc gaaaactacc cgcaactgga ttcacgcatt     960
aagcagtgga atcaggaggg cgtgcagttc ctggcctata tcaacccgta tgttgccagc    1020
gataaagatc tctgcgaaga agcggcacaa cacggctatc tggcaaaaga tgcctctggc    1080
ggtgactatc tggtggagtt tggcgagttt acggcggcg ttgtcgatct cactaatcca     1140
gaagcctacg cctggttcaa ggaagtgatc aaaaagaaca tgattgaact cggctgcggc    1200
ggctggatgg ctgacttcgg cgagtatctg cccaccgaca cgtacttgca taacggcgtc    1260
agtgccgaaa ttatgcataa cgcctggcct gcgctgtggg cgaagtgtaa ctacgaagcc    1320
cttgaagaaa cgggcaagct cggcgagatc cttttcttta tgcgcgccgg ttctaccggt    1380
agccagaaat actccaccat gatgtgggcg gcgaccagaa cgtcgactg gagtctcgac     1440 gatggcctgg cgtcggttgt cccggcggcg ctgtcgctgg caatgaccgg acatggcctg    1500 cacccacagcg acattggcgg ttacaccacc ctgtttgaga tgaagcgcag caaagagctg    1560
ctgctgcgct ggtgcgattt cagcgccttc acgccgatga tgcgcaccca cgaaggtaac    1620
```

```
cgtcctggcg acaactggca gtttgacggc gacgcagaaa ccatcgccca tttcgcccgt    1680
atgaccaccg tcttcaccac cctgaaacct tacctgaaag aggccgtcgc gctgaatgcg    1740
aagtccggcc tgccggttat gcgcccgctg ttcctgcatt acgaagacga tgcgcacact    1800
tacaccctga atatcagta cctgttaggt cgcgacattc tggtcgctcc ggtgcatgaa    1860
gaaggccgta gcgactggac gctctatctg ccggaggata actgggtcca cgcctggacg    1920
ggtgaagcgt tccggggcgg ggaagttacc gttaatgcgc ccatcggcaa gccgccggtc    1980
ttttatcgcg ccgatagcga atgggcggca ctgttcgcgt cgttaaaaag catctaa       2037
```

<210> SEQ ID NO 80
<211> LENGTH: 678
<212> TYPE: PRT
<213> ORGANISM: Escherichia coli

<400> SEQUENCE: 80

```
Met Asp Thr Pro Arg Pro Gln Leu Leu Asp Phe Gln Phe His Gln Asn
 1               5                  10                  15

Asn Asp Ser Phe Thr Leu His Phe Gln Gln Arg Leu Ile Leu Thr His
             20                  25                  30

Ser Lys Asp Asn Pro Cys Leu Trp Ile Gly Ser Gly Ile Ala Asp Ile
         35                  40                  45

Asp Met Phe Arg Gly Asn Phe Ser Ile Lys Asp Lys Leu Gln Glu Lys
     50                  55                  60

Ile Ala Leu Thr Asp Ala Ile Val Ser Gln Ser Pro Asp Gly Trp Leu
 65                  70                  75                  80

Ile His Phe Ser Arg Gly Ser Asp Ile Ser Ala Thr Leu Asn Ile Ser
                 85                  90                  95

Ala Asp Asp Gln Gly Arg Leu Leu Leu Glu Leu Gln Asn Asp Asn Leu
            100                 105                 110

Asn His Asn Arg Ile Trp Leu Arg Leu Ala Ala Gln Pro Glu Asp His
        115                 120                 125

Ile Tyr Gly Cys Gly Glu Gln Phe Ser Tyr Phe Asp Leu Arg Gly Lys
    130                 135                 140

Pro Phe Pro Leu Trp Thr Ser Glu Gln Gly Val Gly Arg Asn Lys Gln
145                 150                 155                 160

Thr Tyr Val Thr Trp Gln Ala Asp Cys Lys Glu Asn Ala Gly Gly Asp
                165                 170                 175

Tyr Tyr Trp Thr Phe Phe Pro Gln Pro Thr Phe Val Ser Thr Gln Lys
            180                 185                 190

Tyr Tyr Cys His Val Asp Asn Ser Cys Tyr Met Asn Phe Asp Phe Ser
        195                 200                 205

Ala Pro Glu Tyr His Glu Leu Ala Leu Trp Glu Asp Lys Ala Thr Leu
    210                 215                 220

Arg Phe Glu Cys Ala Asp Thr Tyr Ile Ser Leu Leu Glu Lys Leu Thr
225                 230                 235                 240

Ala Leu Leu Gly Arg Gln Pro Glu Leu Pro Asp Trp Ile Tyr Asp Gly
                245                 250                 255

Val Thr Leu Gly Ile Gln Gly Gly Thr Glu Val Cys Gln Lys Lys Leu
            260                 265                 270

Asp Thr Met Arg Asn Ala Gly Val Lys Val Asn Gly Ile Trp Ala Gln
        275                 280                 285

Asp Trp Ser Gly Ile Arg Met Thr Ser Phe Gly Lys Arg Val Met Trp
    290                 295                 300
```

```
Asn Trp Lys Trp Asn Ser Glu Asn Tyr Pro Gln Leu Asp Ser Arg Ile
305                 310                 315                 320

Lys Gln Trp Asn Gln Glu Gly Val Gln Phe Leu Ala Tyr Ile Asn Pro
            325                 330                 335

Tyr Val Ala Ser Asp Lys Asp Leu Cys Glu Glu Ala Ala Gln His Gly
        340                 345                 350

Tyr Leu Ala Lys Asp Ala Ser Gly Gly Asp Tyr Leu Val Glu Phe Gly
    355                 360                 365

Glu Phe Tyr Gly Gly Val Val Asp Leu Thr Asn Pro Glu Ala Tyr Ala
370                 375                 380

Trp Phe Lys Glu Val Ile Lys Lys Asn Met Ile Glu Leu Gly Cys Gly
385                 390                 395                 400

Gly Trp Met Ala Asp Phe Gly Glu Tyr Leu Pro Thr Asp Thr Tyr Leu
            405                 410                 415

His Asn Gly Val Ser Ala Glu Ile Met His Asn Ala Trp Pro Ala Leu
        420                 425                 430

Trp Ala Lys Cys Asn Tyr Glu Ala Leu Glu Glu Thr Gly Lys Leu Gly
    435                 440                 445

Glu Ile Leu Phe Phe Met Arg Ala Gly Ser Thr Gly Ser Gln Lys Tyr
450                 455                 460

Ser Thr Met Met Trp Ala Gly Asp Gln Asn Val Asp Trp Ser Leu Asp
465                 470                 475                 480

Asp Gly Leu Ala Ser Val Val Pro Ala Ala Leu Ser Leu Ala Met Thr
            485                 490                 495

Gly His Gly Leu His His Ser Asp Ile Gly Gly Tyr Thr Thr Leu Phe
        500                 505                 510

Glu Met Lys Arg Ser Lys Glu Leu Leu Leu Arg Trp Cys Asp Phe Ser
    515                 520                 525

Ala Phe Thr Pro Met Met Arg Thr His Glu Gly Asn Arg Pro Gly Asp
530                 535                 540

Asn Trp Gln Phe Asp Gly Asp Ala Glu Thr Ile Ala His Phe Ala Arg
545                 550                 555                 560

Met Thr Thr Val Phe Thr Thr Leu Lys Pro Tyr Leu Lys Glu Ala Val
            565                 570                 575

Ala Leu Asn Ala Lys Ser Gly Leu Pro Val Met Arg Pro Leu Phe Leu
        580                 585                 590

His Tyr Glu Asp Asp Ala His Thr Tyr Thr Leu Lys Tyr Gln Tyr Leu
    595                 600                 605

Leu Gly Arg Asp Ile Leu Val Ala Pro Val His Glu Glu Gly Arg Ser
610                 615                 620

Asp Trp Thr Leu Tyr Leu Pro Glu Asp Asn Trp Val His Ala Trp Thr
625                 630                 635                 640

Gly Glu Ala Phe Arg Gly Gly Glu Val Thr Val Asn Ala Pro Ile Gly
            645                 650                 655

Lys Pro Pro Val Phe Tyr Arg Ala Asp Ser Glu Trp Ala Ala Leu Phe
        660                 665                 670

Ala Ser Leu Lys Ser Ile
    675

<210> SEQ ID NO 81
<211> LENGTH: 1404
<212> TYPE: DNA
<213> ORGANISM: Escherichia coli

<400> SEQUENCE: 81
```

```
atgtctgacc ataatccact gacattaaaa ctgaatctgc gggaaaaaat cgcctatggt      60
atgggcgacg tcggttcgaa tttaatgctc tgcatcggta ctctgtatct cctcaaattt     120
tataccgatg aattagggat gcctgcttac tatggcggga ttatctttct ggtggcgaag     180
ttttttaccg cgtttaccga tatgctcacc ggattttttac tcgactcgcg aaaaatatt    240
gggcctaaag gcaaatttcg tccctttatt ttatatgcag cggttccggc ggcgttaatt     300
gcaacgctcc agtttatcgc caccaccttt tgtttgccgg ttaaaacgac gattgccacc     360
gcgctgttta tgatgtttgg actttcatac agtctgatga actgctcgta tggtgcgatg     420
atcccggcaa ttaccaaaaa cccgaatgag cgcgcgcagc tcgcggctta ccgccagggt     480
ggtgcaacca tagggctatt gatttgtacc gtggcgttta ttccgttgca gtcgcttttt     540
tctgactcaa ccgtcggtta tgcctgtgcg gcacttatgt tctccattgg cggctttatt     600
tttatgatgc tgtgctacag aggcgtcaaa gagcattatg tggacacaac gccaaccgga     660
cataaagcca gtattctcaa atcatttttgc gcgatatttc ggaatccgcc attgctggtt     720
ttatgcattg ctaacttgtg taccctggcg gcatttaata tcaaactggc gattcaggtc     780
tattacaccc agtatgtgct gaatgatatt aatttattgt cgtggatggg attcttcagt     840
atgggatgca tcctcatcgg cgtattactg gtgccattaa ctgtaaaatg tttttggtaaa    900
aaacaggttt atctggctgg catggtgctg tgggcggtgg gtgatatact gaattatttc     960
tggggaagta actctttcac tttcgtcatg ttctcttgtg tcgcctttttt tggcacggcc   1020
tttgtaaaca gcctgaactg gcactggta ccagataccg tagattacgg tgaatggaaa    1080
accggtattc gtgccgaagg ttctgtttat accggttata ccttctttcg taaaatttct    1140
gccgcacttg ctggcttctt gccaggcatt atgctgacgc aaattggtta tgttcccaac    1200
atcgcgcaaa gcgatgcgac attacagggt ttgcgtcagc tcattttttat ctggccttgt   1260
gcactggcaa ttattgctgc attgacgatg ggattctttt acacactcaa tgaaaaacgg    1320
tttgcattga ttattgagga aatcaaccaa cgcaaaaata aagagatggc gacagaagaa    1380
aaaacggctt ccgtaacgtt ataa                                           1404
```

<210> SEQ ID NO 82
<211> LENGTH: 467
<212> TYPE: PRT
<213> ORGANISM: Escherichia coli

<400> SEQUENCE: 82

```
Met Ser Asp His Asn Pro Leu Thr Leu Lys Leu Asn Leu Arg Glu Lys
1               5                   10                  15

Ile Ala Tyr Gly Met Gly Asp Val Gly Ser Asn Leu Met Leu Cys Ile
            20                  25                  30

Gly Thr Leu Tyr Leu Leu Lys Phe Tyr Thr Asp Glu Leu Gly Met Pro
        35                  40                  45

Ala Tyr Tyr Gly Gly Ile Ile Phe Leu Val Ala Lys Phe Phe Thr Ala
    50                  55                  60

Phe Thr Asp Met Leu Thr Gly Phe Leu Leu Asp Ser Arg Lys Asn Ile
65                  70                  75                  80

Gly Pro Lys Gly Lys Phe Arg Pro Phe Ile Leu Tyr Ala Ala Val Pro
                85                  90                  95

Ala Ala Leu Ile Ala Thr Leu Gln Phe Ile Ala Thr Phe Cys Leu
            100                 105                 110

Pro Val Lys Thr Thr Ile Ala Thr Ala Leu Phe Met Met Phe Gly Leu
        115                 120                 125
```

```
Ser Tyr Ser Leu Met Asn Cys Ser Tyr Gly Ala Met Ile Pro Ala Ile
            130                 135                 140

Thr Lys Asn Pro Asn Glu Arg Ala Gln Leu Ala Ala Tyr Arg Gln Gly
145                 150                 155                 160

Gly Ala Thr Ile Gly Leu Leu Ile Cys Thr Val Ala Phe Ile Pro Leu
                165                 170                 175

Gln Ser Leu Phe Ser Asp Ser Thr Val Gly Tyr Ala Cys Ala Ala Leu
            180                 185                 190

Met Phe Ser Ile Gly Gly Phe Ile Phe Met Met Leu Cys Tyr Arg Gly
            195                 200                 205

Val Lys Glu His Tyr Val Asp Thr Thr Pro Thr Gly His Lys Ala Ser
            210                 215                 220

Ile Leu Lys Ser Phe Cys Ala Ile Phe Arg Asn Pro Pro Leu Leu Val
225                 230                 235                 240

Leu Cys Ile Ala Asn Leu Cys Thr Leu Ala Ala Phe Asn Ile Lys Leu
                245                 250                 255

Ala Ile Gln Val Tyr Tyr Thr Gln Tyr Val Leu Asn Asp Ile Asn Leu
            260                 265                 270

Leu Ser Trp Met Gly Phe Phe Ser Met Gly Cys Ile Leu Ile Gly Val
            275                 280                 285

Leu Leu Val Pro Leu Thr Val Lys Cys Phe Gly Lys Lys Gln Val Tyr
            290                 295                 300

Leu Ala Gly Met Val Leu Trp Ala Val Gly Asp Ile Leu Asn Tyr Phe
305                 310                 315                 320

Trp Gly Ser Asn Ser Phe Thr Phe Val Met Phe Ser Cys Val Ala Phe
                325                 330                 335

Phe Gly Thr Ala Phe Val Asn Ser Leu Asn Trp Ala Leu Val Pro Asp
            340                 345                 350

Thr Val Asp Tyr Gly Glu Trp Lys Thr Gly Ile Arg Ala Glu Gly Ser
            355                 360                 365

Val Tyr Thr Gly Tyr Thr Phe Phe Arg Lys Ile Ser Ala Ala Leu Ala
            370                 375                 380

Gly Phe Leu Pro Gly Ile Met Leu Thr Gln Ile Gly Tyr Val Pro Asn
385                 390                 395                 400

Ile Ala Gln Ser Asp Ala Thr Leu Gln Gly Leu Arg Gln Leu Ile Phe
                405                 410                 415

Ile Trp Pro Cys Ala Leu Ala Ile Ile Ala Ala Leu Thr Met Gly Phe
            420                 425                 430

Phe Tyr Thr Leu Asn Glu Lys Arg Phe Ala Leu Ile Ile Glu Glu Ile
            435                 440                 445

Asn Gln Arg Lys Asn Lys Glu Met Ala Thr Glu Glu Lys Thr Ala Ser
450                 455                 460

Val Thr Leu
465

<210> SEQ ID NO 83
<211> LENGTH: 693
<212> TYPE: DNA
<213> ORGANISM: Escherichia coli

<400> SEQUENCE: 83
atgaaaaaga ttaatgcaat aatttttatta tcttctctga cctctgcctc ggtatttgct      60
ggcgcatacg tcgaaaacag ggaggcatat aatcttgcct ccgatcaggg cgaggttatg     120
ctacgtgtgg gttataactt cgatatgggc gcgggtatta tgttaaccaa tacctacaac     180
```

```
tttcagcgag aagatgaact aaaacatgga tataacgaaa ttgaaggctg gtatccgtta      240
tttaaaccaa ccgataaatt aaccatccag cccggtggct taattaatga taagagtatc      300
ggttcgggtg gtgcagtgta tctggacgtc aactataaat ttgtaccatg gtttaatctg      360
acagtacgaa atcgctataa ccataataac tatagttcaa cagatttgag cggggaactg      420
gataataatg acacctatga aattggcacc tactggaatt ttaaaatcac cgataaattt      480
tcctatacat ttgagccaca ttacttcatg cgagtgaatg actttaatag tagcaacggg      540
aaagatcatc attgggaaat cactaacacc ttccgttacc gtattaatga acactggctc      600
ccttatttcg aattgcgctg gttagaccgc aacgtcgaac cgtaccaccg cgagcaaaac      660
cagatccgta tcgggacgaa gtatttcttc tga                                   693
```

<210> SEQ ID NO 84
<211> LENGTH: 230
<212> TYPE: PRT
<213> ORGANISM: Escherichia coli

<400> SEQUENCE: 84

```
Met Lys Lys Ile Asn Ala Ile Ile Leu Leu Ser Ser Leu Thr Ser Ala
1               5                   10                  15

Ser Val Phe Ala Gly Ala Tyr Val Glu Asn Arg Glu Ala Tyr Asn Leu
            20                  25                  30

Ala Ser Asp Gln Gly Glu Val Met Leu Arg Val Gly Tyr Asn Phe Asp
        35                  40                  45

Met Gly Ala Gly Ile Met Leu Thr Asn Thr Tyr Asn Phe Gln Arg Glu
    50                  55                  60

Asp Glu Leu Lys His Gly Tyr Asn Glu Ile Glu Gly Trp Tyr Pro Leu
65                  70                  75                  80

Phe Lys Pro Thr Asp Lys Leu Thr Ile Gln Pro Gly Gly Leu Ile Asn
                85                  90                  95

Asp Lys Ser Ile Gly Ser Gly Gly Ala Val Tyr Leu Asp Val Asn Tyr
            100                 105                 110

Lys Phe Val Pro Trp Phe Asn Leu Thr Val Arg Asn Arg Tyr Asn His
        115                 120                 125

Asn Asn Tyr Ser Ser Thr Asp Leu Ser Gly Glu Leu Asp Asn Asn Asp
    130                 135                 140

Thr Tyr Glu Ile Gly Thr Tyr Trp Asn Phe Lys Ile Thr Asp Lys Phe
145                 150                 155                 160

Ser Tyr Thr Phe Glu Pro His Tyr Phe Met Arg Val Asn Asp Phe Asn
                165                 170                 175

Ser Ser Asn Gly Lys Asp His His Trp Glu Ile Thr Asn Thr Phe Arg
            180                 185                 190

Tyr Arg Ile Asn Glu His Trp Leu Pro Tyr Phe Glu Leu Arg Trp Leu
        195                 200                 205

Asp Arg Asn Val Glu Pro Tyr His Arg Glu Gln Asn Gln Ile Arg Ile
    210                 215                 220

Gly Thr Lys Tyr Phe Phe
225                 230
```

<210> SEQ ID NO 85
<211> LENGTH: 1386
<212> TYPE: DNA
<213> ORGANISM: Shigella flexneri

<400> SEQUENCE: 85

```
atgagtcaca tcacaacgga agatccagca actttacgcc tgcccttaa agagaaactc      60
```

| | |
|---|---|
| tcttacggta ttggcgacct ggcctctaac atcctgctgg atatcggtac gctttatctt | 120 |
| ttgaagtttt ataccgacgt tctggggctg ccaggcacct atggcggcat tatcttttg | 180 |
| atttcaaaat tctttactgc gtttaccgat atgggtaccg gcattatgtt ggattcccga | 240 |
| cgcaagatcg gtccaaaagg taagttccgt ccttttattc tgtatgcgtc attcccggtc | 300 |
| accttactgg cgatcgccaa ctttgtcggc acaccgtttg atgtcaccgg taaaacggtg | 360 |
| atggccacta ttctgtttat gctttacgga ctgttttca gcatgatgaa ctgctcctac | 420 |
| ggcgcaatgg tcccggcaat caccaaaaac cccaacgaac gcgcctcact ggcggcatgg | 480 |
| cgtcagggcg gcgctacgct gggcctgctg ctgtgcacgg tgggattcgt gccagttatg | 540 |
| aatcttatcg aaggtaatca gaaacttggc tatatcttcg ccgccacgct gttttcactg | 600 |
| ttcggcctgc tgtttatgtg gatctgctac tcaggcgtga agagcgtta tgtcgaaacc | 660 |
| caaccaacca atccggcgca aaagcctggc ctgttgcaat cttccgcgc aattgccggt | 720 |
| aaccgcccac tgttcattct gtgtattgcc aacctctgca ccttaggggc gtttaacgtc | 780 |
| aagctcgcca ttcaggtcta ttacacccag tacgtactta acgatcccat cctgttgtcg | 840 |
| tatatgggat ttttcagcat gggctgtatt ttcatcggcg tgttcctgat gcctggcgca | 900 |
| gtcagacgtt ttggtaagaa gaaggtctat atcggcggcc tgctgatttg ggtgctgggc | 960 |
| gatctgctca actatttctt cggcggcggc tcggtcagct ttgtggcgtt ctcctgcctg | 1020 |
| gcgttcttcg gctcagcgtt tgttaacagc ctgaactggg cgctggtttc gacaccgtc | 1080 |
| gagtacggag agtggcgcac cggcgtgcgt tcggaaggca cggtctacac cggcttcacc | 1140 |
| ttctttcgca aagtgtctca ggcgctggct ggtttcttcc ccggctggat gctgacgcaa | 1200 |
| attggctatg tgccgaacgt cgcacaggct gaccacacca ttgaagggtt acgccagttg | 1260 |
| atcttcatct acccaagcgc actggcggta gtcaccattg tggcgatggg ttgcttctac | 1320 |
| agcctgaacg agaagatgta tgtccgcatt gtggaagaga tagaagcccg taaacgcacg | 1380 |
| gcgtaa | 1386 |

<210> SEQ ID NO 86
<211> LENGTH: 1383
<212> TYPE: DNA
<213> ORGANISM: Salmonella enterica

<400> SEQUENCE: 86

| | |
|---|---|
| atgagtcaaa catcatcgaa tccggcaacc ctacgcttgc cgtttaaaga aaaacttgcc | 60 |
| tatggactgg gggatttagg ttctaatatc ctgttagata tcggaaccct ctatttactc | 120 |
| aaattttata ccgatgtgct gggtttacca gggacttacg gcgggatcat tttcctgatc | 180 |
| gccaaatttt ttaccgcatt taccgatatg ggtaccggca ttatgctcga ctcgcggcgt | 240 |
| aaaattggtc cgaagggcaa attccgcccg ttcgtgcttt acgcggcatt tccggtaacg | 300 |
| ctactggcga ttgctaactt tgtcggcaca ccgtttgagg tgacgggaaa aaccgtcgtc | 360 |
| gcaacgatgc tgtttatgct gtacgggctg gttttcagca tgatgaactg ctcgtatggc | 420 |
| gcgatggtac ccgcgattac caagaacccg gatgaacgcg cctcgcttgc cgcctggcgt | 480 |
| cagggcggcg ccactctcgg cctgctgctg tgtaccgttg gctttgtgcc ggtcatgaac | 540 |
| ctgatcgaag gcaatgccca actcagctat attttcgccg ccacgctatt tcattgttt | 600 |
| ggcctgctat ttatgtggct gtgctacgcc ggcgttaaag agcgctacgt cgaagtgaaa | 660 |
| cctgtcgata gcgcgcaaaa gcctggatta ttgcagtcgt tccgcgccat cgccggtaac | 720 |
| cgtccgctgt ttattctgtg tatcgccaac ctttgtactc ttggcgcctt caacgtcaaa | 780 |

```
ctggcgattc aggtttatta cacccagtac gttcttaacg acccgatcct cctctcctgg      840
atgggcttct ttagcatggg ctgtattttt atcggcgttt ttttgatgcc cggcgctgta      900
aggcgttttg gcaagaagaa agtctatatc ggcgggctgt taatatgggt ggcaggcgat      960
ctgctcaact acttctttgg cggcggctcg gtcagttttg tcgccttctc ctgcctggcg     1020
ttcttcggtt ccgccttcgt caacagcctg aactgggcgc tggtttccga cacggtggag     1080
tacggtgaat ggcgcaccgg cgtccgctcg aagggacgg tttacaccgg cttcacgttc      1140
ttccgtaagg tctcccaggc gctggcaggg ttcttccccg gctggatgct aacgcaaatc     1200
ggttatatcc cgaatgtggt gcaatcggca ggcaccgtcg aaggcctacg ccagttgatc     1260
tttatttatc cttgcgtgct ggcggtcatc accattattg cgatgggctg tttctacaac     1320
ctcaacgaga agatgtacgt gcgaattgtg gaagagattg aggcccggaa acatacggtt     1380
taa                                                                  1383

<210> SEQ ID NO 87
<211> LENGTH: 1323
<212> TYPE: DNA
<213> ORGANISM: Enterobacter cancerogenus

<400> SEQUENCE: 87
tacgggatgg gcgatctcgg ctctaacatc ctgctggata tcggcacgct gtacctgctg       60
aaattttaca ccgacgtgct gggcctgccg ggcacctacg gcggcattat cttcctgatc      120
gccaagttct ttaccgcctt taccgatatg ggtaccggga tcatgcttga ttcccggcgc      180
aagattgggc cgaagggcaa attccgcccg ttcgtgctgt atgcggcgtt tccggtcacg      240
ctgctggcga ttgcaaactt cgtcggcaca ccgtttgaga tgaccggcaa aacggtgatg      300
gcgacggtgc tgttcatgct gtacggcctg ttcttcagca tgatgaactg ctcttacggc      360
gccatggtgc ccgccattac caaaaacccg gacgagcgcg ccgcgctggc ggcctggcgt      420
cagggtggcg cgacgctggg cctgctgctg tgtaccgtcg gctttgtccc ggtgatgaac      480
ctgattgaag gcaatgatca gctgggctat atctttgccg ccaccctgtt ctcgttgttc      540
gggctgttct ttatgtggtg gtgctataag ggcgtgaccg agcgctacgt cgaggcgcag      600
cccgctaacc ccgctcaaaa accgggcctg ctgcagtcgt ttcgcgccat cgccggcaac      660
cgcccgctgt ttattctctg tattgccaac ctctgcacgc tgggggcctt taacgtcaaa      720
ctcgccatcc aggtctacta cacgcagtac gttttgaacg acccgatcct gctgtcgtac      780
atgggcttct tcagcatggg ctgtatttt atcggcgtgt ttatgatgcc cggcgcggtg      840
cgtcgcttcg gtaagaaaaa ggtctacatc agcgggctga tgatttgggt ggccggcgat      900
ctgctcaact acttcttcgg cggcggctcg gtgagctttg tggcgttctc atgcctggcg      960
ttcttcggct ccgcgtttgt gaacagcctg aactgggcgc tggtgtccga taccgtggag     1020
tacggcgagt ggcgcaccgg cgtacgctcc gaagggacgg tctataccgg gtttaccttc     1080
ttccgtaagg tttcccaggc gctggcgggc ttttttcccgg ggattatgct gacgcaaatc     1140
ggctatgtgc ccaacgtggt gcagtctgac ggaacggttg aagggctacg gcagctgata     1200
tttatctacc cgagcctgct ggcggtcatc accatcgtgg cgatgggctg cttctacaac     1260
ctcaacgaga agatgtatgt gcgcatcgtg aagaaattg aactgcgcaa acgtacagcc      1320
tga                                                                  1323

<210> SEQ ID NO 88
<211> LENGTH: 1383
```

<212> TYPE: DNA
<213> ORGANISM: Citrobacter koseri

<400> SEQUENCE: 88

| | | | | | |
|---|---|---|---|---|---|
| atgagtcaaa | cgtcatcaaa | tccggcgacc | ctacgcttgc | cgtttaaaga | aaaacttgcc | 60 |
| tatgggatgg | gtgatttagg | ctccaatatc | ctgctggata | ttggtacgct | ttatttactt | 120 |
| aagttttata | ccgatgtgct | gggtctaccg | ggcacgtatg | gcggtattat | tttcctgatc | 180 |
| gccaaattct | ttaccgcctt | caccgatatg | ggcaccggga | ttatgctcga | ctcgcggcgt | 240 |
| aaaatcggcc | cgaaaggcaa | gttcgtccg | ttcgtgctct | atgccgcgtt | tccggtgacc | 300 |
| ctgctggcca | tcgccaactt | tgtcggcacg | ccgtttgaaa | tcaccggtaa | gacggtgatg | 360 |
| gcgacggtgc | tgtttatgct | gtacggcctg | ttcttcagca | tgatgaactg | ttcgtatggc | 420 |
| gcgatggtgc | cgccattac | caaaaacccg | gatgagcgcg | cctcgcttgc | cgcctggcgt | 480 |
| cagggcggcg | ccacgctcgg | cctgctgctg | tgcaccgtcg | gttttgttcc | ggtgatgaat | 540 |
| ctgatcgaag | gaacgcaca | gctaagctat | attttcgccg | ccacgctgtt | ctcactgttt | 600 |
| ggcctgctgt | ttatgtggct | ctgctacgca | ggcgtcaaag | agcgttatgt | ggaggtaaaa | 660 |
| ccggttgaag | cgaccgaaaa | accggggctg | ctccagtcgt | ttcgcgccat | tgccgggaac | 720 |
| cgtccgctgt | tcattttatg | tatcgcgaat | ctctgcaccc | tgggcgcttt | caacgttaag | 780 |
| ctggcgatcc | aggtgtatta | cacccagtac | gtactgaatg | acccgatcct | cctctcctgg | 840 |
| atgggttttt | tcagcatggg | ctgcatttc | atcggcgtct | ttttaatgcc | cggcgcggta | 900 |
| agacgcttcg | gcaagaaaaa | ggtctacatc | ggcggcctgc | tggtttgggt | tatcggcgat | 960 |
| cttctcaact | acttctttgg | cggcggctcg | gtcagttttg | tcgcgttttc | ctgcctggcg | 1020 |
| ttttttcggtt | cagcgtttgt | gaacagcctg | aactgggcgc | tggtctccga | cacggtggaa | 1080 |
| tacggtgaat | ggcgcaccgg | cgtgcgttca | gaggaacgg | tatacaccgg | ttttaccttc | 1140 |
| ttccgtaagg | tgtctcaggc | gctggcgggc | ttcttccccg | gttggatgct | gacccaaatc | 1200 |
| ggctacgtgc | ccaatgtggt | gcaatcggca | ggcactgtcg | aaggtttgcg | gcagctgatc | 1260 |
| tttatttatc | cgtgcgcgct | ggcggtgata | accatcatcg | caatgggatg | tttctacaac | 1320 |
| ctcaacgaga | agatgtatgt | ccgcatcgtt | gaagagatag | aagcccgtaa | acaaacggct | 1380 |
| taa | | | | | | 1383 |

<210> SEQ ID NO 89
<211> LENGTH: 1458
<212> TYPE: DNA
<213> ORGANISM: Shigella flexneri

<400> SEQUENCE: 89

| | | | | | |
|---|---|---|---|---|---|
| atgtctgacc | ataatccact | gacattaaaa | ctgaatctgc | gggaaaaaat | cgcctatggt | 60 |
| atgggcgacg | tcggttcgaa | tttaatgctc | tgcatcggta | ctctgtatct | cctcaaactt | 120 |
| tataccgatg | aattagggat | gcctgcttac | tatggcggga | ttatctttct | ggtcgcgaag | 180 |
| tttttttaccg | cgtttaccga | tatgctcacc | ggatttttac | tcgactcgcg | gaaaaatatt | 240 |
| gggcctaaag | gcaaatttcg | tcccttttatt | ttatatgcag | cagttccggc | ggcgttaatt | 300 |
| gcaacgctcc | agtttatcgc | caccaccttt | tgtttgccgg | ttaaaacgac | gattgccacc | 360 |
| acgctgttta | tgatgtttgg | actttcatac | agtctgatga | actgctcgta | tggtgcgatg | 420 |
| atcccggcaa | ttaccaaaaa | cccgaatgag | cgcgcgcagc | tcgcggctta | ccgccagggt | 480 |
| ggtgcaacca | tagggctatt | gatttgtacc | gtggcgttta | ttccgttgca | gtcgcttttt | 540 |
| tctgactcaa | ccgtcggtta | tgcctgtgcg | gcacttatgt | tctccattgg | cggctttatt | 600 |

```
tttatgatgc tgtgctacag aggcgtcaaa gagcattatg tggacacagc gccaaccgga    660
cataaagcca gtattctcaa atcttttgc gcgatatttc gtaatccacc attgctggtt    720
ttatgcattg ctaacctgtg tactctggcg gcatttaata tcaaactggc gattcaggtc    780
tattacaccc agtatgtact gaatgatatt aatttattgt cgtggatggg attcttcagt    840
atgggatgca tcctcgtcgg cgtattactg gtgccagtaa ctgtaaaatg ttttggtaaa    900
aaacaggttt atttagctgg catagtgcta tgggcggtgg gtgatatact gaattctttc    960 tgggaagta actctttcac tttcgtcatg ttctcttgtg tcgcctttt tggcacggcc    1020 tttgtaaaca gcctgaactg ggcactggta ccagataccg tagattacgg tgaatggaaa   1080
accggtattc gtgccgaagg ttctgtttat accggttata ccttctttcg taaaatttct   1140
gccgcacttg ctggcttctt gccaggcatt atgctgacgc aaattggtta tgttcccaac   1200
atcgcgcaaa gcgatgcgac attacagggt ttgcgtcagc tcatttttat ctggccttgt   1260
gcactggcaa ttattgctgc attgacgatg ggattctttt acacactcaa tgaaaaacgg   1320
tttgcattga ttattgagga aatcaaccaa cgcaaaaata agagatggc gacagaaaaa    1380 aaaaacggct tccgtaacgt tataaatgtc aatagccgct atttccatcc tggtgggtgg   1440
cggcctccct acgtttaa                                                 1458

<210> SEQ ID NO 90
<211> LENGTH: 1422
<212> TYPE: DNA
<213> ORGANISM: Salmonella enterica

<400> SEQUENCE: 90
atgtctaatc atgatccgct aacgctaaag ttgagcctgc gggaaaaatg cgcctatggc    60
gtgggcgatt tcggctcaaa tctgatgctg tgtatcggta cgctgtatct actgaagttt   120
tataccgatg aactcgggat gcctgcatat tacggtggaa ttatctttct ggtggcgaaa   180
ttcttcaccg cttttaccga tatgctcacc ggcgtattgc tggactcacg ccgtaatatt   240
ggcgcaaaag gaaagtttcg gcctttttatt ctgtatgcgt catttccagt cgctctggtt   300
gctactgcgc aattctttgc cactcacttt actttacccg ttaaaacagc cttcgcgacg   360
gtgctgttta tgttgttcgg tctgttctac agcctgatga actgctcata cggcgcgatg   420 gtaccccgcta ttaccaaaaa tccgcatgag cgcgcccagc tcgccgcatg gcgacaaggc   480
ggcgctacca ttggccttct tctttgtacc gtaggttta tgcccattca ggcgctgttt   540
acccgttccc cttcgctggg ttatctgatt gcagcagtca tcttttcggt ctgcgggctg   600
ttcagcatgt ggtggtgctt tagcggggta aaagaacggt atatcgaaac cgtacctgac   660
acgcataaac ccagcatatt gaagtccttc tgcgcgattt ttcgtaatcc gccgctgctg   720
gtgctctgcg ttgccaattt gtgcacgctg gccgcctta atatcaagct ggccattcag   780
gtttattaca ctcagtacgt gctgaacgat attcattgt tgtcatggat gggttttttc    840
agcatgggct gtatcctgat tggtgtttta ttagtacctg ctgcggtaaa acgcttcggg   900
aaaaaacagg tttatcttgg tggtctgata ttgtgggccg ttggcgatat cctgaattt    960 atctggggtg aacgtcatt cctgtttgtt attttctctt gtatcgcctt cttcggtacc   1020
gctttcgtca acagctgaa ctgggcgctg gttccggata cggttgacta cggtgaatgg   1080
aaaacgggta ttcgcgctga aggctcggtg tatacgggt ataccttttc ccgcaaaatt   1140
tccgctgcgc ttgctggctt tttgccaggt attatgctga cgcaaatcgg ttatatcccc   1200
aacatagctc aaagtgacac cacgttgctt ggtttgcgtc agctcatttt tttatggcct   1260
```

| | |
|---|---|
| tgcggtcttg ccattatcgc agcactaacg atgggctttt tttataagct caatgaacaa | 1320 |
| cgtttcgctt ttattatcga ggaaattgcc caacgaaaga aaacaggtaa tcaaattgtc | 1380 |
| gcgactaata ataaacaaag tatttctact gtaaataatt aa | 1422 |

<210> SEQ ID NO 91
<211> LENGTH: 1425
<212> TYPE: DNA
<213> ORGANISM: Enterobacter cancerogenus

<400> SEQUENCE: 91

| | |
|---|---|
| atgacacaca ctcctgatcc gttaaccctg aagctgagcc tgcgcgagaa gtgcgcctat | 60 |
| gggatgggcg attttggctc gaacctgatg ctctgtatcg gcacgctgta tctgctgaag | 120 |
| ttttataccg acgagctggg tatgcccgcc ttttacggcg gcattatttt tctggttgcg | 180 |
| aagttttttta ccgcctttac cgacatgctg accggggtgc tgctggactc ccggcgtcat | 240 |
| atcggcgcga ggggaaagtt ccggccattc attctgtatg cctccgtacc ggtggcgctg | 300 |
| gttgccacgg cgcagtttat ggccaacgat tttagcctga cggtgaaaac ggccctcgcc | 360 |
| accgtgctct ttatgatgtt cggcctgtgc tatagcctga tgaactgctc ttacggtgcg | 420 |
| atggtgccag ctatcaccaa aaacccgaac gaacgggcgc agcttgcggc ctggcgtcag | 480 |
| ggcggcgcga cggtggggct gttactctgt accgtcggct ttatgcccat tcaggcgctg | 540 |
| ttcgtcagcc agccctccct cggctatctg gtggccgcgc tggtgtttgt caccggcggc | 600 |
| ttattctgca tgtggtggtg ctacagcggc gtaaaagagc ggtatgtcga gatctcgccc | 660 |
| gatcaccata agcccggcat cctgaagtcc ttctgcgcta tcttccgcaa cccaccgcta | 720 |
| ctggtgctgt gcatcgcgaa cctctgcacc ctggcggcgt taacatcaa gctggcgatt | 780 |
| caggtctatt acacccagta cgtgctcaac gatctgcatt tgctgtcgtg gatgggtttt | 840 |
| ttcagcatgg gctgcattct gattggcgtg tttctggtgc ccgtgcggt gaagcgtttt | 900 |
| ggcaagaagc cggtctatct gggtgggctg gcgctgtggg cgataggcga tgtgctgaac | 960 |
| ttcttctggg ggaccagctc gctgctgttc gtgttctttt cctgtatggc cttttttcggc | 1020 |
| acggcgtttg tgaacagcct gaactgggcg ctggtgccgg atacggttga ttacggcgaa | 1080 |
| tggaaaacgg gcattcgcgc cgaagggtcg gtgtataccg ctataccttt ctcgcgcaaa | 1140 |
| atctccgccg ccctcgccgg attcctgccg ggcataatgc tgacgcagat tgggtatatt | 1200 |
| cctcatgccg tgcagagcgc cagtacgctg ctcggcttgc gccagctgat tttcctctgg | 1260 |
| ccgtgcggcc tggcgattat cgccgccgtg accatgggac tcttctataa actcaacgaa | 1320 |
| gcgcgcttcg cgtttattat cgaggagatc ggcaaacgca aaaaaacagc ggaagttatg | 1380 |
| gccgcgtacg gtccggaaaa gcgggtttcc gccaccagcg tttag | 1425 |

<210> SEQ ID NO 92
<211> LENGTH: 1395
<212> TYPE: DNA
<213> ORGANISM: Citrobacter koseri

<400> SEQUENCE: 92

| | |
|---|---|
| atgtctgacc atgatccgct gacgctaaaa ctgagcctac gggaaaaata tgcctatggc | 60 |
| atgggtgact tcggctcaaa tttgatgctg tgtatcggta cgctgtatct gcttaagttt | 120 |
| tataccgatg aactggggat gcccgcatat tacggtggga ttatctttct ggtggcgaag | 180 |
| ttctttaccg cgttcaccga tatgttgacg ggggtgctgc tggattcccg tcgtcatatt | 240 |
| ggcgctaaag gtaagtttcg ccctttcatt ctgtatgcat catttcctgt cgcgctggtt | 300 |

```
gccagcgcgc agtttctcgc caccgatttt acactgacgg tcaaaacagc gctggcaacc      360
gtactgttca tgctgtttgg cctgttttac agcctgatga attgctcata cggggcgatg      420
gtgcccgcta tcaccagaaa cccgcatgag cgcgcccaac tcgcagcatg cgtcagggc       480 ggcgcaacgc tcggtctgtt gctgtgtacc gttggcttta tgccgattca ggcgctcttc      540
acccagtcat cttctctggg ttatctggta gccgcgttga ttttctccgt ttgcggcctg      600
ttcagtatgt ggtggtgttt cagcggggtg aaagaacggt atatcgatat cgttccggcc      660
caccataagc ccagcattct aaatccttc tgtgcgattt tccgcaatcc gccgctgctg       720
gtgctctgcg tggccaactt atgtacgctg gccgcgttta acatcaaact ggcgattcag      780
gtctattaca cccagtacgt gctgaacgac atccatttgc tgtcatggat gggatttttc      840
agtatggggt gcattctggt cggcgtactg ctggtgcccg taaccgtaaa acggtttggg      900
aaaaagcagg tctacctcgg cggcctgacg ctgtgggcta tcggcgatgt gctgaacttt      960
ctctggggtg gaacctcttt cctgttcgtg atcttctcct gcatggcgtt tttcggcacc     1020
gcgttcgtta acagcctgaa ctgggcgctg gttcctgata cggtcgatta cggcgaatgg     1080
aaaacaggca ttcgtgcgga agggtcggtc tataccggtt ataccttctc acgaaaaatt     1140
tctgcggcgc tggcgggttt cttgcccggc attatgctga cgcaaattgg ctacgtgccg     1200
aacatagcgc aaagcgcgga gacgttactt ggcctacgtc agttgatatt tctctggcca     1260
tgcggcctgg cgattatcgc cgcactcaca atgggctttt tttataagct caatgaaaaa     1320
cgttttgctt ttattattga ggaaattagc caacgaaaga aacaatcgat acaaaccggc     1380
gttgtaagcc attaa                                                      1395

<210> SEQ ID NO 93
<211> LENGTH: 1248
<212> TYPE: DNA
<213> ORGANISM: Artificial Sequence
<220> FEATURE:
<223> OTHER INFORMATION: variant cscB sequence with 408STOP

<400> SEQUENCE: 93
atggcactga atattccatt cagaaatgcg tactatcgtt ttgcatccag ttactcattt       60
ctctttttta tttcctggtc gctgtggtgg tcgttatacg ctatttggct gaaaggacat      120
ctagggttga cagggacgga attaggtaca ctttattcgg tcaaccagtt taccagcatt      180
ctatttatga tgttctacgg catcgttcag gataaactcg gtctgaagaa accgctcatc      240
tggtgtatga gtttcatcct ggtcttgacc ggaccgttta tgatttacgt ttatgaaccg      300
ttactgcaaa gcaattttc tgtaggtcta attctggggg cgctatttt tggcttgggg       360 tatctggcgg gatgcggttt gcttgatagc ttcaccgaaa aaatggcgcg aaattttcat      420
ttcgaatatg aacagcgcg cgcctgggga tcttttggct atgctattgg cgcgttcttt      480
gccggcatat ttttagtat cagtccccat atcaacttct ggttggtctc gctatttggc      540
gctgtattta tgatgatcaa catgcgtttt aaagataagg atcaccagtg cgtagcggca      600
gatgcgggag gggtaaaaaa agaggatttt atcgcagttt tcaaggatcg aaacttctgg      660
gttttcgtca tatttattgt ggggacgtgg tctttctata acattttga tcaacaactt      720 tttcctgtct tttattcagg tttattcgaa tcacacgatg taggaacgcg cctgtatggt      780
tatctcaact cattccaggt ggtactcgaa gcgctgtgca tggcgattat tccttctttt      840
gtgaatcgga tagggccaaa aaatgcatta cttatcggag ttgtgattat ggcgttgcgt      900
atcctttcct gcgcgctgtt cgttaacccc tggattattt cattagtgaa gttgttacat      960
```

```
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg cattttctt cttgagtaaa    1200 aaacgcgagc aaatagttat gtaaacgcct gtaccttcag caatatag                1248
```

<210> SEQ ID NO 94
<211> LENGTH: 407
<212> TYPE: PRT
<213> ORGANISM: Artificial Sequence
<220> FEATURE:
<223> OTHER INFORMATION: variant CscB sequence with 408STOP

<400> SEQUENCE: 94

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320
```

Ala Ile Glu Val Pro Leu Cys Val Ile Ser Val Phe Lys Tyr Ser Val
            325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met
            405

<210> SEQ ID NO 95
<211> LENGTH: 1248
<212> TYPE: DNA
<213> ORGANISM: Artificial Sequence
<220> FEATURE:
<223> OTHER INFORMATION: variant cscB sequence with L61P substitution

<400> SEQUENCE: 95

```
atggcactga atattccatt cagaaatgcg tactatcgtt ttgcatccag ttactcattt      60
ctcttttta tttcctggtc gctgtggtgg tcgttatacg ctatttggct gaaaggacat     120
ctagggttga cagggacgga attaggtaca ctttattcgg tcaaccagtt taccagcatt     180
ccatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt tggcttgggg     360
tatctggcgg atgcggttt gcttgatagc ttcaccgaaa aaatggcgcg aaattttcat     420
ttcgaatatg aacagcgcg cgcctgggga tcttttggct atgctattgg cgcgttcttt     480
gccggcatat tttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tctttctata acatttttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900
atccttttcct gcgcgctgtt cgttaacccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgcgagc aaatagttat ggaaacgcct gtaccttcag caatatag                1248
```

<210> SEQ ID NO 96
<211> LENGTH: 415
<212> TYPE: PRT
<213> ORGANISM: Artificial Sequence
<220> FEATURE:
<223> OTHER INFORMATION: variant CscB sequence with L61P substitution

<400> SEQUENCE: 96

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Pro Phe Met Met
        50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
                100                 105                 110

Gly Ala Leu Phe Phe Gly Leu Gly Tyr Leu Ala Gly Cys Gly Leu Leu
            115                 120                 125

Asp Ser Phe Thr Glu Lys Met Ala Arg Asn Phe His Phe Glu Tyr Gly
        130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415
```

<210> SEQ ID NO 97
<211> LENGTH: 1248
<212> TYPE: DNA
<213> ORGANISM: Artificial Sequence
<220> FEATURE:
<223> OTHER INFORMATION: variant cscB sequence with F159L substitution

<400> SEQUENCE: 97

```
atggcactga atattccatt cagaaatgcg tactatcgtt ttgcatccag ttactcattt      60
ctcttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctatttt tggcttgggg      360
tatctggcgg gatgcggttt gcttgatagc ttcaccgaaa aaatggcgcg aaattttcat     420
ttcgaatatg aacagcgcg cgcctgggga tcttttggct atgctattgg cgcgttattt     480
gccggcatat tttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tcttttctata acatttttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900
atcctttcct gcgcgctgtt cgttaacccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg cattttctt cttgagtaaa    1200
aaacgcgagc aaatagttat ggaaacgcct gtaccttcag caatatag                 1248
```

<210> SEQ ID NO 98
<211> LENGTH: 415
<212> TYPE: PRT
<213> ORGANISM: Artificial Sequence
<220> FEATURE:
<223> OTHER INFORMATION: variant CscB sequence with F159L substitution

<400> SEQUENCE: 98

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
```

```
              100             105             110
Gly Ala Leu Phe Phe Gly Leu Gly Tyr Leu Ala Gly Cys Gly Leu Leu
            115             120             125

Asp Ser Phe Thr Glu Lys Met Ala Arg Asn Phe His Phe Glu Tyr Gly
        130             135             140

Thr Ala Arg Ala Trp Gly Ser Phe Gly Tyr Ala Ile Gly Ala Leu Phe
145             150             155             160

Ala Gly Ile Phe Phe Ser Ile Ser Pro His Ile Asn Phe Trp Leu Val
                165             170             175

Ser Leu Phe Gly Ala Val Phe Met Met Ile Asn Met Arg Phe Lys Asp
            180             185             190

Lys Asp His Gln Cys Val Ala Ala Asp Ala Gly Gly Val Lys Lys Glu
        195             200             205

Asp Phe Ile Ala Val Phe Lys Asp Arg Asn Phe Trp Val Phe Val Ile
    210             215             220

Phe Ile Val Gly Thr Trp Ser Phe Tyr Asn Ile Phe Asp Gln Gln Leu
225             230             235             240

Phe Pro Val Phe Tyr Ser Gly Leu Phe Glu Ser His Asp Val Gly Thr
                245             250             255

Arg Leu Tyr Gly Tyr Leu Asn Ser Phe Gln Val Val Leu Glu Ala Leu
            260             265             270

Cys Met Ala Ile Ile Pro Phe Phe Val Asn Arg Val Gly Pro Lys Asn
        275             280             285

Ala Leu Leu Ile Gly Val Val Ile Met Ala Leu Arg Ile Leu Ser Cys
    290             295             300

Ala Leu Phe Val Asn Pro Trp Ile Ile Ser Leu Val Lys Leu Leu His
305             310             315             320

Ala Ile Glu Val Pro Leu Cys Val Ile Ser Val Phe Lys Tyr Ser Val
                325             330             335

Ala Asn Phe Asp Lys Arg Leu Ser Ser Thr Ile Phe Leu Ile Gly Phe
            340             345             350

Gln Ile Ala Ser Ser Leu Gly Ile Val Leu Leu Ser Thr Pro Thr Gly
        355             360             365

Ile Leu Phe Asp His Ala Gly Tyr Gln Thr Val Phe Phe Ala Ile Ser
    370             375             380

Gly Ile Val Cys Leu Met Leu Leu Phe Gly Ile Phe Leu Ser Lys
385             390             395             400

Lys Arg Glu Gln Ile Val Met Glu Thr Pro Val Pro Ser Ala Ile
                405             410             415

<210> SEQ ID NO 99
<211> LENGTH: 1248
<212> TYPE: DNA
<213> ORGANISM: Artificial Sequence
<220> FEATURE:
<223> OTHER INFORMATION: variant cscB sequence with G162C substitution

<400> SEQUENCE: 99
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gttcatcct ggtcttgacc ggaccgttta tgatttacgt ttatgaaccg     300
ttactgcaaa gcaattttc tgtaggtcta attctggggg cgctattttt tggcttgggg     360
```

```
tatctggcgg gatgcggttt gcttgatagc ttcaccgaaa aaatggcgcg aaatttcat    420 ttcgaatatg aacagcgcg cgcctgggga tcttttggct atgctattgg cgcgttcttt    480
gcctgcatat tttttagtat cagtccccat atcaacttct ggttggtctc gctatttggc   540
gctgtattta tgatgatcaa catgcgtttt aaagataagg atcaccagtg cgtagcggca   600
gatgcgggag gggtaaaaaa agaggatttt atcgcagttt tcaaggatcg aaacttctgg   660
gttttcgtca tatttattgt ggggacgtgg tctttctata acattttga tcaacaactt    720 tttcctgtct tttattcagg tttattcgaa tcacacgatg taggaacgcg cctgtatggt   780
tatctcaact cattccaggt ggtactcgaa gcgctgtgca tggcgattat tccttcttt    840 gtgaatcggg tagggccaaa aaatgcatta cttatcggag ttgtgattat ggcgttgcgt   900
atcctttcct gcgcgctgtt cgttaacccc tggattattt cattagtgaa gttgttacat   960
gccattgagg ttccactttg tgtcatatcc gtcttcaaat acagcgtggc aaactttgat  1020
aagcgcctgt cgtcgacgat ctttctgatt ggttttcaaa ttgccagttc gcttgggatt  1080
gtgctgcttt caacgccgac tgggatactc tttgaccacg caggctacca gacagttttc  1140
ttcgcaattt cgggtattgt ctgcctgatg ttgctatttg cattttctt cttgagtaaa   1200 aaacgcgagc aaatagttat ggaaacgcct gtaccttcag caatatag                1248
```

<210> SEQ ID NO 100
<211> LENGTH: 415
<212> TYPE: PRT
<213> ORGANISM: Artificial Sequence
<220> FEATURE:
<223> OTHER INFORMATION: variant CscB sequence with G162C substitution

<400> SEQUENCE: 100

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Cys Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205
```

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415

<210> SEQ ID NO 101
<211> LENGTH: 1248
<212> TYPE: DNA
<213> ORGANISM: Artificial Sequence
<220> FEATURE:
<223> OTHER INFORMATION: variant cscB sequence with P169H substitution

<400> SEQUENCE: 101
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctatttt tggcttgggg      360 tatctggcgg gatgcggttt gcttgatagc ttcaccgaaa aaatggcgcg aaattttcat     420
ttcgaatatg aacagcgcg cgcctgggga tcttttggct atgctattgg cgcgttcttt     480
gccggcatat tttttagtat cagtcaccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660 gtttttcgtca tatttattgt ggggacgtgg tctttctata acatttttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttcgct     900
atcctttcct gcgcgctgtt cgttaacccc tggattattt cattagtgaa gttgttacat     960

```
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg cattttctt cttgagtaaa    1200 aaacgcgagc aaatagttat ggaaacgcct gtaccttcag caatatag                 1248
```

<210> SEQ ID NO 102
<211> LENGTH: 415
<212> TYPE: PRT
<213> ORGANISM: Artificial Sequence
<220> FEATURE:
<223> OTHER INFORMATION: variant CscB sequence with P169H substitution

<400> SEQUENCE: 102

```
Met Ala Leu Asn Ile Pro Phe Arg Asn Ala Tyr Tyr Arg Phe Ala Ser
1               5                   10                  15

Ser Tyr Ser Phe Leu Phe Ile Ser Trp Ser Leu Trp Ser Leu
            20                  25                  30

Tyr Ala Ile Trp Leu Lys Gly His Leu Gly Leu Thr Gly Thr Glu Leu
            35                  40                  45

Gly Thr Leu Tyr Ser Val Asn Gln Phe Thr Ser Ile Leu Phe Met Met
        50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser His His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320
```

Ala Ile Glu Val Pro Leu Cys Val Ile Ser Val Phe Lys Tyr Ser Val
            325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
            355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415

<210> SEQ ID NO 103
<211> LENGTH: 1248
<212> TYPE: DNA
<213> ORGANISM: Artificial Sequence
<220> FEATURE:
<223> OTHER INFORMATION: variant cscB sequence with L61W substitution

<400> SEQUENCE: 103
atggcactga atattccatt cagaaatgcg tactatcgtt ttgcatccag ttactcattt      60
ctctttttta tttcctggtc gctgtggtgg tcgttatacg ctatttggct gaaaggacat    120
ctagggttga cagggacgga attaggtaca ctttattcgg tcaaccagtt taccagcatt    180
tggtttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctggggg cgctattttt tggcttgggg    360
tatctggcgg atgcggttt gcttgatagc ttcaccgaaa aaatggcgcg aaattttcat    420
ttcgaatatg aacagcgcg cgcctgggga tcttttggct atgctattgg cgcgttcttt    480
gccggcatat tttttagtat cagtccccat atcaacttct ggttggtctc gctatttggc    540
gctgtattta tgatgatcaa catgcgtttt aaagataagg atcaccagtg cgtagcggca    600
gatgcgggag gggtaaaaaa agaggatttt atcgcagttt tcaaggatcg aaacttctgg    660
gttttcgtca tatttattgt ggggacgtgg tctttctata acattttga tcaacaactt    720
tttcctgtct tttattcagg tttattcgaa tcacacgatg taggaacgcg cctgtatggt    780
tatctcaact cattccaggt ggtactcgaa gcgctgtgca tggcgattat tcctttcttt    840
gtgaatcggg taggccaaa aaatgcatta cttatcggag ttgtgattat ggcgttgcgt    900
atcctttcct gcgcgctgtt cgttaacccc tggattattt cattagtgaa gttgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg gcattttctt cttgagtaaa   1200
aaacgcgagc aaatagttat ggaaacgcct gtaccttcag caatatag                1248

<210> SEQ ID NO 104
<211> LENGTH: 415
<212> TYPE: PRT
<213> ORGANISM: Artificial Sequence
<220> FEATURE:
<223> OTHER INFORMATION: variant CscB sequence with L61W substitution

<400> SEQUENCE: 104

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Trp Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415
```

-continued

<210> SEQ ID NO 105
<211> LENGTH: 1248
<212> TYPE: DNA
<213> ORGANISM: Artificial Sequence
<220> FEATURE:
<223> OTHER INFORMATION: variant cscB sequence with L61H substitution

<400> SEQUENCE: 105

```
atggcactga atattccatt cagaaatgcg tactatcgtt ttgcatccag ttactcattt      60
ctctttttta tttcctggtc gctgtggtgg tcgttatacg ctatttggct gaaaggacat     120
ctagggttga cagggacgga attaggtaca ctttattcgg tcaaccagtt taccagcatt     180
cattttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt tggcttgggg     360
tatctggcgg gatgcggttt gcttgatagc ttcaccgaaa aaatggcgcg aaattttcat     420
ttcgaatatg aacagcgcg cgcctgggga tcttttggct atgctattgg cgcgttcttc     480
gccggcatat ttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tctttctata acattttga tcaacaactt     720
tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900
atcctttcct gcgcgctgtt cgttaaccc tggattattt cattagtgaa gttgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgcgagc aaatagttat ggaaacgcct gtaccttcag caatatag                1248
```

<210> SEQ ID NO 106
<211> LENGTH: 415
<212> TYPE: PRT
<213> ORGANISM: Artificial Sequence
<220> FEATURE:
<223> OTHER INFORMATION: variant CscB sequence with L61H substitution

<400> SEQUENCE: 106

Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile His Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu

```
                100             105                 110
Gly Ala Leu Phe Phe Gly Leu Gly Tyr Leu Ala Gly Cys Gly Leu Leu
            115                 120             125

Asp Ser Phe Thr Glu Lys Met Ala Arg Asn Phe His Phe Glu Tyr Gly
        130                 135             140

Thr Ala Arg Ala Trp Gly Ser Phe Gly Tyr Ala Ile Gly Ala Phe Phe
145                 150             155                 160

Ala Gly Ile Phe Phe Ser Ile Ser Pro His Ile Asn Phe Trp Leu Val
                165             170              175

Ser Leu Phe Gly Ala Val Phe Met Met Ile Asn Met Arg Phe Lys Asp
            180              185                 190

Lys Asp His Gln Cys Val Ala Ala Asp Ala Gly Gly Val Lys Lys Glu
            195                 200             205

Asp Phe Ile Ala Val Phe Lys Asp Arg Asn Phe Trp Val Phe Val Ile
        210             215                 220

Phe Ile Val Gly Thr Trp Ser Phe Tyr Asn Ile Phe Asp Gln Gln Leu
225                 230              235                 240

Phe Pro Val Phe Tyr Ser Gly Leu Phe Glu Ser His Asp Val Gly Thr
                245             250                 255

Arg Leu Tyr Gly Tyr Leu Asn Ser Phe Gln Val Val Leu Glu Ala Leu
            260             265                 270

Cys Met Ala Ile Ile Pro Phe Phe Val Asn Arg Val Gly Pro Lys Asn
            275             280                 285

Ala Leu Leu Ile Gly Val Val Ile Met Ala Leu Arg Ile Leu Ser Cys
            290             295                 300

Ala Leu Phe Val Asn Pro Trp Ile Ile Ser Leu Val Lys Leu Leu His
305                 310             315                 320

Ala Ile Glu Val Pro Leu Cys Val Ile Ser Val Phe Lys Tyr Ser Val
                325             330                 335

Ala Asn Phe Asp Lys Arg Leu Ser Ser Thr Ile Phe Leu Ile Gly Phe
            340             345                 350

Gln Ile Ala Ser Ser Leu Gly Ile Val Leu Leu Ser Thr Pro Thr Gly
            355             360                 365

Ile Leu Phe Asp His Ala Gly Tyr Gln Thr Val Phe Phe Ala Ile Ser
370                 375             380

Gly Ile Val Cys Leu Met Leu Leu Phe Gly Ile Phe Phe Leu Ser Lys
385                 390             395                 400

Lys Arg Glu Gln Ile Val Met Glu Thr Pro Val Pro Ser Ala Ile
            405             410                 415

<210> SEQ ID NO 107
<211> LENGTH: 1248
<212> TYPE: DNA
<213> ORGANISM: Artificial Sequence
<220> FEATURE:
<223> OTHER INFORMATION: variant cscB sequence with L61F substitution

<400> SEQUENCE: 107
atggcactga atattccatt cagaaatgcg tactatcgtt ttgcatccag ttactcattt     60 ctcttttta tttcctggtc gctgtggtgg tcgttatacg ctatttggct gaaaggacat    120
ctagggttga cagggacgga attaggtaca ctttattcgg tcaaccagtt taccagcatt    180
ttttttatga tgttctacgg catcgttcag gataaactcg gtctgaagaa accgctcatc    240
tggtgtatga gttcatcct ggtcttgacc ggaccgttta tgatttacgt ttatgaaccg    300
ttactgcaaa gcaattttc tgtaggtcta attctggggg cgctattttt tggcttgggg    360
```

```
tatctggcgg gatgcggttt gcttgatagc ttcaccgaaa aaatggcgcg aaattttcat      420
ttcgaatatg aacagcgcg cgcctgggga tcttttggct atgctattgg cgcgttcttt      480
gccggcatat ttttagtat cagtccccat atcaacttct ggttggtctc gctatttggc      540
gctgtattta tgatgatcaa catgcgtttt aaagataagg atcaccagtg cgtagcggca      600
gatgcgggag gggtaaaaaa agaggatttt atcgcagttt tcaaggatcg aaacttctgg      660
gttttcgtca tatttattgt ggggacgtgg tctttctata acattttga tcaacaactt      720 tttcctgtct tttattcagg tttattcgaa tcacacgatg taggaacgcg cctgtatggt      780
tatctcaact cattccaggt ggtactcgaa gcgctgtgca tggcgattat tcctttcttt      840
gtgaatcggg tagggccaaa aaatgcatta cttatcggag ttgtgattat ggcgttgcgt      900
atcctttcct gcgcgctgtt cgttaacccc tggattattt cattagtgaa gttgttacat      960
gccattgagg ttccactttg tgtcatatcc gtcttcaaat acagcgtggc aaactttgat     1020
aagcgcctgt cgtcgacgat cttctctgatt ggttttcaaa ttgccagttc gcttgggatt     1080
gtgctgcttt caacgccgac tgggatactc tttgaccacg caggctacca gacagttttc     1140
ttcgcaattt cgggtattgt ctgcctgatg ttgctatttg cattttctt cttgagtaaa     1200 aaacgcgagc aaatagttat ggaaacgcct gtaccttcag caatatag                 1248
```

<210> SEQ ID NO 108
<211> LENGTH: 415
<212> TYPE: PRT
<213> ORGANISM: Artificial Sequence
<220> FEATURE:
<223> OTHER INFORMATION: variant CscB sequence with L61F substitution

<400> SEQUENCE: 108

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Phe Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205
```

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
                260                 265                 270

Cys Met Ala Ile Ile Pro Phe Phe Val Asn Arg Val Gly Pro Lys Asn
    275                 280                 285

Ala Leu Leu Ile Gly Val Val Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
    355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 109
<211> LENGTH: 1248
<212> TYPE: DNA
<213> ORGANISM: Artificial Sequence
<220> FEATURE:
<223> OTHER INFORMATION: variant cscB sequence with 403STOP

<400> SEQUENCE: 109
atggcactga atattccatt cagaaatgcg tactatcgtt ttgcatccag ttactcattt      60 ctcttttta tttcctggtc gctgtggtgg tcgttatacg ctatttggct gaaaggacat     120
ctagggttga cagggacgga attaggtaca ctttattcgg tcaaccagtt taccagcatt     180
ctatttatga tgttctacgg catcgttcag gataaactcg gtctgaagaa accgctcatc     240
tggtgtatga gtttcatcct ggtcttgacc ggaccgttta tgatttacgt ttatgaaccg     300
ttactgcaaa gcaattttc tgtaggtcta attctggggg cgctattttt tggcttgggg     360
tatctggcgg gatgcggttt gcttgatagc ttcaccgaaa aaatggcgcg aaattttcat     420
ttcgaatatg aacagcgcg cgcctgggga tcttttggct atgctattgg cgcgttcttt     480
gccggcatat tttttagtat cagtccccat atcaacttct ggttggtctc gctatttggc     540
gctgtattta tgatgatcaa catgcgtttt aaagataagg atcaccagtg cgtagcggca     600
gatgcgggag gggtaaaaaa agaggatttt atcgcagttt tcaaggatcg aaacttctgg     660
gttttcgtca tatttattgt ggggacgtgg tctttctata acattttga tcaacaactt     720 tttcctgtct tttattcagg tttattcgaa tcacacgatg taggaacgcg cctgtatggt     780
tatctcaact cattccaggt ggtactcgaa gcgctgtgca tggcgattat tcctttcttt     840
gtgaatcggg tagggccaaa aaatgcatta cttatcggag ttgtgattat ggcgttgcgt     900 atccttttcct gcgcgctgtt cgttaacccc tggattattt cattagtgaa gttgttacat     960

```
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgctagc aaatagttat ggaaacgcct gtaccttcag caatatag                 1248
```

<210> SEQ ID NO 110
<211> LENGTH: 402
<212> TYPE: PRT
<213> ORGANISM: Artificial Seqquence
<220> FEATURE:
<223> OTHER INFORMATION: variant CscB sequence with 403STOP

<400> SEQUENCE: 110

```
Met Ala Leu Asn Ile Pro Phe Arg Asn Ala Tyr Tyr Arg Phe Ala Ser
1               5                   10                  15

Ser Tyr Ser Phe Leu Phe Ile Ser Trp Ser Leu Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320
```

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg

<210> SEQ ID NO 111
<211> LENGTH: 921
<212> TYPE: DNA
<213> ORGANISM: Escherichia coli

<400> SEQUENCE: 111
atgagcgcaa gagtatgggt actcggtgat gcggttgttg atttattacc cgaaagccag      60
gggagactac tacagtgtcc tggcggggcg cctgctaatg ttgcagtcgg tatcgcaagg     120
ctggggggga aaagtgcctt tattggcaaa gttggcgatg atcctttcgg tcgctttatg     180
tatcagacac tgagtacaga aaatgttgat acacattata tgtctcttga tcctcaacaa     240
cgcacctcaa ttgtggctgt aggacttgat gagcaaggag aaagaaactt tacctttatg     300
gtacgcccaa gtgccgatct ttttttacaa cctggtgacc ttcctgcatt tgggccgggt     360
gaatggctcc atctttgttc cattgcgctc agtgcagaac cttcccgaag taccgcattt     420
ctggctatgg agaaaatacg tcaggctggc ggaaacatca gttttgatcc caatatccgc     480
agcgatctct ggcagagtga agcgctatta aggaaatacc ttgatcgcgc actttcgctg     540
gcgaatatcg ctaaattgtc cgaagaagag ttgctattca tcagtggcga aagccaggtt     600
cagcaaggcg catattcatt agtacaacgt tattcgttga cttttattgct tattacacaa     660 ggaaaaaatg gcgtacttgt gtattttcag ggcagttta tccactatcc cgccaaacct     720
gtttctgtcg tcgatacgac cggggcagga gatgcttttg tcgctggatt acttgcaggt     780
ctggctgatt ctggaatacc aacaaatacc agacagcttg aacgaatcat tgcacaagct     840
cagatttgtg gtgctctggc gaccacggct aaaggcgcga taaccgcctt accccgacaa     900
cacgatctcc cttcacaata g                                              921

<210> SEQ ID NO 112
<211> LENGTH: 306
<212> TYPE: PRT
<213> ORGANISM: Escherichia coli

<400> SEQUENCE: 112

Met Ser Ala Arg Val Trp Val Leu Gly Asp Ala Val Val Asp Leu Leu
1               5                   10                  15

Pro Glu Ser Gln Gly Arg Leu Leu Gln Cys Pro Gly Gly Ala Pro Ala
            20                  25                  30

Asn Val Ala Val Gly Ile Ala Arg Leu Gly Gly Lys Ser Ala Phe Ile
        35                  40                  45

Gly Lys Val Gly Asp Asp Pro Phe Gly Arg Phe Met Tyr Gln Thr Leu
    50                  55                  60

Ser Thr Glu Asn Val Asp Thr His Tyr Met Ser Leu Asp Pro Gln Gln
65                  70                  75                  80

```
Arg Thr Ser Ile Val Ala Val Gly Leu Asp Glu Gln Gly Glu Arg Asn
                85                  90                  95
Phe Thr Phe Met Val Arg Pro Ser Ala Asp Leu Phe Leu Gln Pro Gly
            100                 105                 110
Asp Leu Pro Ala Phe Gly Pro Gly Glu Trp Leu His Leu Cys Ser Ile
        115                 120                 125
Ala Leu Ser Ala Glu Pro Ser Arg Ser Thr Ala Phe Leu Ala Met Glu
    130                 135                 140
Lys Ile Arg Gln Ala Gly Gly Asn Ile Ser Phe Asp Pro Asn Ile Arg
145                 150                 155                 160
Ser Asp Leu Trp Gln Ser Glu Ala Leu Leu Arg Lys Tyr Leu Asp Arg
                165                 170                 175
Ala Leu Ser Leu Ala Asn Ile Ala Lys Leu Ser Glu Glu Leu Leu
            180                 185                 190
Phe Ile Ser Gly Glu Ser Gln Val Gln Gln Gly Ala Tyr Ser Leu Val
        195                 200                 205
Gln Arg Tyr Ser Leu Thr Leu Leu Ile Thr Gln Gly Lys Asn Gly
    210                 215                 220
Val Leu Val Tyr Phe Gln Gly Gln Phe Ile His Tyr Pro Ala Lys Pro
225                 230                 235                 240
Val Ser Val Val Asp Thr Thr Gly Ala Gly Asp Ala Phe Val Ala Gly
                245                 250                 255
Leu Leu Ala Gly Leu Ala Asp Ser Gly Ile Pro Thr Asn Thr Arg Gln
            260                 265                 270
Leu Glu Arg Ile Ile Ala Gln Ala Gln Ile Cys Gly Ala Leu Ala Thr
        275                 280                 285
Thr Ala Lys Gly Ala Ile Thr Ala Leu Pro Arg Gln His Asp Leu Pro
    290                 295                 300
Ser Gln
305

<210> SEQ ID NO 113
<211> LENGTH: 924
<212> TYPE: DNA
<213> ORGANISM: Klebsiella pneumoniae

<400> SEQUENCE: 113
atgaatggaa aaatctgggt actcggcgat gcggtcgtcg atctcctgcc cgatggagag    60
ggccgcctgc tgcaatgccc cggcggcgcg ccggccaacg tggcggtcgg cgtggcgcgg   120
ctcggcggtg acagcgggtt tatcggccgc gtcggcgacg atcccttcgg ccgttttatg   180
cgtcacaccc tggcgcagga gcaagtggat gtgaactata tgcgcctcga tgcggcgcag   240
cgcacctcca cggtggtggt cgatctcgat agccacgggg agcgcacctt taccttttatg   300 gtccgtccga gcgccgacct gttccttcag cccgaggatc tcccgccgtt tgccgccggt   360
cagtggctgc acgtctgctc catcgctctc agcgcggagc cgagccgcag cacgacattc   420
gcggcgatgg aggcgataaa gcgcgccggg ggctatgtca gcttcgaccc caatatccgc   480
agcgacctgt ggcaggatcc gcaggacctt cgcgactgtc tcgaccgggc gctggccctc   540
gccgacgcca taaaactttc ggaagaggag ctggcgttta tcagcggcag cgacgacatc   600
gtcagcggca ccgcccggct gaacgcccgc ttccagccga cgctactgct ggtgacccag   660
ggtaaagcgg gggtccaggc cgccctgcgc gggcaggtta gccacttccc tgcccgcccg   720
gtggtggccg tcgataccac cggcgccggc gatgcctttg tcgccgggct actcgccggc   780
```

```
ctcgccgccc acggtatccc ggacaacctc gcagccctgg ctcccgacct cgcgctggcg      840
caaacctgcg gcgccctggc caccaccgcc aaaggcgcca tgaccgccct gccctacagg      900
gacgatcttc agcgctcgct gtga                                              924
```

<210> SEQ ID NO 114
<211> LENGTH: 307
<212> TYPE: PRT
<213> ORGANISM: Klebsiella pneumoniae

<400> SEQUENCE: 114

```
Met Asn Gly Lys Ile Trp Val Leu Gly Asp Ala Val Val Asp Leu Leu
1               5                   10                  15

Pro Asp Gly Glu Gly Arg Leu Leu Gln Cys Pro Gly Gly Ala Pro Ala
            20                  25                  30

Asn Val Ala Val Gly Val Ala Arg Leu Gly Gly Asp Ser Gly Phe Ile
        35                  40                  45

Gly Arg Val Gly Asp Asp Pro Phe Gly Arg Phe Met Arg His Thr Leu
    50                  55                  60

Ala Gln Glu Gln Val Asp Val Asn Tyr Met Arg Leu Asp Ala Ala Gln
65                  70                  75                  80

Arg Thr Ser Thr Val Val Asp Leu Asp Ser His Gly Glu Arg Thr
                85                  90                  95

Phe Thr Phe Met Val Arg Pro Ser Ala Asp Leu Phe Leu Gln Pro Glu
            100                 105                 110

Asp Leu Pro Pro Phe Ala Ala Gly Gln Trp Leu His Val Cys Ser Ile
        115                 120                 125

Ala Leu Ser Ala Glu Pro Ser Arg Ser Thr Thr Phe Ala Ala Met Glu
130                 135                 140

Ala Ile Lys Arg Ala Gly Gly Tyr Val Ser Phe Asp Pro Asn Ile Arg
145                 150                 155                 160

Ser Asp Leu Trp Gln Asp Pro Gln Asp Leu Arg Asp Cys Leu Asp Arg
                165                 170                 175

Ala Leu Ala Leu Ala Asp Ala Ile Lys Leu Ser Glu Glu Glu Leu Ala
            180                 185                 190

Phe Ile Ser Gly Ser Asp Asp Ile Val Ser Gly Thr Ala Arg Leu Asn
        195                 200                 205

Ala Arg Phe Gln Pro Thr Leu Leu Leu Val Thr Gln Gly Lys Ala Gly
    210                 215                 220

Val Gln Ala Ala Leu Arg Gly Gln Val Ser His Phe Pro Ala Arg Pro
225                 230                 235                 240

Val Val Ala Val Asp Thr Thr Gly Ala Gly Asp Ala Phe Val Ala Gly
                245                 250                 255

Leu Leu Ala Gly Leu Ala Ala His Gly Ile Pro Asp Asn Leu Ala Ala
            260                 265                 270

Leu Ala Pro Asp Leu Ala Leu Ala Gln Thr Cys Gly Ala Leu Ala Thr
        275                 280                 285

Thr Ala Lys Gly Ala Met Thr Ala Leu Pro Tyr Arg Asp Asp Leu Gln
    290                 295                 300

Arg Ser Leu
305
```

<210> SEQ ID NO 115
<211> LENGTH: 60
<212> TYPE: DNA
<213> ORGANISM: Artificial Sequence
<220> FEATURE:

```
<223> OTHER INFORMATION: Primer

<400> SEQUENCE: 115
tagacgtgaa acaggagtca taatgaattt tcatcatctg ggatcccttg cccgctgttg      60

<210> SEQ ID NO 116
<211> LENGTH: 60
<212> TYPE: DNA
<213> ORGANISM: Artificial Sequence
<220> FEATURE:
<223> OTHER INFORMATION: Primer

<400> SEQUENCE: 116
catttcaggc ctccaggctt atccagatgg ttttcagttc gaattcgcag gaccgtgata      60

<210> SEQ ID NO 117
<211> LENGTH: 24
<212> TYPE: DNA
<213> ORGANISM: Artificial Sequence
<220> FEATURE:
<223> OTHER INFORMATION: Primer

<400> SEQUENCE: 117
tgagcgaatc ccgatgagct tact                                             24

<210> SEQ ID NO 118
<211> LENGTH: 24
<212> TYPE: DNA
<213> ORGANISM: Artificial Sequence
<220> FEATURE:
<223> OTHER INFORMATION: Primer

<400> SEQUENCE: 118
atacgttcgc ggatgatctc acca                                             24

<210> SEQ ID NO 119
<211> LENGTH: 60
<212> TYPE: DNA
<213> ORGANISM: Artificial Sequence
<220> FEATURE:
<223> OTHER INFORMATION: Primer

<400> SEQUENCE: 119
accattgtgg cgatgggttg cttctacagc ctgaacgaga ggatcccttg cccgctgttg      60

<210> SEQ ID NO 120
<211> LENGTH: 60
<212> TYPE: DNA
<213> ORGANISM: Artificial Sequence
<220> FEATURE:
<223> OTHER INFORMATION: Primer

<400> SEQUENCE: 120
ttacgggctt ctatctcttc cacaatgcgg acatacatct gaattcgcag gaccgtgata      60

<210> SEQ ID NO 121
<211> LENGTH: 24
<212> TYPE: DNA
<213> ORGANISM: Artificial Sequence
<220> FEATURE:
<223> OTHER INFORMATION: Primer

<400> SEQUENCE: 121
tgctgggcga tctgctcaac tatt                                             24

<210> SEQ ID NO 122
```

```
<211> LENGTH: 24
<212> TYPE: DNA
<213> ORGANISM: Artificial Sequence
<220> FEATURE:
<223> OTHER INFORMATION: Primer

<400> SEQUENCE: 122
taatcccgcc atagtaagca ggca                                           24

<210> SEQ ID NO 123
<211> LENGTH: 4146
<212> TYPE: DNA
<213> ORGANISM: Escherichia coli

<400> SEQUENCE: 123
ggatcccttg cccgctgttg atccgttgtt ccacctgata ttatgttaac ccagtagcca     60
gagtgctcca tgttgcagca cagccactcc gtgggaggca taaagcgaca gttcccgttc    120
ttctggctgc ggatagattc gactactcat caccgcttcc ccgtcgttaa taaatacttc    180
cacggatgat gtatcgataa atatccttag ggcgagcgtg tcacgctgcg ggagggggaat   240 actacggtag ccgtctaaat tctcgtgtgg gtaataccgc cacaaaacaa gtcgctcaga    300
ttggttatca atatacagcc gcattccagt gccgagctgt aatccgtaat gttcggcatc    360
actgttcttc agcgcccact gcaactgaat ctcaactgct gcgcgtttt cctgcaaaac     420 atatttattg ctgattgtgc ggggagagac agattgatgc tgctggcgta acgactcagc    480
ttcgtgtacc gggcgttgta gaagtttgcc attgctctct gatagctcgc gcgcagcgt    540 catgcagcct gcccatcctt cacgttttga gggcattggc gattcccaca tatccatcca    600
gccgataaca atacgccgac catccttcgc taaaaagctt tgtggtgcat aaaagtcatg    660
cccgttatca agttcagtaa aatgcccgga ttgtgcaaaa agtcgtcctg gcgaccacat    720
tccgggtatt acgccacttt gaaagcgatt tcggtaactg tatccctcgg cattcattcc    780
ctgcggggaa aacatcagat aatgctgatc gccaaggctg aaaaagtccg gacattccca    840
catatagctt tcacccgcat cagcgtgggc cagtacgcga tcgaaggtcc attcacgcaa    900
cgaactgccg cgataaagca ggatctgccc cgtgttgcct ggatctttcg ccccgactac    960
catccaccat gtgtcggctt cacgccacac tttaggatcg cggaagtgca tgattccttc   1020
tggtggagtg aggatcacac cctgtttctc gaaatgaata ccatcccgac tggtagccag   1080
acattgtact cgcgaattg catcgtcatt acctgcacca tcgagccaga cgtgtccggt    1140
gtagataagt gagaggacac cattgtcatc gacagcacta cctgaaaaac acccgtcttt    1200
gtcattatcg tctcctggcg ctagcgcaat aggctcatgc tgccagtgga tcatatcgtc    1260
gctggtggca tgtccccagt gcattggccc ccagtgttcg ctcatcggat gatgttgata    1320
aaacgcgtga taacgatcgt taaaccagat caggccgttt ggatcgttca tccacccggc    1380
aggaggcgcg aggtgaaaat ggggatagaa agtgttaccc cggtgctcat gaagttttgc    1440
tagggcgttt tgcgccgcat gcaatcgaga ttgcgtcatt ttaatcatcc tggttaagca    1500
aatttggtga attgttaacg ttaactttta taaaataaa gtcccttact ttcataaatg     1560
cgatgaatat cacaaatgtt aacgttaact atgacgtttt gtgatcgaat atgcatgttt    1620
tagtaaatcc atgacgattt tgcgaaaaag aggtttatca ctatgcgtaa ctcagatgaa    1680
tttaagggaa aaaaatgtca gccaaagtat gggttttagg ggatgcggtc gtagatctct    1740
tgccagaatc agacgggcgc ctactgcctt gtcctggcgg cgcgccagct aacgttgcgg    1800
tgggaatcgc cagattaggc ggaacaagtg ggtttatagg tcgggtgggg gatgatcctt    1860
```

```
ttggtgcgtt aatgcaaaga acgctgctaa ctgagggagt cgatatcacg tatctgaagc    1920
aagatgaatg gcaccggaca tccacggtgc ttgtcgatct gaacgatcaa ggggaacgtt    1980
catttacgtt tatggtccgc cccagtgccg atctttttt  agagacgaca gacttgccct    2040
gctggcgaca tggcgaatgg ttacatctct gttcaattgc gttgtctgcc gagccttcgc    2100
gtaccagcgc atttactgcg atgacggcga tccggcatgc cggaggtttt gtcagcttcg    2160
atcctaatat tcgtgaagat ctatggcaag acgagcattt gctccgcttg tgtttgcggc    2220
aggcgctaca actggcggat gtcgtcaagc tctcggaaga agaatggcga cttatcagtg    2280
gaaaaacaca gaacgatcag gatatatgcg ccctggcaaa agagtatgag atcgccatgc    2340
tgttggtgac taaaggtgca gaagggggtgg tggtctgtta tcgaggacaa gttcaccatt    2400
ttgctggaat gtctgtgaat tgtgtcgata gcacggggggc gggagatgcg ttcgttgccg    2460
ggttactcac aggtctgtcc tctacgggat tatctacaga tgagagagaa atgcgacgaa    2520
ttatcgatct cgctcaacgt tgcggagcgc ttgcagtaac ggcgaaaggg gcaatgacag    2580
cgctgccatg tcgacaagaa ctggaatagt gagaagtaaa cggcgaagtc gctcttatct    2640
ctaaatagga cgtgaatttt taacgacag  gcaggtaatt atggcactga atattccatt    2700
cagaaatgcg tactatcgtt ttgcatccag ttactcattt ctcttttta  tttcctggtc    2760 gctgtggtgg tcgttatacg ctatttggct gaaaggacat ctaggggttga cagggacgga    2820 attaggtaca ctttattcgg tcaaccagtt taccagcatt ctatttatga tgttctacgg    2880
catcgttcag gataaactcg gtctgaagaa accgctcatc tggtgtatga gtttcatcct    2940
ggtcttgacc ggaccgttta tgatttacgt ttatgaaccg ttactgcaaa gcaattttc    3000 tgtaggtcta attctggggg cgctattttt tggcttgggg tatctggcgg gatgcggttt    3060
gcttgatagc ttcaccgaaa aaatggcgcg aaatttttcat ttcgaatatg aacagcgcg    3120 cgcctgggga tcttttggct atgctattgg cgcgttcttt gccggcatat ttttttagtat    3180 cagtccccat atcaacttct ggttggtctc gctatttggc gctgtattta tgatgatcaa    3240
catgcgtttt aaagataagg ataccagtg  cgtagcggca gatgcgggag gggtaaaaaa    3300
agaggatttt atcgcagttt tcaaggatcg aaacttctgg gttttcgtca tatttattgt    3360
ggggacgtgg tctttctata acattttga  tcaacaactt tttcctgtct tttattcagg    3420
tttattcgaa tcacacgatg taggaacgcg cctgtatggt tatctcaact cattccaggt    3480
ggtactcgaa gcgctgtgca tggcgattat tcctttcttt gtgaatcggg tagggccaaa    3540 aaaatgcatta cttatcggag ttgtgattat ggcgttgcgt atcctttcct gcgcgctgtt    3600
cgttaacccc tggattattt cattagtgaa gttgttacat gccattgagg ttccactttg    3660
tgtcatatcc gtcttcaaat acagcgtggc aaactttgat aagcgcctgt cgtcgacgat    3720
ctttctgatt ggttttcaaa ttgccagttc gcttgggatt gtgctgcttt caacgccgac    3780
tgggatactc tttgaccacg caggctacca gacagttttc ttcgcaattt cgggtattgt    3840
ctgcctgatg ttgctatttg gcatttttct cttgagtaaa aaacgcgagc aaatagttat    3900
ggaaacgcct gtaccttcag caatatagac gtaaactttt tccggttgtt gtcgatagct    3960
ctatatccct caaccggaaa ataataatag taaaatgctt agccctgcta ataatcgcct    4020
aatccaaacg cctcattcat gttctggtac agtcgctcaa atgtacttca gatgcgcggt    4080
tcgctgattt ccaggacatt gtcgtcattc agtgacctgt cccgtgtatc acggtcctgc    4140
gaattc                                                              4146
```

<210> SEQ ID NO 124

<211> LENGTH: 9317
<212> TYPE: DNA
<213> ORGANISM: Artificial Sequence
<220> FEATURE:
<223> OTHER INFORMATION: Plasmid

<400> SEQUENCE: 124

| | | | | | |
|---|---|---|---|---|---|
| tcgaggaatt | cgcaggaccg | tgatacacgg | gacaggtcac | tgaatgacga | caatgtcctg | 60 |
| gaaatcagcg | aaccgcgcat | ctgaagtaca | tttgagcgac | tgtaccagaa | catgaatgag | 120 |
| gcgtttggat | taggcgatta | ttagcagggc | taagcatttt | actattatta | ttttccggtt | 180 |
| gagggatata | gagctatcga | caacaaccgg | aaaaagttta | cgtctatatt | gctgaaggta | 240 |
| caggcgtttc | cataactatt | tgctcgcgtt | ttttactcaa | gaagaaaatg | ccaaatagca | 300 |
| acatcaggca | gacaatacc | gaaattgcga | agaaaactgt | ctggtagcct | gcgtggtcaa | 360 |
| agagtatccc | agtcggcgtt | gaaagcagca | caatcccaag | cgaactggca | atttgaaaac | 420 |
| caatcagaaa | gatcgtcgac | gacaggcgct | tatcaaagtt | tgccacgctg | tatttgaaga | 480 |
| cggatatgac | acaaagtgga | acctcaatgg | catgtaacaa | cttcactaat | gaaataatcc | 540 |
| aggggttaac | gaacagcgcg | caggaaagga | tacgcaacgc | cataatcaca | actccgataa | 600 |
| gtaatgcatt | ttttggccct | acccgattca | caaagaaagg | aataatcgcc | atgcacagcg | 660 |
| cttcgagtac | cacctggaat | gagttgagat | aaccatacag | gcgcgttcct | acatcgtgtg | 720 |
| attcgaataa | acctgaataa | aagacaggaa | aaagttgttg | atcaaaaatg | ttatagaaag | 780 |
| accacgtccc | cacaataaat | atgacgaaaa | cccagaagtt | tcgatccttg | aaaactgcga | 840 |
| taaaatcctc | ttttttttacc | cctcccgcat | ctgccgctac | gcactggtga | tccttatctt | 900 |
| taaaacgcat | gttgatcatc | ataaatacag | cgccaaatag | cgagaccaac | cagaagttga | 960 |
| tatgggact | gatactaaaa | aatatgccgg | caaagaacgc | gccaatagca | tagccaaaag | 1020 |
| atccccaggc | gcgcgctgtt | ccatattcga | atgaaaaatt | tcgcgccatt | ttttcggtga | 1080 |
| agctatcaag | caaaccgcat | cccgccagat | accccaagcc | aaaaaatagc | gcccccagaa | 1140 |
| ttagacctac | agaaaaattg | ctttgcagta | acggttcata | aacgtaaatc | ataaacggtc | 1200 |
| cggtcaagac | caggatgaaa | ctcatacacc | agatgagcgg | tttcttcaga | ccagttttat | 1260 |
| cctgaacgat | gccgtagaac | atcataaata | gaatgctggt | aaactggttg | accgaataaa | 1320 |
| gtgtacctaa | ttccgtccct | gtcaaccccta | gatgtccttt | cagccaaata | gcgtataacg | 1380 |
| accaccacag | cgaccaggaa | ataaaaaaga | gaaatgagta | actggatgca | aaacgatagt | 1440 |
| acgcatttct | gaatggaata | ttcagtgcca | taattacctg | cctgtcgtta | aaaaattcac | 1500 |
| gtcctattta | gagataagag | cgacttcgcc | gtttacttct | cactattcca | gttcttgtcg | 1560 |
| acatggcagc | gctgtcattg | ccccttttcgc | cgttactgca | agcgctccgc | aacgttgagc | 1620 |
| gagatcgata | attcgtcgca | tttctctctc | atctgtagat | aatcccgtag | aggacagacc | 1680 |
| tgtgagtaac | ccggcaacga | acgcatctcc | cgccccgtg | ctatcgacac | aattcacaga | 1740 |
| cattccagca | aaatggtgaa | cttgtcctcg | ataacagacc | accacccctt | ctgcaccttt | 1800 |
| agtcaccaac | agcatggcga | tctcatactc | ttttgccagg | gcgcatatat | cctgatcgtt | 1860 |
| ctgtgttttt | ccactgataa | gtcgccattc | ttcttccgag | agcttgacga | catccgccag | 1920 |
| ttgtagcgcc | tgccgcaaac | acaagcggag | caaatgctcg | tcttgccata | gatcttcacg | 1980 |
| aatattagga | tcgaagctga | caaaaccctcc | ggcatgccgg | atcgccgtca | tcgcagtaaa | 2040 |
| tgcgctggta | cgcgaaggct | cggcagacaa | cgcaattgaa | cagagatgta | accattcgcc | 2100 |
| atgtcgccag | cagggcaagt | ctgtcgtctc | taaaaaaga | tcggcactgg | ggcggaccat | 2160 |

```
aaacgtaaat gaacgttccc cttgatcgtt cagatcgaca agcaccgtgg atgtccggtg    2220
ccattcatct tgcttcagat acgtgatatc gactccctca gttagcagcg ttctttgcat    2280
taacgcacca aaaggatcat cccccacccg acctataaac ccacttgttc cgcctaatct    2340
ggcgattccc accgcaacgt tagctggcgc gccgccagga caaggcagta ggcgcccgtc    2400
tgattctggc aagagatcta cgaccgcatc ccctaaaacc catactttgg ctgacatttt    2460
tttcccttaa attcatctga gttacgcata gtgataaacc tcttttcgc aaaatcgtca     2520 tggatttact aaaacatgca tattcgatca caaaacgtca tagttaacgt taacatttgt    2580
gatattcatc gcatttatga aagtaaggga ctttatttt  ataaaagtta acgttaacaa    2640
ttcaccaaat ttgcttaacc aggatgatta aaatgacgca atctcgattg catgcggcgc    2700
aaaacgccct agcaaaactt catgagcacc ggggtaacac tttctatccc cattttcacc    2760
tcgcgcctcc tgccgggtgg atgaacgatc caaacggcct gatctggttt aacgatcgtt    2820
atcacgcgtt ttatcaacat catccgatga gcgaacactg ggggccaatg cactgggac     2880 atgccaccag cgacgatatg atccactggc agcatgagcc tattgcgcta gcgccaggag    2940
acgataatga caaagacggg tgttttttcag gtagtgctgt cgatgacaat ggtgtcctct   3000
cacttatcta caccggacac gtctggctcg atggtgcagg taatgacgat gcaattcgcg    3060
aagtacaatg tctggctacc agtcgggatg gtattcattt cgagaaacag ggtgtgatcc    3120
tcactccacc agaaggaatc atgcacttcc gcgatcctaa agtgtggcgt gaagccgaca    3180
catggtggat ggtagtcggg gcgaaagatc caggcaacac ggggcagatc ctgctttatc    3240
gcggcagttc gttgcgtgaa tggaccttcg atcgcgtact ggcccacgct gatgcgggtg    3300
aaagctatat gtgggaatgt ccggactttt tcagccttgg cgatcagcat tatctgatgt    3360
tttccccgca gggaatgaat gccgagggat acagttaccg aaatcgcttt caaagtggcg    3420
taatacccgg aatgtggtcg ccaggacgac tttttgcaca atccgggcat tttactgaac    3480
ttgataacgg gcatgacttt tatgcaccac aaagctttt  agcgaaggat ggtcggcgta    3540
ttgttatcgg ctggatggat atgtgggaat cgccaatgcc ctcaaaacgt gaaggatggg    3600
caggctgcat gacgctggcg cgcgagctat cagagagcaa tggcaaactt ctacaacgcc    3660
cggtacacga agctgagtcg ttacgccagc agcatcaatc tgtctctccc cgcacaatca    3720
gcaataaata tgttttgcag gaaaacgcgc aagcagttga gattcagttg cagtgggcgc    3780
tgaagaacag tgatgccgaa cattacggat tacagctcgg cactggaatg cggctgtata    3840
ttgataacca atctgagcga cttgttttgt ggcggtatta cccacacgag aatttagacg    3900
gctaccgtag tattcccctc ccgcagcgtg acacgctcgc cctaaggata tttatcgata    3960
catcatccgt ggaagtattt attaacgacg gggaagcggt gatgagtagt cgaatctatc    4020
cgcagccaga agaacgggaa ctgtcgcttt atgcctccca cggagtggct gtgctgcaac    4080
atggagcact ctggctactg ggttaacata atatcaggtg gaacaacgga tcaacagcgg    4140
gcaagggatc cacgaagctt cccatggtga cgtcaccggt aaaccagcaa tagacataag    4200
cggctattta acgaccctgc cctgaaccga cgaccgggtc gaatttgctt tcgaatttct    4260
gccattcatc cgcttattat acttattcag gcgtagcacc aggcgtttaa gggcaccaat    4320
aactgcctta aaaaaattac gccccgccct gccactcatc gcagtactgt tgtaattcat    4380
taagcattct gccgacatgg aagccatcac agacggcatg atgaacctga atcgccagcg    4440
gcatcagcac cttgtcgcct tgcgtataat atttgcccat ggtgaaaacg ggggcgaaga    4500
agttgtccat attggccacg tttaaatcaa aactggtgaa actcacccag ggattggctg    4560
```

```
agacgaaaaa catattctca ataaaccctt tagggaaata ggccaggttt tcaccgtaac   4620
acgccacatc ttgcgaatat atgtgtagaa actgccggaa atcgtcgtgg tattcactcc   4680
agagcgatga aaacgtttca gtttgctcat ggaaacggt gtaacaaggg tgaacactat   4740
cccatatcac cagctcaccg tctttcattg ccatacggaa ttccggatga gcattcatca   4800
ggcgggcaag aatgtgaata aaggccggat aaaacttgtg cttattttc tttacggtct   4860 ttaaaaggc cgtaatatcc agctgaacgg tctggttata ggtacattga gcaactgact   4920
gaaatgcctc aaaatgttct ttacgatgcc attgggatat atcaacggtg gtatatccag   4980 tgatttttt ctccatttta gcttccttag ctcctgaaaa tctcgataac tcaaaaaata   5040
cgcccggtag tgatcttatt tcattatggt gaaagttgga acctcttacg tgccgatcaa   5100
cgtctcattt tcgccaaaag ttgggccagg gcttcccggt atcaacaggg acaccaggat   5160
ttatttattc tgcgaagtga tcttccgtca caggtattta ttcggcgcaa agggcctcgt   5220
gatacgccta tttttatagg ttaatgtcat gataataatg gtttcttaga cgtcaggtgg   5280
cacttttcgg ggaaatgtgc gcgcccgcgt tcctgctggc gctgggcctg tttctggcgc   5340
tggacttccc gctgttccgt cagcagcttt tcgcccacgg ccttgatgat cgcggcggcc   5400
ttggcctgca tatcccgatt caacggcccc agggcgtcca gaacgggctt caggcgctcc   5460
cgaaggtctc gggccgtctc ttgggcttga tcggccttct tgcgcatctc acgcgctcct   5520
gcggcggcct gtagggcagg ctcataccc tgccgaaccg cttttgtcag ccggtcggcc   5580
acggcttccg gcgtctcaac gcgctttgag attcccagct tttcggccaa tcctgcggt   5640 gcataggcgc gtggctcgac cgcttgcggg ctgatggtga cgtggcccac tggtggccgc   5700
tccagggcct cgtagaacgc ctgaatgcgc gtgtgacgtg ccttgctgcc ctcgatgccc   5760
cgttgcagcc ctagatcggc cacagcggcc gcaaacgtgg tctggtcgcg ggtcatctgc   5820
gctttgttgc cgatgaactc cttggccgac agcctgccgt cctgcgtcag cggcaccacg   5880
aacgcggtca tgtgcgggct ggtttcgtca cggtggatgc tggccgtcac gatgcgatcc   5940
gccccgtact tgtccgccag ccacttgtgc gccttctcga agaacgccgc ctgctgttct   6000
tggctggccg acttccacca ttccgggctg ccgtcatga cgtactcgac cgccaacaca   6060
gcgtccttgc gccgcttctc tggcagcaac tcgcgcagtc ggcccatcgc ttcatcggtg   6120
ctgctggccg cccagtgctc gttctctggc gtcctgctgg cgtcagcgtt gggcgtctcg   6180
cgctcgcggt aggcgtgctt gagactggcc gccacgttgc ccattttcgc cagcttcttg   6240
catcgcatga tcgcgtatgc cgccatgcct gcccctccct tttggtgtcc aaccggctcg   6300 acggggcag cgcaaggcgg tgcctccggc gggccactca atgcttgagt atactcacta   6360
gactttgctt cgcaaagtcg tgaccgccta cggcggctgc ggcgccctac gggcttgctc   6420
tccgggcttc gccctgcgcg gtcgctgcgc tcccttgcca gccgtggat atgtggacga   6480 tggccgcgag cggccaccgg ctggctcgct tcgctcggcc cgtggacaac cctgctggac   6540
aagctgatgg acaggctgcg cctgcccacg agcttgacca cagggattgc ccaccggcta   6600
cccagccttc gaccacatac ccaccggctc caactgcgcg gcctgcggcc ttgccccatc   6660 aatttttta attttctctg gggaaaagcc tccggcctgc ggcctgcgcg cttcgcttgc   6720
cggttggaca ccaagtggaa ggcgggtcaa ggctcgcgca gcgaccgcgc agcggcttgg   6780
ccttgacgcg cctggaacga cccaagccta tgcgagtggg ggcagtcgaa ggcgaagccc   6840
gcccgcctgc ccccgagac ctgcaggggg gggggggcgc tgaggtctgc ctcgtgaaga   6900
aggtgttgct gactcatacc aggcctgaat cgccccatca tccagccaga aagtgaggga   6960
```

```
gccacggttg atgagagctt tgttgtaggt ggaccagttg gtgattttga acttttgctt    7020
tgccacggaa cggtctgcgt tgtcgggaag atgcgtgatc tgatccttca actcagcaaa    7080
agttcgattt attcaacaaa gccgccgtcc cgtcaagtca gcgtaatgct ctgccagtgt    7140
tacaaccaat taaccaattc tgattagaaa aactcatcga gcatcaaatg aaactgcaat    7200
ttattcatat caggattatc aataccatat ttttgaaaaa gccgtttctg taatgaagga    7260
gaaaactcac cgaggcagtt ccataggatg gcaagatcct ggtatcggtc tgcgattccg    7320
actcgtccaa catcaataca acctattaat ttcccctcgt caaaaataag gttatcaagt    7380
gagaaatcac catgagtgac gactgaatcc ggtgagaatg gcaaaagctt atgcatttct    7440
ttccagactt gttcaacagg ccagccatta cgctcgtcat caaaatcact cgcatcaacc    7500
aaaccgttat tcattcgtga ttgcgcctga gcgagacgaa atacgcgatc gctgttaaaa    7560
ggacaattac aaacaggaat cgaatgcaac cggcgcagga acactgccag cgcatcaaca    7620
atattttcac ctgaatcagg atattcttct aatacctgga atgctgtttt cccgggggatc    7680 gcagtggtga gtaaccatgc atcatcagga gtacggataa aatgcttgat ggtcggaaga    7740
ggcataaatt ccgtcagcca gtttagtctg accatctcat ctgtaacatc attggcaacg    7800
ctacctttgc catgtttcag aaacaactct ggcgcatcgg gcttcccata caatcgatag    7860
attgtcgcac ctgattgccc gacattatcg cgagcccatt tatacccata taaatcagca    7920
tccatgttgg aatttaatcg cggcctcgag caagacgttt cccgttgaat atggctcata    7980 acacccttg tattactgtt tatgtaagca gacagtttta ttgttcatga tgatatattt    8040
ttatcttgtg caatgtaaca tcagagattt tgagacacaa cgtggctttc cccccccccc    8100
ctgcaggtcc cgagcctcac ggcggcgagt gcggggggttc caaggggggca gcgccacctt    8160 gggcaaggcc gaaggccgcg cagtcgatca acaagccccg gaggggccac ttttttgccgg    8220 aggggggagcc gcgccgaagg cgtggggggaa ccccgcaggg gtgccccttct ttgggcacca    8280 aagaactaga tatagggcga aatgcgaaag acttaaaaat caacaactta aaaaggggg    8340 gtacgcaaca gctcattgcg gcacccccccg caatagctca ttgcgtaggt taaagaaaat    8400
ctgtaattga ctgccacttt tacgcaacgc ataattgttg tcgcgctgcc gaaaagttgc    8460
agctgattgc gcatggtgcc gcaaccgtgc ggcaccctac cgcatggaga taagcatggc    8520
cacgcagtcc agagaaatcg gcattcaagc caagaacaag cccggtcact gggtgcaaac    8580
ggaacgcaaa gcgcatgagg cgtgggccgg gcttattgcg aggaaaccca cggcggcaat    8640
gctgctgcat cacctcgtgg cgcagatggg ccaccagaac gccgtggtgg tcagccagaa    8700
gacactttcc aagctcatcg gacgttcttt gcggacggtc caatacgcag tcaaggactt    8760
ggtggccgag cgctggatct ccgtcgtgaa gctcaacggc cccggcaccg tgtcggccta    8820
cgtggtcaat gaccgcgtgg cgtggggcca gccccgcgac cagttgcgcc tgtcggtgtt    8880
cagtgccgcc gtggtggttg atcacgacga ccaggacgaa tcgctgttgg ggcatggcga    8940
cctgcgccgc atcccgaccc tgtatccggg cgagcagcaa ctaccgaccg gccccggcga    9000
ggagccgccc agccagcccg gcattccggg catggaacca gacctgccag ccttgaccga    9060
aacggaggaa tgggaacggc gcgggcagca gcgcctgccg atgcccgatg agccgtgttt    9120 tctgacgat ggcgagccgt tggagccgcc gacacgggtc acgctgccgc gccggtagca    9180
cttgggttgc gcagcaaccc gtaagtgcgc tgttccagac tatcggctgt agccgcctcg    9240 ccgcccctata ccttgtctgc ctccccgcgt tgcgtcgcgg tgcatggagc cgggccacct    9300
cgacctgaat ggaagcc                                                  9317
```

1

RECOMBINANT BACTERIA HAVING IMPROVED SUCROSE UTILIZATION

FIELD OF THE INVENTION

The invention relates to the fields of microbiology and molecular biology. More specifically, recombinant bacteria having an improved ability to utilize sucrose are provided.

BACKGROUND OF THE INVENTION

Many commercially useful microorganisms use glucose as their main carbohydrate source. However, a disadvantage of the use of glucose by microorganisms developed for production of commercially desirable products is the high cost of glucose. The use of sucrose and mixed feedstocks containing sucrose and other sugars as carbohydrate sources for microbial production systems would be more commercially desirable because these materials are readily available at a lower cost.

A production microorganism can function more efficiently when it can utilize any sucrose present in a mixed feedstock. Therefore, when a production microorganism does not have the ability to utilize sucrose efficiently as a major carbon source, it cannot operate as efficiently. For example, bacterial cells typically show preferential sugar use, with glucose being the most preferred. In artificial media containing mixtures of sugars, glucose is typically metabolized to its entirety ahead of other sugars. Moreover, many bacteria lack the ability to utilize sucrose. For example, less than 50% of *Escherichia coli* strains have the ability to utilize sucrose. Thus, when a production microorganism cannot utilize sucrose as a carbohydrate source, it is desirable to engineer the microorganism so that it can utilize sucrose.

Recombinant bacteria that have been engineered to utilize sucrose by incorporation of sucrose utilization genes have been reported. For example, Livshits et al. (U.S. Pat. No. 6,960,455) describe the production of amino acids using *Escherichia coli* strains containing genes encoding a metabolic pathway for sucrose utilization. Additionally, Olson et al. (*Appl. Microbiol. Biotechnol.* 74:1031-1040, 2007) describe *Escherichia coli* strains carrying genes responsible for sucrose degradation, which produce L-tyrosine or L-phenylalanine using sucrose as a carbon source. Additionally, Eliot et al. (U.S. Patent Application Publication No. 2011/0136190) describe recombinant bacteria that are capable of producing glycerol and glycerol-derived products from sucrose. However, there is still a need for bacterial strains that have an improved ability to utilize sucrose. Additionally, there is a need for bacterial strains having an improved capability of producing glycerol and glycerol-derived products using sucrose as carbon source.

SUMMARY OF THE INVENTION

One embodiment provides a recombinant bacterium comprising in its genome:
  (a) one or more nucleotide sequences encoding a polypeptide or a polypeptide complex having sucrose transporter activity;
  (b) a nucleotide sequence encoding a polypeptide having fructokinase activity; and
  (c) a nucleotide sequence encoding a polypeptide having sucrose hydrolase activity;
wherein:
  (i) (a), (b) and (c) are each operably linked to the same or a different promoter;
  (ii) (a), (b), and (c) are integrated into the genome between the yihP gene or its homolog and the yihO gene or its homolog; and
  (iii) said bacterium metabolizes sucrose at a greater rate than a bacterium comprising (a), (b), and (c) integrated at a different location in the genome.

Another embodiment provides a process for making glycerol, 1,3-propanediol and/or 3-hydroxypropionic acid from sucrose comprising:
  a) culturing the recombinant bacterium disclosed herein in the presence of sucrose; and
  b) recovering the glycerol, 1,3-propanediol and/or 3-hydroxypropionic acid produced.

BRIEF DESCRIPTION OF THE FIGURE AND SEQUENCE DESCRIPTIONS

The invention can be more fully understood from the following detailed description, FIGURE, and the accompanying sequence descriptions, which form a part of this application.

FIG. 1 is a diagram showing chromosomal locations where the sucrose gene cluster was integrated. The chromosomal genes are shown in striped arrows. The sucrose genes are shown in open arrows. The direction of arrows indicates the direction of gene expression.

The following sequences conform with 37 C.F.R. 1.821 1.825 ("Requirements for Patent Applications Containing Nucleotide Sequences and/or Amino Acid Sequence Disclosures—the Sequence Rules") and consistent with World Intellectual Property Organization (WIPO) Standard ST.25 (2009) and the sequence listing requirements of the EPO and PCT (Rules 5.2 and 49.5(a bis), and Section 208 and Annex C of the Administrative Instructions). The symbols and format used for nucleotide and amino acid sequence data comply with the rules set forth in 37 C.F.R. §1.822.

TABLE A

Summary of Gene and Protein SEQ ID Numbers

| Gene | Coding Sequence SEQ ID NO: | Encoded Protein SEQ ID NO: |
| --- | --- | --- |
| GPD1 from *Saccharomyces cerevisiae* | 1 | 2 |
| GPD2 from *Saccharomyces cerevisiae* | 3 | 4 |
| GPP1 from *Saccharomyces cerevisiae* | 5 | 6 |
| GPP2 from *Saccharomyces cerevisiae* | 7 | 8 |
| dhaB1 from *Klebsiella pneumoniae* | 9 | 10 |
| dhaB2 from *Klebsiella pneumoniae* | 11 | 12 |
| dhaB3 from *Klebsiella pneumoniae* | 13 | 14 |
| aldB from *Escherichia coli* | 15 | 16 |
| aldA from *Escherichia coli* | 17 | 18 |
| aldH from *Escherichia coli* | 19 | 20 |
| galP from *Escherichia coli* | 21 | 22 |
| cscB from *Escherichia coli* EC3132 | 23 | 24 |
| cscB from *Escherichia coli* ATCC ®13281 | 25 | 26 |
| cscB from *Bifidobacterium lactis* | 27 | 28 |
| susT1 from *Streptococcus pneumoniae* strain TIGR4 | 29 | 30 |
| susT2 from *Streptococcus pneumoniae* strain TIGR4 | 31 | 32 |
| susX from *Streptococcus pneumoniae* strain TIGR4 | 33 | 34 |
| malE from *Streptococcus mutans* | 35 | 36 |
| malF from *Streptococcus mutans* | 37 | 38 |
| malG from *Streptococcus mutans* | 39 | 40 |
| malK from *Streptococcus mutans* | 41 | 42 |
| scrK from *Agrobacterium tumefaciens* | 43 | 44 |
| scrK from *Streptococcus mutans* | 45 | 46 |
| cscK from *Escherichia coli* | 47 | 48 |
| cscK from *Enterococcus faecalis* | 49 | 50 |

TABLE A-continued

Summary of Gene and Protein SEQ ID Numbers

| Gene | Coding Sequence SEQ ID NO: | Encoded Protein SEQ ID NO: |
|---|---|---|
| HXK1 from *Saccharomyces cerevisiae* | 51 | 52 |
| HXK2 from *Saccharomyces cerevisiae* | 53 | 54 |
| cscA from *Escherichia coli* EC3132 | 55 | 56 |
| cscA from *Escherichia coli* ATCC ®13281 | 57 | 58 |
| brfA from *Bifidobacterium lactis* strain DSM 10140$^T$ | 59 | 60 |
| SUC2 from *Saccharomyces cerevisiae* | 61 | 62 |
| scrB from *Corynebacterium glutamicum* | 63 | 64 |
| sucrose phosphorylase gene from *Leuconostoc mesenteroides* DSM 20193 | 65 | 66 |
| sucP *Bifidobacterium adolescentis* DSM 20083 | 67 | 68 |
| dhaT from *Klebsiella pneumoniae* | 69 | 70 |
| yihP from *Escherichia coli* | 77 | 78 |
| yihQ from *Escherichia coli* | 79 | 80 |
| yihO from *Escherichia coli* | 81 | 82 |
| ompL from *Escherichia coli* | 83 | 84 |
| cscB variant 408STOP | 93 | 94 |
| cscB variant L61P | 95 | 96 |
| cscB variant F159L | 97 | 98 |
| cscB variant G162C | 99 | 100 |
| cscB variant P169H | 101 | 102 |
| cscB variant L61W | 103 | 104 |
| cscB variant L61H | 105 | 106 |
| cscB variant L61F | 107 | 108 |
| cscB variant 403STOP | 109 | 110 |
| scrK From *Escherichia coli* | 111 | 112 |
| scrK from *Klebsiella pneumoniae* | 113 | 114 |

SEQ ID NO:71 is the nucleotide sequence of the coding region of the dhaX gene from *Klebsiella pneumoniae*.

SEQ ID NO:72 is the nucleotide sequence of plasmid pSYCO101.

SEQ ID NO:73 is the nucleotide sequence of plasmid pSYCO103.

SEQ ID NO:74 is the nucleotide sequence of plasmid pSYCO106.

SEQ ID NO:75 is the nucleotide sequence of plasmid pSYCO109.

SEQ ID NO:76 is the nucleotide sequence of plasmid pSYCO400/AGRO.

SEQ ID NO:85 is the nucleotide sequence encoding putative permease YP_690957 of *Shigella flexneri*.

SEQ ID NO:86 is the nucleotide sequence encoding GPH family transport protein NP_462898 of *Salmonella enterica*.

SEQ ID NO:87 is the nucleotide sequence encoding hypothetical protein ENCANT_09547 of *Enterobacter cancerogenus* ATCC® 35316.

SEQ ID NO:88 is the nucleotide sequence encoding hypothetical protein CKO_03136 of *Citrobacter koseri* ATCC® BAA-895.

SEQ ID NO:89 is the nucleotide sequence encoding putative permease YP_690958 of *Shigella flexneri*.

SEQ ID NO:90 is the nucleotide sequence encoding GPH family transport protein NP_462897 of *Salmonella enterica*.

SEQ ID NO:91 is the nucleotide sequence encoding hypothetical protein ENCANT_09546 of *Enterobacter cancerogenus* ATCC® 35316.

SEQ ID NO:92 is the nucleotide sequence encoding hypothetical protein CKO_03137 of *Citrobacter koseri* ATCC® BAA-895.

SEQ ID NOs:115-122 are the nucleotide sequences of primers used in the Examples herein.

SEQ ID NO:123 is the nucleotide sequence of the cscAKB gene cluster *Escherichia coli* ATCC® 3281.

SEQ ID NO:124 is nucleotide sequence of plasmid pBHR-cscBKA.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

The term "recombinant glycerol-producing bacterium" refers to a bacterium that has been genetically engineered to be capable of producing glycerol and/or glycerol-derived products such as 1,3-propanediol and 3-hydroxypropionic acid.

The term "polypeptide or polypeptide complex having sucrose transporter activity" refers to a polypeptide or polypeptide complex that is capable of mediating the transport of sucrose into microbial cells. Examples of polypeptides having sucrose transporter activity include, but are not limited to, sucrose:H+ symporters. Examples of polypeptide complexes having sucrose transporter activity include, but are not limited to, ABC-type transporters. Sucrose:H+ symporters are encoded by, for example, the cscB gene found in *E. coli* strains such as EC3132 (Jahreis et al., *J. Bacteriol.* 184:5307-5316, 2002) or ATCC® 13281 (Olson et al., *Appl. Microbiol. Biotechnol.* 74:1031-1040, 2007), and *Bifidobacterium lactis* strain DSM 10140$^T$ (Ehrmann et al., *Curr. Microbiol.* 46(6): 391-397, 2003). An example of an ABC-type transporter with activity towards sucrose is the complex encoded by the genes susT1, susT2 and susX in *Streptococcus pneumoniae* strain TIGR4 (Iyer and Camilli, *Molecular Microbiology* 66:1-13, 2007). Polypeptides or polypeptide complexes having sucrose transporter activity may also have activity towards other saccharides. An example is the maltose transporter complex of *Streptococcus mutans* encoded by malEFGK (Kilic et al., *FEMS Microbiol Lett.* 266:218, 2007).

The term "variant sucrose transporter polypeptide" refers to a polypeptide having sucrose transporter activity that has an amino acid sequence that differs from the sequence of a wild-type sucrose transporter polypeptide. The difference in the sequence of the variant sucrose transporter polypeptide may be any one of the following: (i) an amino acid substitution in at least one position of the wild-type sequence, (ii) the sequence of the variant sucrose transporter polypeptide may be shortened from that of the wild-type sequence, or (iii) the sequence of the variant sucrose transporter polypeptide may be shortened from that of the wild-type sequence and contain an amino acid substitution in at least one position of the wild-type sequence.

The term "polypeptide having fructokinase activity" refers to a polypeptide that has the ability to catalyze the conversion of D-fructose+ATP to fructose-phosphate+ADP. Typical of fructokinase is EC 2.7.1.4. Enzymes that have some ability to phosphorylate fructose, whether or not this activity is their predominant activity, may be referred to as a fructokinase.

Abbreviations used for genes encoding fructokinases and proteins having fructokinase activity include, for example, "Frk", "scrK", "cscK", "FK", and "KHK". Fructokinase is encoded by the scrK gene in *Agrobacterium tumefaciens* and *Streptococcus mutans*; and by the cscK gene in certain *Escherichia coli* strains.

The term "polypeptide having sucrose hydrolase activity" refers to a polypeptide that has the ability to catalyze the hydrolysis of sucrose to produce glucose and fructose. Such polypeptides are often referred to as "invertases" or "β-fructofuranosidases". Typical of these enzymes is EC 3.2.1.26. Examples of genes encoding polypeptides having sucrose hydrolase activity are the cscA gene found in *E. coli* strains EC3132 (Jahreis et al. supra) or ATCC® 3281 (Olson et al., supra), the bfrA gene from *Bifidobacterium lactis* strain DSM 10140$^T$, and the SUC2 gene from *Saccharomyces cerevisiae* (Carlson and Botstein, *Cell* 28:145, 1982). A polypeptide having sucrose hydrolase activity may also have sucrose phosphate hydrolase activity. An example of such a peptide is encoded by scrB in *Corynebacterium glutamicum* (Engels et al., *FEMS Microbiol Lett.* 289:80-89, 2008). A polypeptide having sucrose hydrolase activity may also have sucrose phosphorylase activity. Typical of such an enzyme is EC 2.4.1.7. Examples of genes encoding sucrose phosphorylases having sucrose hydrolase activity are found in *Leuconostoc mesenteroides* DSM 20193 (Goedl et al., *Journal of Biotechnology* 129:77-86, 2007) and *Bifidobacterium adolescentis* DSM 20083 (van den Broek et al., *Appl. Microbiol. Biotechnol.* 65:219-227, 2004), among others.

The terms "glycerol derivative" and "glycerol-derived products" are used interchangeably herein and refer to a compound that is synthesized from glycerol or in a pathway that includes glycerol. Examples of such products include 3-hydroxypropionic acid, methylglyoxal, 1,2-propanediol, and 1,3-propanediol.

The term "microbial product" refers to a product that is microbially produced, i.e., the result of a microorganism metabolizing a substance. The product may be naturally produced by the microorganism, or the microorganism may be genetically engineered to produce the product.

The terms "phosphoenolpyruvate-sugar phosphotransferase system", "PTS system", and "PTS" are used interchangeably herein and refer to the phosphoenolpyruvate-dependent sugar uptake system.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to enzymes designated as EC 2.7.1.69, encoded by crr in *E. coli*. PtsH, PtsI, and Crr comprise the PTS system.

The term "PTS minus" refers to a microorganism that does not contain a PTS system in its native state or a microorganism in which the PTS system has been inactivated through the inactivation of a PTS gene.

The terms "glycerol-3-phosphate dehydrogenase" and "G3PDH" refer to a polypeptide responsible for an enzyme activity that catalyzes the conversion of dihydroxyacetone phosphate (DHAP) to glycerol 3-phosphate (G3P). In vivo G3PDH may be NAD- or NADP-dependent. When specifically referring to a cofactor specific glycerol-3-phosphate dehydrogenase, the terms "NAD-dependent glycerol-3-phosphate dehydrogenase" and "NADP-dependent glycerol-3-phosphate dehydrogenase" will be used. As it is generally the case that NAD-dependent and NADP-dependent glycerol-3-phosphate dehydrogenases are able to use NAD and NADP interchangeably (for example by the enzyme encoded by gpsA), the terms NAD-dependent and NADP-dependent glycerol-3-phosphate dehydrogenase will be used interchangeably. The NAD-dependent enzyme (EC 1.1.1.8) is encoded, for example, by several genes including GPD1, also referred to herein as DAR1 (coding sequence set forth in SEQ ID NO:1; encoded protein sequence set forth in SEQ ID NO:2), or GPD2 (coding sequence set forth in SEQ ID NO:3; encoded protein sequence set forth in SEQ ID NO:4), or GPD3. The NADP-dependent enzyme (EC 1.1.1.94) is encoded, for example, by gpsA.

The terms "glycerol 3-phosphatase", "sn-glycerol 3-phosphatase", "D,L-glycerol phosphatase", and "G3P phosphatase" refer to a polypeptide having an enzymatic activity that is capable of catalyzing the conversion of glycerol 3-phosphate and water to glycerol and inorganic phosphate. G3P phosphatase is encoded, for example, by GPP1 (coding sequence set forth in SEQ ID NO:5; encoded protein sequence set forth in SEQ ID NO:6), or GPP2 (coding sequence set forth in SEQ ID NO:7; encoded protein sequence set forth in SEQ ID NO:8).

The term "glycerol dehydratase" or "dehydratase enzyme" refers to a polypeptide having enzyme activity that is capable of catalyzing the conversion of a glycerol molecule to the product, 3-hydroxypropionaldehyde (3-HPA).

For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium, Klebsiella oxytoca*, and *Lactobacillus reuteri*, among others. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" (alpha) subunit of glycerol dehydratase include dhaB1 (coding sequence set forth in SEQ ID NO:9, encoded protein sequence set forth in SEQ ID NO:10), gldA and dhaB; genes encoding the medium or "β" (beta) subunit include dhaB2 (coding sequence set forth in SEQ ID NO:11, encoded protein sequence set forth in SEQ ID NO:12), gldB, and dhaC; genes encoding the small or "γ" (gamma) subunit include dhaB3 (coding sequence set forth in SEQ ID NO:13, encoded protein sequence set forth in SEQ ID NO:14), gldC, and dhaE. Other genes encoding the large or "α" subunit of diol dehydratase include pduC and pddA; other genes encoding the medium or "β" subunit include pduD and pddB; and other genes encoding the small or "γ" subunit include pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" and "regenerating the dehydratase activity" are used interchangeably and refer to the phenomenon of converting a dehydratase not capable of catalysis of a reaction to one capable of catalysis of a reaction or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., U.S. Pat. No. 6,013,494 and references therein; Daniel et al., supra; Toraya and Mori, *J. Biol. Chem.* 274, 3372 (1999);

and Tobimatsu et al., *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" and "DhaT" are used interchangeably herein and refer to the polypeptide(s) having an enzymatic activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Genes encoding a 1,3-propanediol oxidoreductase include, but are not limited to, dhaT from *Klebsiella pneumoniae*, *Citrobacter freundii*, and *Clostridium pasteurianum*. Each of these genes encode a polypeptide belonging to the family of type III alcohol dehydrogenases, which exhibits a conserved iron-binding motif, and has a preference for the $NAD^+/NADH$ linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated polynucleotides or open reading frames encoding polypeptides having various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described in U.S. Pat. No. 7,371,558.

The terms "aldehyde dehydrogenase" and "Ald" refer to a polypeptide that catalyzes the conversion of an aldehyde to a carboxylic acid. Aldehyde dehydrogenases may use a redox cofactor such as NAD, NADP, FAD, or PQQ. Typical of aldehyde dehydrogenases is EC 1.2.1.3 (NAD-dependent); EC 1.2.1.4 (NADP-dependent); EC 1.2.99.3 (PQQ-dependent); or EC 1.2.99.7 (FAD-dependent). An example of an NADP-dependent aldehyde dehydrogenase is AldB (SEQ ID NO:16), encoded by the *E. coli* gene aldB (coding sequence set forth in SEQ ID NO:15). Examples of NAD-dependent aldehyde dehydrogenases include AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence set forth in SEQ ID NO:19).

The terms "glucokinase" and "Glk" are used interchangeably herein and refer to a protein that catalyzes the conversion of D-glucose+ATP to glucose 6-phosphate+ADP. Typical of glucokinase is EC 2.7.1.2. Glucokinase is encoded by glk in *E. coli*.

The terms "phosphoenolpyruvate carboxylase" and "Ppc" are used interchangeably herein and refer to a protein that catalyzes the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde-3-phosphate dehydrogenase" and "GapA" are used interchangeably herein and refer to a protein having an enzymatic activity capable of catalyzing the conversion of glyceraldehyde 3-phosphate+phosphate+$NAD^+$ to 3-phospho-D-glyceroyl-phosphate+$NADH+H^+$. Typical of glyceraldehyde-3-phosphate dehydrogenase is EC 1.2.1.12. Glyceraldehyde-3-phosphate dehydrogenase is encoded by gapA in *E. coli*.

The terms "aerobic respiration control protein" and "ArcA" are used interchangeably herein and refer to a global regulatory protein. The aerobic respiration control protein is encoded by arcA in *E. coli*.

The terms "methylglyoxal synthase" and "MgsA" are used interchangeably herein and refer to a protein having an enzymatic activity capable of catalyzing the conversion of dihydroxyacetone phosphate to methylglyoxal+phosphate. Typical of methylglyoxal synthase is EC 4.2.3.3. Methylglyoxal synthase is encoded by mgsA in *E. coli*.

The terms "phosphogluconate dehydratase" and "Edd" are used interchangeably herein and refer to a protein having an enzymatic activity capable of catalyzing the conversion of 6-phospho-gluconate to 2-keto-3-deoxy-6-phospho-gluconate+$H_2O$. Typical of phosphogluconate dehydratase is EC 4.2.1.12. Phosphogluconate dehydratase is encoded by edd in *E. coli*.

The term "YciK" refers to a putative enzyme encoded by yciK which is translationally coupled to btuR, the gene encoding Cob(I)alamin adenosyltransferase in *E. coli*.

The term "cob(I)alamin adenosyltransferase" refers to an enzyme capable of transferring a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" in *E. coli*, "cobA" in *Salmonella typhimurium*, and "cobO" in *Pseudomonas denitrificans*.

The terms "galactose-proton symporter" and "GalP" are used interchangeably herein and refer to a protein having an enzymatic activity capable of transporting a sugar and a proton from the periplasm to the cytoplasm. D-glucose is a preferred substrate for GalP. Galactose-proton symporter is encoded by galP in *Escherichia coli* (coding sequence set forth in SEQ ID NO:21, encoded protein sequence set forth in SEQ ID NO:22).

The term "non-specific catalytic activity" refers to the polypeptide(s) having an enzymatic activity capable of catalyzing the interconversion of 3-HPA and 1,3-propanediol and specifically excludes 1,3-propanediol oxidoreductase(s). Typically these enzymes are alcohol dehydrogenases. Such enzymes may utilize cofactors other than $NAD^+/NADH$, including but not limited to flavins such as FAD or FMN. A gene for a non-specific alcohol dehydrogenase (yqhD) is found, for example, to be endogenously encoded and functionally expressed within *E. coli* K-12 strains.

The terms "1.6 long GI promoter", "1.20 short/long GI Promoter", and "1.5 long GI promoter" refer to polynucleotides or fragments containing a promoter from the *Streptomyces lividans* glucose isomerase gene as described in U.S. Pat. No. 7,132,527. These promoter fragments include a mutation which decreases their activities as compared to the wild type *Streptomyces lividans* glucose isomerase gene promoter.

The terms "function" and "enzyme function" are used interchangeably herein and refer to the catalytic activity of an enzyme in altering the rate at which a specific chemical reaction occurs without itself being consumed by the reaction. It is understood that such an activity may apply to a reaction in equilibrium where the production of either product or substrate may be accomplished under suitable conditions.

The terms "polypeptide" and "protein" are used interchangeably herein.

The terms "carbon substrate" and "carbon source" are used interchangeably herein and refer to a carbon source capable of being metabolized by the recombinant bacteria disclosed herein and, particularly, carbon sources comprising sucrose. The carbon source may further comprise monosaccharides, other disaccharides, oligosaccharides; or polysaccharides.

The terms "host cell" and "host bacterium" are used interchangeably herein and refer to a bacterium capable of receiving foreign or heterologous genes and capable of expressing those genes to produce an active gene product.

The term "production microorganism" as used herein refers to a microorganism, including, but not limited to, those that are recombinant, used to make a specific product such as 1,3-propanediol, glycerol, 3-hydroxypropionic acid, polyunsaturated fatty acids, and the like.

As used herein, "nucleic acid" means a polynucleotide and includes a single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise genes inserted into a non-native organism, genes introduced into a new location within the native host, or chimeric genes.

The term "native nucleotide sequence" refers to a nucleotide sequence that is normally found in the host microorganism.

The term "non-native nucleotide sequence" refers to a nucleotide sequence that is not normally found in the host microorganism.

The term "native polypeptide" refers to a polypeptide that is normally found in the host microorganism.

The term "non-native polypeptide" refers to a polypeptide that is not normally found in the host microorganism.

The terms "encoding" and "coding" are used interchangeably herein and refer to the process by which a gene, through the mechanisms of transcription and translation, produces an amino acid sequence.

The term "coding sequence" refers to a nucleotide sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (e.g., a terminator) that, in eukaryotes, usually contains a polyadenylation site. The expression cassette(s) is usually included within a vector, to facilitate cloning and transformation. Different organisms, including bacteria, yeast, and fungi, can be transformed with different expression cassettes as long as the correct regulatory sequences are used for each host.

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms transformed with the nucleic acid fragments are referred to as "recombinant" or "transformed" organisms or "transformants". "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. Chimeric genes can be designed for use in suppression by linking a nucleic acid fragment or subfragment thereof, whether or not it encodes an active enzyme, in the sense or antisense orientation relative to a promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein.

The terms "substantially similar" and "corresponds substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. Moreover, the skilled artisan recognizes that substantially similar nucleic acid sequences encompassed by this invention are also defined by their ability to hybridize (under moderately stringent conditions, e.g., 0.5×SSC (standard sodium citrate), 0.1% SDS (sodium dodecyl sulfate), 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences are two nucleotide sequences wherein the complement of one of the nucleotide sequences typically has about at least 80% sequence identity, or 90% sequence identity, up to and including 100% sequence identity (i.e., fully complementary) to the other nucleotide sequence.

The term "stringent conditions" or "stringent hybridization conditions" includes reference to conditions under which a probe will selectively hybridize to its target sequence. Probes are typically single stranded nucleic acid sequences which are complementary to the nucleic acid sequences to be detected. Probes are "hybridizable" to the nucleic acid sequence to be detected. Generally, a probe is less than about 1000 nucleotides in length, optionally less than 500 nucleotides in length.

Hybridization methods are well defined. Typically the probe and sample are mixed under conditions which will permit nucleic acid hybridization. This involves contacting the probe and sample in the presence of an inorganic or organic salt under the proper concentration and temperature conditions. Optionally a chaotropic agent may be added. Nucleic acid hybridization is adaptable to a variety of assay formats. One of the most suitable is the sandwich assay format. A primary component of a sandwich-type assay is a solid support. The solid support has adsorbed to it or covalently coupled to it an immobilized nucleic acid probe that is unlabeled and complementary to one portion of the sequence.

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the thermal melting point ($T_m$) can be approximated from the equation of Meinkoth et al., *Anal. Biochem.* 138:267-284 (1984): $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, CABIOS. 5:151-153 (1989); Higgins, D. G. et al., Comput. Appl. Biosci. 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, supra; Higgins, D. G. et al., supra) and found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Thus, the invention encompasses more than the specific exemplary nucleotide sequences disclosed herein. For example, alterations in the gene sequence which reflect the degeneracy of the genetic code are contemplated. Also, it is well known in the art that alterations in a gene which result in the production of a chemically equivalent amino acid at a given site, but do not affect the functional properties of the encoded protein are common. Substitutions are defined for the discussion herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize under stringent conditions, as defined above.

Preferred substantially similar nucleic acid fragments of the instant invention are those nucleic acid fragments whose nucleotide sequences are at least 70% identical to the nucleotide sequence of the nucleic acid fragments reported herein. More preferred nucleic acid fragments are at least 90% identical to the nucleotide sequence of the nucleic acid fragments reported herein. Most preferred are nucleic acid fragments that are at least 95% identical to the nucleotide sequence of the nucleic acid fragments reported herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine. Accordingly, the instant invention may make use of isolated nucleic acid molecules that are complementary to the complete sequences as reported in the accompanying Sequence Listing and the specification as well as those substantially similar nucleic acid sequences.

The term "isolated" refers to a polypeptide or nucleotide sequence that is removed from at least one component with which it is naturally associated.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

"3' non-coding sequences", "transcription terminator" and "termination sequences" are used interchangeably herein and refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "genetically altered" refers to the process of changing hereditary material by genetic engineering, transformation and/or mutation.

The term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The term "variant bacterium" refers to a wild-type bacterium that has undergone a spontaneous mutation, natural transformation, natural transduction, or natural transposition; or has been modified by mutagenesis.

The terms "recombinant construct", "expression construct", "chimeric construct", "construct", and "recombinant DNA construct", are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events may result in different levels and patterns of expression (Jones et al., *EMBO J.* 4:2411-2418 (1985); De Almeida et al., *Mol. Gen. Genetics* 218:78-86 (1989)), and thus that multiple events may need be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "homologous" refers to proteins or polypeptides of common evolutionary origin with similar catalytic function. The invention may include bacteria producing homologous proteins via recombinant technology.

Disclosed herein are recombinant bacteria comprising in their genome one or more nucleotide sequences encoding a polypeptide or a polypeptide complex having sucrose transporter activity; a nucleotide sequence encoding a polypeptide having fructokinase activity; and a nucleotide sequence encoding a polypeptide having sucrose hydrolase activity. These nucleotide sequences are each operably linked to the same or a different promoter. Additionally, the nucleotide sequences are integrated into the genome between the yihP gene or its homolog and the yihO gene or its homolog, as shown in FIG. 1. Integration at this particular site in the genome results in a greater rate of sucrose metabolism by the recombinant bacterium compared to integration at other sites in the genome, for example, at aldH (coding sequence set forth in SEQ ID NO:19), as shown in Examples 5 and 7-10 herein.

The yihP gene of *Escherichia coli* (coding sequence set forth in SEQ ID NO:77) encodes a putative inner membrane transport protein (SEQ ID NO:78) that appears to be part of a sugar utilization locus. The upstream yihQ gene (coding sequence set forth in SEQ ID NO:79) encodes an α-glycosidase (SEQ ID NO:80). The downstream yihO gene (coding sequence set forth in SEQ ID NO:81) and ompL gene (coding sequence set forth in SEQ ID NO:83) encode a putative inner membrane transport protein (SEQ ID NO:82) and an outer membrane porin (SEQ ID NO:84), respectively. The aldH gene (coding sequence set forth in SEQ ID NO:19, synonym of puuC) encodes a γ-glutamyl-γ-aminobutyraldehyde dehydrogenase (SEQ ID NO:20) that is part of the putrescine utilization pathway. The downstream puuB and puuE genes encode γ-glutamylputrescine oxidase and 4-aminobutyrate aminotransferase, respectively.

Homologs of the *Escherichia coli* yihP and yihO genes in other host bacteria may be identified using methods known in the art. For example, homologs of yihP and yihO genes can be identified using sequence analysis software, such as BLASTN, to search publically available nucleic acid sequence databases. Additionally, the isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci. USA* 82, 1074, 1985); or strand displacement amplification (SDA), Walker, et al., *Proc. Natl. Acad. Sci. U.S.A.*, 89: 392, (1992)). For example, the nucleotide sequence encoding the polypeptides described above may be employed as a hybridization probe for the identification of homologs.

Examples of homologs of yihP include, but are not limited to, putative permease YP_690957 of *Shigella flexneri* (coding sequence set forth in SEQ ID NO:85), GPH family transport protein NP_462898 of *Salmonella enterica* (coding sequence set forth in SEQ ID NO:86), hypothetical protein ENTCAN_09547 of *Enterobacter cancerogenus* ATCC® 35316 (coding sequence set forth in SEQ ID NO:87), and hypothetical protein CKO_03136 of *Citrobacter koseri* ATCC® BAA-895 (coding sequence set forth in SEQ ID NO:88). Examples of homologs of yihO include, but are not limited to, putative permease YP_690958 of *Shigella flexneri* (coding sequence set forth in SEQ ID NO:89), GPH family transport protein NP_462897 of *Salmonella enterica* (coding sequence set forth in SEQ ID NO:90), hypothetical protein ENTCAN_09546 of *Enterobacter cancerogenus* ATCC® 35316 (coding sequence set forth in SEQ ID NO:91), and hypothetical protein CKO_03137 of *Citrobacter koseri* ATCC® BAA-895 (coding sequence set forth in SEQ ID NO:92). These yihP and yihO homologs are adjacent to each other in each of the host chromosomes, as in *E. coli*.

Suitable host bacteria for use in the construction of the recombinant bacteria disclosed herein include, but are not limited to organisms of the genera: *Escherichia, Streptococcus, Agrobacterium, Bacillus, Corynebacterium, Lactobacillus, Clostridium, Gluconobacter, Citrobacter, Enterobacter, Klebsiella, Aerobacter, Methylobacter, Salmonella, Streptomyces,* and *Pseudomonas.*

In one embodiment the host bacterium is selected from the genera: *Escherichia, Klebsiella, Citrobacter,* and *Aerobacter.*

In another embodiment, the host bacterium is *Escherichia coli.*

In some embodiments, the host bacterium is PTS minus. In these embodiments, the host bacterium is PTS minus in its native state, or may be rendered PTS minus through inactivation of a PTS gene as described below.

In production microorganisms, it is sometimes desirable to unlink the transport of sugars and the use of phosphoenolpyruvate (PEP) for phosphorylation of the sugars being transported.

The term "down-regulated" refers to reduction in, or abolishment of, the activity of active protein(s), as compared to the activity of the wildtype protein(s). The PTS may be inactivated (resulting in a "PTS minus" organism) by down-regulating expression of one or more of the endogenous genes encoding the proteins required in this type of transport. Down-regulation typically occurs when one or more of these genes has a "disruption", referring to an insertion, deletion, or targeted mutation within a portion of that gene, that results in either a complete gene knockout such that the gene is deleted from the genome and no protein is translated or a protein has been translated such that it has an insertion, deletion, amino acid substitution or other targeted mutation. The location of the disruption in the protein may be, for example, within the N-terminal portion of the protein or within the C-terminal portion of the protein. The disrupted protein will have impaired activity with respect to the protein that was not disrupted, and can be non-functional. Down-regulation that results in low or lack of expression of the protein, could also result via manipulating the regulatory sequences, transcription and translation factors and/or signal transduction pathways or by use of sense, antisense or RNAi technology, etc.

Sucrose transporter polypeptides or polypeptide complexes are polypeptides or polypeptide complexes that are capable of mediating the transport of sucrose into microbial cells. Sucrose transport polypeptides and polypeptide complexes are known, as described above. Examples of polypeptides having sucrose transporter activity include, but are not limited to, CscB from *E. coli* wild-type strain EC3132 (set forth in SEQ ID NO:24), encoded by gene cscB (coding sequence set forth in SEQ ID NO:23); CscB from *E. coli* ATCC® 3281 (set forth in SEQ ID NO:26), encoded by gene cscB (coding sequence set forth in SEQ ID NO:25); and CscB from *Bifidobacterium lactis* (set forth in SEQ ID NO:28), encoded by gene cscB (coding sequence set forth in SEQ ID NO:27). Examples of polypeptide complexes having sucrose transporter activity include, but are not limited to, the sucrose ABC-type transporter complex from *Streptococcus pneumoniae* strain TIGR4 comprising three polypeptide subunits set forth in SEQ ID NOs:30, 32, and 34, encoded by genes susT1 (coding sequence set forth in SEQ ID NO:29), susT2 (coding sequence set forth in SEQ ID NO:31), and susX (coding sequence set forth in SEQ ID NO: 33); and the maltose transporter complex of *Streptococcus mutans* comprising four polypeptide subunits set forth in SEQ ID NOs:36, 38, 40, and 42, encoded by genes malE (coding sequence set forth in SEQ ID NO:35), malF (coding sequence set forth in SEQ ID NO:37), malG (coding sequence set forth in SEQ ID NO:39), and malK (coding sequence set forth in SEQ ID NO:41), respectively.

In one embodiment, the polypeptide having sucrose transporter activity has at least 95% sequence identity, based on the Clustal W method of alignment, to an amino acid sequence as set forth in SEQ ID NO:24, SEQ ID NO:26, or SEQ ID NO:28.

In another embodiment, the sucrose transporter polypeptide is a variant of the wild-type sucrose transporter polypeptide CscB from *E. coli* ATCC® 3281 (set forth in SEQ ID NO:26, nucleotide coding sequence set forth in SEQ ID NO:25) that enables faster sucrose utilization in bacteria. These variant sucrose transporter polypeptides were isolated from variant *E. coli* strains that exhibited faster growth on sucrose, or were identified by saturation mutagenesis, as described in copending and commonly owned U.S. patent application Ser. No. 13/210,488. The variant sucrose transporter polypeptides have an amino acid sequence that has at least 95% identity to an amino acid sequence as set forth in SEQ ID NO:26 based on a Clustal W method of alignment and having at least one amino acid change selected from the group consisting of:

(i) leucine to proline at position 61;
(ii) phenylalanine to leucine at position 159;
(iii) glycine to cysteine at position 162;
(iv) proline to histidine at position 169;
(v) leucine to tryptophan at position 61;
(vi) leucine to histidine at position 61;
(vii) leucine to phenylalanine at position 61; and
(viii) leucine to tyrosine at position 61.

In another embodiment, the variant sucrose transporter polypeptides have an amino acid sequence that has at least 95% identity to an amino acid sequence as set forth in SEQ ID NO:94 (coding sequence set forth in SEQ ID NO: 93) based on a Clustal W method of alignment and having a length of 402 to 407 amino acids from the N-terminus.

In another embodiment, the variant sucrose transporter polypeptides have an amino acid sequence that has at least 95% identity to an amino acid sequence as set forth in SEQ ID NO:94 based on a Clustal W method of alignment, having a length of 402 to 407 amino acids from the N-terminus, and having at least one of the amino acid changes listed above.

In another embodiment, the variant sucrose transporter polypeptides have an amino acid sequence selected from the group consisting of: SEQ ID NO:94, SEQ ID NO:96, SEQ ID NO:98, SEQ ID NO:100, SEQ ID NO:102, SEQ ID NO:104, SEQ ID NO:106, SEQ ID NO:108, and SEQ ID NO:110.

In another embodiment, the polypeptide complex having sucrose transporter activity comprises: a first subunit having at least 95% sequence identity, based on a Clustal W method of alignment, when compared to an amino acid sequence as set forth in SEQ ID NO:30; a second subunit having at least 95% sequence identity, based on a Clustal W method of alignment, when compared to an amino acid sequence as set forth in SEQ ID NO:32; and a third subunit having at least 95% sequence identity, based on a Clustal W method of alignment, when compared to an amino acid sequence as set forth in SEQ ID NO:34.

In another embodiment, the polypeptide complex having sucrose transporter activity comprises: a first subunit having at least 95% sequence identity, based on a Clustal W method of alignment, when compared to an amino acid sequence as set forth in SEQ ID NO:36; a second subunit having at least 95% sequence identity, based on a Clustal W method of alignment, when compared to an amino acid sequence as set forth in SEQ ID NO:38; a third subunit having at least 95% sequence identity, based on a Clustal W method of alignment, when compared to an amino acid sequence as set forth in SEQ ID NO:40; and a fourth subunit having at least 95% sequence identity, based on a Clustal W method of alignment, when compared to an amino acid sequence as set forth in SEQ ID NO:42.

In another embodiment, the polypeptide having sucrose transporter activity corresponds substantially to the amino acid sequence set forth in SEQ ID NO:26 or SEQ ID NO:96.

Polypeptides having fructokinase activity include fructokinases (designated EC 2.7.1.4) and various hexose kinases having fructose phosphorylating activity (EC 2.7.1.3 and EC 2.7.1.1). Fructose phosphorylating activity may be exhibited by hexokinases and ketohexokinases. Representative genes encoding polypeptides from a variety of microorganisms, which may be used to construct the recombinant bacteria disclosed herein, are listed in Table 1. One skilled in the art will know that proteins that are substantially similar to a protein which is able to phosphorylate fructose (such as encoded by the genes listed in Table 1) may also be used.

TABLE 1

Sequences Encoding Enzymes with Fructokinase Activity

| Source | Gene Name | EC Number | Nucleotide SEQ ID NO: | Protein SEQ ID NO: |
|---|---|---|---|---|
| *Agrobacterium tumefaciens* | scrK (fructokinase) | 2.7.1.4 | 43 | 44 |
| *Streptococcus mutans* | scrK (fructokinase) | 2.7.1.4 | 45 | 46 |
| *Escherichia coli* | scrK (fructokinase | 2.7.1.4 | 111 | 112 |
| *Klebsiella pneumoniae* | scrK (fructokinase | 2.7.1.4 | 113 | 114 |
| *Escherichia coli* | cscK (fructokinase) | 2.7.1.4 | 47 | 48 |
| *Enterococcus faecalis* | cscK (fructokinase) | 2.7.1.4 | 49 | 50 |
| *Saccharomyces cerevisiae* | HXK1 (hexokinase) | 2.7.1.1 | 51 | 52 |
| *Saccharomyces cerevisiae* | HXK2 (hexokinase) | 2.7.1.1 | 53 | 54 |

In one embodiment, the polypeptide having fructokinase activity has at least 95% sequence identity, based on the Clustal W method of alignment, to an amino acid sequence as set forth in SEQ ID NO:44, SEQ ID NO:46, SEQ ID NO:48, SEQ ID NO:50, SEQ ID NO:52, SEQ ID NO:54, SEQ ID NO:112, or SEQ ID NO:114.

In another embodiment, the polypeptide having fructokinase activity corresponds substantially to the sequence set forth in SEQ ID NO:48

Polypeptides having sucrose hydrolase activity have the ability to catalyze the hydrolysis of sucrose to produce fructose and glucose. Polypeptides having sucrose hydrolase activity are known, as described above, and include, but are not limited to CscA from *E. coli* wild-type strain EC3132 (set forth in SEQ ID NO:56), encoded by gene cscA (coding sequence set forth in SEQ ID NO:55), CscA from *E. coli* ATCC® 13821 (set forth in SEQ ID NO:58), encoded by gene cscA (coding sequence set forth in SEQ ID NO:57); BfrA from *Bifidobacterium lactis* strain DSM 10140$^T$ (set forth in SEQ ID NO:60), encoded by gene bfrA (coding sequence set forth in SEQ ID NO:59); Suc2p from *Saccharomyces cerevisiae* (set forth in SEQ ID NO:62), encoded by gene SUC2 (coding sequence set forth in SEQ ID NO:61); ScrB from *Corynebacterium glutamicum* (set forth in SEQ ID NO:64), encoded by gene scrB (coding sequence set forth in SEQ ID NO:63); sucrose phosphorylase from *Leuconostoc mesenteroides* DSM 20193 (set forth in SEQ ID NO:66), coding sequence of encoding gene set forth in SEQ ID NO:65; and sucrose phosphorylase from *Bifidobacterium adolescentis* DSM 20083 (set forth in SEQ ID NO:68), encoded by gene sucP (coding sequence set forth in SEQ ID NO:67).

In one embodiment, the polypeptide having sucrose hydrolase activity has at least 95% sequence identity, based on the Clustal W method of alignment, to an amino acid sequence as set forth in SEQ ID NO:56, SEQ ID NO:58, SEQ ID NO:60, SEQ ID NO:62, SEQ ID NO:64, SEQ ID NO:66, or SEQ ID NO:68.

In another embodiment, the polypeptide having sucrose hydrolase activity corresponds substantially to the amino acid sequence set forth in SEQ ID NO:58.

The coding sequence of genes encoding polypeptides or polypeptide complexes having sucrose transporter activity, polypeptides having fructokinase activity, and polypeptides having sucrose hydrolase activity may be used to isolate nucleotide sequences encoding homologous polypeptides from the same or other microbial species. For example, homologs of the genes may be identified using methods known in the art, as described above.

One of ordinary skill in the art will appreciate that genes encoding these polypeptides isolated from other sources may also be used in the recombinant bacteria disclosed herein. Additionally, variations in the nucleotide sequences encoding the polypeptides may be made without affecting the amino acid sequence of the encoded polypeptide due to codon degeneracy, and that amino acid substitutions, deletions or additions that produce a substantially similar protein may be included in the encoded protein.

The nucleotide sequences encoding polypeptides or polypeptide complexes having sucrose transporter activity, polypeptides having fructokinase activity, and polypeptides having sucrose hydrolase activity may be isolated using PCR (see, e.g., U.S. Pat. No. 4,683,202) and primers designed to bound the desired sequence, if this sequence is known. Other methods of gene isolation are well known to one skilled in the art such as by using degenerate primers or heterologous probe hybridization. The nucleotide sequences can also be chemically synthesized or purchased from vendors such as DNA2.0 Inc. (Menlo Park, Calif.). Additionally, the entire wild type csc operon may be isolated from the genomic DNA of *E. coli* strain ATCC® 3281 or a variant csc operon may be isolated from a variant bacterium and integrated into the genome of the host bacterium between the yihP gene or its homolog and the yihO gene or its homolog, as described in detail in Examples 1 and 3 herein.

The nucleotide sequences encoding the polypeptides described above are introduced into the host bacterium by integrating one or more copies of the coding sequences into the host genome between the yihP gene or its homolog and the yihO gene or its homolog using site-specific recombination systems known in the art, such as for example, as described in Examples 1-4 and 7-10 herein. The introduced coding regions in the genome may be expressed from at least one highly active promoter. An integrated coding region may either be introduced as a part of a chimeric gene having its own promoter, or it may be integrated adjacent to a highly active promoter that is endogenous to the genome or in a highly expressed operon. Suitable promoters include, but are not limited to, CYC1, HIS3, GAL1, GAL10, ADH1, PGK, PHO5, GAPDH, ADC1, TRP1, URA3, LEU2, ENO, and lac, ara, tet, trp, $IP_L$, $IP_R$, T7, tac, and trc (useful for expression in *Escherichia coli*) as well as the amy, apr, npr promoters and various phage promoters useful for expression in *Bacillus*. The promoter may also be the *Streptomyces lividans* glucose isomerase promoter or a variant thereof, described by Payne et al. (U.S. Pat. No. 7,132,527).

In one embodiment, the recombinant bacteria disclosed herein are capable of producing glycerol. Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis. In the method of producing glycerol disclosed herein, host bacteria may be used that naturally produce glycerol. In addition, bacteria may be engineered for production of glycerol and glycerol derivatives. The capacity for glycerol production from a variety of substrates may be provided through the expression of the enzyme activities glycerol-3-phosphate dehydrogenase (G3PDH) and/or glycerol-3-phosphatase as described in U.S. Pat. No. 7,005,291. Genes encoding these proteins that may be used for expressing the enzyme activities in a host bacterium are described in U.S. Pat. No. 7,005,291. Suitable examples of genes encoding polypeptides having glycerol-3-phosphate dehydrogenase activity include, but are not limited to, GPD1 from *Saccharomyces cerevisiae* (coding sequence set forth in SEQ ID NO:1, encoded protein sequence set forth in SEQ ID NO:2) and GPD2 from *Saccharomyces cerevisiae* (coding sequence set forth in SEQ ID NO:3, encoded protein sequence set forth in SEQ ID NO:4). Suitable examples of genes encoding polypeptides having glycerol-3-phosphatase activity include, but are not limited to, GPP1 from *Saccharomyces cerevisiae* (coding sequence set forth in SEQ ID NO:5, encoded protein sequence set forth in SEQ ID NO:6) and GPP2 from *Saccharomyces cerevisiae* (coding sequence set forth in SEQ ID NO:7, encoded protein sequence set forth in SEQ ID NO:8).

Increased production of glycerol may be attained through reducing expression of target endogenous genes. Down-regulation of endogenous genes encoding glycerol kinase and glycerol dehydrogenase activities further enhance glycerol production as described in U.S. Pat. No. 7,005,291. Increased channeling of carbon to glycerol may be accomplished by reducing the expression of the endogenous gene encoding glyceraldehyde 3-phosphate dehydrogenase, as described in U.S. Pat. No. 7,371,558. Down-regulation may be accomplished by using any method known in the art, for example, the methods described above for down-regulation of genes of the PTS system.

Glycerol provides a substrate for microbial production of useful products. Examples of such products, i.e., glycerol derivatives include, but are not limited to, 3-hydroxypropionic acid, methylglyoxal, 1,2-propanediol, and 1,3-propanediol.

In another embodiment, the recombinant bacteria disclosed herein are capable of producing 1,3-propanediol. The glycerol derivative 1,3-propanediol is a monomer having potential utility in the production of polyester fibers and the manufacture of polyurethanes and cyclic compounds. 1,3-Propanediol can be produced by a single microorganism by bioconversion of a carbon substrate other than glycerol or dihydroxyacetone, as described in U.S. Pat. No. 5,686,276. In this bioconversion, glycerol is produced from the carbon substrate, as described above. Glycerol is converted to the intermediate 3-hydroxypropionaldehyde by a dehydratase enzyme, which can be encoded by the host bacterium or can be introduced into the host by recombination. The dehydratase can be glycerol dehydratase (E.C. 4.2.1.30), diol dehydratase (E.C. 4.2.1.28) or any other enzyme able to catalyze this conversion. A suitable example of genes encoding the "α" (alpha), "β" (beta), and "γ" (gamma) subunits of a glycerol dehydratase include, but are not limited to dhaB1 (coding sequence set forth in SEQ ID NO:9), dhaB2 (coding sequence set forth in SEQ ID NO:11), and dhaB3 (coding sequence set forth in SEQ ID NO:13), respectively, from *Klebsiella pneumoniae*. The further conversion of 3-hydroxypropionaldehyde to 1,3-propandeiol can be catalyzed by 1,3-propanediol dehydrogenase (E.C. 1.1.1.202) or other alcohol dehydrogenases. A suitable example of a gene encoding a 1,3-propanediol dehydrogenase is dhaT from *Klebsiella pneumoniae* (coding sequence set forth in SEQ ID NO:69, encoded protein sequence set forth in SEQ ID NO:70).

Bacteria can be recombinantly engineered to provide more efficient production of glycerol and the glycerol derivative 1,3-propanediol. For example, U.S. Pat. No. 7,005,291 discloses transformed microorganisms and a method for production of glycerol and 1,3-propanediol with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase.

U.S. Pat. No. 6,013,494 describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). U.S. Pat. No. 6,136,576 discloses a method for the production of 1,3-propanediol comprising a recombinant microorganism further comprising a dehydratase and protein X (later identified as being a dehydratase reactivation factor peptide).

U.S. Pat. No. 6,514,733 describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. Additionally, U.S. Pat. No. 7,132,527 discloses vectors and plasmids useful for the production of 1,3-propanediol.

Increased production of 1,3-propanediol may be achieved by further modifications to a host bacterium, including down-regulating expression of some target genes and up-regulating, expression of other target genes, as described in U.S. Pat. No. 7,371,558. For utilization of glucose as a carbon source in a PTS minus host, expression of glucokinase activity may be increased.

Additional genes whose increased or up-regulated expression increases 1,3-propanediol production include genes encoding:
  phosphoenolpyruvate carboxylase typically characterized as EC 4.1.1.31
  cob(I)alamin adenosyltransferase, typically characterized as EC 2.5.1.17
  non-specific catalytic activity that is sufficient to catalyze the interconversion of 3-HPA and 1,3-propanediol, and specifically excludes 1,3-propanediol oxidoreductase(s), typically these enzymes are alcohol dehydrogenases Genes whose reduced or down-regulated expression increases 1,3-propanediol production include genes encoding:
  aerobic respiration control protein
  methylglyoxal synthase
  acetate kinase
  phosphotransacetylase
  aldehyde dehydrogenase A
  aldehyde dehydrogenase B
  triosephosphate isomerase
  phosphogluconate dehydratase In another embodiment, the recombinant bacteria disclosed herein are capable of producing 3-hydroxypropionic acid. 3-Hydroxypropionic acid has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction. 3-Hydroxypropionic acid may be produced biologically from a fermentable carbon source by a single microorganism, as described in copending and commonly owned U.S. Patent Application No. 61/187,476. In one representative biosynthetic pathway, a carbon substrate is converted to 3-hydroxypropionaldehyde, as described above for the production of 1,3-propanediol. The 3-hydroxypropionaldehyde is converted to 3-hydroxypropionic acid by an aldehyde dehydrogenase. Suitable examples of aldehyde dehydrogenases include, but are not limited to, AldB (SEQ ID NO:16), encoded by the *E. coli* gene aldB (coding sequence set forth in SEQ ID NO:15); AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence asset forth in SEQ ID NO:19).

Many of the modifications described above to improve 1,3-propanediol production by a recombinant bacterium can also be made to improve 3-hydroxypropionic acid production. For example, the elimination of glycerol kinase prevents glycerol, formed from G3P by the action of G3P phosphatase, from being re-converted to G3P at the expense of ATP. Also, the elimination of glycerol dehydrogenase (for example, gldA) prevents glycerol, formed from DHAP by the action of NAD-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating (disrupting) genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Furthermore, down-regulation of gene expression may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/regulatory (promoter) regions, and 3) altering coding regions and/or regulatory (promoter) regions (for example, by making DNA base pair changes). Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, *Curr. Opin. Biotechnol.* (1999) 10:411; Ross, et al., *J. Bacteriol.* (1998) 180:5375; deHaseth, et al., *J. Bacteriol.* (1998) 180:3019; Smolke and Keasling, *Biotechnol. Bioeng.* (2002) 80:762; Swartz, *Curr. Opin. Biotech.* (2001) 12:195; and Ma, et al., *J. Bacteriol.* (2002) 184:5733.

Recombinant bacteria containing the necessary changes in gene expression for metabolizing sucrose in the production of microbial products including glycerol and glycerol derivatives, as described above, may be constructed using techniques well known in the art, some of which are exemplified in the Examples herein.

The construction of the recombinant bacteria disclosed herein may be accomplished using a variety of vectors and transformation and expression cassettes suitable for the cloning, transformation and expression of coding regions that confer the ability to utilize sucrose in the production of glycerol and its derivatives in a suitable host microorganism. Suitable vectors are those which are compatible with the bacterium employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host bacterium are numerous and familiar to those skilled in the art. Virtually any promoter capable of driving expression is suitable for use herein. For example, any of the promoters listed above may be used.

Termination control regions may also be derived from various genes native to the preferred hosts. Optionally, a termination site may be unnecessary; however, it is most preferred if included.

For effective expression of the instant polypeptides, nucleotide sequences encoding the polypeptides are linked operably through initiation codons to selected expression control regions such that expression results in the formation of the appropriate messenger RNA.

Particularly useful in the present invention are the vectors pSYCO101, pSYCO103, pSYCO106, and pSYCO109, described in U.S. Pat. No. 7,371,558, and pSYCO400/AGRO, described in U.S. Pat. No. 7,524,660. The essential elements of these vectors are derived from the dha regulon isolated from *Klebsiella pneumoniae* and from *Saccharomyces cerevisiae*. Each vector contains the open reading frames dhaB1, dhaB2, dhaB3, dhaX (coding sequence set forth in SEQ ID NO:71), orfX, DAR1, and GPP2 arranged in three separate operons. The nucleotide sequences of pSYCO101, pSYCO103, pSYCO106, pSYCO109, and pSYCO400/AGRO are set forth in SEQ ID NO:72, SEQ ID NO:73, SEQ ID NO:74, SEQ ID NO:75, and SEQ ID NO:76, respectively. The differences between the vectors are illustrated in the chart below [the prefix "p-" indicates a promoter; the open reading frames contained within each "( )" represent the composition of an operon]:

pSYCO101 (SEQ ID NO:72):
    p-trc (Dar1_GPP2) in opposite orientation compared to the other 2 pathway operons,
    p-1.6 long GI (dhaB1_dhaB2_dhaB3_dhaX), and
    p-1.6 long GI (orfY_orfX_orfW).

pSYCO103 (SEQ ID NO:73):
  p-trc (Dar1_GPP2) same orientation compared to the other 2 pathway operons,
  p-1.5 long GI (dhaB1_dhaB2_dhaB3_dhaX), and
  p-1.5 long GI (orfY_orfX_orfW).
pSYCO106 (SEQ ID NO:74):
  p-trc (Dar1_GPP2) same orientation compared to the other 2 pathway operons,
  p-1.6 long GI (dhaB1_dhaB2_dhaB3_dhaX), and
  p-1.6 long GI (orfY_orfX_orfW).
pSYCO109 (SEQ ID NO:75):
  p-trc (Dar1_GPP2) same orientation compared to the other 2 pathway operons,
  p-1.6 long GI (dhaB1_dhaB2_dhaB3_dhaX), and
  p-1.6 long GI (orfY_orfX).
pSYCO400/AGRO (SEQ ID NO:76):
  p-trc (Dar1_GPP2) same orientation compared to the other 2 pathway operons,
  p-1.6 long GI (dhaB1_dhaB2_dhaB3_dhaX), and
  p-1.6 long GI (orfY_orfX).
  p-1.20 short/long GI (scrK) opposite orientation compared to the pathway operons.

Once suitable expression cassettes are constructed, they are used to transform appropriate host bacteria. Introduction of the cassette containing the coding regions into the host bacterium may be accomplished by known procedures such as by transformation (e.g., using calcium-permeabilized cells, or electroporation) or by transfection using a recombinant phage virus (Sambrook et al., supra). Expression cassettes may be maintained on a stable plasmid in a host cell. In addition, expression cassettes may be integrated into the genome of the host bacterium through homologous or random recombination using vectors and methods well known to those skilled in the art. Site-specific recombination systems may also be used for genomic integration of expression cassettes.

In addition to the cells exemplified, cells having single or multiple mutations specifically designed to enhance the production of microbial products including glycerol and/or its derivatives may also be used. Cells that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Pat. No. 7,371,558. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Fermentation media in the present invention comprise sucrose as a carbon substrate. Other carbon substrates such as glucose and fructose may also be present.

In addition to the carbon substrate, a suitable fermentation medium contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol.

Adenosyl-cobalamin (coenzyme $B_{12}$) is an important cofactor for dehydratase activity. Synthesis of coenzyme $B_{12}$ is found in prokaryotes, some of which are able to synthesize the compound de novo, for example, *Escherichia blattae*, *Klebsiella* species, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, needs be provided in *E. coli* fermentations. Vitamin $B_{12}$ may be added continuously to *E. coli* fermentations at a constant rate or staged as to coincide with the generation of cell mass, or may be added in single or multiple bolus additions.

Although vitamin $B_{12}$ is added to the transformed *E. coli* described herein, it is contemplated that other bacteria, capable of de novo vitamin $B_{12}$ biosynthesis will also be suitable production cells and the addition of vitamin $B_{12}$ to these bacteria will be unnecessary.

Typically bacterial cells are grown at 25 to 40° C. in an appropriate medium containing sucrose. Examples of suitable growth media for use herein are common commercially prepared media such as Luria Bertani (LB) broth, Sabouraud Dextrose (SD) broth or Yeast medium (YM) broth. Other defined or synthetic growth media may also be used, and the appropriate medium for growth of the particular bacterium will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is typical as the initial condition.

Reactions may be performed under aerobic, anoxic, or anaerobic conditions depending on the requirements of the recombinant bacterium. Fed-batch fermentations may be performed with carbon feed, for example, carbon substrate, limited or excess.

Batch fermentation is a commonly used method. Classical batch fermentation is a closed system where the composition of the medium is set at the beginning of the fermentation and is not subject to artificial alterations during the fermentation. Thus, at the beginning of the fermentation, the medium is inoculated with the desired bacterium and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable for use herein and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by the turbidity of the medium, is kept constant. Continuous systems strive to maintain steady state growth conditions, and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, such as 1,3-propanediol.

In one embodiment, a process for making glycerol, 1,3-propanediol, and/or 3-hydroxypropionic acid from sucrose is provided. The process comprises the steps of culturing a recombinant bacterium, as described above, in the presence of sucrose, and optionally recovering the glycerol, 1,3-propanediol, and/or 3-hydroxypropionic acid produced. The product may be recovered using methods known in the art. For example, solids may be removed from the fermentation medium by centrifugation, filtration, decantation, or the like. Then, the product may be isolated from the fermentation medium, which has been treated to remove solids as described above, using methods such as distillation, liquid-liquid extraction, or membrane-based separation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology*, 5$^{th}$ Ed. Current Protocols, John Wiley and Sons, Inc., N.Y., 2002.

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds.), American Society for Microbiology: Washington, D.C. (1994)); or in *Manual of Industrial Microbiology and Biotechnology*, 3$^{rd}$ Edition (Richard H. Baltz, Julian E. Davies, and Arnold L. Demain Eds.), ASM Press, Washington, D.C., 2010. All reagents, restriction enzymes and materials described for the growth and maintenance of bacterial cells may be obtained from Aldrich Chemicals (Milwaukee, Wis.), BD Diagnostic Systems (Sparks, Md.), Life Technologies (Rockville, Md.), New England Biolabs (Beverly, Mass.), or Sigma Chemical Company (St. Louis, Mo.).

The meaning of abbreviations is as follows: "sec" means second(s), "min" means minute(s), "h" means hour(s), "nm" means nanometer(s), "µL" means microliter(s), "mL" means milliliter(s), "L" means liter(s), "mM" means millimolar, "M" means molar, "g" means gram(s), "µg" means microgram(s), "ng" means nanogram(s), "bp" means base pair(s), "kbp" means kilobase pair(s), "rpm" means revolutions per minute, "ATCC" means American Type Culture Collection, Manassas, Va., "OD" means optical density, "g" means the gravitation constant, "HPLC" means high performance liquid chromatography.

TABLE 2

Primers used in the Examples

| Primer | Sequence | SEQ ID NO: |
|---|---|---|
| aldH cscA | TAGACGTGAAACAGGAGTCATAATGAATTT TCATCATCTGGGATCCCTTGCCCGCTGTTG | 115 |
| aldH cscB | CATTTCAGGCCTCCAGGCTTATCCAGATGG TTTTCAGTTCGAATTCGCAGGACCGTGATA | 116 |
| aldH_check_up | TGAGCGAATCCCGATGAGCTTACT | 117 |
| aldH_check_dn | ATACGTTCGCGGATGATCTCACCA | 118 |
| yihP cscA | ACCATTGTGGCGATGGGTTGCTTCTACAGC CTGAACGAGAGGATCCCTTGCCCGCTGTTG | 119 |
| yihP cscB | TTACGGGCTTCTATCTCTTCCACAATGCGG ACATACATCTGAATTCGCAGGACCGTGATA | 120 |
| yihPA For | TGC TGG GCG ATC TGC TCA ACT ATT | 121 |
| yihPB Rev | TAA TCC CGC CAT AGT AAG CAG GCA | 122 |

Examples 1-4

Integration of Sucrose Gene Clusters in the E. coli Chromosome

These Examples describe the integration of sucrose gene clusters in two locations within the genome of E. coli, at the aldH gene or between the yihP gene and the yihO gene, to enable sucrose utilization.

Wild type or variant cscAKB gene clusters from E. coli ATCC® 13281 were introduced into PDO producing strain TTab pSYCO400/AGRO to enable PDO production from sucrose. E. coli strain TTab pSYCO400/AGRO, a PTS minus strain, was constructed as follows. Strain TTab was generated by deletion of the aldB gene from strain TT aldA, described in U.S. Pat. No. 7,371,558 (Example 17). Briefly, an aldB deletion was made by first replacing 1.5 kbp of the coding region of aldB in E. coli strain MG1655 with the FRT-CmR-FRT cassette of the pKD3 plasmid (Datsenko and Wanner, Proc. Natl. Acad. Sci. USA 97:6640-6645, 2000). A replacement cassette was amplified with the primer pair SEQ ID NO:58 and SEQ ID NO:59 using pKD3 as the template. The primer SEQ ID NO:58 contains 80 bp of homology to the 5'-end of aldB and 20 bp of homology to pKD3. Primer SEQ ID NO:59 contains 80 bp of homology to the 3' end of aldB and 20 bp homology to pKD3. The PCR products were gel-purified and electroporated into MG1655/pKD46 competent cells (U.S. Pat. No. 7,371,558). Recombinant strains were selected on LB plates with 12.5 mg/L of chloramphenicol. The deletion of the aldB gene was confirmed by PCR, using the primer pair SEQ ID NO:60 and SEQ ID NO:61. The wild-type strain gave a 1.5 kbp PCR product while the recombinant strain gave a characteristic 1.1 kbp PCR product. A P1 lysate was prepared and used to move the mutation to the TT aldA strain to form the TT aldAΔaldB::Cm strain. A chloramphenicol-resistant clone was checked by genomic PCR with the primer pair SEQ ID NO:60 and SEQ ID NO:61 to ensure that the mutation was present. The chloramphenicol resistance marker was removed using the FLP recombinase (Datsenko and Wanner, supra) to create TTab. Strain TTab was then transformed with pSYCO400/AGRO (set forth in SEQ ID NO:55), described in U.S. Pat. No. 7,524,660 (Example 4), to generate strain TTab pSYCO400/AGRO.

As described in the cited references, strain TTab is a derivative of E. coli strain FM5 (ATCC® No. 53911) containing the following modifications:
deletion of glpK, gldA, ptsHI, crr, edd, arcA, mgsA, qor, ackA, pta, aldA and aldB genes;
upregulation of galP, glk, btuR, ppc, and yqhD genes; and downregulation of gapA gene.

Plasmid pSYCO400/AGRO contains genes encoding a glycerol production pathway (DAR1 and GPP2) and genes encoding a glycerol dehydratase and associated reactivating factor (dhaB123, dhaX, orfX, orfY), as well as a gene encoding a fructokinase (scrK).

The wild type or a variant sucrose gene cluster from E. coli ATCC® 13281 was integrated at the aldH gene or the yihP gene in TTab pSYCO400/AGRO by the Lambda Red method. FIG. 1 shows the chromosomal regions where the sucrose gene cluster was integrated. The wild type cscAKB gene cluster (SEQ ID NO: 123) was amplified from plasmid pBHR-cscBKA (SEQ ID NO:124), which was constructed as described in Example 1 of U.S. Patent Application Publication No. 2011/0136190 A1. The variant sucrose gene cluster containing a leucine to proline substitution at codon 61 (L61P) in the cscB gene (SEQ ID NO:95) was amplified from an isolate of a TTab pSYCO400/AGRO strain transformed with the cscAKB gene cluster from E. coli ATCC® 3281 at the aldH gene, which exhibited enhanced growth on sucrose.

Integration at the aldH gene was achieved using aldH cscA primer (SEQ ID NO:115) and aldH cscB primer (SEQ ID NO:116) containing flanking homology for both regions outside of the aldH gene in the chromosome. Integration of the sucrose gene cluster at the aldH gene replaced the aldH gene with the sucrose gene cluster. Integration between the yihP gene and the yihO gene was achieved using yihP cscA primer (SEQ ID NO:119) and yihP cscB primer (SEQ ID NO:120) containing flanking homology for the yihP gene. The sucrose gene cluster was inserted at a site close to the C-terminal end of yihP without removing the yihP sequence from the chromosome. Plasmid pBHR-cscBKA, linearized by PstI digest, was used as the PCR template for the wild type cluster. Cells containing the L61P substitution in cscB of the sucrose gene cluster were used as the PCR template for the variant cluster. High fidelity PfuUltra® II Fusion HS DNA polymerase (Stratagene; La Jolla, Calif.) was used in the PCR reaction. PCR was performed using the following cycling conditions: 95° C. for 2 min; 35 cycles of 95° C. for 30 sec, 60° C. for 30 sec, and 72° C. for 4 min; and then 72° C. for 7 min. The resulting PCR product was stored at 4° C. The PCR product was purified using a QIAquick PCR Purification kit (Qiagen, Valencia, Calif.). The PCR product was electroporated into the TTab pSYCO400/AGRO strain containing the pKD46 plasmid (Red recombinase plasmid, GenBank Acc. No. AY048746), encoding lambda recombinases, following the lambda red recombination procedure (Datsenko, K. A. and Wanner, B. L., 2000, Proc. Natl. Acad. Sci. USA 97: 6640-6645). The transformation mixture was plated on MOPS minimal plates containing 10 g/L sucrose and 100 µg/mL spectinomycin. The MOPS minimal plates contained 1XMOPS buffer (Technova, Hollister, Calif.), 1.32 mM KH$_2$PO$_4$ (Technova), 50 µg/L uracil and 1.5 g/L Bacto agar. Plates were incubated at 37° C. for 2-3 days. Colonies grown on minimal sucrose plates were picked and purified by streaking on LB spectinomycin plates. Integration of the sucrose gene cluster at the aldH gene was confirmed by PCR using primer aldH_check_up (SEQ ID NO: 117) and primer aldH_check_dn (SEQ ID NO:118). Integration of the sucrose gene cluster between the yihP gene and the yihO gene was confirmed by PCR using primer yihPA For (SEQ ID NO: 121) and primer yihPB Rev (SEQ ID NO:122). The integrated sucrose gene cluster was confirmed by sequencing to ensure that the isolated strains contained no unexpected mutation. The strains constructed are summarized in Table 3.

TABLE 3

Recombinant E. coli Strains Containing an Integrated Sucrose Gene Cluster

| Example | Strain | cscAKB | Location in Genome |
|---|---|---|---|
| 1 | PDO3083 | wild type | between yihP and yihO |
| 2, Comparative | PDO3084 | wild type | aldH |
| 3 | PDO3096 | L61P variant | between yihP and yihO |
| 4, Comparative | PDO3097 | L61P variant | aldH |

Example 5

Growth Rates of Recombinant E. coli Strains

This Example demonstrates the enhanced growth on sucrose of the E. coli strains having a sucrose gene cluster integrated between the yihP gene and the yihO gene compared to E. coli strains having the sucrose gene cluster integrated at the aldH gene.

The maximum growth rates of the integrated E. coli strains in sucrose containing minimal medium was determined using the Bioscreen C instrument (Bioscreen, Helsinki, Finland). Two isolates from each integrated strain were picked for the assay. The E. coli strains were individually grown in 3 mL of LA medium (1% tryptone, 0.5% yeast extract, 0.05% sodium chloride) containing 100 μg/mL spectinomycin at 37° C. for 16 hours. For the Bioscreen assay, the fresh overnight cultures were diluted 1:100 into MOPS minimal medium containing 2.5 g/L, 5 g/L or 10 g/L sucrose and 100 μg/mL spectinomycin in a Bioscreen honeycomb plate. Vitamin $B_{12}$ was added to the medium to a concentration of 0.1 mg/L. Blank wells containing the growth medium were also included. The honeycomb plate was placed into the Bioscreen C instrument according to the manufacturer's instructions. The plate was incubated at 33° C. with constant shaking and the OD was recorded every 15 min. The maximum growth rate ($\mu_{max}$) was estimated using the following procedure. First, the background was removed by subtracting the averaged OD values in the blank wells from the OD values of non-blank wells. Then, the growth rate parameter was estimated using a sliding window consisting of 8 data points (covering 2 hours of growth) by fitting the data points to an exponential curve using non-linear regression. In each sliding window, the estimated growth rate was recorded only if the fit was good (i.e., $R^2 > 0.95$). The largest value from all the recorded growth rates was the $\mu_{max}$. The $\mu_{max}$ of both isolates of each strain are given in Table 4. Strains containing integration of the sucrose gene cluster between the yihP gene and the yihO gene showed faster growth on sucrose than strains containing the cluster at the aldH gene, particularly at low sucrose levels.

Example 6

Production of PDO and Glycerol by Recombinant E. coli Strains Grown on Sucrose This Example describes the production of PDO and glycerol by the E. coli strains described in Examples 1-4 when grown on sucrose.

The molar yield for production of PDO and glycerol was determined in shake flask studies. Fresh overnight cultures of the E. coli isolates were inoculated into 12.5 mL MOPS medium containing 10 g/L sucrose plus 100 ng/mL Vitamin B12 and 100 μg/mL spectinomycin to an initial OD of 0.01. Cells were grown at 33° C. with shaking at 250 rpm for 44 hours. Cultures were centrifuged and the supernatants were added to 0.22 μm Spin-X centrifuge tube filters (Corning Inc., Corning, N.Y.) and centrifuged at 10,000 g for 1 min. The filtrates were analyzed by HPLC using a Waters Alliance 2690 HPLC system (Waters Corp., Milford, Mass.) with an Aminex HPX-87C HPLC carbohydrate analysis column (Bio-Rad Laboratories, Hercules, Calif., Cat #125-0095) heated to 85° C. in a separated Waters TCM heating chamber. A Bio-Rad carbo-C micro-guard column (Bio-Rad, Cat #125-0128) was used before the analysis column. The mobile phase was composed of 0.05 mM CaO (Sigma, #208159), 0.5 mM MES (Sigma, #M3671), 0.05 mM $HNO_3$ (EMD Chemicals, Gibbstown, N.J., Cat #NX0409), pH 5.3. The flow rate was 0.5 mL/min. Typically, the retention times of PDO and glycerol were 17.5 min and 19.3 min, respectively. The retention times of sucrose, glucose and fructose were 10.3 min, 12.5 min and 15.9 min, respectively.

E. coli strains containing the sucrose gene cluster integration between the yihP gene and the yihO gene showed slightly higher molar yield for production of PDO and glycerol (i.e., moles of PDO and glycerol per mole of sucrose) than the strains containing the sucrose gene cluster integrated at the aldH gene for both the wild type gene cluster and the variant gene cluster, as shown in Table 4.

TABLE 4

Growth Rate and Molar Yield for the Production of PDO and Glycerol by Recombinant E. coli Strains

| TTab-derived strains | cscAKB* | Location | Growth rate ($\mu_{max}$, hour$^{-1}$) on sucrose | | | Molar yield (mol PDO + Gly/ mol sucrose) |
|---|---|---|---|---|---|---|
| | | | 2.5 g/L | 5 g/L | 10 g/L | |
| Example 1-isolate 7 | wild type | between yihP and yihO | 0.127 | 0.165 | 0.197 | 1.10 |
| Example 1-isolate 8 | wild type | between yihP and yihO | 0.124 | 0.183 | 0.185 | 1.14 |
| Example 2 Comparative, isolate 7 | wild type | aldH | 0.102 | 0.151 | 0.234 | 1.09 |
| Example 2 Comparative, isolate 18 | wild type | aldH | 0.084 | 0.146 | 0.228 | 1.08 |
| Example 3 - isolate 13 | L61P variant | between yihP and yihO | 0.251 | 0.258 | 0.255 | 1.26 |
| Example 3 - isolate 14 | L61P variant | between yihP and yihO | 0.253 | 0.276 | 0.263 | 1.26 |
| Example 4 Comparative, isolate 15 | L61P variant | aldH | 0.233 | 0.272 | 0.275 | 1.25 |
| Example 4 Comparative, isolate 19 | L61P variant | aldH | 0.232 | 0.270 | 0.275 | 1.25 |

Examples 7-10

Integration of Sucrose Gene Clusters in a Wild Type E. coli Strain

These Examples describe the integration of sucrose gene clusters in a non-PDO producing wild type *E. coli*. Integration between the yihP gene and the yihO gene also resulted in faster growth in sucrose than integration at the aldH gene in this *E. coli* strain.

Integration of the wild type or the variant sucrose gene cluster at aldH or yihP gene in *E. coli* strain FM5 (ATCC® No. 53911) was done as described in Examples 1-4, except that *E. coli* strain FM5 was used as the host for integration. The colonies were also purified and cured of pKD46. The integration site was confirmed by PCR and the integrated clusters were sequenced to ensure that no unexpected mutation occurred. Growth rates of the FM5 derived strains on sucrose were determined using the Bioscreen assay as described in Example 5. The results (i.e., the mean and standard deviation of triplicate determinations) are shown in Table 5. The strains having the sucrose gene cluster, both the wild type and the variant gene cluster, integrated between the yihP gene and the yihO gene exhibited higher growth rates than strains having the sucrose gene cluster integrated at the aldH gene.

TABLE 5

Growth Rates of *E. coli* strain FM5 Derived Strains Containing Sucrose Gene Clusters integrated at the aldH or between the yihP gene and the yihO gene

| | | | | Growth rate ($\mu_{max}$, hour$^{-1}$) on sucrose | | |
|---|---|---|---|---|---|---|
| Example | Strain | cscAKB* | Location | 1 g/L | 2.5 g/L | 10 g/L |
| 7, Comparative | PDO3257 | wild type | aldH | 0.107 ± 0.004 | 0.235 ± 0.001 | 0.444 ± 0.007 |
| 8 | PDO3085 | wild type | between yihP and yihO | 0.133 ± 0.004 | 0.284 ± 0.008 | 0.456 ± 0.012 |
| 9, Comparative | PDO3094 | L61P variant | aldH | 0.229 ± 0.012 | 0.415 ± 0.004 | 0.448 ± 0.004 |
| 10 | PDO3099 | L61P variant | between yihP and yihO | 0.259 ± 0.002 | 0.428 ± 0.003 | 0.439 ± 0.009 |

What is claimed is:

1. A recombinant bacterium comprising in its genome:
   (a) one or more nucleotide sequences encoding a polypeptide or a polypeptide complex having sucrose transporter activity, wherein the polypeptide or the polypeptide complex having sucrose transporter activity has (i) at least 95% sequence identity based on the Clustal W method of alignment to an amino acid sequence set forth in SEQ ID NO:24, SEQ ID NO:26, SEQ ID NO:28, SEQ ID NO:94, SEQ ID NO:96, SEQ ID NO:98, SEQ ID NO:100, SEQ ID NO:102, SEQ ID NO:104, SEQ ID NO:106, SEQ ID NO:108, or SEQ ID NO:110 or (ii) polypeptide subunits having at least 95% sequence identity, based on the Clustal W method of alignment, to the amino acid sequences set forth in SEQ ID NOs: 30, 32, and 34 or the amino acid sequences set forth in SEQ ID NOs:36, 38, 40, and 42;
   (b) a nucleotide sequence encoding a polypeptide having fructokinase activity, wherein the polypeptide having fructokinase activity is classified as EC 2.7.1.4, EC 2.7.1.3, or EC 2.7.1.1; and
   (c) a nucleotide sequence encoding a polypeptide having sucrose hydrolase activity, wherein the polypeptide having sucrose hydrolase activity is classified as EC 3.2.1.26 or EC 2.4.1.7;

wherein:
   (i) (a), (b) and (c) are each operably linked to the same or a different promoter;
   (ii) (a), (b), and (c) are integrated into the genome between the yihP gene or its homolog and the yihO gene or its homolog; and
   (iii) said bacterium metabolizes sucrose at a greater rate than a bacterium comprising (a), (b), and (c) integrated at a different location in the genome.

2. The recombinant bacterium of claim 1 wherein the bacterium is selected from the group consisting of the genera: *Escherichia, Klebsiella, Citrobacter*, and *Aerobacter*.

3. The recombinant bacterium of claim 2 wherein the bacterium is *Escherichia coli*.

4. The recombinant bacterium of claim 1 wherein the bacterium produces 1,3-propanediol, glycerol, and/or 3-hydroxypropionic acid.

5. A process for making glycerol, 1,3-propanediol and/or 3-hydroxypropionic acid from sucrose comprising:
   a) culturing the recombinant bacterium of claim 4 in the presence of sucrose; and
   b) recovering the glycerol, 1,3-propanediol and/or 3-hydroxypropionic acid produced.

* * * * *